US009650340B2

(12) United States Patent
Lücking et al.

(10) Patent No.: US 9,650,340 B2
(45) Date of Patent: May 16, 2017

(54) 5-FLUORO-N-(PYRIDIN-2-YL)PYRIDIN-2-AMINE DERIVATIVES CONTAINING A SULFOXIMINE GROUP

(71) Applicant: BAYER PHARMA AKTIENGESELLSCHAFT, Berlin (DE)

(72) Inventors: Ulrich Lücking, Berlin (DE); Niels Böhnke, Berlin (DE); Arne Scholz, Berlin (DE); Philip Lienau, Berlin (DE); Gerhard Siemeister, Berlin (DE); Ulf Bömer, Glienicke (DE); Dirk Kosemund, Berlin (DE); Rolf Bohlmann, Berlin (DE); Ludwig Zorn, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/443,279

(22) PCT Filed: Nov. 12, 2013

(86) PCT No.: PCT/EP2013/073637
§ 371 (c)(1),
(2) Date: May 15, 2015

(87) PCT Pub. No.: WO2014/076091
PCT Pub. Date: May 22, 2014

(65) Prior Publication Data
US 2015/0291528 A1 Oct. 15, 2015

(30) Foreign Application Priority Data
Nov. 15, 2012 (EP) .................... 12192852

(51) Int. Cl.
*C07D 405/14* (2006.01)
*C07D 213/72* (2006.01)
*C07D 401/12* (2006.01)
*A61K 31/444* (2006.01)

(52) U.S. Cl.
CPC .......... *C07D 213/72* (2013.01); *A61K 31/444* (2013.01); *C07D 401/12* (2013.01)

(58) Field of Classification Search
CPC ............................ C07D 213/72; C07D 405/14
USPC ........................... 546/256, 264; 514/332, 333
See application file for complete search history.

(56) References Cited

U.S. PATENT DOCUMENTS 9,242,937 B2 * 1/2016 Ruhter ................ C07D 213/74
2004/0209895 A1 10/2004 Luecking et al.
2005/0176743 A1 8/2005 Luecking et al.

2010/0184789 A1 7/2010 Wabnitz et al.
2011/0028492 A1 2/2011 Barsanti et al.
2011/0306602 A1 12/2011 Wabnitz et al.

FOREIGN PATENT DOCUMENTS

| EP | 2527332 | 11/2012 |
|---|---|---|
| WO | WO-02059110 | 8/2002 |
| WO | WO-2005037800 | 4/2005 |
| WO | WO-2006064251 | 6/2006 |
| WO | WO-2008028590 | 3/2008 |
| WO | WO-2008060248 | 5/2008 |
| WO | WO-2008079918 | 7/2008 |
| WO | WO-2008079933 | 7/2008 |
| WO | WO-2008129070 | 10/2008 |
| WO | WO-2008129071 | 10/2008 |
| WO | WO-2008129080 | 10/2008 |
| WO | WO-2008132138 | 11/2008 |
| WO | WO-2009029998 | 3/2009 |
| WO | WO-2009118567 | 10/2009 |
| WO | WO-2011116951 | 9/2011 |
| WO | WO-2012117059 | 9/2012 |
| WO | WO-2013037894 | 3/2013 |
| WO | WO-2013037896 | 3/2013 |
| WO | WO-2014060376 | 4/2014 |
| WO | WO-2014076028 | 5/2014 |
| WO | WO-2014076091 | 5/2014 |
| WO | WO-2015001021 | 1/2015 |
| WO | WO-2015136028 | 9/2015 |

OTHER PUBLICATIONS

Jordan "Tamoxifen " Nature Rev. v.2, p. 205-213 (2003).*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . ." J. Royal Soc. Chem. Commun. p. 3635-3645 (2005).*
Bernstein, "Polymorphism in . . ." p. 115-118, 272 (2002).*
Davidovich et al., "Detection of polymorphism . . ." Am. Pharm. Rev. v.&(1) p. 10, 12, 14, 16, 100 (2004).*
Dean "Analytical Chem . . ." p. 10.24-10.26 (1995).*
Ivanisevic et al. "Use of X-ray . . ." Pharm. Sci. Encycl. p. 1-42 (2010).*
Seddon "Pseudopolymorph . . ." Crystal Growth & design v.4(6) p. 1087 (2004) (2 pages from internet).*

(Continued)

*Primary Examiner* — Patricia L Morris
(74) *Attorney, Agent, or Firm* — Morrison and Foerster LLP

(57) ABSTRACT

The present invention relates to 5-fluoro-N-(pyridin-2-yl) pyridin-2-amine derivatives containing a sulfoximine group of general formula (I) as described and defined herein, and methods for their preparation, their use for the treatment and/or prophylaxis of disorders, in particular of hyperproliferative disorders and/or virally induced infectious diseases and/or of cardiovascular diseases. The invention further relates to intermediate compounds useful in the preparation of said compounds of general formula (I).

9 Claims, No Drawings

(56) References Cited

OTHER PUBLICATIONS

Jain et al., "Polymorphism in Pharmacy", Indian Drugs, 1986, 23(6) 315-329.*

Dorwald, Side Reactions in Organic Synthesis, 2005, Wiley: VCH Weinheim Preface, pp. 1-15 & Chapter 8, pp. 279-308.*

Allenmark, S. et al. (1983). "Enantioselective Liquid Chromatographic retention of a Series of Sulfoxides and N-substituted Sulfoximines on Chiral Stationary Phases," Acta Chemica Scandinavica B 37: 325-328.

Bark-Jones, S.J. et al. (2006). "EBV EBNA 2 stimulates CDK9-dependent transcription and RNA polymerase II phosphorylation on serine 5," Oncogene 25: 1775-1785.

Barnes, A.C. et al. (1979). "Pharmacologically Active Sulfoximides: 5-Hexyl-7-(S-methylsulfonimidoyl)xanthone-2-carboxylic Acid, a Potent Antiallergic Agent," Journal of Medicinal Chemistry 22(4): 418-424.

Bauer, V.J. et al. (Oct. 1966). "The Reactions of Carbamoyl Azides with Sulfur Nucleophiles," Journal of Organic Chemisty 31: 3440-3441.

Berge, S.M. et al. (Jan. 1977). "Pharmaceutical Salts," Journal of Pharmaceutical Sciences 66(1): 1-19.

Bolm, C. et al. (1998). "Palladium-Catalyzed Carbon-Nitrogen Bond Formation: A Novel, Catalytic Approach towards N-Arylated Sulfoximines," Tetrahendron Letters 39: 5731-5734.

Bolm, C. et al. (2000). "Palladium-Catalyzed N-Arylation of Sulfoximines with Aryl Bromides and Aryl Iodides," Journal of Organic Chemistry 65: 169-175.

Bolm, C. et al. (Feb. 2000). "Catalytic Coupling of Aryl Sulfonates with $Sp^2$-Hybridized Nitrogen Nucleophiles: Palladium- and Nickel-catalyzed Synthesis of N-Aryl Sulfoximines," Synthesis 7:911-913.

Bolm, C. et al. (2001). "Synthesis of Pseudopeptides with Sulfoximines as Chiral Backbone Modifying Elements," Chem. Eur. J. 7(5): 1118-1128.

Bolm, C. et al. (2002). "A Mild Synthetic Procedure for the Preparation of N-Alkylated Sulfoximines," Synthesis 7: 879-887.

Cho, G.Y., et al. (2005). "Synthesis and Palladium-Catalyzed Coupling Reaction of Enantiopure p-Bromophenyl Methyl Sulfoximine," J. Org. Chem. 70(6): 2346-2349.

Cho, S. et al. (May 1, 2010). "CYCLINg through transcription Posttranslational modification of P-TEFb regulate transcription elongation," Cell Cycle 9(9): 1697-1705.

Copeland, R. A. et al. (2006). "Drug-target residence time and its implications for lead optimization," Nature Reviews Drug Discovery 5: 730-739.

Craig, D. et al. (1995). "Asymmetric Intramolecular Diels-Alder Reactions of Sulfoximine-activated Trienes," Tetrahedron 51(21): 6071-6098.

Cram, D.J. (Dec. 16, 1970). "Stereochemistry of Sulfur Compounds. I. Stereochemical Reactions Cycles Involving an Open chain Sulfoxide, Sulfimide, and Sulfoximide," Journal of the American Chemical Society 92(25): 7369-7384.

De Meijere, A. et al. (2004). "Metal-Catalyzed Cross-Coupling Reactions," WILEY-VCH Verlag GmbH & Co. KGaA, Weinheim, pp. 83-91.

Dey, A. et al. (Aug. 1, 2007). "HEXIM1 and the Control of Transcription Elongation from Cancer and Inflammation to AIDS and Cardiac Hypertrophy," Cell Cycle 6(15): 1856-1863.

Füger, B. et al. (2009). "Ring-Closing Enyne Metathesis (RCEYM) for the Synthesis of Cyclic Sulfoximines," Synlett 10: 1601-1604.

Hackenberger, C.P.R., et al. (2004). "Synthetic and Spectroscopic Investigation of N-Acylated Sulfoximines," Chem. Eur. J. 10: 2942-2952.

He, N. et al. (Mar. 14, 2008). "A La-Related Protein Modulates 7SK snRNP Integrity to Suppress P-TEFb-Dependent Transcriptional Elongation and Tumorigenesis," Molecular Cell 29: 588-599.

International Preliminary Report on Patentablility dated May 19, 2015 for PCT Application No. PCT/EP2013/073637, filed on Nov. 12, 2013, 8 pages.

Johnson, C.R. (Nov. 4, 1970). "Preparation and Synthetic Applications of (Dimethylamino) phenyloxosulfonium Methylide," Journal of the American Chemical Society 92(22): 6594-6598.

Johnson, C.R. (1978). "Preparation of α-Halo Sulfoximines," Journal of Organic Chemistry 43(21): 4136-4140.

Johnson, C.R. et al. (1993). "Alkylation of Sulfoximines and Related Compounds at the Imino Nitrogen under Phase-Transfer Conditions," Journal of Organic Chemistry 58(7): 1922-1923.

Jones, M.R. et al. (Apr. 3, 1974). "Stereochemisty of Sulfur Compounds. VII. Course of Substitution at Sulfur Attached to Four Different Ligands," Journal of the American Chemical Society 96(7): 2183-2190.

Mancheño, O.G. et al. (2007). "Synthesis of N-(1H)-Tetrazole Sulfoximines," Organic Letters 9(15)" 2951-2954.

Okamura, H. et al. (2004). "Rhodium-Catalyzed Imination of Sulfoxides and Sulfides: Efficient Preparation of N-Unsubstituted Sulfoximines and Sulfilimines," Organic Letters 6(8): 1305-1307.

Polla, M.O. et al. (2004). "Design and synthesis of potent, orally active, inhibitors of carboxypeptidase U (TAFIa)," Bioorganic & Medicinal Chemistry Letters 12: 1151-1175.

Sammond, D.M. et al. (2005). "Discovery of a novel and potent series of dianilinopyrimidineurea and urea isostere inhibitors of VEGFR2 tyrosine kinase," Bioorganic & Medicinal Chemistry Letters 15: 3519-3523.

Sauer, D.T. et al. (1972). "Bis(perfluoroalkyl)sulfur oxyimines and silver Bis(trifluoromethyl)sulfur Oxyimine," Inorganic Chemistry 11(2): 238-242.

Stoss, P. et al. (1978). "Transannulare Acylwanderungen in cyclischen Sulfoximiden," Chem. Ber. 111: 1453-1463.

Wang, S. et al. (2008). "Cyclin-dependent kinase 9: a key transcriptional regulator and potential drug target in oncology, virology and cardiology," Trends in Pharmacological Sciences 29(6): 302-313.

Wang, S. et al. (2010). "Discovery and Characterization of 2-Anilino-4-(Thiazol-5-yl)Pyrimidine Transcriptional CDK Inhibitors as Anticancer Agents," Chemistry & Biology 17: 1111-1121.

Yang, Z. et al. (Aug. 19, 2005). "Recruitment of P-TEFb for Stimulation of Transcriptional Elongation by the Bromodomain Protein Brd4," Molecular Cell 19: 535-545.

Zhou, M. et al. (Dec. 2004). "Coordination of Transcription Factor Phosphorylation and Histone Methylation by the P-TEFb Kinase during Human Inmmunodeficiency Virus Type 1 Transcription," Journal of Virology 78(24): 13522-13533.

Zhou, Q. et al. (Sep. 2006). "The Yin and Yang of P-TEFb Regulation: Implications for Human Immunodeficiency Virus Gene Expression and Global Control of Cell Growth and Differentiation," Microbiology and Molecular Biology Reviews 70(3): 646-659.

* cited by examiner

5-FLUORO-N-(PYRIDIN-2-YL)PYRIDIN-2-AMINE DERIVATIVES CONTAINING A SULFOXIMINE GROUP

CROSS REFERENCE TO RELATED APPLICATIONS

This application is a National Phase application under 35 U.S.C. §371 of International Application No. PCT/EP2013/073637, filed Nov. 12, 2013, which claims priority benefit of European Application No. 12192852.7, filed Nov. 15, 2012, the disclosures of each of which are hereby incorporated by reference in their entireties for all purposes.

The present invention relates to 5-fluoro-N-(pyridin-2-yl)pyridin-2-amine derivatives containing a sulfoximine group of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol Mol Biol Rev 70, 646, 2006). Furthermore, the activity of P-TEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the P-TEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of P-TEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data is presented. These compounds do not contain a fluoro atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heteroaryl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluoro atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO 2012101064 discloses N-acyl pyrimidine biaryl compounds as inhibitors of CDK9.

WO 2012101065 discloses pyrimidine biaryl compounds as inhibitors of CDK9. The biaryl core mandatorily consists of two heteroaromatic rings.

WO 2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

WO 2013037896 discloses disubstituted 5-fluoropyrimidines as selective inhibitors of CDK9.

WO 2013037894 discloses disubstituted 5-fluoropyrimidine derivatives containing a sulfoximine group as selective inhibitors of CDK9.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618,968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBKL and/or IKK epsilon. The specific examples mainly focus on compounds having a pyrimidine core.

WO2012142329 concerns amino-pyrimidine compounds as inhibitors of TBKL and/or IKK epsilon.

WO2012139499 discloses urea substituted anilino-pyrimidines as inhibitors of various protein kinases.

Despite the fact that various inhibitors of CDKs are known, there remains a need for selective CDK9 inhibitors to be used for the treatment of diseases such as hyperproliferative diseases, viral diseases, and/or diseases of the heart, which offer one or more advantages over the compounds known from prior art, such as:
- improved activity and/or efficacy
- beneficial kinase selectivity profile according to the respective therapeutic need
- improved side effect profile, such as fewer undesired side effects, lower intensity of side effects, or reduced (cyto)toxicity, e.g. via reduced inhibition of Carbonic anhydrase
- improved physicochemical properties, such as solubility in water body fluids, and aqueous formulations, e.g. for intravenous administration s
- improved pharmacokinetic properties, allowing e.g. for dose reduction or an easier dosing scheme
- easier drug substance manufacturing e.g. by shorter synthetic routes or easier purification.

A particular object of the invention is to provide CDK9 kinase inhibitors which, compared to the compounds known from prior art, show an increased selectivity for CDK9/Cyclin T1 as compared to CDK2/Cyclin E.

Another object of the invention is to provide CDK9 kinase inhibitors which show an increased potency to inhibit CDK9 activity (demonstrated by a lower $IC_{50}$ value for CDK9/Cyclin T1) compared to the compounds known from prior art.

Another object of the invention is to provide CDK9 kinase inhibitors which show an increased potency to inhibit CDK9 activity at high ATP concentrations compared to the compounds known from prior art.

Another object of the invention is to provide CDK9 kinase inhibitors, which show an improved anti-proliferative activity in tumor cell lines such as HeLa compared to the compounds known from prior art.

Further, it is also an object of the present invention to provide CDK9 kinase inhibitors, which, compared to the compounds known from prior art, are highly selective for CDK9/Cyclin T1 as compared to CDK2/Cyclin E, and/or which show an increased potency to inhibit CDK9 activity and/or which show an improved anti-proliferative activity in tumor cell lines such as HeLa and/or which show an increased potency to inhibit CDK9 activity at high ATP concentrations compared to the compounds known from prior art.

The present invention relates to compounds of general formula (I)

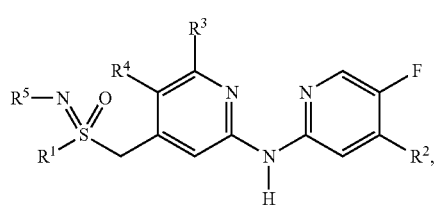

(I)

wherein
$R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(O)(OH)$_2$, —C(O)OH, —C(O)NH$_2$;
$R^2$ represents a group selected from

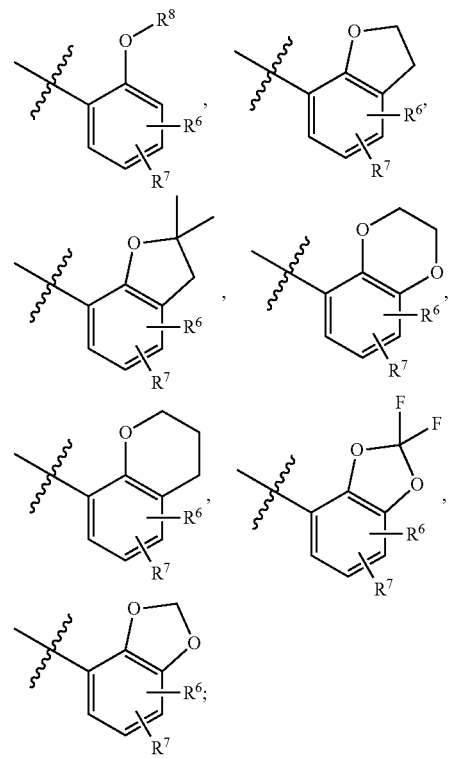

$R^3$, $R^4$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-;
$R^5$ represents a group selected from a hydrogen atom, cyano, —C(O)R$^9$, —C(O)OR$^9$, —S(O)$_2$R$^9$, —C(O)NR$^{10}$R$^{11}$, —P(O)(OR$^{12}$)$_2$, —CH$_2$OP(OR$^{12}$)$_2$, $C_1$-$C_6$-alkyl-, $C_3$-$C_7$-cycloalkyl-, heterocyclyl-, phenyl, heteroaryl,
wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;
$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;
$R^8$ represents a group selected from
a) a $C_1$-$C_6$-alkyl group, which is optionally substituted with one or two or three substituents, identically or differently, selected from halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-, C$_3$-C$_7$-cycloalkyl-, heterocyclyl-, phenyl, heteroaryl, wherein said C$_3$-C$_7$-cycloalkyl-, heterocyclyl-, phenyl or heteroaryl group is optionally substituted with one, two or three substituents, identically or differently, selected from halogen, hydroxy, C$_1$-C$_3$-alkyl-, C$_1$-C$_3$-alkoxy-, —NH$_2$, alkylamino-, dialkylamino-, acetylamino-, N-methyl-N-acetylamino-, cyclic amines, halo-C$_1$-C$_3$-alkyl-, C$_1$-C$_3$-fluoroalkoxy-;

b) a C$_3$-C$_7$-cycloalkyl- group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-;

c) a heterocyclyl- group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-, C$_2$-C$_3$-alkenyl-, C$_2$-C$_3$-alkynyl-;

d) a phenyl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

e) a heteroaryl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

f) a phenyl-C$_1$-C$_3$-alkyl- group, the phenyl group of which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

g) a heteroaryl-C$_1$-C$_3$-alkyl- group, the heteroaryl group of which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, C$_1$-C$_3$-alkyl-, halo-C$_1$-C$_3$-alkyl-, C$_1$-C$_3$-fluoroalkoxy-, C$_1$-C$_3$-alkoxy-;

h) a C$_3$-C$_6$-cycloalkyl-C$_1$-C$_3$-alkyl- group, the C$_3$-C$_6$-cycloalkyl group of which is optionally substituted with one or two or three substituents, identically or differently, selected from halogen, C$_1$-C$_3$-alkyl-, C$_1$-C$_3$-alkoxy-, halo-C$_1$-C$_3$-alkyl-, C$_1$-C$_3$-fluoroalkoxy-;

i) a heterocyclyl-C$_1$-C$_3$-alkyl- group, the heterocyclyl group of which is optionally substituted with one or two or three substituents, identically or differently, selected from halogen, C$_1$-C$_3$-alkyl-, C$_1$-C$_3$-alkoxy-, halo-C$_1$-C$_3$-alkyl-, C$_1$-C$_3$-fluoroalkoxy-;

R$^9$ represents a group selected from C$_1$-C$_6$-alkyl-, halo-C$_1$-C$_3$-alkyl-, C$_3$-C$_7$-cycloalkyl-, heterocyclyl-, phenyl, benzyl or heteroaryl, wherein said group is optionally substituted with one, two or three substituents, identically or differently, selected from halogen, hydroxy, C$_1$-C$_3$-alkyl-, C$_1$-C$_3$-alkoxy-, —NH$_2$, alkylamino-, dialkylamino-, acetylamino-, N-methyl-N-acetylamino-, cyclic amines, halo-C$_1$-C$_3$-alkyl-, C$_1$-C$_3$-fluoroalkoxy-;

R$^{10}$, R$^{11}$ represent, independently from each other, a group selected from hydrogen, C$_1$-C$_6$-alkyl-, C$_3$-C$_7$-cycloalkyl-, heterocyclyl-, phenyl, benzyl or heteroaryl, wherein said C$_1$-C$_6$-alkyl-, C$_3$-C$_7$-cycloalkyl, heterocyclyl-, phenyl, benzyl or heteroaryl group is optionally substituted with one, two or three substituents, identically or differently, selected from halogen, hydroxy, C$_1$-C$_3$-alkyl-, C$_1$-C$_3$-alkoxy-, —NH$_2$, alkylamino-, dialkylamino-, acetylamino-, N-methyl-N-acetylamino-, cyclic amines, halo-C$_1$-C$_3$-alkyl-, C$_1$-C$_3$-fluoroalkoxy-, or R$^{10}$ and R$^{11}$, together with the nitrogen atom they are attached to, form a cyclic amine;

R$_{12}$ represents a group selected from hydrogen, C$_1$-C$_4$-alkyl or benzyl, and the enantiomers, diastereomers, salts, solvates or salts of solvates thereof.

The present invention relates to compounds of general formula (I)

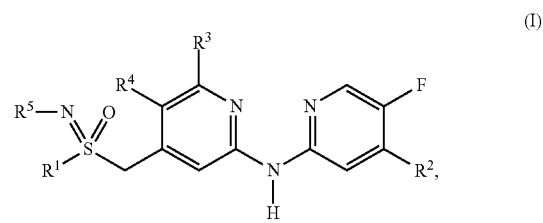

wherein

R$^1$ represents a group selected from C$_1$-C$_6$-alkyl-, C$_3$-C$_7$-cycloalkyl-, heterocyclyl-, phenyl, heteroraryl, phenyl-C$_1$-C$_3$-alkyl- or heteroaryl-C$_1$-C$_3$-alkyl-, wherein said group is optionally substituted with one or two or three substituents, identically or differently, selected from the group of hydroxy, cyano, halogen, halo-C$_1$-C$_3$-alkyl-, C$_1$-C$_6$-alkoxy-, C$_1$-C$_3$-fluoroalkoxy-, —NH$_2$, alkylamino-, dialkylamino-, acetylamino-, N-methyl-N-acetylamino-, cyclic amines, —OP(O)(OH)$_2$, —C(O)OH, —C(O)NH$_2$;

R$^2$ represents a group selected from

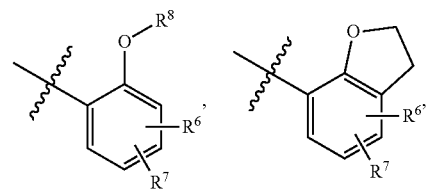

-continued

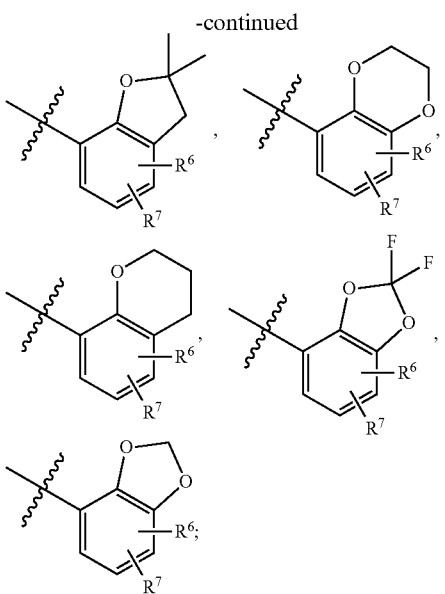

$R^3$, $R^4$ represent, independently from each other, a group selected from a hydrogen atom, fluoro atom, chloro atom, bromo atom, cyano, $C_1$-$C_3$-alkyl, $C_1$-$C_3$-alkoxy-, halo-$C_1$-$C_3$-alkyl-, $C_1$-$C_3$-fluoroalkoxy-;

$R^5$ represents a group selected from a hydrogen atom, cyano, —C(O)$R^9$, —C(O)O$R^9$, —S(O)$_2R^9$, —C(O)N$R^{10}R^{11}$, —P(O)(O$R$)$_2$, —CH$_2$OP(O$R$)$_2$, $C_1$-$C_6$-alkyl-, $C_3$-$C_7$-cycloalkyl-, heterocyclyl-, phenyl, heteroaryl,
  wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
  a) a $C_1$-$C_6$-alkyl group, which is optionally substituted with one or two or three substituents, identically or differently, selected from halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1C_3$-fluoroalkoxy-;
  b) a $C_3$-$C_7$-cycloalkyl- group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
  c) a heterocyclyl- group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-;
  d) a phenyl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  e) a heteroaryl group, which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  f) a phenyl-$C_1$-$C_3$-alkyl- group, the phenyl group of which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  g) a heteroaryl-$C_1$-$C_3$-alkyl- group, the heteroaryl group of which is optionally substituted with one or two or three substituents, identically or differently, selected from the group of halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;
  h) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;
  i) a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, $C_3$-$C_7$-cycloalkyl-, heterocyclyl-, phenyl, benzyl or heteroaryl,
  wherein said group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, phenyl, benzyl or heteroaryl,
  wherein said $C_1$-$C_6$-alkyl-, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

and the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents like lower alkylhalides such as methyl-, ethyl-, propyl-, and butylchlorides, -bromides and -iodides; dialkylsulfates like dimethyl-, diethyl-, dibutyl- and diamylsulfates, long chain halides such as decyl-, lauryl-, myristyl- and stearylchlorides, -bromides and -iodides, aralkylhalides like benzyl- and phenethylbromides and others. Examples of suitable quarternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{13}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen", "halogen atom" or "halo" represents fluorine, chlorine, bromine and iodine, particularly chlorine or fluorine, preferably fluorine.

The term "alkyl" represents a linear or branched alkyl radical having the number of carbon atoms specifically indicated, e.g. $C_1$-$C_{10}$ one, two, three, four, five, six, seven, eight, nine or ten carbon atoms, e.g. methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. If the number of carbon atoms is not specifically indicated the term "alkyl" represents a linear or branched alkyl radical having, as a rule, 1 to 9, particularly 1 to 6, preferably 1 to 4 carbon atoms. Particularly, the alkyl group has 1, 2, 3, 4, 5 or 6 carbon atoms ("$C_1$-$C_6$-alkyl"), e.g. methyl, ethyl, n-propyl-, isopropyl, n-butyl, tert-butyl, pentyl, isopentyl, hexyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl. Preferably, the alkyl group has 1, 2 or 3 carbon atoms ("$C_1$-$C_3$-alkyl"), methyl, ethyl, n-propyl or isopropyl.

The term "$C_2$-$C_3$-alkenyl" is to be understood as preferably meaning a linear or branched, monovalent hydrocarbon group, which contains one double bond, and which has 2 or 3 carbon atoms ("$C_2$-$C_3$-alkenyl"). Said alkenyl group is, for example, a vinyl, allyl, (E)-2-methylvinyl, (Z)-2-methylvinyl or isopropenyl group.

The term "$C_2$-$C_3$-alkynyl" is to be understood as preferably meaning a linear, monovalent hydrocarbon group which contains one triple bond, and which contains 2 or 3 carbon atoms. Said $C_2$-$C_3$-alkynyl group is, for example, ethynyl, prop-1-ynyl or prop-2-ynyl group.

The term "$C_3$-$C_7$-cycloalkyl" is to be understood as preferably meaning a saturated, monovalent, monocyclic hydrocarbon ring which contains 3, 4, 5, 6 or 7 carbon atoms. Said $C_3$-$C_7$-cycloalkyl group is for example, a monocyclic hydrocarbon ring, e.g. a cyclopropyl, cyclobutyl, cyclopentyl, cyclohexyl or cycloheptyl group. Said cycloalkyl ring is non-aromatic but can optionally contain one or more double bonds e.g. cycloalkenyl, such as a cyclopropenyl, cyclobutenyl, cyclopentenyl, cyclohexenyl or cycloheptenyl group, wherein the bond between said ring with the rest of the molecule may be to any carbon atom of said ring, be it saturated or unsaturated. Particularly, said cycloalkyl group is a $C_4$-$C_6$-cycloalkyl, a $C_5$-$C_6$-cycloalkyl or a cyclohexyl group.

The term "$C_3$-$C_5$-cycloalkyl" is to be understood as preferably meaning a saturated, monovalent, monocyclic hydrocarbon ring which contains 3, 4 or 5 carbon atoms. In particular said $C_3$-$C_5$-cycloalkyl group is a monocyclic hydrocarbon ring such as a cyclopropyl, cyclobutyl or cyclopentyl group. Preferably said "$C_3$-$C_5$-cycloalkyl" group is a cyclopropyl group.

The term "$C_3$-$C_6$-cycloalkyl" is to be understood as preferably meaning a saturated, monovalent, monocyclic hydrocarbon ring which contains 3, 4, 5 or 6 carbon atoms. In particular said $C_3$-$C_6$-cycloalkyl group is a monocyclic hydrocarbon ring such as a cyclopropyl, cyclobutyl, cyclopentyl or cyclohexyl group.

The term "$C_3$-$C_6$-cycloalkyl-$C_1$-$C_3$-alkyl-" group is to be understood as preferably meaning a $C_3$-$C_6$-cycloalkyl group as defined supra, in which one of the hydrogen atoms is replaced by a $C_1$-$C_3$-alkyl group, as defined supra, that links the $C_3$-$C_6$-cycloalkyl-$C_1$-$C_3$-alkyl- group to the molecule. Particularly, the "$C_3$-$C_6$-cycloalkyl-$C_1$-$C_3$-alkyl-" is a "$C_3$-$C_6$-cycloalkyl-$C_1$-$C_2$-alkyl-", preferably it is a "$C_3$-$C_6$-cycloalkyl-methyl-" group.

The term "heterocyclyl" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen. A $C_3$-$C_9$-heterocyclyl is to be understood as meaning a heterocyclyl which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl, azetidinyl, tetrahydrofuranyl, pyrrolidinyl, 1,3-dioxolanyl, imidazolidinyl, pyrazolidinyl, oxazolidinyl, isoxazolidinyl, 1,4-dioxanyl, pyrrolinyl, tetrahydropyranyl, piperidinyl, morpholinyl, 1,3-dithianyl, thiomorpholinyl, piperazinyl, or chinuclidinyl group. Optionally, said heterocyclic ring can contain one or more double bonds, e.g. 4H-pyranyl, 2H-pyranyl, 2,5-dihydro-1H-pyrrolyl, 1,3-dioxolyl, 4H-1,3,4-thiadiazinyl, 2,5-dihydrofuranyl, 2,3-dihydrofuranyl, 2,5-dihydrothienyl, 2,3-dihydrothienyl, 4,5-dihydrooxazolyl, 4,5-dihydroisoxazolyl, or 4H-1,4-thiazinyl group, or, it may be benzo fused.

Particularly a $C_3$-$C_7$-heterocyclyl is to be understood as meaning a heterocyclyl which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly a $C_3$-$C_6$-heterocyclyl is to be understood as meaning a heterocyclyl which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl" is to be understood as being a heterocyclic ring which contains 3, 4 or 5 carbon atoms, and 1, 2 or 3 of the above-mentioned heteroatom-containing groups (a "4- to 8-membered heterocyclic ring"), more particularly said ring can contain 4 or 5 carbon atoms, and 1, 2 or 3 of the above-mentioned heteroatom-containing groups (a "5- to 8-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "heterocyclyl-$C_1$-$C_3$-alkyl-" group is to be understood as preferably meaning a heterocyclyl, preferably a 4- to 7-membered heterocyclic ring, more preferably a 5- to 7-membered heterocyclic ring, each as defined supra, in which one of the hydrogen atoms is replaced by a $C_1$-$C_3$-alkyl group, as defined supra, that links the heterocyclyl-$C_1$-$C_3$-alkyl- group to the molecule. Particularly, the "heterocyclyl-$C_1$-$C_3$-alkyl-" is a "heterocyclyl-$C_1$-$C_2$-alkyl-", preferably it is a heterocyclyl-methyl- group.

The term "$C_1$-$C_6$-alkoxy-" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentyloxy, iso-pentyloxy, n-hexyloxy group, or an isomer thereof. Particularly, the "$C_1$-$C_6$-alkoxy-" group is a "$C_1$-$C_4$-alkoxy-", a "$C_1$-$C_3$-alkoxy-", a methoxy, ethoxy, or propoxy group, preferably a methoxy, ethoxy or propoxy group. Further preferred is a "$C_1$-$C_2$-alkoxy-" group, particularly a methoxy or ethoxy group.

The term "$C_1$-$C_3$-fluoroalkoxy-" is to be understood as preferably meaning a linear or branched, saturated, monovalent, $C_1$-$C_3$-alkoxy- group, as defined supra, in which one or more of the hydrogen atoms is replaced, identically or differently, by one or more fluoro atoms. Said $C_1$-$C_3$-fluoroalkoxy-group is, for example a 1,1-difluoromethoxy-, a 1,1,1-trifluoromethoxy-, a 2-fluoroethoxy-, a 3-fluoro-propoxy-, a 2,2,2-trifluoroethoxy-, a 3,3,3-trifluoropropoxy-particularly a "$C_1$-$C_2$-fluoroalkoxy-" group.

The term "alkylamino-" is to be understood as preferably meaning an alkylamino group with one linear or branched alkyl group as defined supra. ($C_1$-$C_3$)-alkylamino- for example means a monoalkylamino group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert.-butylamino-, n-pentylamino- or n-hexylamino-.

The term "dialkylamino-" is to be understood as preferably meaning an alkylamino group having two linear or branched alkyl groups as defined supra, which are independent from each other. ($C_1$-$C_3$)-dialkylamino—for example represents a dialkylamino group with two alkyl groups each of them having 1 to 3 carbon atoms per alkyl group. The term "dialkylamino-" comprises for example: N,N-Dimethylamino-, N,N-Diethylamino-, N-Ethyl-N-methylamino-, N-Methyl-N-n-propylamino-, N-Isopropyl-N-n-propylamino-, N-tert-Butyl-N-methylamino-, N-Ethyl-N-n-pentylamino- and N-n-Hexyl-N-methylamino-.

The term "cyclic amine" is to be understood as preferably meaning a cyclic amine group. Preferably, a cyclic amine means a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-", or, used synonymously, "$C_1$-$C_3$-haloalkyl-", is to be understood as preferably meaning a linear or branched, saturated, monovalent hydrocarbon group in which the term "$C_1$-$C_3$-alkyl" is defined supra, and in which one or more hydrogen atoms is replaced by a halogen atom, identically or differently, i.e. one halogen atom being independent from another. Particularly, said halogen atom is fluorine. Preferred halo-$C_1$-$C_3$-alkyl- group is a fluoro-$C_1$-$C_3$-alkyl- group, such as for example —$CH_3$, —$CHF_2$, —$CH_2F$, —$CF_2CF_3$, or —$CH_2CF_3$, preferably it is —$CF_3$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, that links the phenyl-$C_1$-$C_3$-alkyl- group to the molecule. Particularly, the "phenyl-$C_1$-$C_3$-alkyl-" is a phenyl-$C_1$-$C_2$-alkyl-, preferably it is a benzyl- group.

The term "heteroaryl" is to be understood as preferably meaning a monovalent, aromatic ring system having 5, 6, 7, 8, 9, 10, 11, 12, 13 or 14 ring atoms (a "5- to 14-membered heteroaryl" group), particularly 5 (a "5-membered heteroaryl") or 6 (a "6-membered heteroaryl") or 9 (a "9-membered heteroaryl") or 10 ring atoms (a "10-membered heteroaryl"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, or oxepinyl, etc. Preferably, heteroaryl is selected from monocyclic heteroaryl, 5-membered heteroaryl or 6-membered heteroaryl.

The term "5-membered heteroaryl" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl.

The term "6-membered heteroaryl" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl" is selected from pyridyl, pyridazinyl, pyrimidinyl, pyrazinyl, triazinyl.

The term "heteroaryl-$C_1$-$C_3$-alkyl-" is to be understood as preferably meaning a heteroaryl, a 5-membered heteroaryl or a 6-membered heteroaryl group, each as defined supra, in which one of the hydrogen atoms is replaced by a $C_1$-$C_3$-alkyl group, as defined supra, that links the heteroaryl-$C_1$-$C_3$-alkyl- group to the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, -a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl- group.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms. It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$. Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol ⌁ at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment the present invention concerns compounds of general formula (I), wherein $R^1$ represents a group selected from $C_1$-$C_6$-alkyl-, $C_3$-$C_5$-cycloalkyl-,
  wherein said group is optionally substituted with one substituent selected from the group of hydroxy, $C_1$-$C_3$-alkoxy-, halo-$C_1$-$C_2$-alkyl-, $C_1$-$C_2$-fluoroalkoxy-, —$NH_2$, alkylamino-, dialkylamino-, cyclic amines, —OP(O)(OH)$_2$, —C(O)OH, —C(O)NH$_2$;

$R^2$ represents a group selected from

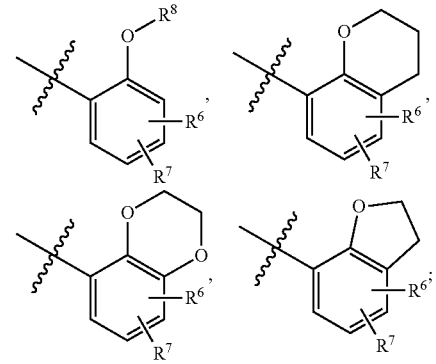

$R^3$ represents a hydrogen atom, a fluoro atom, a chloro atom, a bromo atom, or a $C_1$-$C_3$-alkyl, $C_1$-$C_3$-alkoxy or a halo-$C_1$-$C_3$-alkyl group;

$R^4$ represents a hydrogen atom, a fluoro atom, a chloro atom, or a bromo atom;

$R^5$ represents a group selected from a hydrogen atom, cyano, —C(O)$R^9$, —C(O)O$R^9$, —S(O)$_2R^9$, —C(O)N$R^{10}R^{11}$, —P(O)(O$R^{12}$)$_2$, —CH$_2$OP(O$R^{12}$)$_2$, $C_1$-$C_6$-alkyl-, $C_3$-$C_7$-cycloalkyl-, heterocyclyl-, phenyl, heteroaryl,
  wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
  a) a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, $C_1$-$C_3$-fluoroalkoxy-;

b) a phenyl-$C_1$-$C_3$-alkyl- group, the phenyl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, the heteroaryl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

d) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

e) a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, halo-$C_1$-$C_3$-alkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, benzyl, phenyl or heteroaryl,
wherein said $C_1$-$C_6$-alkyl, $C_3$-$C_7$-cycloalkyl-, heterocyclyl-, benzyl, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine;

$R^{12}$ represents a group selected from hydrogen or $C_1$-$C_4$-alkyl,
and the enantiomers, diastereomers, salts, solvates or salts of solvates thereof.

In another embodiment the present invention concerns compounds of general formula (I), wherein
$R^1$ represents a group selected from $C_1$-$C_6$-alkyl-, $C_3$-$C_5$-cycloalkyl-, wherein said group is optionally substituted with one substituent selected from the group of hydroxy, $C_1$-$C_2$-alkoxy-, halo-$C_1$-$C_2$-alkyl-, $C_1$-$C_2$-fluoroalkoxy-, —$NH_2$, alkylamino-, dialkylamino-, cyclic amines, —OP(O)(OH)$_2$, —C(O)OH, —C(O)NH$_2$;

$R^2$ represents a group selected from

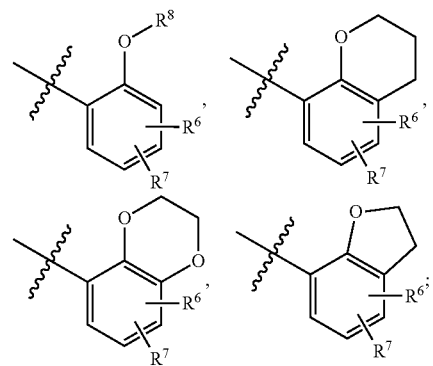

$R^3$ represents a hydrogen atom, a fluoro atom or a chloro atom, or a $C_1$-$C_3$-alkyl group;

$R^4$ represents a hydrogen atom or a fluoro atom;

$R^5$ represents a group selected from a hydrogen atom, cyano, —C(O)$R^9$, —C(O)O$R^9$, —S(O)$_2R^9$, —C(O)N$R^{10}R^{11}$, —P(O)(OR)$_2$, —CH$_2$OP(OR)$_2$, $C_1$-$C_6$-alkyl-, $C_3$-$C_7$-cycloalkyl-, heterocyclyl-, phenyl, heteroaryl,
wherein said $C_1$-$C_6$-alkyl-, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclicamines, halo-$C_1$-$C_3$-alkyl-, $C_1$-$C_3$-fluoroalkoxy-;

$R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-;

$R^8$ represents a group selected from
a) a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, dialkylamino-, acetylamino-, N-methyl-N-acetylamino-, cyclic amines, halo-$C_1$-$C_3$-alkyl-, $C_1$-$C_3$-fluoroalkoxy-;

b) a phenyl-$C_1$-$C_3$-alkyl- group, the phenyl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

c) a heteroaryl-$C_1$-$C_3$-alkyl- group, the heteroaryl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

d) a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

e) a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-;

$R^9$ represents a group selected from $C_1$-$C_6$-alkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^{10}$, $R^{11}$ represent, independently from each other, a group selected from hydrogen, $C_1$-$C_6$-alkyl-, $C_3$-$C_7$-cycloalkyl-, heterocyclyl-, benzyl, phenyl or heteroaryl,
wherein said $C_1$-$C_6$-alkyl, $C_3$-$C_7$-cycloalkyl-, heterocyclyl-, benzyl, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines , halo-$C_1$-$C_3$-alkyl-, $C_1$-$C_3$-fluoroalkoxy-, or $R^{10}$ and $R^{11}$, together with the nitrogen atom they are attached to, form a cyclic amine;

and the enantiomers, diastereomers, salts, solvates or salts of solvates thereof.

In a preferred embodiment the present invention concerns compounds of general formula (I), wherein $R^1$ represents a $C_1$-$C_6$-alkyl- or $C_3$-$C_5$-cycloalkyl group,
wherein said group is optionally substituted with one substituent selected from the group of hydroxy, $C_1$-$C_3$-alkoxy-, —$NH_2$, alkylamino-, dialkylamino-, cyclic amines, —$OP(O)(OH)_2$;

$R^2$ represents a group selected from

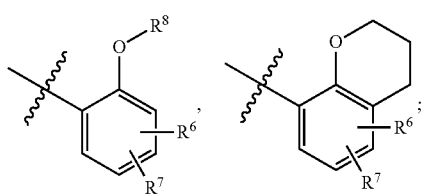

$R^3$ represents a hydrogen atom, a fluoro atom or a chloro atom, or a $C_1$-$C_3$-alkyl, $C_1$-$C_3$-alkoxy or a fluoro-$C_1$-$C_3$-alkyl group;

$R^4$ represents a hydrogen atom, a fluoro atom or a bromo atom;

$R^5$ represents a group selected from a hydrogen atom, cyano, —$C(O)R^9$, —$C(O)OR^9$, —$C(O)NR^{10}R^{11}$, —$P(O)(OR^{12})_2$, —$CH_2OP(OR^{12})_2$ or $C_1$-$C_3$-alkyl-,
wherein said $C_1$-$C_3$-alkyl group is optionally substituted with one substituent, selected from —$NH_2$, alkylamino-, dialkylamino-, or cyclic amines;

$R^6$, $R^7$ represent, independently from each other, a group selected from a hydrogen atom, a fluoro atom or a chloro atom;

$R^8$ represents a group selected from
a) a $C_1$-$C_3$-alkyl group, which is optionally substituted with one or two or three substituents, identically or differently, selected from halogen, halo-$C_1$-$C_3$-alkyl-;
b) a phenyl-$C_1$-$C_3$-alkyl- group, the phenyl group of which is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
c) a heteroaryl-$C_1$-$C_3$-alkyl- group, the heteroaryl group of which is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

$R^9$ represents a group selected from $C_1$-$C_3$-alkyl-, halo-$C_1$-$C_3$-alkyl-, or a benzyl group, the phenyl group of which is optionally substituted with one or two substituents, identically or differently, selected from the group of halogen, $C_1$-$C_3$-alkyl-, $C_1$-$C_3$-alkoxy-, —$NH_2$, alkylamino-, dialkylamino-;

$R^{10}$, $R^{11}$ represent, independently from each other, a group selected from hydrogen, $C_1$-$C_3$-alkyl-, benzyl, or $R^{10}$ and $R^{11}$, together with the nitrogen atom they are attached to, form a cyclic amine;

$R^{12}$ represents a group selected from hydrogen or $C_1$-$C_2$-alkyl, and the enantiomers, diastereomers, salts, solvates or salts of solvates thereof.

In a preferred embodiment the present invention concerns compounds of general formula (I), wherein $R^1$ represents a $C_1$-$C_6$-alkyl- or $C_3$-$C_5$-cycloalkyl group,
wherein said group is optionally substituted with one substituent selected from the group of hydroxy, $C_1$-$C_6$-alkoxy-, —$NH_2$, alkylamino-, dialkylamino-, cyclic amines, —$OP(O)(OH)_2$;

$R^2$ represents a group selected from

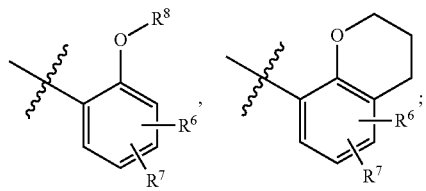

$R^3$ represents a hydrogen atom, fluoro atom or chloro atom, or a $C_1$-$C_3$-alkyl group;

$R^4$ represents a hydrogen atom or a fluoro atom;

$R^5$ represents a group selected from a hydrogen atom, cyano, —$C(O)R^9$, —$C(O)OR^9$, —$C(O)NR^{10}R^{11}$, —$P(O)(OR)_2$, —$CH_2OP(OR)_2$ or $C_1$-$C_3$-alkyl-,
wherein said $C_1$-$C_3$-alkyl group is optionally substituted with one substituent, selected from —$NH_2$, alkylamino-, dialkylamino-, or cyclic amines;

$R^6$, $R^7$ represent, independently from each other, a group selected from a hydrogen atom, a fluoro atom or a chloro atom;

R⁸ represents a group selected from
  a) a $C_1$-$C_3$-alkyl group, which is optionally substituted with one or two or three substituents, identically or differently, selected from halogen, halo-$C_1$-$C_3$-alkyl-;
  b) a phenyl-$C_1$-$C_3$-alkyl- group, the phenyl group of which is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
  c) a heteroaryl-$C_1$-$C_3$-alkyl- group, the heteroaryl group of which is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;
R⁹ represents a group selected from $C_1$-$C_3$-alkyl-, $C_1$-$C_3$-haloalkyl-, or benzyl group, the phenyl group of which is optionally substituted with one or two substituents, identically or differently, selected from the group of halogen, $C_1$-$C_3$-alkyl-, $C_1$-$C_3$-alkoxy-, —NH₂, alkylamino-, dialkylamino-;
R¹⁰, R¹¹ represent, independently from each other, a group selected from hydrogen, $C_1$-$C_3$-alkyl-, benzyl, or R¹⁰ and R¹¹, together with the nitrogen atom they are attached to, form a cyclic amine;
and the enantiomers, diastereomers, salts, solvates or salts of solvates thereof.

In another preferred embodiment the present invention concerns compounds of general formula (I), wherein
R¹ represents a $C_1$-$C_6$-alkyl group,
  wherein said group is optionally substituted with one substituent, selected from the group of hydroxy, $C_1$-$C_3$-alkoxy, —NH₂, alkylamino-, dialkylamino-, or cyclic amines;
R² represents a group selected from

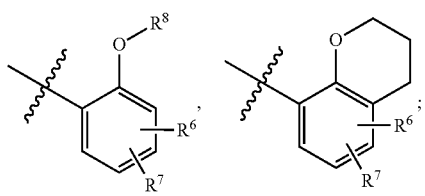

R³ represents a hydrogen atom, a fluoro atom or a chloro atom, or a methyl, methoxy, difluoromethyl or trifluoromethyl group;
R⁴ represents a hydrogen atom or a bromo atom;
R⁵ represents a group selected from a hydrogen atom, cyano, —C(O)R⁹, —C(O)OR⁹, —C(O)NR¹⁰R¹¹;
R⁶, R⁷ represent, independently from each other, a group selected from a hydrogen atom, fluoro atom or chloro atom;
R⁸ represents a $C_1$-$C_3$-alkyl group;
R⁹ represents a $C_1$-$C_3$-alkyl group, a benzyl group, or trifluoromethyl;
R¹⁰, R¹¹ represent, independently from each other, a group selected from hydrogen, $C_1$-$C_2$-alkyl-;
and the enantiomers, diastereomers, salts, solvates or salts of solvates thereof.

In another preferred embodiment the present invention concerns compounds of general formula (I), wherein
R¹ represents a $C_1$-$C_6$-alkyl group,
  wherein said group is optionally substituted with one substituent, selected from the group of $C_1$-$C_3$-alkoxy, —NH₂, alkylamino-, dialkylamino-, or cyclic amines;
R² represents a group selected from

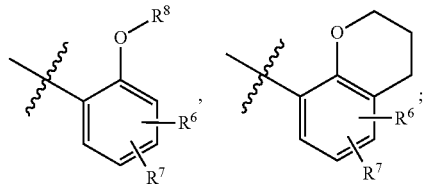

R³ represents a hydrogen atom, fluoro atom or chloro atom;
R⁴ represents a hydrogen atom or fluoro atom;
R⁵ represents a group selected from a hydrogen atom, cyano, —C(O)R⁹, —C(O)OR⁹, —C(O)NR¹⁰R¹¹;
R⁶, R⁷ represent, independently from each other, a group selected from a hydrogen atom, fluoro atom or chloro atom;
R⁸ represents a $C_1$-$C_3$-alkyl group;
R⁹ represents a $C_1$-$C_3$-alkyl group, a benzyl group, or trifluoromethyl;
R¹⁰, R¹¹ represent, independently from each other, a group selected from hydrogen, $C_1$-$C_2$-alkyl-;
and the enantiomers, diastereomers, salts, solvates or salts of solvates thereof.

In a particularly preferred embodiment the present invention concerns compounds of general formula (I), wherein
R¹ represents a $C_1$-$C_3$-alkyl group,
  wherein said group is optionally substituted with one substituent, selected from the group of hydroxy, —NH₂;
R² represents a group

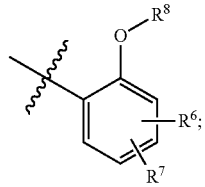

R³ represents a hydrogen atom, a fluoro atom or a chloro atom, or a methyl, methoxy, difluoromethyl or trifluoromethyl group;
R⁴ represents a hydrogen atom or a bromo atom;
R⁵ represents a group selected from a hydrogen atom, cyano, —C(O)R⁹, —C(O)OR⁹, —C(O)NR¹⁰R¹¹;
R⁶ represents a fluoro atom;
R⁷ represents hydrogen;
R⁸ represents a methyl or ethyl group;
R⁹ represents a methyl, ethyl or trifluoromethyl group;
R¹⁰, R¹¹ represent, independently from each other, a group selected from hydrogen, $C_1$-$C_2$-alkyl-;
and the enantiomers, diastereomers, salts, solvates or salts of solvates thereof.

In a particularly preferred embodiment the present invention concerns compounds of general formula (I), wherein
R¹ represents a $C_1$-$C_3$-alkyl group;
R² represents a group

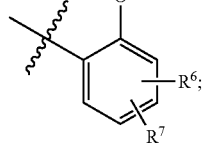

R³ represents a hydrogen atom or a chloro atom;
R⁴ represents a hydrogen atom;

$R^5$ represents a group selected from a hydrogen atom, —C(O)$R^9$;
$R^6$ represents hydrogen, para-fluoro, or para-chloro, whereby para refers to the point of attachment of $R^2$ to the rest of the molecule;
$R^7$ represents hydrogen;
$R^8$ represents a methyl group;
$R^9$ represents a trifluoromethyl group;
and the enantiomers, diastereomers, salts, solvates or salts of solvates thereof.

In another particular preferred embodiment the present invention concerns compounds of general formula (I), wherein
$R^1$ represents a methyl, ethyl, 2-hydroxyethyl or 2-aminoethyl group;
$R^2$ represents a 4-fluoro-2-methoxyphenyl or 4-fluoro-2-ethoxyphenyl group;
$R^3$ represents a hydrogen atom, a fluoro atom or a chloro atom, or a methyl, methoxy, difluoromethyl or trifluoromethyl group;
$R^4$ represents a hydrogen atom or a bromo atom;
$R^5$ represents a hydrogen atom, or a group selected from cyano, —C(O)CH$_3$, —C(O)CF$_3$, —C(O)OC$_2$H, —C(O)N(H)C$_2$H$_5$;
and the enantiomers, diastereomers, salts, solvates or salts of solvates thereof.

In another particular preferred embodiment the present invention concerns compounds of general formula (I), wherein
$R^1$ represents a methyl group;
$R^2$ represents a 4-fluoro-2-methoxyphenyl group;
$R^3$ represents a hydrogen atom or a chloro atom;
$R^4$ represents a hydrogen atom;
$R^5$ represents a hydrogen atom;
and the enantiomers, diastereomers, salts, solvates or salts of solvates thereof.

In another embodiment the invention relates to compounds of formula (I), in which $R^1$ represents a group selected from $C_1$-$C_6$-alkyl-, $C_3$-$C_7$-cycloalkyl-, heterocyclyl-, phenyl, heteroaryl, phenyl-$C_1$-$C_3$-alkyl- or heteroaryl-$C_1$-$C_3$-alkyl-,
wherein said group is optionally substituted with one or two or three substituents, identically or differently, selected from the group of hydroxy, cyano, halogen, halo-$C_1$-$C_3$-alkyl-, $C_1$-$C_6$-alkoxy-, $C_1$-$C_3$-fluoroalkoxy-, —NH$_2$, alkylamino-, dialkylamino-, acetylamino-, N-methyl-N-acetylamino-, cyclic amines, —OP(O)(OH)$_2$, —C(O)OH, —C(O)NH$_2$.

In another embodiment the invention relates to compounds of formula (I), in which $R^1$ represents a $C_1$-$C_3$-alkyl-, a $C_3$-$C_5$-cycloalkyl-, a 4- to 7-membered heterocyclic ring, a phenyl, a heteroaryl, a phenyl-$C_1$-$C_2$-alkyl- or a heteroaryl-$C_1$-$C_2$-alkyl- group,
wherein said group is optionally substituted with one or two or three substituents, identically or differently, selected from the group of hydroxy, cyano, halogen, halo-$C_1$-$C_2$-alkyl-, $C_1$-$C_3$-alkoxy , $C_1$-$C_2$-fluoroalkoxy-, —NH$_2$, alkylamino-, dialkylamino-, acetylamino-, N-methyl-N-acetylamino-, cyclic amines.

In another embodiment the invention relates to compounds of formula (I), in which $R^1$ represents a group selected from $C_1$-$C_6$-alkyl-, $C_3$-$C_5$-cycloalkyl-,
wherein said group is optionally substituted with one substituent selected from the group of hydroxy, $C_1$-$C_2$-alkoxy-, halo-$C_1$-$C_2$-alkyl-, $C_1$-$C_2$-fluoroalkoxy-, —NH$_2$, alkylamino-, dialkylamino-, cyclic amines, —OP(O)(OH)$_2$, —C(O)OH, —C(O)NH$_2$.

In another embodiment the invention relates to compounds of formula (I), in which $R^1$ represents a group selected from $C_1$-$C_6$-alkyl-, $C_3$-$C_5$-cycloalkyl-,
wherein said group is optionally substituted with one substituent selected from the group of hydroxy, $C_1$-$C_3$-alkoxy-, halo-$C_1$-$C_2$-alkyl-, $C_1$-$C_2$-fluoroalkoxy-, —NH$_2$, alkylamino-, dialkylamino-, cyclic amines, —OP(O)(OH)$_2$, —C(O)OH, —C(O)NH$_2$.

In another embodiment the invention relates to compounds of formula (I), in which $R^1$ represents a phenyl or a heteroaryl group,
wherein said group is optionally substituted with one or two or three substituents, identically or differently, selected from the group of hydroxy, cyano, halogen, halo-$C_1$-$C_2$-alkyl-, $C_1$-$C_3$-alkoxy-, $C_1$-$C_2$-fluoroalkoxy-, —NH$_2$, alkylamino-, dialkylamino-, acetylamino-, N-methyl-N-acetylamino-, cyclic amines.

In another embodiment the present invention relates to compounds of general formula (I), wherein $R^1$ represents a group selected from $C_1$-$C_6$-alkyl-, $C_3$-$C_5$-cycloalkyl-,
wherein said group is optionally substituted with one or two substituents, identically or differently, selected from the group of hydroxy, $C_1$-$C_2$-alkoxy-, halo-$C_1$-$C_2$-alkyl-, $C_1$-$C_2$-fluoroalkoxy-, —NH$_2$, —OP(O)(OH)$_2$, —C(O)OH, —C(O)NH$_2$.

In another embodiment the invention relates to compounds of formula (I), in which $R^1$ represents a group selected from methyl, ethyl, propan-2-yl, tert-butyl, cyclopropyl, cyclohexyl or phenyl,
wherein said group is optionally substituted with one substituent selected from the group of hydroxy or methoxy.

In another embodiment the invention relates to compounds of formula (I), in which $R^1$ represents a group selected from $C_1$-$C_6$-alkyl-, $C_3$-$C_7$-cycloalkyl or phenyl-$C_1$-$C_3$-alkyl-,
wherein said group is optionally substituted with one or two or three substituents, identically or differently, selected from the group of hydroxy or $C_1$-$C_6$-alkoxy.

In another embodiment the invention relates to compounds of formula (I), in which $R^1$ represents a group selected from $C_1$-$C_4$-alkyl-, $C_3$-$C_6$-cycloalkyl or phenyl-$C_1$-$C_2$-alkyl-,
wherein said group is optionally substituted with one or two or three substituents, identically or differently, selected from the group of hydroxy or $C_1$-$C_3$-alkoxy.

In a preferred embodiment the present invention concerns compounds of general formula (I), wherein $R^1$ represents a $C_1$-$C_6$-alkyl- or $C_3$-$C_5$-cycloalkyl group,
wherein said group is optionally substituted with one substituent selected from the group of hydroxy, $C_1$-$C_6$-alkoxy-, —NH$_2$, alkylamino-, dialkylamino-, cyclic amines, —OP(O)(OH)$_2$.

In a preferred embodiment the present invention concerns compounds of general formula (I), wherein $R^1$ represents a $C_1$-$C_6$-alkyl- or $C_3$-$C_5$-cycloalkyl group,
wherein said group is optionally substituted with one substituent selected from the group of hydroxy, $C_1$-$C_3$-alkoxy-, —NH$_2$, alkylamino-, dialkylamino-, cyclic amines, —OP(O)(OH)$_2$.

In another preferred embodiment the invention relates to compounds of formula (I), in which $R^1$ represents a $C_1$-$C_6$-alkyl group,
wherein said group is optionally substituted with one substituent selected from the group of hydroxy, $C_1$-$C_6$-alkoxy-, —NH$_2$, —OP(O)(OH)$_2$.

In another preferred embodiment the present invention concerns compounds of general formula (I), in which $R^1$ represents a $C_1$-$C_6$-alkyl group,
  wherein said group is optionally substituted with one substituent, selected from the group of $C_1$-$C_3$-alkoxy, —$NH_2$, alkylamino-, dialkylamino-, or cyclic amines.

In another preferred embodiment the present invention concerns compounds of general formula (I), in which $R^1$ represents a $C_1$-$C_6$-alkyl group,
  wherein said group is optionally substituted with one substituent, selected from the group of hydroxy, $C_1$-$C_3$-alkoxy, —$NH_2$, alkylamino-, dialkylamino-, or cyclic amines.

In another preferred embodiment the invention relates to compounds of formula (I), in which $R^1$ represents a group selected from methyl, ethyl, propan-2-yl, cyclopropyl, tert-butyl, cyclopentyl, cyclohexyl or phenyl,
  wherein said group is optionally substituted with one substituent, selected from the group of $C_1$-$C_3$-alkoxy, —$NH_2$, alkylamino-, dialkylamino-, or cyclic amines.

In another preferred embodiment the invention relates to compounds of formula (I), in which $R^1$ represents a group selected from methyl, ethyl, propan-2-yl, cyclopropyl, or tert-butyl,
  wherein said group is optionally substituted with one substituent, selected from the group of $C_1$-$C_3$-alkoxy, —$NH_2$, alkylamino-, dialkylamino-, or cyclic amines.

In a preferred embodiment the present invention concerns compounds of general formula (I), wherein $R^1$ represents a $C_1$-$C_6$-alkyl group,
  wherein said group is optionally substituted with one substituent, selected from the group of hydroxy or —OP(O)(OH)$_2$.

In a particularly preferred embodiment the present invention concerns compounds of general formula (I), wherein $R^1$ represents a $C_1$-$C_3$-alkyl group.

In a particularly preferred embodiment the present invention concerns compounds of general formula (I), wherein $R^1$ represents a $C_1$-$C_3$-alkyl group,
  wherein said group is optionally substituted with one substituent, selected from the group of hydroxy, —$NH_2$.

In a particularly preferred embodiment the present invention concerns compounds of general formula (I), wherein $R^1$ represents a methyl, ethyl, 2-hydroxyethyl or 2-aminoethyl group.

In another particularly preferred embodiment the present invention concerns compounds of general formula (I), wherein $R^1$ represents a methyl group.

In another embodiment the invention relates to compounds of formula (I), in which $R^2$ represents a group selected from

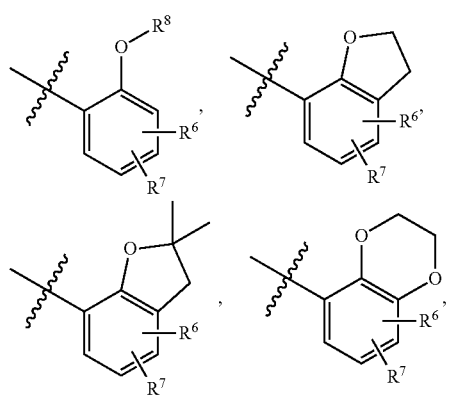

In another embodiment the invention relates to compounds of formula (I), in which $R^2$ represents a group selected from

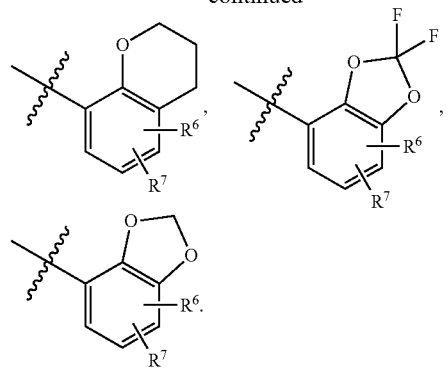

In another embodiment the invention relates to compounds of formula (I), in which $R^2$ represents a group selected from

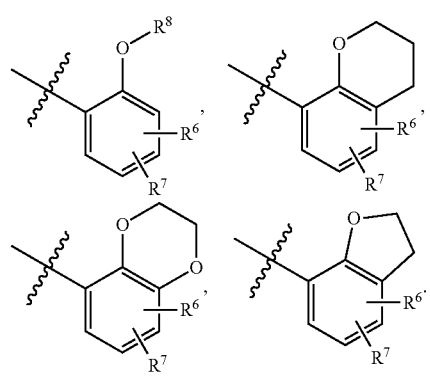

In another embodiment the invention relates to compounds of formula (I), in which $R^2$ represents a group selected from

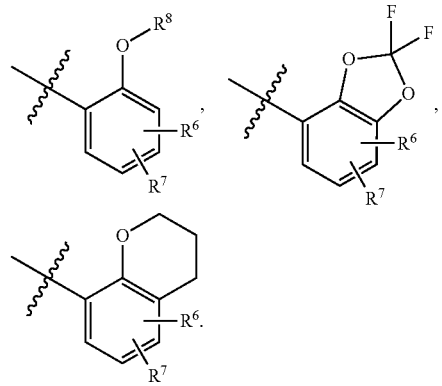

In a preferred embodiment the invention relates to compounds of formula (I), in which $R^2$ represents a group selected from

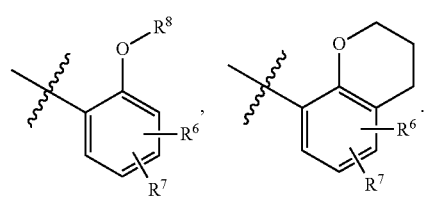

In a particularly preferred embodiment the invention relates to compounds of formula (I), in which $R^2$ represents

[Chemical structure: a phenyl ring with substituents — $OR^8$ at one position, $R^6$ and $R^7$ at other positions, with two wavy bond attachments]

In another particularly preferred embodiment the invention relates to compounds of formula (I), in which $R^2$ represents a 4-fluoro-2-methoxyphenyl- group.

In another particularly preferred embodiment the invention relates to compounds of formula (I), in which $R^2$ represents a 4-fluoro-2-methoxyphenyl- or 4-fluoro-2-ethoxyphenyl- group.

In another particularly preferred embodiment the invention relates to compounds of formula (I), in which $R^2$ represents a 4-fluoro-2-ethoxyphenyl- group.

In another embodiment the invention relates to compounds of formula (I), in which $R^3$ and $R^4$ represent, independently from each other, a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In a preferred embodiment the invention relates to compounds of formula (I), in which $R^3$ represents a hydrogen atom, fluoro atom or chloro atom, or a $C_1$-$C_3$-alkyl group, and $R^4$ represents a hydrogen atom or a fluoro atom.

In another preferred embodiment the invention relates to compounds of formula (I), in which $R^3$ represents a hydrogen atom, a fluoro atom, a chloro atom, a bromo atom, or a $C_1$-$C_3$-alkyl, $C_1$-$C_3$-alkoxy or a halo-$C_1$-$C_3$-alkyl group, and $R^4$ represents a hydrogen atom, a fluoro atom, a chloro atom or a bromo atom.

In another preferred embodiment the invention relates to compounds of formula (I), in which $R^3$ represents a hydrogen atom, a fluoro atom or a chloro atom, or a $C_1$-$C_3$-alkyl, $C_1$-$C_3$-alkoxy or a fluoro-$C_1$-$C_3$-alkyl group, and $R^4$ represents a hydrogen atom, a fluoro atom or a bromo atom.

In another preferred embodiment the invention relates to compounds of formula (I), in which $R^3$ represents a hydrogen atom, fluoro atom or chloro atom, and $R^4$ represents a hydrogen atom or a fluoro atom.

In another preferred embodiment the invention relates to compounds of formula (I), in which $R^3$ represents a hydrogen atom, a fluoro atom or a chloro atom, or a methyl, methoxy, difluoromethyl or a trifluoromethyl group, and $R^4$ represents a hydrogen atom or a bromo atom.

In a particularly preferred embodiment the invention relates to compounds of formula (I), in which $R^3$ represents a hydrogen atom or a chloro atom, and $R^4$ represents a hydrogen atom.

In another embodiment the invention relates to compounds of formula (I), in which $R^3$ represents a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another preferred embodiment the invention relates to compounds of formula (I), in which $R^3$ represents a hydrogen atom, a fluoro atom, a chloro atom, a bromo atom, or a $C_1$-$C_3$-alkyl, $C_1$-$C_3$-alkoxy or a halo-$C_1$-$C_3$-alkyl group.

In a preferred embodiment the invention relates to compounds of formula (I), in which $R^3$ represents a hydrogen atom, a fluoro atom or a chloro atom, or a $C_1$-$C_3$-alkyl- group.

In another preferred embodiment the invention relates to compounds of formula (I), in which $R^3$ represents a $C_1$-$C_3$-alkyl, $C_1$-$C_3$-alkoxy or a halo-$C_1$-$C_3$-alkyl group.

In another preferred embodiment the invention relates to compounds of formula (I), in which $R^3$ represents a $C_1$-$C_3$-alkyl- group.

In another preferred embodiment the invention relates to compounds of formula (I), in which $R^3$ represents a group selected from a hydrogen, a fluoro, or a chloro atom.

In another preferred embodiment the invention relates to compounds of formula (I), in which $R^3$ represents a hydrogen atom, a fluoro atom or a chloro atom, or a $C_1$-$C_3$-alkyl, $C_1$-$C_3$-alkoxy or a fluoro-$C_1$-$C_3$-alkyl group.

In another preferred embodiment the invention relates to compounds of formula (I), in which $R^3$ represents a hydrogen atom or a $C_1$-$C_3$-alkyl, $C_1$-$C_3$-alkoxy or a fluoro-$C_1$-$C_3$-alkyl group.

In another preferred embodiment the invention relates to compounds of formula (I), in which $R^3$ represents a hydrogen atom or a $C_1$-$C_3$-alkyl or a fluoro-$C_1$-$C_3$-alkyl group.

In another preferred embodiment the invention relates to compounds of formula (I), in which $R^3$ represents a hydrogen atom or a $C_1$-$C_3$-alkyl group.

In another preferred embodiment the invention relates to compounds of formula (I), in which $R^3$ represents a hydrogen atom or a fluoro-$C_1$-$C_3$-alkyl group.

In another preferred embodiment the invention relates to compounds of formula (I), in which $R^3$ represents a $C_1$-$C_3$-alkyl, $C_1$-$C_3$-alkoxy or a fluoro-$C_1$-$C_3$-alkyl group.

In another preferred embodiment the invention relates to compounds of formula (I), in which $R^3$ represents a a fluoro-$C_1$-$C_3$-alkyl group.

In another preferred embodiment the invention relates to compounds of formula (I), in which $R^3$ represents a hydrogen atom, a fluoro atom or a chloro atom, or a methyl, methoxy, difluoromethyl or a trifluoromethyl group.

In another preferred embodiment the invention relates to compounds of formula (I), in which $R^3$ represents a methyl, methoxy, difluoromethyl or a trifluoromethyl group.

In another preferred embodiment the invention relates to compounds of formula (I), in which $R^3$ represents a difluoromethyl or a trifluoromethyl group.

In another preferred embodiment the invention relates to compounds of formula (I), in which $R^3$ represents a methyl group.

In another preferred embodiment the invention relates to compounds of formula (I), in which $R^3$ represents a methoxy group.

In another preferred embodiment the invention relates to compounds of formula (I), in which $R^3$ represents a trifluoromethyl group.

In another preferred embodiment the invention relates to compounds of formula (I), in which $R^3$ represents a difluoromethyl group.

In another preferred embodiment the invention relates to compounds of formula (I), in which $R^3$ represents a fluoro or a chloro atom.

In another preferred embodiment the invention relates to compounds of formula (I), in which $R^3$ represents a hydrogen atom or a fluoro atom.

In another preferred embodiment the invention relates to compounds of formula (I), in which $R^3$ represents a fluoro atom.

In a particularly preferred embodiment the invention relates to compounds of formula (I), in which $R^3$ represents a hydrogen atom or chloro atom.

In another particularly preferred embodiment the invention relates to compounds of formula (I), in which $R^3$ represents a hydrogen atom.

In another particularly preferred embodiment the invention relates to compounds of formula (I), in which $R^3$ represents a chloro atom.

In another embodiment the invention relates to compounds of formula (I), in which $R^4$ represents a group selected from a hydrogen atom, fluoro atom, chloro atom, bromo atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^4$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In another embodiment the invention relates to compounds of formula (I), in which $R^4$ represents a group selected from a hydrogen, a fluoro or a chloro atom.

In another embodiment the invention relates to compounds of formula (I), in which $R^4$ represents a fluoro or a chloro atom.

In another embodiment the invention relates to compounds of formula (I), in which $R^4$ represents a group selected from a hydrogen atom, a fluoro atom, a chloro atom or a bromo atom.

In another embodiment the invention relates to compounds of formula (I), in which $R^4$ represents a group selected from a hydrogen atom, a fluoro atom or a bromo atom.

In another embodiment the invention relates to compounds of formula (I), in which $R^4$ represents a bromo atom.

In a preferred embodiment the invention relates to compounds of formula (I), in which $R^4$ represents a group selected from a hydrogen atom or fluoro atom.

In another preferred embodiment the invention relates to compounds of formula (I), in which $R^4$ represents a group selected from a hydrogen atom or a bromo atom.

In another preferred embodiment the invention relates to compounds of formula (I), in which $R^4$ represents a fluoro atom.

In a particularly preferred preferred embodiment the invention relates to compounds of formula (I), in which $R^4$ represents a hydrogen atom.

In another embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(OR)$_2$, —CH$_2$OP(OR)$_2$, $C_1$-$C_6$-alkyl-, $C_3$-$C_7$-cycloalkyl-, heterocyclyl-, phenyl, heteroaryl, wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(OR)$_2$, —CH$_2$OP(OR$^{12}$)$_2$, $C_1$-$C_6$-alkyl-, $C_3$-$C_7$-cycloalkyl-, heterocyclyl-, phenyl, heteroaryl, wherein said $C_1$-$C_6$-alkyl, $C_3$-$C_7$-cycloalkyl-, heterocyclyl-, phenyl or heteroaryl group is optionally substituted with one, two or three substituents, identically or differently, selected from halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^5$ represents a group selected from a hydrogen atom, cyano, —C(O)$R^9$, —C(O)O$R^9$, —C(O)N$R_{10}R^{11}$, —P(O)(OR)$_2$, —CH$_2$OP(OR)$_2$ or $C_1$-$C_3$-alkyl-, wherein said $C_1$-$C_3$-alkyl group is optionally substituted with one substituent, selected from —NH$_2$, alkylamino-, dialkylamino-, or cyclic amines.

In another preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$, —P(O)(OR$^{12}$)$_2$, —CH$_2$OP(OR$^{12}$)$_2$ or $C_1$-$C_3$-alkyl-, wherein said $C_1$-$C_3$-alkyl group is optionally substituted with one substituent, selected from —NH$_2$, alkylamino-, dialkylamino-, or cyclic amines.

In another preferred embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(OR)$_2$, —CH$_2$OP(OR)$_2$, methyl-.

In another preferred embodiment the invention relates to compounds of formula (I), in which $R^5$ represents a group selected from a hydrogen atom, cyano, —C(O)$R^9$, —C(O)O$R^9$, —S(O)$_2R^9$, —C(O)N$R^{10}R^{11}$, —P(O)(OR$^{12}$)$_2$, —CH$_2$OP(OR$^{12}$)$_2$, methyl-.

In another preferred embodiment the invention relates to compounds of formula (I), in which $R^5$ represents a group selected from cyano, —C(O)$R^9$, —C(O)O$R^9$, —S(O)$_2R^9$, —C(O)N$R^{10}R^{11}$, —P(O)(OR)$_2$, —CH$_2$OP(OR)$_2$, methyl-.

In another preferred embodiment the invention relates to compounds of formula (I), in which $R^5$ represents a group selected from cyano, —C(O)$R^9$, —C(O)O$R^9$, —S(O)$_2R^9$, —C(O)N$R^{10}R^{11}$, —P(O)(OR$^{12}$)$_2$, —CH$_2$OP(OR$^{12}$)$_2$, methyl-.

In another preferred embodiment the invention relates to compounds of formula (I), in which $R^5$ represents a group selected from cyano, —S(O)$_2R^9$, —C(O)N$R^{10}R^{11}$, —P(O)(OR)$_2$, —CH$_2$OP(OR)$_2$.

In another preferred embodiment the invention relates to compounds of formula (I), in which $R^5$ represents a group selected from cyano, —S(O)$_2R^9$, —C(O)N$R^{10}R^{11}$, —P(O)(OR$^{12}$)$_2$, —CH$_2$OP(OR$^{12}$)$_2$.

In a preferred embodiment the invention relates to compounds of formula (I), in which $R^5$ represents a group selected from a hydrogen atom, cyano, —C(O)$R^9$, —C(O)O$R^9$, —C(O)N$R^{10}R^{11}$.

In another preferred embodiment the invention relates to compounds of formula (I), in which $R^5$ represents a group selected from cyano, —C(O)O$R^9$, —C(O)N$R^{10}R^{11}$.

In another embodiment the invention relates to compounds of formula (I), in which $R^5$ represents a group selected from cyano or —C(O)O$R^9$.

In another embodiment the invention relates to compounds of formula (I), in which $R^5$ represents a group selected from a hydrogen atom or a cyano group.

In another embodiment the invention relates to compounds of formula (I), in which $R^5$ represents a group selected from a hydrogen atom or —C(O)O$R^9$.

In another embodiment the invention relates to compounds of formula (I), in which $R^5$ represents —C(O)O$R^9$.

In another embodiment the invention relates to compounds of formula (I), in which $R^5$ represents —C(O)N$R^{10}R^{11}$.

In another preferred embodiment the invention relates to compounds of formula (I), in which $R^5$ represents a cyano group.

In a particularly preferred embodiment the invention relates to compounds of formula (I), in which $R^5$ represents a group selected from a hydrogen atom or —C(O)$R^9$.

In another particularly preferred embodiment the invention relates to compounds of formula (I), in which $R^5$ represents —C(O)$R^9$.

In another particularly preferred embodiment the invention relates to compounds of formula (I), in which $R^5$ represents a hydrogen atom.

In another particularly preferred embodiment the invention relates to compounds of formula (I), in which $R^5$ represents a hydrogen atom, or a group selected from cyano, —C(O)CH$_3$, —C(O)CF$_3$, —C(O)OC$_2$H$_5$, —C(O)N(H)C$_2$H$_5$.

In another particularly preferred embodiment the invention relates to compounds of formula (I), in which $R^5$ represents a hydrogen atom, or a group selected from —C(O)CH$_3$ or —C(O)CF$_3$.

In another particularly preferred embodiment the invention relates to compounds of formula (I), in which $R^5$ represents a group selected from —C(O)CH$_3$ or —C(O)CF$_3$.

In another embodiment the invention relates to compounds of formula (I), in which $R^6$, $R^7$ represent, independently from each other, a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ and $R^7$ represent, independently from each other, a group selected from a hydrogen or fluoro atom or $C_1$-$C_3$-alkoxy-.

In a preferred embodiment the invention relates to compounds of formula (I), in which $R^6$ and $R^7$ represent, independently from each other, a group selected from a hydrogen atom, a fluoro atom or a chloro atom.

In another preferred embodiment the invention relates to compounds of formula (I), in which $R^6$ and $R^7$ represent, independently from each other, a group selected from a hydrogen or fluoro atom.

In a particularly preferred embodiment the invention relates to compounds of formula (I), in which $R^6$ represents hydrogen, para-fluoro, or para-chloro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents para-fluoro, whereby para refers to the point of attachment of $R^2$ to the rest of the molecule, and in which $R^7$ represents a hydrogen atom.

In another particularly preferred embodiment the invention relates to compounds of formula (I), in which $R^6$ represents a fluoro atom, and in which $R^7$ represents a hydrogen atom.

In another embodiment the invention relates to compounds of formula (I), in which $R^6$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^6$ represents a group selected from a hydrogen atom, fluoro atom, chloro atom, $C_1$-$C_2$-alkyl-, $C_1$-$C_2$-alkoxy-, halo-$C_1$-$C_2$-alkyl-, $C_1$-$C_2$-fluoroalkoxy-.

In a preferred embodiment the invention relates to compounds of formula (I), in which $R^6$ represents a group selected from a hydrogen atom, fluoro atom, chloro atom.

In another preferred embodiment the invention relates to compounds of formula (I), in which $R^6$ represents a hydrogen atom.

In another preferred embodiment the invention relates to compounds of formula (I), in which $R^6$ represents a fluoro atom.

In another preferred embodiment the invention relates to compounds of formula (I), in which $R^6$ represents a chloro atom.

In a particularly preferred embodiment the invention relates to compounds of formula (I), in which $R^6$ represents hydrogen, para-fluoro, or para-chloro, whereby para refers to the point of attachment of $R^2$ to the rest of the molecule.

In another particularly preferred embodiment the invention relates to compounds of formula (I), in which $R^6$ represents para-fluoro, whereby para refers to the point of attachment of $R^2$ to the rest of the molecule.

In another embodiment the invention relates to compounds of formula (I), in which $R^7$ represents a group selected from a hydrogen atom, fluoro atom, chloro atom, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^7$ represents a group selected from a hydrogen atom, fluoro atom, chloro atom, $C_1$-$C_2$-alkyl-, halo-$C_1$-$C_2$-alkyl-, $C_1$-$C_2$-fluoroalkoxy-.

In a preferred embodiment the invention relates to compounds of formula (I), in which $R^7$ represents a group selected from a hydrogen atom, fluoro atom, chloro atom.

In another preferred embodiment the invention relates to compounds of formula (I), in which $R^7$ represents a fluoro atom.

In another preferred embodiment the invention relates to compounds of formula (I), in which $R^7$ represents a chloro atom.

In a particularly preferred embodiment the invention relates to compounds of formula (I), in which $R^7$ represents a hydrogen atom.

In another embodiment the invention relates to compounds of formula (I), in which $R^8$ represents a $C_1$-$C_6$-alkyl group, which is optionally substituted with one or two or three substituents, identically or differently, selected from halogen, hydroxy, —NH$_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_6$-alkyl group, which is optionally substituted with one or two or three substituents, identically or differently, selected from halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_3$-alkyl group, which is optionally substituted with one or two or three substituents, identically or differently, selected from halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-, $C_3$-$C_7$-cycloalkyl-, heterocyclyl-, phenyl, heteroaryl, wherein said $C_3$-$C_7$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^8$ represents a $C_1$-$C_6$-alkyl-group, which is optionally substituted with one or two or three substituents, identically or differently, selected from the group of halogen atom, $C_1$-$C_3$-alkyl-, $C_3$-$C_6$-cycloalkyl-, $C_3$-$C_6$-heterocyclyl-, phenyl, heteroaryl, wherein said $C_3$-$C_6$-cycloalkyl-, $C_3$-$C_6$-heterocyclyl-, phenyl- or heteroaryl group is optionally substituted with one substituent selected from halogen.

In a preferred embodiment the invention relates to compounds of formula (I), in which $R^8$ represents a $C_1$-$C_3$-alkyl group, which is optionally substituted with one or two or three substituents, identically or differently, selected from halogen, halo-$C_1$-$C_3$-alkyl-.

In another preferred embodiment the invention relates to compounds of formula (I), in which $R^8$ represents a $C_1$-$C_3$-alkyl group.

In another preferred embodiment the invention relates to compounds of formula (I), in which $R^8$ represents a group selected from methyl, ($^2H_3$)methyl.

In a particularly preferred embodiment the invention relates to compounds of formula (I), in which $R^8$ represents a methyl group.

In a particularly preferred embodiment the invention relates to compounds of formula (I), in which $R^8$ represents a methyl or ethyl group.

In a particularly preferred embodiment the invention relates to compounds of formula (I), in which $R^8$ represents an ethyl group.

In another embodiment the invention relates to compounds of formula (I), in which $R^8$ represents a $C_3$-$C_7$-cycloalkyl- group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^8$ represents a cyclopentyl or cyclohexyl group, which is optionally substituted with one or two or three substituents, identically or differently, selected from the group of fluoro, chloro, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-, $C_2$-$C_3$-alkenyl-, $C_2$-$C_3$-alkynyl-.

In another embodiment the invention relates to compounds of formula (I), in which $R^8$ represents a heterocyclyl-group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^8$ represents a 4- to 7-membered heterocyclic ring, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-, $C_2$-$C_3$-alkenyl-, $C_2$-$C_3$-alkynyl-.

In another embodiment the invention relates to compounds of formula (I), in which $R^8$ represents a phenyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_{1-3}$-alkoxy-.

In another embodiment the invention relates to compounds of formula (I), in which $R^8$ represents a phenyl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a phenyl group, which is optionally substituted with one or two or three substituents, identically or differently, selected from the group of halogen, dialkylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl group, which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a heteroaryl group, which is optionally substituted with one or two or three substituents, identically or differently, selected from the group of halogen, dialkylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-$C_1$-$C_3$-alkyl- group, the phenyl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-$C_1$-$C_2$-alkyl- group, the phenyl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-$C_1$-$C_2$-alkyl- group, the phenyl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a benzyl group, the phenyl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In another embodiment the invention relates to compounds of formula (I), in which $R^8$ represents a phenyl-$C_1$-$C_3$-alkyl- group, the phenyl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a phenyl-$C_1$-$C_3$-alkyl- group, the phenyl group of which is optionally substituted with one or two or three substituents, identically or differently, selected from the group of halogen, cyano, dialkylamino-, acetylamino-, N-methyl-N-acetylamino-, cyclic amines.

In a preferred embodiment the invention relates to compounds of formula (I), in which $R^8$ represents a phenyl-$C_1$-$C_3$-alkyl- group, the phenyl group of which is optionally substituted with one or two or three substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-.

In another preferred embodiment the invention relates to compounds of formula (I), in which $R^8$ represents a phenyl-$C_1$-$C_3$-alkyl- group, the phenyl group of which is optionally substituted with one or two or three substituents, identically or differently, selected from the group of halogen or $C_1$-$C_3$-alkoxy-.

In another preferred embodiment the invention relates to compounds of formula (I), in which $R^8$ represents a phenyl-$C_1$-$C_3$-alkyl- group.

In another preferred embodiment the invention relates to compounds of formula (I), in which $R^8$ represents a phenyl-$C_1$-$C_2$-alkyl- group, the phenyl group of which is optionally substituted with one or two or three substituents, identically or differently, selected from the group of halogen or $C_1$-$C_3$-alkoxy-.

In another preferred embodiment the invention relates to compounds of formula (I), in which $R^8$ represents a phenyl-$C_1$-$C_2$-alkyl- group.

In another preferred embodiment the invention relates to compounds of formula (I), in which $R^8$ represents a benzyl group, the phenyl group of which is optionally substituted with one or two or three substituents, identically or differently, selected from the group of halogen or $C_1$-$C_3$-alkoxy-.

In another preferred embodiment the invention relates to compounds of formula (I), in which $R^8$ represents a benzyl group.

In another embodiment the invention relates to compounds of formula (I), in which $R^8$ represents a heteroaryl-$C_1$-$C_3$-alkyl- group, the heteroaryl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a heteroaryl-$C_1$-$C_3$-alkyl- group, the heteroaryl group of which is optionally substituted with one or two or three substituents, identically or differently, selected from the group of halogen, hydroxy, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-;

In another embodiment the invention relates to compounds of formula (I), in which $R^8$ represents a heteroaryl-$C_1$-$C_2$-alkyl- group, the heteroaryl group of which is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_3$-alkyl-, halo-$C_1$-$C_3$-alkyl-, $C_1$-$C_3$-fluoroalkoxy-, $C_1$-$C_3$-alkoxy-.

In another embodiment the invention relates to compounds of formula (I), in which $R^8$ represents a pyridyl-$C_1$-$C_2$-alkyl- group, which pyridyl group is optionally substituted with one or two or three substituents, identically or differently, selected from the group of halogen, hydroxy, —$NH_2$, alkylamino-, dialkylamino-, acetylamino-, N-methyl-N-acetylamino-, cyclic amines, cyano, $C_1$-$C_2$-alkyl-, halo-$C_1$-$C_2$-alkyl-, $C_1$-$C_2$-fluoroalkoxy-, $C_1$-$C_2$-alkoxy-.

In a preferred embodiment the invention relates to compounds of formula (I), in which $R^8$ represents a heteroaryl-$C_1$-$C_3$-alkyl- group, the heteroaryl group of which is optionally substituted with one or two substituents, identically or differently, selected from the group of halogen, cyano, $C_1$-$C_3$-alkyl-, halo-$C_1$-$C_3$-alkyl-, $C_1$-$C_3$-fluoroalkoxy-, $C_1$-$C_3$-alkoxy-;

In another preferred embodiment the invention relates to compounds of formula (I), in which $R^8$ represents a pyridyl-$C_1$-$C_3$-alkyl- group, the pyridyl group of which is optionally substituted with one or two or three substituents, identically or differently, selected from the group of halogen or $C_1$-$C_3$-alkoxy-.

In another embodiment the invention relates to compounds of formula (I), in which $R^8$ represents a pyridyl-$CH_2$- group, the pyridyl group of which is optionally substituted with one or two or three substituents, identically or differently, selected from the group of halogen, $C_1$-$C_2$-alkyl-, halo-$C_1$-$C_2$-alkyl, —$C_1$-$C_2$-fluoroalkoxy-, $C_1$-$C_2$-alkoxy-.

In another preferred embodiment the invention relates to compounds of formula (I), in which $R^8$ represents a pyridyl-$CH_2$— group, the pyridyl group of which is optionally substituted with one or two substituents, identically or differently, selected from the group of halogen or $C_1$-$C_3$-alkoxy-.

In another embodiment the invention relates to compounds of formula (I), in which $R^8$ represents a $C_3$-$C_6$-cycloalkyl-$C_1$-$C_3$-alkyl- group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a $C_3$-$C_6$-cycloalkyl-$CH_2$— group, the $C_3$-$C_6$-cycloalkyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^8$ represents a cyclohexyl-$CH_2$— or cyclopentyl-$CH_2$— group, the cyclohexyl or cyclopentyl group of which is optionally substituted with one or two or three substituents, identically or differently, selected from fluoro, $C_1$-$C_3$-alkyl-, $C_1$-$C_3$-alkoxy-, trifluoromethyl-, $C_1$-$C_3$-fluoroalkoxy-.

In another embodiment the invention relates to compounds of formula (I), in which $R^8$ represents a heterocyclyl-$C_1$-$C_3$-alkyl- group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another preferred embodiment the invention relates to compounds of formula (I), in which $R^8$ represents a heterocyclyl-$CH_2$— group, the heterocyclyl group of which is optionally substituted with one or two or three substituents, identically or differently, selected from halogen, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^9$ represents a group selected from $C_1$-$C_6$-alkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^9$ represents a group selected from $C_1$-$C_6$-alkyl-, halo-$C_1$-$C_3$-alkyl-, $C_3$-$C_7$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^9$ represents a group selected from $C_1$-$C_5$-alkyl-, $C_3$-$C_6$-cycloalkyl-, heterocyclyl-, phenyl, benzyl or heteroaryl,
wherein said group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^9$ represents a group selected from $C_1$-$C_3$-alkyl-, halo-$C_1$-$C_3$-alkyl, or a benzyl group, the phenyl group of which is optionally substituted with one or two substituents, identically or differently, selected from the group of halogen, $C_1$-$C_3$-alkyl-, $C_1$-$C_3$-alkoxy-, —$NH_2$, alkylamino-, dialkylamino-.

In a preferred embodiment the invention relates to compounds of formula (I), in which $R^9$ represents a group selected from $C_1$-$C_3$-alkyl-, $C_1$-$C_3$-haloalkyl, benzyl group, the phenyl group of which is optionally substituted with one or two substituents, identically or differently, selected from the group of halogen, $C_1$-$C_3$-alkyl-, $C_1$-$C_3$-alkoxy-, —$NH_2$, alkylamino-, dialkylamino-.

In another preferred embodiment the invention relates to compounds of formula (I), in which $R^9$ represents a group selected from $C_1$-$C_6$-alkyl-.

In another preferred embodiment the invention relates to compounds of formula (I), in which $R^9$ represents a group selected from $C_1$-$C_3$-alkyl- which is optionally substituted with $C_1$-$C_3$-alkoxy-.

In another preferred embodiment the invention relates to compounds of formula (I), in which $R^9$ represents a group selected from $C_1$-$C_3$-alkyl-, benzyl, or trifluoromethyl.

In another preferred embodiment the invention relates to compounds of formula (I), in which $R^9$ represents a $C_1$-$C_3$-alkyl- group.

In another particularly preferred embodiment the invention relates to compounds of formula (I), in which $R^9$ represents a methyl, ethyl or trifluoromethyl group.

In another particularly preferred embodiment the invention relates to compounds of formula (I), in which $R^9$ represents a trifluoromethyl group.

In another particularly preferred embodiment the invention relates to compounds of formula (I), in which $R^9$ represents a methyl group.

In another particularly preferred embodiment the invention relates to compounds of formula (I), in which $R^9$ represents an ethyl group.

In another embodiment the invention relates to compounds of formula (I), in which $R^{10}$, $R^{11}$ represent, independently from each other, a group selected from hydrogen, $C_1$-$C_6$-alkyl-, $C_3$-$C_7$-cycloalkyl-, heterocyclyl-, phenyl, benzyl or heteroaryl, wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^{10}$ and $R^{11}$, together with the nitrogen atom they are attached to, form a cyclic amine.

In another embodiment the invention relates to compounds of formula (I), in which $R^{10}$ and $R^{11}$ represent, independently from each other, a group selected from hydrogen, $C_1$-$C_5$-alkyl-, $C_3$-$C_6$-cycloalkyl-, heterocyclyl-, phenyl or heteroaryl wherein said $C_1$-$C_5$-alkyl, $C_3$-$C_6$-cycloalkyl-, heterocyclyl-, phenyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^{10}$ and $R^{11}$ represent, independently from each other, a group selected from hydrogen, $C_1$-$C_3$-alkyl-, benzyl, or $R^{10}$ and $R^{11}$, together with the nitrogen atom they are attached to, form a cyclic amine.

In another preferred embodiment the invention relates to compounds of formula (I), in which $R^{10}$ and $R^{11}$ represent, independently from each other, a group selected from hydrogen or $C_1$-$C_2$-alkyl-.

In another preferred embodiment the invention relates to compounds of formula (I), in which $R^{10}$ and $R^{11}$ represent, independently from each other, hydrogen or a $C_1$-$C_6$-alkyl-.

In a particularly preferred embodiment the invention relates to compounds of formula (I), in which $R^{10}$ and $R^{11}$ represent hydrogen.

In another embodiment the invention relates to compounds of formula (I), in which $R^{10}$ represents a group selected from hydrogen, $C_1$-$C_6$-alkyl-, $C_3$-$C_7$-cycloalkyl-, heterocyclyl-, phenyl, benzyl or heteroaryl, wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^{10}$ represents a group selected from hydrogen, $C_1$-$C_3$-alkyl-, benzyl.

In another preferred embodiment the invention relates to compounds of formula (I), in which $R^{10}$ represents a group selected from hydrogen, $C_1$-$C_6$-alkyl-.

In another preferred embodiment the invention relates to compounds of formula (I), in which $R^{10}$ represents a group selected from hydrogen or $C_1$-$C_2$-alkyl-.

In another preferred embodiment the invention relates to compounds of formula (I), in which $R^{10}$ represents $C_1$-$C_2$-alkyl-.

In a particularly preferred embodiment the invention relates to compounds of formula (I), in which $R^{10}$ represents hydrogen.

In another embodiment the invention relates to compounds of formula (I), in which $R^{11}$ represents a group selected from hydrogen, $C_1$-$C_6$-alkyl-, $C_3$-$C_7$-cycloalkyl-, heterocyclyl-, phenyl, benzyl or heteroaryl, wherein said $C_1$-$C_6$-alkyl, $C_3$-$C_7$-cycloalkyl-, heterocyclyl-, phenyl, benzyl or heteroaryl group is optionally substituted with one, two or three substituents, identically or differently, selected from halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^{11}$ represents a group selected from hydrogen, $C_1$-$C_3$-alkyl-, benzyl.

In another preferred embodiment the invention relates to compounds of formula (I), in which $R^{11}$ represents a group selected from hydrogen, $C_1$-$C_6$-alkyl-.

In another preferred embodiment the invention relates to compounds of formula (I), in which $R^{11}$ represents a group selected from hydrogen or $C_1$-$C_2$-alkyl.

In another preferred embodiment the invention relates to compounds of formula (I), in which $R^{11}$ represents $C_1$-$C_2$-alkyl.

In a particularly preferred embodiment the invention relates to compounds of formula (I), in which $R^{11}$ represents hydrogen.

In another embodiment the invention relates to compounds of formula (I), in which $R^{12}$ represents a group selected from hydrogen, $C_1$-$C_4$-alkyl or benzyl.

In another preferred embodiment the invention relates to compounds of formula (I), in which $R^{12}$ represents a group selected from hydrogen or $C_1$-$C_4$-alkyl.

In another preferred embodiment the invention relates to compounds of formula (I), in which $R^{12}$ represents a group selected from hydrogen or $C_1$-$C_2$-alkyl.

It is to be understood that the present invention relates to any sub-combination within any embodiment of the present invention of compounds of formula (I), supra.

In another preferred embodiment the invention relates to a specific stereoisomer of compounds of the formula (I) featuring a lower $IC_{50}$ vs CDK9 as compared to other stereoisomers of the respective compound, determined according to Method 1a described in the Materials and Methods section below.

In another preferred embodiment the invention relates to a specific stereoisomer of compounds of the formula (I) featuring a lower $IC_{50}$ vs CDK9 at high ATP concentration as compared to other stereoisomers of the respective compound, determined according to Method 1b described in the Materials and Methods section below.

In another preferred embodiment the invention relates to a specific stereoisomer of compounds of the formula (I) featuring a higher selectivity in favor of CDK9 over CDK2 as compared to other stereoisomers of the respective compound, determined according to Methods 1a (CDK9) and 2 (CDK2) described in the Materials and Methods section below.

In another preferred embodiment the invention relates to a specific stereoisomer of compounds of the formula (I) featuring a higher anti-proliferative activity in tumor cell lines such as HeLa as compared to other stereoisomers of the respective compound, determined according to Method 3 described in the Materials and Methods section below.

In another preferred embodiment the invention relates to a specific stereoisomer of compounds of the formula (I) featuring a aqueous solubility, e.g. in water at pH 6.5, as compared to other stereoisomers of the respective compound, determined according to Method 4 described in the Materials and Methods section below.

In another preferred embodiment the invention relates to a specific stereoisomer of compounds of the formula (I) featuring a higher an increased apparent Caco-2 permeability ($P_{app}$ A-B) across Caco-2 cell monolayers compared to other stereoisomers of the respective compound, determined according to Method 5 described in the Materials and Methods section below.

More particularly still, the present invention covers compounds of formula (I) which are disclosed in the Example section of this text, infra.

Very specially preferred are combinations of two or more of the abovementioned preferred embodiments.

In particular, preferred subjects of the present invention are the compounds selected from:

- (rac)-5-Fluoro-4-(4-fluoro-2-methoxyphenyl)-N-{4-[(S-methylsulfonimidoyl)methyl]pyridin-2-yl}pyridin-2-amine;
- (+)-5-Fluoro-4-(4-fluoro-2-methoxyphenyl)-N-{4-[(S-methylsulfonimidoyl)methyl]pyridin-2-yl}pyridin-2-amine;
- (−)-5-Fluoro-4-(4-fluoro-2-methoxyphenyl)-N-{4-[(S-methylsulfonimidoyl)methyl]pyridin-2-yl}pyridin-2-amine;
- (rac)-5-Fluoro-4-(4-fluoro-2-methoxyphenyl)-N-{6-methyl-4-[(S-methylsulfonimidoyl)methyl]pyridin-2-yl}pyridin-2-amine;
- (rac)-5-Bromo-N-[5-fluoro-4-(4-fluoro-2-methoxyphenyl)pyridin-2-yl]-6-methyl-4-[(S-methylsulfonimidoyl)methyl]pyridin-2-amine;
- (rac)-5-Fluoro-4-(4-fluoro-2-methoxyphenyl)-N-{6-methoxy-4-[(S-methylsulfonimidoyl)methyl]pyridin-2-yl}pyridin-2-amine;
- (rac)-N-{6-Chloro-4-[(S-methylsulfonimidoyl)methyl]pyridin-2-yl}-5-fluoro-4-(4-fluoro-2-methoxyphenyl)pyridin-2-amine;
- (rac)-2-{S-[(2-{[5-Fluoro-4-(4-fluoro-2-methoxyphenyl)pyridin-2-yl]amino}pyridin-4-yl)methyl]sulfonimidoyl}ethanol;
- (rac)-N-(4-{[S-(2-Aminoethyl)sulfonimidoyl]methyl}pyridin-2-yl)-5-fluoro-4-(4-fluoro-2-methoxyphenyl)pyridin-2-amine;
- {[(2-{[5-Fluoro-4-(4-fluoro-2-methoxyphenyl)pyridin-2-yl]amino}pyridin-4-yl)methyl](methyl)oxido-$\lambda^6$-sulfanylidene}cyanamide;
- (rac)-Ethyl{[(2-{[5-fluoro-4-(4-fluoro-2-methoxyphenyl)pyridin-2-yl]amino}pyridin-4-yl)methyl](methyl)oxido-$\lambda^6$-sulfanylidene}carbamate;
- (rac)-1-Ethyl-3-{[(2-{[5-fluoro-4-(4-fluoro-2-methoxyphenyl)pyridin-2-yl]amino}pyridin-4-yl)methyl](methyl)oxido-$\lambda^6$-sulfanylidene}urea;
- (rac)-N-{[(2-{[5-Fluoro-4-(4-fluoro-2-methoxyphenyl)pyridin-2-yl]amino}pyridin-4-yl)methyl](methyl)oxido-$\lambda^6$-sulfanylidene}acetamide;
- 5-Fluoro-4-(4-fluoro-2-methoxyphenyl)-N-{4-[(S-methylsulfonimidoyl)methyl]pyridin-2-yl}pyridin-2-amine hydrochloride; enantiomer 2;
- (rac)-Ethyl{[(2-{[5-fluoro-4-(4-fluoro-2-methoxyphenyl)pyridin-2-yl]amino}-6-methoxypyridin-4-yl)methyl](methyl)oxido-$\lambda^6$-sulfanylidene}carbamate;
- 5-Fluoro-4-(4-fluoro-2-methoxyphenyl)-N-{4-[(S-methylsulfonimidoyl)methyl]pyridin-2-yl}pyridin-2-amine hydrochloride; enantiomer 1;
- (rac)-5-Fluoro-4-(4-fluoro-2-methoxyphenyl)-N-{6-fluoro-4-[(S-methylsulfonimidoyl)methyl]pyridin-2-yl}pyridin-2-amine;
- (rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)oxido-$\lambda^6$-sulfanylidene}acetamide;
- (+)-5-Fluoro-4-(4-fluoro-2-methoxyphenyl)-N-{6-fluoro-4-[(S-methylsulfonimidoyl)methyl]pyridin-2-yl}pyridin-2-amine;
- (−)-5-Fluoro-4-(4-fluoro-2-methoxyphenyl)-N-{6-fluoro-4-[(S-methylsulfonimidoyl)methyl]pyridin-2-yl}pyridin-2-amine;
- (rac)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
- (+)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
- (−)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
- (+)-2,2,2-Trifluoro-N-[{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide;
- (−)-2,2,2-Trifluoro-N-[{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide;
- (rac)-4-(2-Ethoxy-4-fluorophenyl)-5-fluoro-N-{6-fluoro-4-[(S-methylsulfonimidoyl)methyl]pyridin-2-yl}pyridin-2-amine;
- (rac)-N-{[(2-{[4-(2-Ethoxy-4-fluoro-phenyl)-5-fluoropyridin-2-yl]amino}-6-fluoropyridin-4-yl)methyl]-(methyl)oxido-$\lambda^6$-sulfanylidene}-2,2,2-trifluoroacetamide;
- (+)-4-(2-Ethoxy-4-fluorophenyl)-5-fluoro-N-{6-fluoro-4-[(S-methylsulfonimidoyl)methyl]pyridin-2-yl}pyridin-2-amine;
- (−)-4-(2-Ethoxy-4-fluorophenyl)-5-fluoro-N-{6-fluoro-4-[(S-methylsulfonimidoyl)methyl]pyridin-2-yl}pyridin-2-amine;
- (rac)-N-{4-[(S-Ethylsulfonimidoyl)-methyl]pyridin-2-yl}-5-fluoro-4-(4-fluoro-2-methoxyphenyl)pyridin-2-amine;
- (rac)-N-{6-(Difluoromethyl)-4-[(S-methylsulfonimidoyl)methyl]pyridin-2-yl}-5-fluoro-4-(4-fluoro-2-methoxyphenyl)pyridin-2-amine;
- (+)-5-Fluoro-4-(4-fluoro-2-methoxyphenyl)-N-{6-methyl-4-[(S-methylsulfonimidoyl)methyl]pyridin-2-yl}pyridin-2-amine;
- (−)-5-Fluoro-4-(4-fluoro-2-methoxyphenyl)-N-{6-methyl-4-[(S-methylsulfonimidoyl)methyl]pyridin-2-yl}pyridin-2-amine, and the enantiomers, diastereomers, salts, solvates or salts of solvates thereof.

The above mentioned definitions of radicals which have been detailed in general terms or in preferred ranges also apply to the end products of the formula (I) and, analogously, to the starting materials or intermediates required in each case for the preparation.

The invention furthermore relates to a process for the preparation of the compounds of formula (I) according to the invention, in which N-unprotected sulfoximines of formula (I), in which $R^5$ represents hydrogen, are reacted with suitable agents to give N-functionalized sulfoximines of formula (I), in which $R^5$ is as defined for the compound of formula (I) according to the invention but is different from hydrogen,

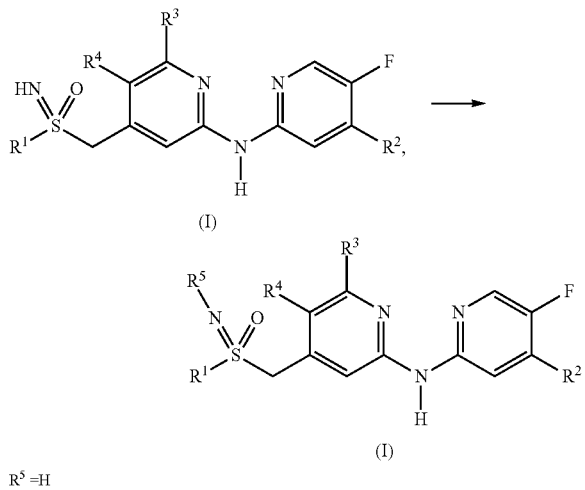

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (6), in which $R^1$, $R^2$, $R^3$, and $R^4$ are as defined for the compound of the formula (I) according to the present invention, in which method compounds of formula (5), in which $R^1$, $R^2$, $R^3$, and $R^4$ are as defined for the compound of the formula (I) according to the present invention.

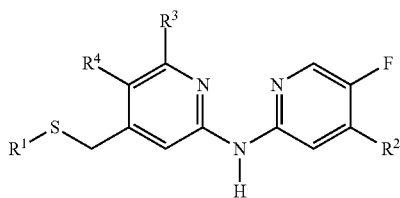

are reacted with trifluoroacetamide and 1,3-dibromo-5,5-dimethylhydantoin in the presence of an alkali salt of tert-butanol in a cyclic ether as a solvent, to give compounds of the formula (6),

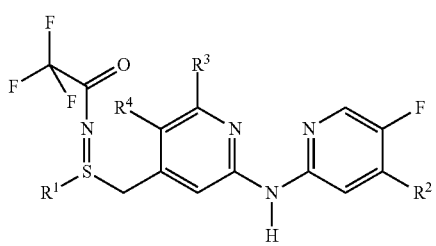

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (6),

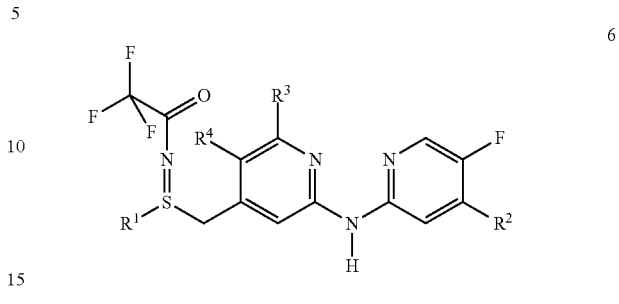

in which $R^1$, $R^2$, $R^3$, and $R^4$ are as defined for the compound of the formula (I) according to the present invention, are oxidised with an alkali salt of permanganic acid in an aliphatic ketone of the formula $C_1$-$C_2$—C(O)—$C_1$-$C_2$-alkyl as a solvent, followed, if the trifluoroacetyl group present in the compounds of formula (6) has not been cleaved off during abovementioned oxidation process, by the removal of said trifluoroacetyl group by treatment of the resulting intermediate with a suitable base in an alcoholic solvent, to give compounds of the formula (I), in which $R^5$ is hydrogen,

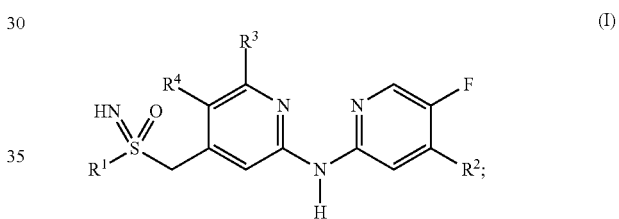

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (6),

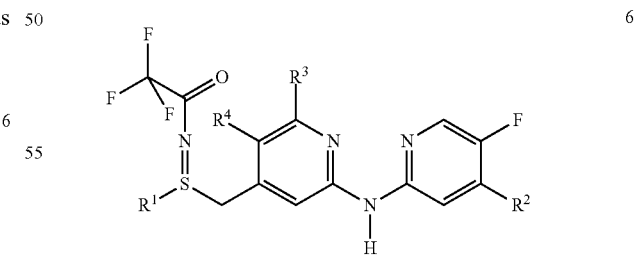

in which $R^1$, $R^2$, $R^3$, and $R^4$ are as defined for the compound of the formula (I) according to the present invention, are oxidised with a peroxomonosulfate based oxidant in a solvent selected from an aliphatic alcohol of the formula $C_1$-$C_3$-alkyl-OH, water, and N,N-dimethylformamide, or a mixture thereof, to give compounds of the formula (I), in which $R^5$ is hydrogen,

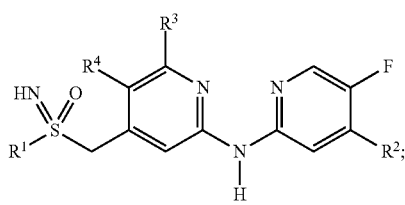

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (5), in which $R^1$, $R^2$, $R^3$, and $R^4$ are as defined for the compound of the formula (I) according to the present invention,

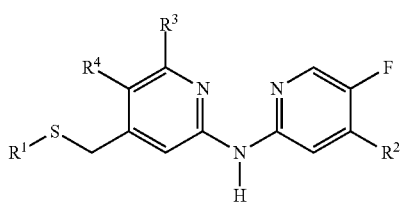

are reacted with trifluoroacetamide and 1,3-dibromo-5,5-dimethylhydantoin in the presence of an alkali salt of tert-butanol in a cyclic ether as a solvent, to give compounds of the formula (6),

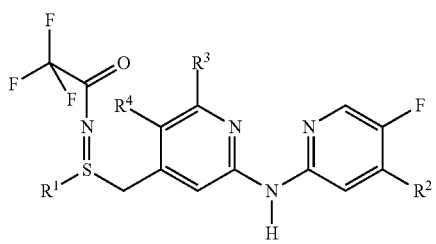

and in which method subsequently said compounds of the formula (6) are oxidised by a suitable oxidising agent, selected from an alkali salt of permanganic acid and a peroxomonosulfate based oxidant, in a solvent selected from an aliphatic ketone of the formula $C_1$-$C_2$—C(O)—$C_1$-$C_2$-alkyl, an aliphatic alcohol of the formula $C_1$-$C_3$-alkyl-OH, water, and N,N-dimethylformamide, or a mixture thereof, to give compounds of the formula (I), in which $R^5$ is hydrogen,

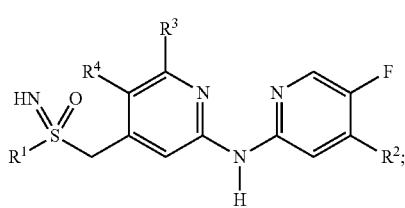

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (14),

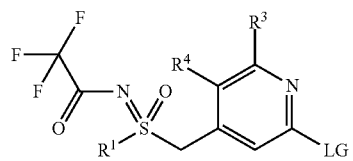

in which $R^1$, $R^3$, and $R^4$ are as defined for the compound of the formula (I), according to the present invention, and in which LG stands for a leaving group, is reacted with a compound of the formula (10),

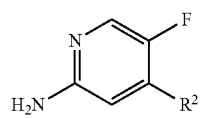

in which $R^2$ is as defined for the compound of the formula (I), according to the present invention, in a Palladium-catalyzed C—N cross-coupling reaction in the presence of chloro(2-dicyclohexylphosphino-2',4',6'-tri-iso-propyl-1,1'-biphenyl)[2-(2-aminoethyl)phenyl]palladium(II) methyl-tert-butylether adduct and 2-(dicyclohexylphosphino)-2',4',6'-triisopropylbiphenyl as catalyst and Palladium ligand, potassium phosphate as a base, in a mixture of toluene and N-methylpyrrolidin-2-one as a solvent, to give compounds of the formula (I), in which $R^5$ is hydrogen,

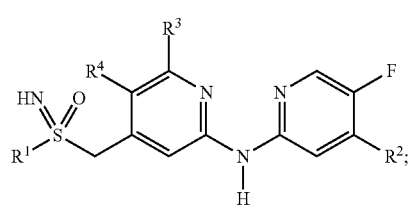

and in which method the resulting compounds are optionally, if appropriate, converted with the corresponding (i) solvents and/or (ii) bases or acids to the solvates, salts and/or solvates of the salts thereof.

The present invention further relates to a method for the preparation of the compounds of formula (I), in which method compounds of formula (16),

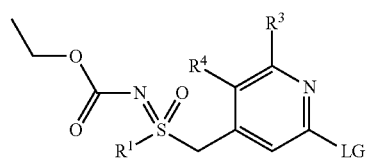

in which $R^1$, $R^3$, and $R^4$ are as defined for the compound of the formula (I), according to the present invention, and in which LG stands for a leaving group, is reacted with a compound of the formula (10),

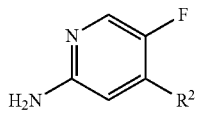

10 in which $R^2$ is as defined for the compound of the formula (I), according to the present invention, a Palladium-catalyzed C—N cross-coupling reaction in the presence of chloro(2-dicyclohexylphosphino-2',4',6'-tri-iso-propyl-1,1'-biphenyl)[2-(2-aminoethyl)phenyl]palladium(II) methyl-tert-butylether adduct and 2-(dicyclohexylphosphino)-2',4',6'-triisopropylbiphenyl as catalyst and Palladium ligand, potassium phosphate as a base, in a mixture of toluene and N-methylpyrrolidin-2-one as a solvent, to give compounds of formula (I) in which $R^5$ is C(O)OEt, followed by the reaction of said compounds of formula (I) in which $R^5$ is C(O)OEt, with an alkali salt of an aliphatic alcohol of the formula $C_1$-$C_4$-alkyl-OH in the corresponding aliphatic alcohol, to give compounds of the formula (I), in which $R^5$ is hydrogen,

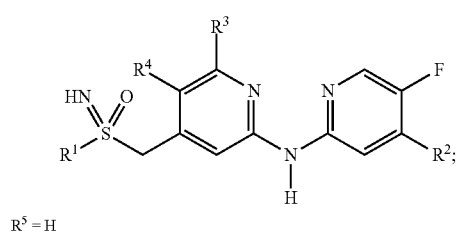

(I)

$R^5 = H$ and in which method the resulting compounds are optionally, if appropriate, converted with the corresponding (i) solvents and/or (ii) bases or acids to the solvates, salts and/or solvates of the salts thereof.

The invention further relates to compounds of the formula (5), in which $R^1$, $R^2$, $R^3$ and $R^4$ are as defined for the compounds of formula (I) according to the present invention,

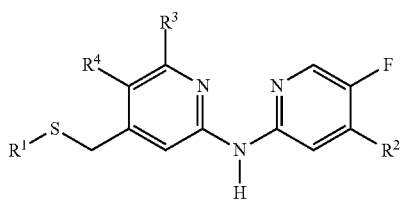

5 and the salts, solvates or salts of solvates thereof.

The invention further relates to compounds of the formula (6), in which $R^1$, $R^2$, $R^3$ and $R^4$ are as defined for the compounds of formula (I) according to the present invention,

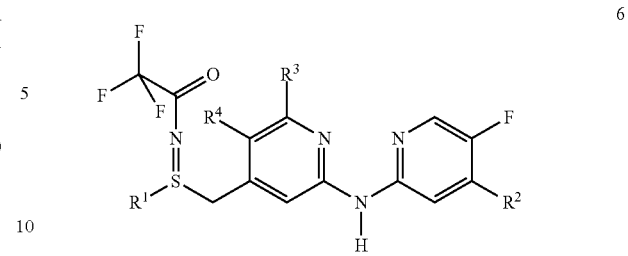

6 and the salts, solvates or salts of solvates thereof.

The invention further relates to compounds of the formula (14), in which $R^1$, $R^3$ and $R^4$ are as defined for the compounds of formula (I) according to the present invention, and in which LG stands for a leaving group,

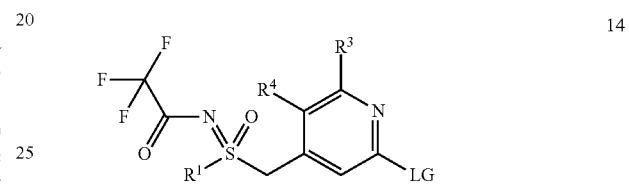

14 and the salts, solvates or salts of solvates thereof.

The invention further relates to compounds of the formula (16), in which $R^1$, $R^3$ and $R^4$ are as defined for the compounds of formula (I) according to the present invention, and in which LG stands for a leaving group,

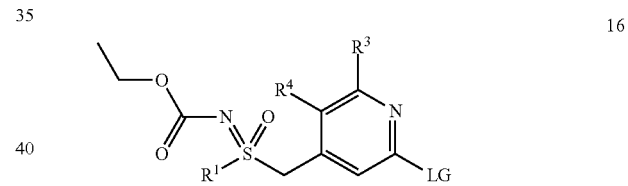

16 and the salts, solvates or salts of solvates thereof.

The compounds according to the invention show a valuable pharmacological and pharmacokinetic spectrum of action which could not have been predicted.

They are therefore suitable for use as medicaments for the treatment and/or prophylaxis of disorders in humans and animals.

Within the scope of the present invention, the term "treatment" includes prophylaxis.

The pharmaceutical activity of the compounds according to the invention can be explained by their action as inhibitors of CDK9. Thus, the compounds according to the general formula (I) as well as the enantiomers, diastereomers, salts, solvates and salts of solvates thereof are used as inhibitors for CDK9. Furthermore, the compounds according to the invention show a particularly high potency (demonstrated by a low $IC_{50}$ value in the CDK9/CycT1 assay) for inhibiting CDK9 activity.

In context of the present invention, the $IC_{50}$ value with respect to CDK9 can be determined by the methods described in the method section below. Preferably, it is determined according to Method 1a. ("CDK9/CycT1 kinase assay") described in the Materials and Method section below.

Surprisingly it turned out that the compounds according to the general formula (I) as well as the enantiomers, diastereomers, salts, solvates and salts of solvates thereof selectively inhibit CDK9 in comparison to other cyclin-dependent protein kinases, preferably in comparison to CDK2. Thus, the compounds according to the general formula (I) as well as pharmaceutically acceptable salts thereof are preferably used as selective inhibitors for CDK9.

Compounds of the present invention according to general formula (I) show a significantly stronger CDK9 than CDK2 inhibition.

In context of the present invention, the $IC_{50}$ value with respect to CDK2 can be determined by the methods described in the method section below. Preferably, it is determined according to Method 2. ("CDK2/CycE kinase assay") described in the Materials and Method section below.

Further, as compared to the CDK9 inhibitors described in the prior art, preferred compounds of the present invention according to general formula (I) show a surprisingly high potency for inhibiting CDK9 activity at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

Further, preferred compounds of the present invention according to formula (I) show an improved anti-proliferative activity in tumor cell lines such as HeLa compared to the CDK9 inhibitors described in the prior art. In context of the present invention, the anti-proliferative activity in tumor cell lines such as HeLa is preferably determined according to Method 3. ("Proliferation Assay") as described in the Materials and Method section below.

Further, preferred compounds of the present invention according to formula (I) surprisingly show an increased solubility in water at pH 6.5 compared to the compounds described in the prior art.

In context of the present invention the solubility in water at pH 6.5 is preferably determined according to Method 4a. ("Equilibrium Shake Flask Solubility Assay, Thermodynamic solubility in water") described in the Materials and Method section below.

Further, preferred compounds of the present invention according to formula (I) are characterized by improved pharmacokinetic properties, such as an increased apparent Caco-2 permeability ($P_{app}$ A-B) across Caco-2 cell monolayers, compared to the compounds known from the prior art.

Further, preferred compounds of the present invention according to formula (I) are characterized by improved pharmacokinetic properties, such as a decreased efflux ratio (efflux ratio=$P_{app}$ B-A/$P_{app}$ A-B) from the basal to apical compartment across Caco-2 cell monolayers, compared to the compounds known from the prior art.

In context of the present invention, the apparent Caco-2 permeability values from the basal to apical compartment ($P_{app}$ A-B) or the efflux ratio (defined as the ratio (($P_{app}$ B-A)/($P_{app}$ A-B)) are preferably determined according to Method 5. ("Caco-2 Permeation Assay") described in the Materials and Method section below.

Further, preferred compounds of the present invention according to formula (I) show no significant inhibition of carbonic anhydrase-1 or -2 ($IC_{50}$ values of more than 10 μM) and therefore show an improved side effect profile as compared to those CDK inhibitors described in the prior art containing a sulfonamide group, which inhibit carbonic anhydrase-1 or -2. In context of the present invention, the carbonic anhydrase-1 and -2 inhibition is preferably determined according to Method 6. ("Carbonic anhydrase Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit the activity or expression of CDK9. Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways. The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, anal gland adenocarcinomas, and mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip and oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention for the treatment and/or prophylaxis of disorders, in particular of the disorders mentioned above.

A further subject matter of the present invention is the use of the compounds of general formula (I) according to the invention for the treatment and/or prophylaxis of disorders, in particular lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A further subject matter of the present invention are the compounds according to the invention for use in a method for the treatment and/or prophylaxis of the disorders mentioned above.

A preferred subject matter of the present invention are the compounds according to the invention for the use in a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A further subject matter of the present invention is the use of the compounds according to the invention in the manufacture of a medicament for the treatment and/or prophylaxis of disorders, in particular the disorders mentioned above.

A preferred subject matter of the present invention is the use of the compounds according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

A further subject matter of the present invention is a method for the treatment and/or prophylaxis of disorders, in particular the disorders mentioned above, using an effective amount of the compounds according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemia.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Compounds of formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-la and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds of the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro pharmacological properties of the compounds can be determined according to the following assays and methods.

1a. CDK9/CyeT1 Kinase Assay:

CDK9/CycT1-inhibitory activity of compounds of the present invention was quantified employing the CDK9/CycT1 TR-FRET assay as described in the following paragraphs:

Recombinant full-length His-tagged human CDK9 and CycT1, expressed in insect cells and purified by Ni-NTA affinity chromatography, were purchased from Invitrogen (Cat. No PV4131). As substrate for the kinase reaction biotinylated peptide biotin-Ttds-YISPLKSPYKISEG (C-terminus in amid form) was used which can be purchased e.g. form the company JERINI Peptide Technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium orthovanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 µg/mL The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC$_{50}$ values were calculated by a 4 parameter fit using an inhouse software.

1b. CDK9/CyeT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany). For the assay 50 nl of a 100 fold concentrated solution of the test compound in DMSO was pipetted into a black low volume 384 well microtiter plate (Greiner Bio-One, Frickenhausen, Germany), 2 µl of a solution of CDK9/CycT1 in aqueous assay buffer [50 mM Tris/HCl pH 8.0, 10 mM MgCl$_2$, 1.0 mM dithiothreitol, 0.1 mM sodium orthovanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (1.67 µM=>final conc. in the 5 µl assay volume is 1 µM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 µg/mL The reaction was stopped by the addition of 5 µl of a solution of TR-FRET detection reagents (0.2 µM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC$_{50}$ values were calculated by a 4 parameter fit using an inhouse software.

2a. CDK2/CycE Kinase Assay:

CDK2/CycE-inhibitory activity of compounds of the present invention was quantified employing the CDK2/CycE TR-FRET assay as described in the following paragraphs:

Recombinant fusion proteins of GST and human CDK2 and of GST and human CycE, expressed in insect cells (Sf9) and purified by Glutathion-Sepharose affinity chromatography, were purchased from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI Peptide Technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/mL The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

2b. CDK2/CycE High ATP Kinase Assay:

CDK2/CycE-inhibitory activity of compounds of the present invention at 2 mM adenosine-tri-phosphate (ATP) was quantified employing the CDK2/CycE TR-FRET (TR-FRET=Time Resolved Fluorescence Energy Transfer) assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 µl of a solution ATP (3.33 mM=>final conc. in the 5 µl assay volume is 2 mM) and substrate (1.25 µM=>final conc. in the 5 µl assay volume is 0.75 µM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 15 ng/ml. The reaction was stopped by the addition of 5 µl of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and $IC_{50}$ values were calculated by a 4 parameter fit using an inhouse software.

3. Proliferation Assay:

Cultivated tumour cells (HeLa, human cervical tumour cells, ATCC CCL-2; NCI-H460, human non-small cell lung carcinoma cells, ATCC HTB-177; A2780, human ovarian carcinoma cells, ECACC #93112519; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 2,500 cells/well (A2780), 1,500 cells/well (Caco-2), or 1,000 cells/well (B16F10) in a 96-well multititer plate in 200 μL of their respective growth medium supplemented 10% fetal calf serum. After 24 hours, the cells of one plate (zero-point plate) were stained with crystal violet (see below), while the medium of the other plates was replaced by fresh culture medium (200 μl), to which the test substances were added in various concentrations (0 μM, as well as in the range of 0.001-10 μM; the final concentration of the solvent dimethyl sulfoxide was 0.5%). The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 μm) cells (=100%). The $IC_{50}$ values (inhibitory concentration at 50% of maximal effect) were determined by means of a 4 parameter fit. Non-adherent MOLM-13 human acute myeloid leukemia cells (DSMZ ACC 554) were seeded at a density of 5,000 cells/well in a 96-well multititer plate in 100 μL of growth medium supplemented 10% fetal calf serum. After 24 hours, cell viability of one plate (zero-point plate) was determined with the Cell Titre-Glo Luminescent Cell Viability Assay (Promega), while 50 μL of test compound containing medium was added to the wells of the other plates (final concentrations in the range of 0.001-10 μM and DMSO controls; the final concentration of the solvent dimethyl sulfoxide was 0.5%). Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Equilibrium Shake Flask Solubility Assay:
4a) Thermodynamic Solubility in Water The thermodynamic solubility of compounds in water was determined by an equilibrium shake flask method (see for example: E. H. Kerns, L. Di: Drug-like Properties: Concepts, Structure Design and Methods, 276-286, Burlington, Mass., Academic Press, 2008). A saturated solution of the drug was prepared and the solution was mixed for 24 h to ensure that equilibrium was reached. The solution was centrifuged to remove the insoluble fraction and the concentration of the compound in solution was determined using a standard calibration curve. To prepare the sample, 2 mg solid compound was weighed in a 4 mL glass vial. 1 mL phosphate buffer pH 6.5 was added. The suspension was stirred for 24 hrs at room temperature. The solution was centrifuged afterwards. To prepare the sample for the standard calibration, 2 mg solid sample was dissolved in 30 mL acetonitrile. After sonification the solution was diluted with water to 50 mL. Sample and standards were quantified by HPLC with UV-detection. For each sample two injection volumes (5 and 50 μl) in triplicates were made. Three injection volumes (5 μl, 10 μl and 20 μl) were made for the standard.

| Chromatographic conditions: | |
|---|---|
| HPLC column: | Xterra MS C18 2.5 μm 4.6 × 30 mm |
| Injection volume: | Sample: 3 × 5 μl and 3 × 50 μl |
| | Standard: 5 μl, 10 μl, 20 μl |
| Flow: | 1.5 mL/min |
| Mobile phase: | acidic gradient: |
| | A: Water/0.01% TFA |
| | B: Acetonitrile/0.01% TFA |
| | 0 min → 95% A 5% B |
| | 0-3 min → 35% A 65% B, linear gradient |
| | 3-5 min → 35% A 65% B, isocratic |
| | 5-6 min → 95% A 5% B, isocratic |
| UV detector: | wavelength near the absorption maximum (between 200 and 400 nm) |

The areas of sample- and standard injections as well as the calculation of the solubility value (in mg/l) were determined by using HPLC software (Waters Empower 2 FR).

4b) Thermodynamic Solubility in Citrate Buffer pH 4

Thermodynamic solubility was determined by an equilibrium shake flask method [Literature: Edward H. Kerns and Li Di (2008) Solubility Methods in: Drug-like Properties: Concepts, Structure Design and Methods, p276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 1.5 mg solid compound was weighed in a 4 ml glass vial. 1 ml Citrate buffer pH 4 was added. The suspension was put on a stirrer and mixed for 24 hrs at room temperature. The solution was centrifuged afterwards. To prepare the sample for the standard calibration, 0.6 mg solid sample was dissolved in 19 ml acetonitrile/water 1:1. After sonification the solution was filled up with acetonitrile/water 1:1 to 20 ml.

Sample and standards were quantified by HPLC with UV-detection. For each sample two injection volumes (5 and 50 μl) in triplicates were made. Three injection volumes (5 μl, 10 μl and 20 μl) were made for the standard.

| Chemicals: | |
|---|---|
| Citrate buffer pH 4 (MERCK Art. 109435; 1 L buffer consisting of 11,768 g citric acid, 4,480 g sodium hydroxide, 1,604 g hydrogen chloride) | |

| Chromatographic conditions were as follows: | |
|---|---|
| HPLC column: | Xterra MS C18 2.5 μm 4.6 × 30 mm |
| Injection volume: | Sample: 3 × 5 μl and 3 × 50 μl |
| | Standard: 5 μl, 10 μl, 20 μl |
| Flow: | 1.5 ml/min |
| Mobile phase: | acidic gradient: |
| | A: Water/0.01% TFA |
| | B: Acetonitrile/0.01% TFA |
| | 0 min: 95% A 5% B |
| | 0-3 min: 35% A 65% B, linear gradient |
| | 3-5 min: 35% A 65% B, isocratic |
| | 5-6 min: 95% A 5% B, isocratic |

| UV detector: | wavelength near the absorption maximum (between 200 and 400 nm) |

The areas of sample- and standard injections as well as the calculation of the solubility value (in mg/l) were determined by using HPLC software (Waters Empower 2 FR).

The areas of sample- and standard injections as well as the calculation of the solubility value (in mg/l) were determined by using HPLC software (Waters Empower 2 FR).

5. Caco-2 Permeation Assay:

Caco-2 cells (purchased from DSMZ Braunschweig, Germany) were seeded at a density of $4.5 \times 10^4$ cells per well on 24 well insert plates, 0.4 µm pore size, and grown for 15 days in DMEM medium supplemented with 10% fetal bovine serum, 1% GlutaMAX (100×, GIBCO), 100 U/mL penicillin, 100 µg/mL streptomycin (GIBCO) and 1% non essential amino acids (100 ×). Cells were maintained at 37° C. in a humified 5% $CO_2$ atmosphere. Medium was changed every 2-3 day. Before running the permeation assay, the culture medium was replaced by a FCS—free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 µM in transport buffer. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$Papp=(Vr/Po)(1/S)(P2/t)$$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2 h of incubation, and t is the incubation time. The efflux ratio basolateral (B) to apical (A) was calculated by dividing the Papp B-A by the Papp A-B. In addition the compound recovery was calculated. The following reference compounds were used for the classification of the permeability class: Antipyrine, Pyrazosin, Verapamil, Fluvastatin, Cimetidine, Ranitidine, Atenolol, Sulfasalazine.

6. Carbonic Anhydrase Assay

The principle of the assay is based on the hydrolysis of 4-nitrophenyl acetate by carbonic anhydrases (Pocker & Stone, Biochemistry, 1967, 6, 668), with subsequent photometric determination of the dye product 4-nitrophenolate at 400 nm by means of a 96-channel spectral photometer.

2 µL of the test compounds, dissolved in DMSO (100-fold final concentration), in a concentration range of 0.03-10 µmol/L (final), was pipetted as quadruplicates into the wells of a 96-hole microtiter plate. Wells that contained the solvent without test compounds were used as reference values (1. Wells without carbonic anhydrase for correction of the non-enzymatic hydrolysis of the substrate, and 2. Wells with carbonic anhydrase for determining the activity of the non-inhibited enzyme).

188 µL of assay buffer (10 mmol/L of Tris/HCl, pH 7.4, 80 mmol/L of NaCl), with or without 3 units/well of carbonic anhydrase-1 [=human carbonic anhydrase-1 (Sigma, #C4396)] in order to determine carbonic anhydrase-1 inhibition or 3 units/well of carbonic anhydrase-2 [=human carbonic anhydrase-2 (Sigma, #C6165)] for measuring carbonic anhydrase-2 inhibition, was pipetted into the wells of the microtiter plate. The enzymatic reaction was started by the addition of 10 microL of the substrate solution (1 mmol/L of 4-nitrophenyl acetate (Fluka #4602), dissolved in anhydrous acetonitrile (final substrate concentration: 50 µmol/L). The plate was incubated at room temperature for 15 minutes. Absorption was measured by photometry at a wavelength of 400 nm. The enzyme inhibition was calculated after the measured values were normalized to the absorption of the reactions in the wells without enzyme (=100% inhibition) and to the absorption of reactions in the wells with non-inhibited enzyme (=0% inhibition). $IC_{50}$ values were determined by means of a 4 parameter fit using the company's own software.

PREPARATIVE EXAMPLES

Syntheses of Compounds

The syntheses of the 5-fluoro-N-(pyridin-2-yl)pyridin-2-amine derivatives of formula (I) according to the present invention are preferably carried out according to the general synthetic sequences as shown in Schemes 1-6.

In addition to said routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, interconversion of any of the substituents $R^1$, $R^2$, $R^3$, $R^4$ and/or $R^5$ can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art.

The geometry of the sulfoximine moiety renders the compounds of the general formula (I) chiral. Separation of racemic sulfoximines into their enantiomers can be achieved by methods known to the person skilled in the art, preferably by means of preparative HPLC on chiral stationary phase.

Scheme 1

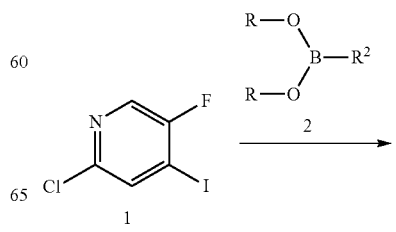

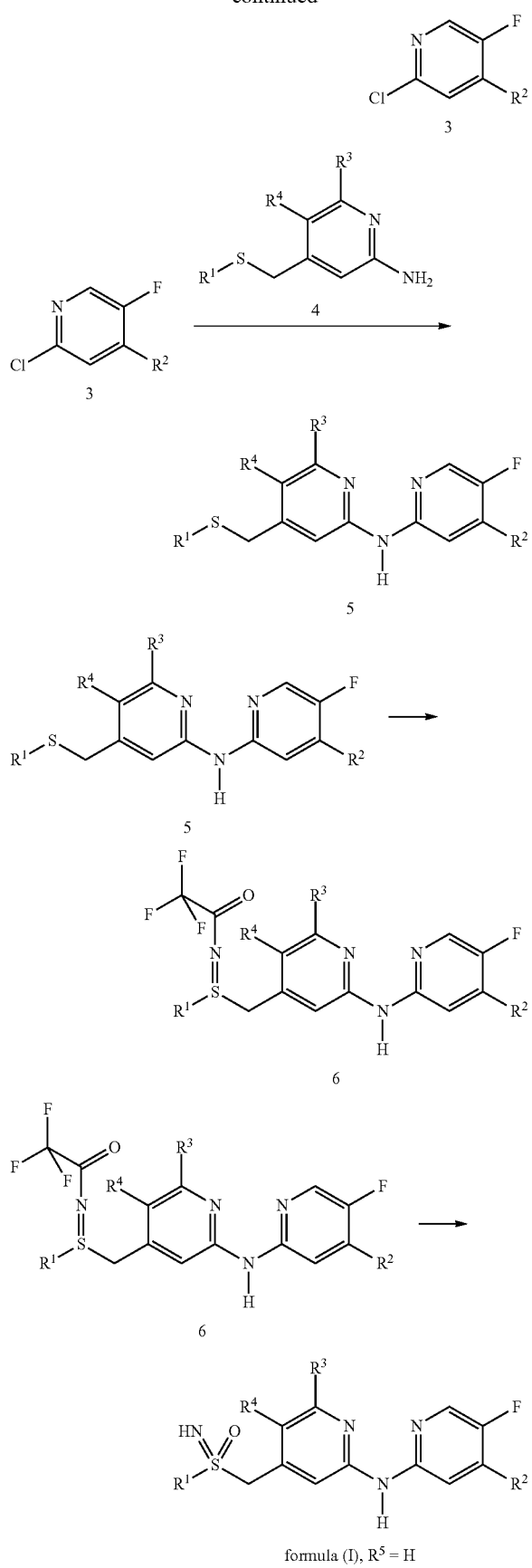
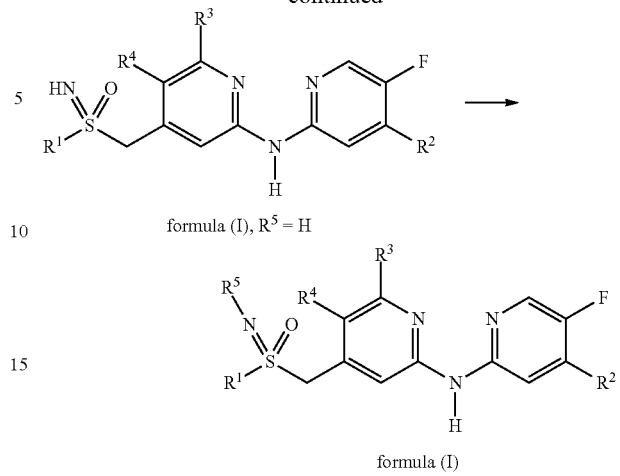

Scheme 1 illustrates a preferred synthetic approach to the compounds of the general formula (I). In the first step, 2-chloro-5-fluoro-4-iodopyridine (1; CAS #884494-49-9) is reacted with a boronic acid derivative $R^2$—$B(OR)_2$ of formula (2), in which $R^2$ is as defined for the compound of general formula (I), to give a compound of formula (3). The boronic acid derivative (2) may be a boronic acid (R=—H) or an ester of the boronic acid, e.g. its isopropyl ester (R=—CH(CH$_3$)$_2$), preferably an ester derived from pinacol in which the boronic acid intermediate forms a 2-aryl-4,4,5,5-tetramethyl-1,3,2-dioxaborolane (R—R=—C(CH$_3$)$_2$—C(CH$_3$)$_2$—).

The coupling reaction is catalyzed by palladium catalysts, e.g. by Pd(0) catalysts like tetrakis(triphenylphosphine)palladium(0) [Pd(PPh$_3$)$_4$], tris(dibenzylideneacetone)di-palladium(0) [Pd$_2$(dba)$_3$], or by Pd(II) catalysts like dichlorobis(triphenylphosphine)-palladium(II) [Pd(PPh$_3$)$_2$Cl$_2$], palladium(II) acetate and triphenylphosphine or by [1,1'-bis(diphenylphosphino)ferrocene]palladium dichloride.

The reaction is preferably carried out in a mixture of a solvent like 1,2-dimethoxyethane, dioxane, DMF, DME, THF, or isopropanol with water and in the presence of a base like potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction is performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

In the second step, a compound of formula (3) is reacted with a suitable pyridin-2-amine of formula (4), in which $R^1$, $R^3$ and $R^4$ are as defined for the compound of general formula (I), to give a compound of formula (5). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of tris(dibenzylideneacetone)dipalladium(0), (9,9-dimethyl-9H-xanthene-4,5-diyl)bis(diphenylphosphane) and and cesium carbonate in dioxane. The reactions are preferably run under an atmosphere of argon for 3-48 hours at 100° C. in a microwave oven or in an oil bath.

In the third step, imination of a compound of formula (5) gives the corresponding sulfilimine of formula (6) (see for examples: a) C. Bolm et al, Organic Letters, 2004, 6, 1305; b) J. Krüger et al, WO 2012/038411). Said imination is preferably performed by reacting a compound of the formula (5) with trifluoroacetamide and a suitable oxidant, such as 1,3-dibromo-5,5-dimethylhydantoin, in the presence of an alkali salt of tert-butanol, such as sodium tert.-butoxide, in a cyclic ether, such as tetrahydrofuran and dioxane, or mixtures thereof, as a solvent.

Oxidation of the sulfilimine of formula (6) followed by deprotection of the trifluoroacetyl group gives the N-unprotected sulfoximine of formula (I) ($R^5$=H) (see for examples: a) A. Plant et al, WO 2006/037945; b) J. Krüger et al, WO 2012/038411). Said oxidation is preferably performed by reacting compounds of formula (6) with an alkali salt of permanganic acid, such as potassium permanganate, in an aliphatic ketone of the formula $C_1$-$C_2$—C(O)—$C_1$-$C_2$-alkyl, such as acetone, as a solvent. Unless the trifluoroacetyl group present in the compounds of formula (6) has been cleaved off during the abovementioned oxidation process, it can be removed by treatment of the resulting intermediate with a suitable base, such as a carbonate of an alkali or earth alkali metal, preferably potassium carbonate, in a suitable alcohol, such as an aliphatic alcohol $C_1$-$C_6$-alkyl-OH, preferably methanol. Said oxidation is also preferably performed by reacting compounds of formula (6) with a peroxomonosulfate based oxidant, such as Oxone® (CAS No. 37222-66-5), in a suitable solvent mixture, such as methanol/water and as the circumstances require additional DMF, while controlling the pH of the reaction mixture with aqueous potassium hydroxide solution to give N-unprotected sulfoximine of formula (I) ($R^5$=H).

Pyridine-2-amines of formula (4) are commercially available in certain cases, or can be prepared by methods known to the person skilled in the art, e.g. from the corresponding 4-hydroxymethylpyridine-2-amine via conversion of the hydroxy group contained therein into a suitable leaving group, such as chloro or bromo, followed by nucleophilic displacement with a thiol of the general formula $R^1$—SH, in which R' is defined as defined for the compound of general formula (I). If needed, the amino group present in said 4-hydroxymethylpyridine-2-amine can be protected by a suitable protecting group. Protecting groups for amino groups present in analogues and methods for their introduction and removal are well known to the person skilled in the art, see e.g. T. W. Greene and P. G. M. Wuts in: Protective Groups in Organic Synthesis, 3$^{rd}$ edition, Wiley (1999). Thiols of formula $R^1$—SH are known to the person skilled in the art and are commercially available in considerable variety.

N-unprotected sulfoximines of formula (I) ($R^5$=H) may be reacted to give N-functionalized derivatives of formula (I). There are multiple methods for the preparation of N-functionalized sulfoximines by functionalization of the nitrogen of the sulfoximine group:

Alkylation: see for example: a) U. Lücking et al, US 2007/0232632; b) C. R. Johnson, J. Org. Chem. 1993, 58, 1922; c) C. Bolm et al, Synthesis 2009, 10, 1601.
Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.
Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.
Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.
Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/ 191393.
Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.
Reaction with bromocyane: see for example: a) D. T. Sauer et al, Inorganic Chemistry 1972, 11, 238; b) C. Bolm et al, Org. Lett. 2007, 9, 2951; c) U. Lücking et al, WO 2011/29537.

An alternative synthesis approach to the 5-fluoro-N-(pyridin-2-yl)pyridin-2-amine derivatives of formula (I) according to the present invention is described in Scheme 2.

In the first step, a compound of formula (3), in which $R^2$ is as defined for the compound of general formula (I), is reacted with a suitable pyridin-2-amine of formula (7), in which $R^3$ and $R^4$ are as defined for the compound of general formula (I), to give a compound of formula (8). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', 2$^{nd}$ ed.: A. de Meijere, F. Diederich, Eds.: Wiley-VCH: Weinheim, Germany, 2004).

Preferred is the herein described use of tris(dibenzylideneacetone)dipalladium(0), (9,9-dimethyl-9H-xanthene-4,5-diyl)bis(diphenylphosphane) and and cesium carbonate in dioxane. The reactions are preferably run under an atmosphere of argon for 3-48 hours at 100° C. in a microwave oven or in an oil bath.

Pyridine-2-amines of formula (7) are commercially available in certain cases, or can be prepared by methods known to the person skilled in the art, e.g. by reduction of the corresponding carboxylic acids or esters thereof.

Scheme 2

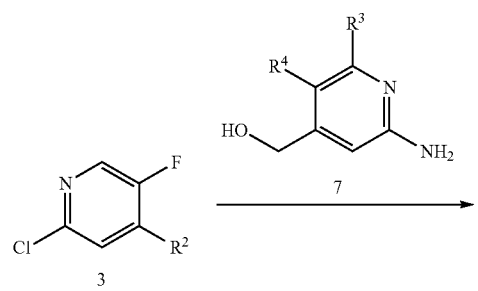

-continued

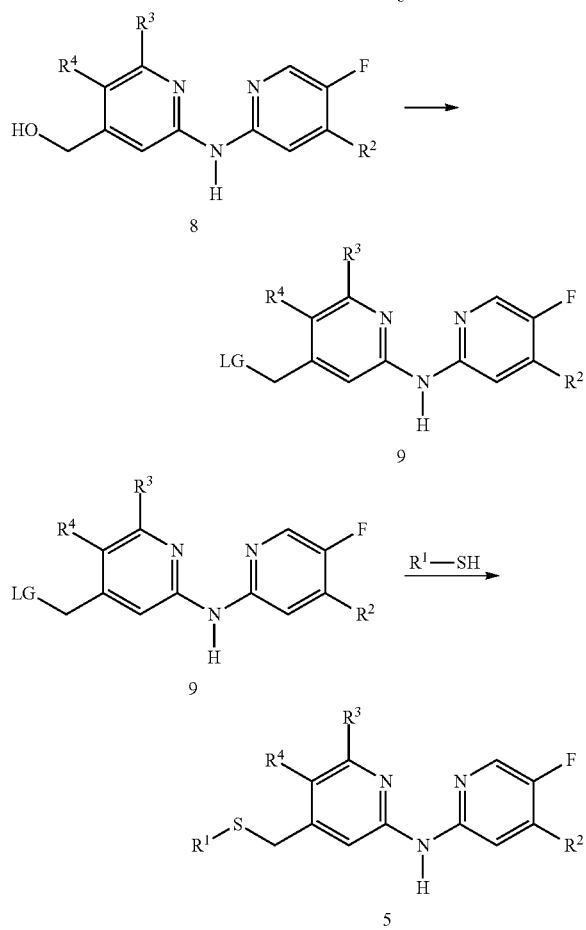

In the final steps, the thioether of formula (5) is converted to the corresponding sulfoximine of formula (I) as described in Scheme 1.

Another alternative synthesis approach to the 5-fluoro-N-(pyridin-2-yl)pyridin-2-amine derivatives of formula (I) according to the present invention is described in Scheme 3.

Scheme 3

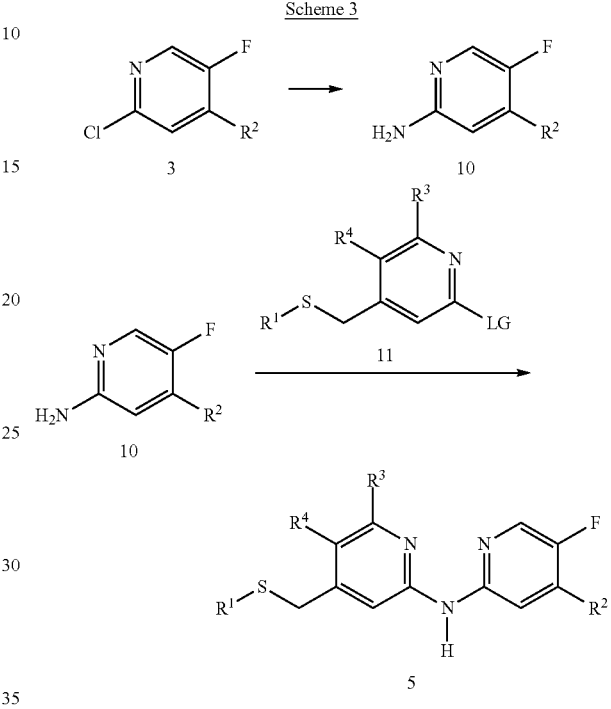

In the second step, a compound of formula (8), in which $R^2$, $R^3$ and $R^4$ are as defined for the compound of general formula (I), is converted to a compound of formula (9), in which $R^2$, $R^3$ and $R^4$ are as defined for the compound of general formula (I) and in which LG represents a leaving group, preferably chloro or bromo. Preferred is the herein described use of thionylchloride in NMP or DMF and DCM for the formation of benzylchloride derivatives (LG=Cl). A possibility for the formation of benzylbromide derivatives (LG=Br) is the use of tetrabromomethane and triphenylphosphane in DCM (see for example: Polla et al, Bioorganic and Medicinal Chemistry, 2004, 12, 1151).

In the third step, a compound of formula (9) is converted to a thioether of formula (5), in which $R^1$, $R^2$, $R^3$ and $R^4$ are as defined for the compound of general formula (I), by reaction with suitable thiol of formula $R^1$SH, in which $R^1$ is as defined for the compound of formula (I), under basic conditions, yielding the corresponding thioether of formula (5) (see for example: Sammond et al, Bioorg. Med. Chem. Lett. 2005, 15, 3519). Thiols of formula $R^1$—SH are known to the person skilled in the art and are commercially available in considerable variety.

In the first step, a compound of formula (3), in which $R^2$ is as defined for the compound of general formula (I), is converted to a 5-fluoro-pyridine-2-amine of formula (10). This reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of lithium bis(trimethylsilyl)amide, tris(dibenzylideneacetone)dipalladium(0) and 2-(dicyclohexylphosphino)-2',4',6'-triisopropylbiphenyl in THF. The reactions are preferably run under an atmosphere of argon for 3-24 hours at 60° C. in an oil bath.

In the second step, a compound of formula (10) is reacted with a suitable pyridine derivative of formula (11), in which $R^1$, $R^3$ and $R^4$ are as defined for the compound of general formula (I), and in which LG represents a leaving group, preferably chloro, to give a compound of formula (5). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of tris(dibenzylideneacetone)dipalladium(0), (9,9-dimethyl-9H-xanthene-4,5-diyl)bis(diphenylphosphane) and cesium carbonate in dioxane. The reactions are preferably run under an atmosphere of argon for 3-48 hours at 100° C. in a microwave oven or in an oil bath. Preferred is also the herein described use of chloro(2-dicyclohexylphosphino-2',4',6'-tri-iso-propyl-1,1'-biphenyl)[2-(2-aminoethyl)phenyl]palladium(II) methyl-tert-butylether adduct, 2-(dicyclohexylphosphino)-2',4',6'-triisopropylbiphenyl and potassium phosphate in toluene and NMP. The reactions are preferably run under an atmosphere of argon for 2-24 hours at 100-130° C. in a microwave oven or in an oil bath.

In the final steps, the thioether of formula (5) is converted to the corresponding sulfoximine of formula (I) as described in Scheme 1.

Pyridine derivatives of the formula (11) can be prepared according to methods known to the person skilled in the art, e.g. by conversion of a halomethyl group into the thioether present in compound of the formula (11) using a thiol of the formula $R^1$—SH, in which $R^1$ is as defined for the compound of general formula (I), in a similar fashion as described supra for pyridine amines of the formula (4) and for the conversion of intermediates of formula (9) into thioethers of formula (5) in Scheme 2. Said halomethyl pyridine precursors are known to the person skilled in the art, and are commercially available in certain cases.

Another alternative synthesis approach to the 5-fluoro-N-(pyridin-2-yl)pyridin-2-amine derivatives of formula (I) according to the present invention is described in Scheme 4.

reactions are preferably run under an atmosphere of argon for 2-24 hours at 100-130° C. in a microwave oven or in an oil bath.

In the subsequent steps, the benzylic alcohol of formula (8) is first converted to the corresponding thioether of formula (5) as described in Scheme 2, and then transformed into the corresponding sulfoximine of formula (I) as described in Scheme 1.

Pyridine derivatives of the formula (12) are known to the person skilled in the art, and are commercially available in considerable variety.

Another alternative synthesis approach to the 5-fluoro-N-(pyridin-2-yl)pyridin-2-amine derivatives of formula (I) according to the present invention is described in Scheme 5.

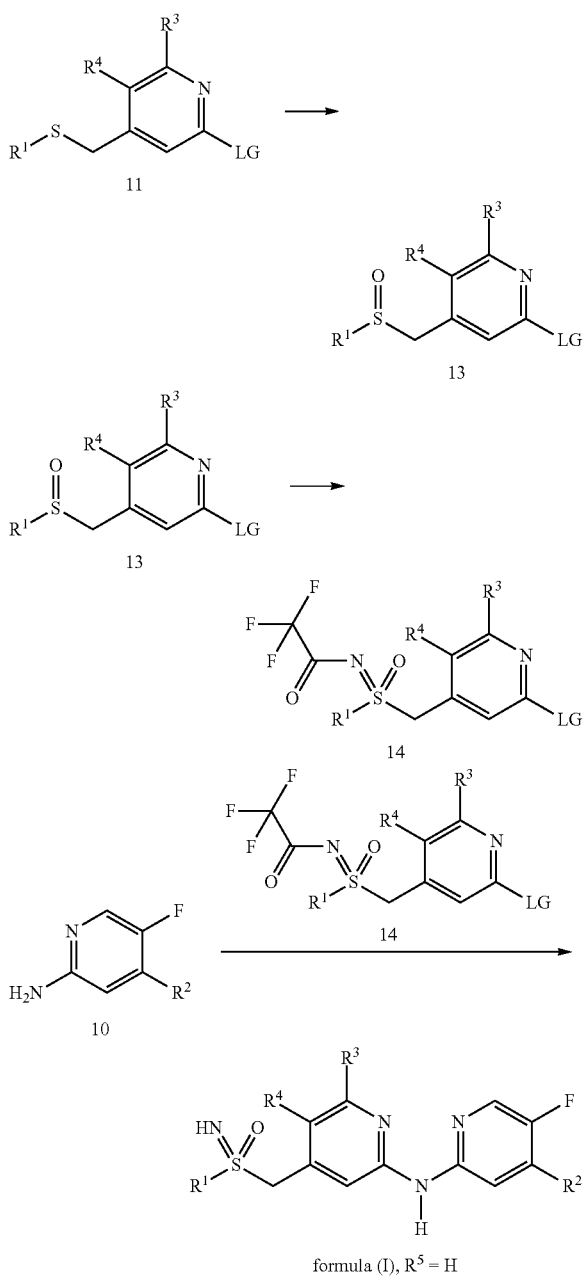

In the first step, a compound of formula (10), in which $R^2$ is as defined for the compound of general formula (I), is reacted with a suitable pyridine derivative of formula (12), in which $R^3$ and $R^4$ are as defined for the compound of general formula (I), and in which LG represents a leaving group, preferably chloro, to give a compound of formula (8). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use chloro(2-dicyclohexylphosphino-2',4',6'-tri-iso-propyl-1,1'-biphenyl)[2-(2-aminoethyl)phenyl]palladium(II) methyl-tert-butylether adduct, 2-(dicyclohexylphosphino)-2',4',6'-triisopropylbiphenyl and potassium phosphate in toluene and NMP. The In the first step, a thioether of formula (11), in which R¹, R³ and R⁴ are as defined for the compound of general formula (I), and in which LG represents a leaving group, preferably chloro, is oxidized to the corresponding sulfoxide of formula (13). There are numerous methods for the oxidation of a thioether to the corresponding sulfoxide (see for example: (a) M. H. Ali et al, Synthesis 1997, 764; (b) M. C. Carreno, Chem. Rev. 1995, 95, 1717; (c) I. Patel et al, Org. Proc. Res. Dev. 2002, 6, 225; (d) N. Khiar et al, Chem. Rev. 2003, 103, 3651). Preferred is the herein described use of periodic acid and iron(III)chloride.

In the second step, rhodium-catalyzed imination of the sulfoxide of formula (13) gives the corresponding sulfoximine of formula (14) (see for example: Bolm et al, Org. Lett. 2004, 6, 1305).

In the third step, a compound of formula (10), in which $R^2$ is as defined for the compound of general formula (I), is reacted with a sulfoximine of formula (14), to give an unprotected sulfoximine of formula (I) ($R^5$=H). This coupling reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use chloro(2-dicyclohexylphosphino-2',4',6'-tri-iso-propyl-1,1'-biphenyl)[2-(2-aminoethyl)phenyl]palladium(II) methyl-tert-butylether adduct, 2-(dicyclohexylphosphino)-2',4',6'-triisopropylbiphenyl and potassium phosphate in toluene and NMP. The reactions are preferably run under an atmosphere of argon for 1-24 hours at 100-130° C. in a microwave oven or in an oil bath.

Another alternative synthesis approach to the 5-fluoro-N-(pyridin-2-yl)pyridin-2-amine derivatives of formula (I) according to the present invention is described in Scheme 6.

In the first step, a sulfoxide of formula (13), in which R¹, R³ and R⁴ are as defined for the compound of general formula (I), and in which LG represents a leaving group, preferably chloro, is converted to the unprotected sulfoximine of formula (15) by a rhodium-catalyzed imination followed by a deprotection under basic conditions (see for example: Bolm et al, Org. Lett. 2004, 6, 1305).

In the second step, the unprotected sulfoximine of formula (15), in which R¹, R³ and R⁴ are as defined for the compound of general formula (I), is converted to the protected sulfoximine of formula (16) by the reaction with ethyl chloroformate in pyridine (see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800).

Scheme 6

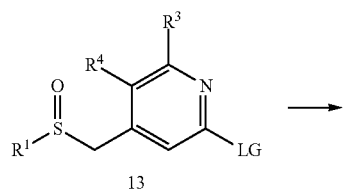

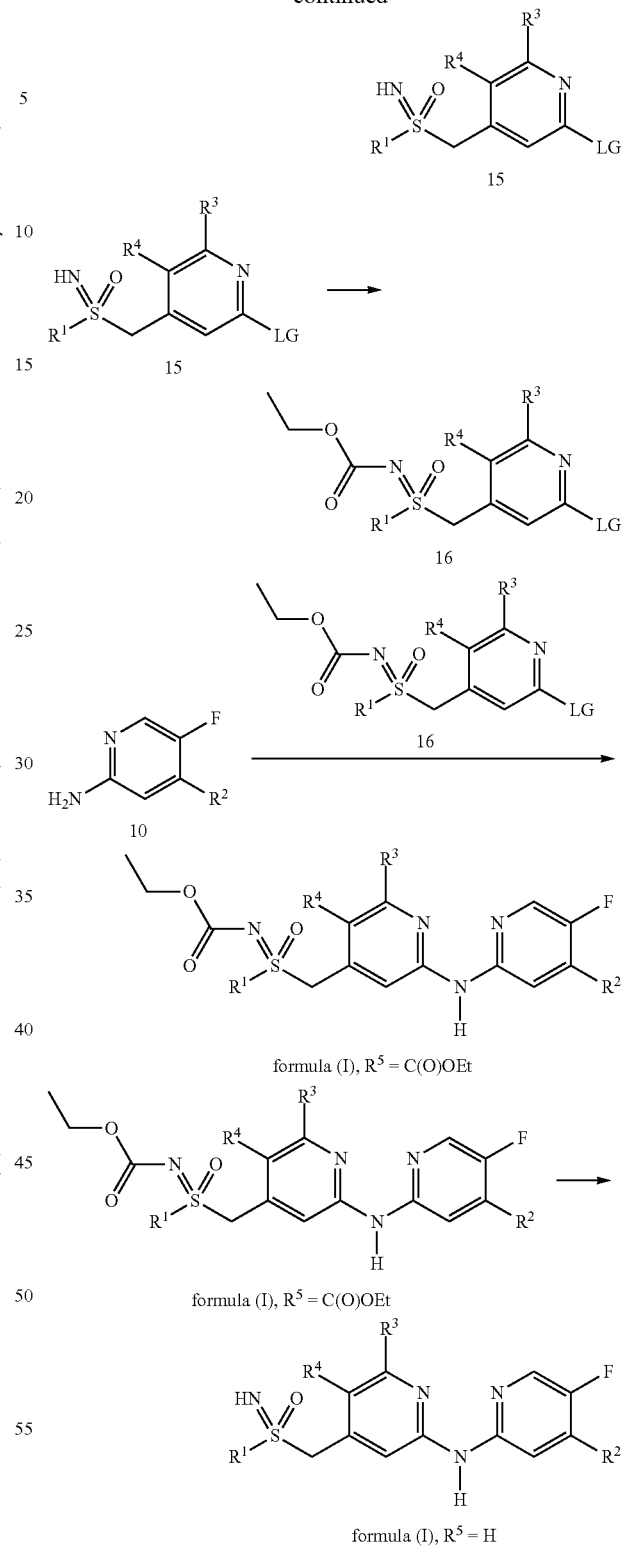

In the third step, a compound of formula (10), in which $R^2$ is as defined for the compound of general formula (I), is reacted with a sulfoximine of formula (16), to give an protected sulfoximine of formula (I) ($R^5$=C(O)OEt). This coupling reaction can be carried out by a Palladium-catalyzed C—N cross-coupling reaction (for a review on C—N cross coupling reactions see for example: a) L. Jiang, S. L.

Buchwald in 'Metal-Catalyzed Cross-Coupling Reactions', 2nd ed.: A. de Meijere, F. Diederich, Eds.: Wiley-VCH: Weinheim, Germany, 2004).

Preferred is the herein described use chloro(2-dicyclohexylphosphino-2',4',6'-tri-iso-propyl-1,1'-biphenyl)[2-(2-aminoethyl)phenyl]palladium(II) methyl-tert-butylether adduct, 2-(dicyclohexylphosphino)-2',4',6'-triisopropylbiphenyl and potassium phosphate in toluene and NMP. The reactions are preferably run under an atmosphere of argon for 1-24 hours at 100-130° C. in a microwave oven or in an oil bath.

In the last step, the protected sulfoximine of formula (I) ($R^5$=C(O)OEt) is converted to an unprotected sulfoximine of formula (I) ($R^5$=H) by the reaction with an alkali salt of an aliphatic alcohol of the formula $C_1$-$C_4$-alkyl-OH in the corresponding aliphatic alcohol. Preferred is the herein described use of sodium ethoxide in ethanol at 60° C.

Preparation of Compounds:
Abbreviations Used in the Description of the Chemistry and in the Examples that Follow are:
br (broad); CDCl₃ (deuterated chloroform); cHex (cyclohexane); d (doublet); dd (doublet of doublets); dtr (doublet of triplets); DCM (dichloromethane); DIPEA (di-iso-propylethylamine); DME (1,2-dimethoxyethane), DMF (N,N-dimethylformamide); DMSO (dimethyl sulfoxide); eq (equivalent); ES (electrospray); EtOAc (ethyl acetate); EtOH (ethanol); iPrOH (iso-propanol); mCPBA (meta-chloroperoxybenzoic acid), MeCN (acetonitrile), MeOH (methanol); MS (mass spectrometry); NMP (N-Methylpyrrolidin-2-one); NBS (N-bromosuccinimide), NMR (nuclear magnetic resonance); Oxone® (triple salt 2KHSO₅*KHSO₄*K₂SO₄); p (pentet); Pd(dppf)Cl₂ ([1,1'-bis(diphenylphosphino)ferrocene]dichloro palladium(II) complex with dichloromethane); q (quartet); RT (room temperature); s (singlet); sat. aq. (saturated aqueous); SiO₂ (silica gel); TFA (trifluoroacetic acid); TFAA (trifluoroacetic anhydride), THF (tetrahydrofuran); tr (triplet); trd (triplet of doublets).

The IUPAC names of the examples were generated using the program 'ACD/Name batch version 12.01' from ACD LABS.

Example 1

(rac)-5-Fluoro-4-(4-fluoro-2-methoxyphenyl)-N-{4-[(S-methylsulfonimidoyl)methyl]pyridin-2-yl}pyridin-2-amine

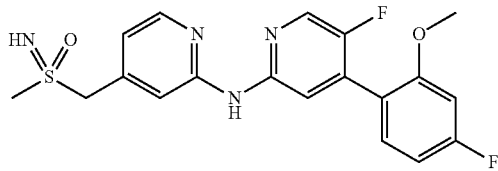 [SMILES: COc1cc(F)ccc1-c1cc(Nc2cc(CS(C)(=N)=O)ccn2)ncc1F]

Preparation of Intermediate 1.1

2-Chloro-5-fluoro-4-(4-fluoro-2-methoxyphenyl)pyridine

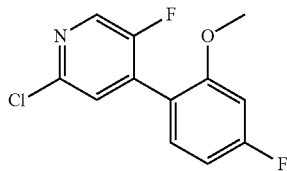 [SMILES: COc1cc(F)ccc1-c1cc(Cl)ncc1F]

A batch with 2-chloro-5-fluoro-4-iodopyridine (1000 mg; 3.88 mmol; APAC Pharmaceutical, LLC), (4-fluoro-2-methoxyphenyl)boronic acid (660 mg; 3.88 mmol; Aldrich Chemical Company Inc.) and tetrakis(triphenylphosphin) palladium(0) (449 mg; 0.38 mmol) in 1,2-dimethoxyethane (10.0 mL) and 2 M aqueous solution of potassium carbonate (5.8 mL) was degassed using argon. The batch was stirred under an atmosphere of argon for 4 hours at 100° C. After cooling, the batch was diluted with ethyl acetate and THF and washed with a saturated aqueous solution of sodium chloride. The organic phase was filtered using a Whatman filter and concentrated. The residue was purified by column chromatography (hexane to hexane/ethyl acetate 50%) to give the desired product (947 mg; 3.70 mmol).

$^1$H NMR (400 MHz, CDCl₃, 300K) δ=8.27 (m, 1H), 7.33 (m, 1H), 7.24 (m, 1H), 6.75 (m, 2H), 3.83 (s, 3H).

Preparation of Intermediate 1.2

5-Fluoro-4-(4-fluoro-2-methoxyphenyl)-N-{4-[(methylsulfanyl)methyl]pyridin-2-yl}pyridin-2-amine

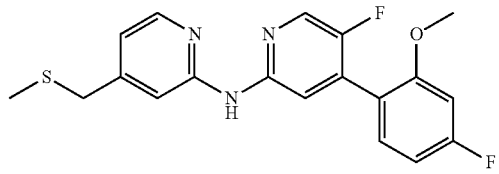 [SMILES: COc1cc(F)ccc1-c1cc(Nc2cc(CSC)ccn2)ncc1F]

A batch containing 2-chloro-5-fluoro-4-(4-fluoro-2-methoxyphenyl)pyridine (400 mg; 1.57 mmol), 4-[(methylsulfanyl)methyl]pyridin-2-amine (483 mg; 3.13 mmol; UkrOrgSynthesis Ltd.), (9,9-dimethyl-9H-xanthene-4,5-diyl)bis(diphenylphosphane) (40 mg; 0.07 mmol) and cesium carbonate (765 mg; 2.35 mmol) in dioxane (6.0 mL) was degassed using argon. Tris(dibenzylideneacetone)dipalladium(0) (21 mg; 0.02 mmol) was added under argon and the batch was stirred in a closed pressure tube for 5 hours at 100° C. After cooling, the batch was diluted with an aqueous solution of sodium chloride and extracted with DCM (3×). The combined organic phases were filtered using a Whatman filter and concentrated. The residue was purified by chromatography (hexane to hexane/ethyl acetate 30%) to give the desired product (556 mg; 1.48 mmol).

$^1$H NMR (400 MHz, CDCl₃, 300K) δ=8.15 (m, 2H), 7.61 (m, 1H), 7.40 (s, 1H), 7.35 (br, 1H), 7.29 (m, 1H), 6.82 (m, 1H), 6.75 (m, 2H), 3.83 (s, 3H), 3.62 (s, 2H), 2.03 (s, 3H).

Preparation of end product:

Under argon, a solution of 2,2,2-trifluoroacetamide (195 mg; 1.73 mmol) in dioxane (0.5 mL) was added dropwise to a solution of sodium tert.-butoxide (111 mg; 1.15 mmol) in dioxane (0.6 mL), so that the temperature of the mixture remained below 10° C. Subsequently, a freshly prepared solution of 1,3-dibromo-5,5-dimethylhydantoin (247 mg; 0.86 mmol) in dioxane (0.6 mL)/THF (1.0 mL) was added dropwise to the stirred mixture, so that the temperature of the mixture remained below 10° C. Then the mixture was stirred for 10 minutes at 10° C. Finally, a solution of 5-fluoro-4-(4-fluoro-2-methoxyphenyl)-N-{4-[(methylsulfanyl)methyl]pyridin-2-yl}pyridin-2-amine (430 mg; 1.15 mmol) in dioxane (1.0 mL) was added dropwise to the stirred mixture, so that the temperature of the mixture remained below 10° C. The mixture was stirred for 60 minutes at 10° C. The batch was diluted with toluene (2.0 mL) under cooling and an aqueous solution of sodium sulfite (145 mg; 1.15 mmol in 2.0 mL water) was added so that the temperature of the mixture remained below 15° C. An aqueous solution of sodium chloride was added and the batch was extracted with ethyl acetate (3×). The combined organic phases were filtered using a Whatman filter and concentrated to give crude 2,2,2-trifluoro-N-{[(2-{[5-fluoro-4-(4-fluoro-2-methoxyphenyl)pyridin-2-yl]amino}pyridin-4-yl)methyl](methyl)-λ⁴-sulfanylidene}acetamide, that was used without further purification.

Acetone (6.0 mL) and potassium permanganate (814 mg; 5.15 mmol) were added to the residue and the mixture was stirred at 50° C. for 90 minutes. Additional potassium permanganate (223 mg; 1.42 mmol) was added and stirring was continued at 50° C. for 4 hours. Finally, additional potassium permanganate (305 mg; 1.93 mmol) was added and stirring was continued at 50° C. for 150 minutes. After cooling, the batch was filtered, the residue was washed with acetone and the combined filtrates were concentrated. The residue was dissolved in MeOH (60 mL), potassium carbonate (182 mg; 1.32 mmol) was added and the reaction mixture was stirred for 20 minutes at RT. The batch was diluted with an aqueous solution of sodium chloride and extracted with DCM (3×). The combined organic phases were filtered using a Whatman filter and concentrated. The residue was purified by preparative HPLC to give the desired product (50 mg; 0.12 mmol).

| System: | Waters Autopurificationsystem: Pump 254, Sample Manager 2767, CFO, DAD 2996, SQD 3100 |
|---|---|
| Column: | XBrigde C18 5 μm 100 × 30 mm |
| Solvent: | A = H₂O + 0.2% NH₃ (32%) |
|  | B = MeCN |
| Gradient: | 0-8 min 15-50% B |
| Flow: | 50 mL/min |
| Temperature: | RT |
| Solution: | 132 mg/2 mL DMF/MeOH 1:1 |
| Injection: | 2 × 1 mL |
| Detection: | DAD scan range 210-400 nm |
|  | MS ESI+, ESI−, scan range 160-1000 m/z |
| Retention: | 3.39-3.88 min |
| MS(ES+): | m/z = 404 |

¹H NMR (400 MHz, d₆-DMSO, 300K) δ=9.80 (s, 1H), 8.20 (m, 1H), 8.16 (m, 1H), 7.79 (m, 1H), 7.59 (m, 1H), 7.34 (m, 1H), 7.09 (m, 1H), 6.91 (m, 2H), 4.36 (m, 2H), 3.80 (s, 3H), 3.72 (s, 1H), 2.88 (s, 3H).

Alternative Procedure for the Preparation of Intermediate 1.2

5-Fluoro-4-(4-fluoro-2-methoxyphenyl)-N-{4-[(methylsulfanyl)methyl]pyridin-2-yl}pyridin-2-amine

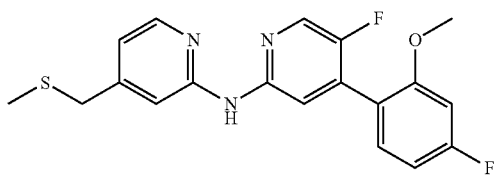 [SMILES: COc1cc(F)ccc1-c1cc(Nc2cc(CSC)ccn2)ncc1F]

Preparation of Intermediate 1.3

(2-{[5-Fluoro-4-(4-fluoro-2-methoxyphenyl)pyridin-2-yl]amino}pyridin-4-yl)methanol

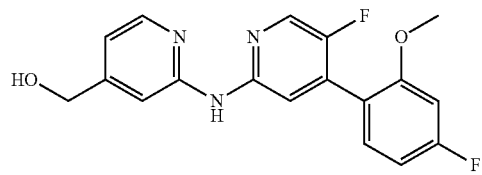 [SMILES: COc1cc(F)ccc1-c1cc(Nc2cc(CO)ccn2)ncc1F]

A batch containing 2-chloro-5-fluoro-4-(4-fluoro-2-methoxyphenyl)pyridine (411 mg; 1.61 mmol), (2-aminopyridin-4-yl)methanol (200 mg; 1.61 mmol; ABCR GmbH & CO. KG), (9,9-dimethyl-9H-xanthene-4,5-diyl)bis(diphenylphosphane) (418 mg; 0.72 mmol) and cesium carbonate (784 mg; 2.41 mmol) in dioxane (8.0 mL) was degassed using argon. Tris(dibenzylideneacetone)dipalladium(0) (147 mg; 0.16 mmol) was added under an atmosphere of argon and the batch was stirred for 29 hours at 100° C. After cooling, additional (2-aminopyridin-4-yl)methanol (100 mg; 0.81 mmol), (9,9-dimethyl-9H-xanthene-4,5-diyl)bis(diphenylphosphane) (118 mg; 0.20 mmol) and tris(dibenzylideneacetone)dipalladium(0) (74 mg; 0.08 mmol) were added and the mixture was stirred for 19 hours at 100° C. After cooling, the batch was diluted with ethyl acetate and washed with an aqueous solution of sodium chloride. The organic phase was filtered using a Whatman filter and concentrated. The residue was purified by chromatography (DCM/EtOH 9:1) to give the desired product (389 mg; 1.13 mmol).

¹H NMR (400 MHz, d₆-DMSO, 300K) δ=9.66 (s, 1H), 8.17 (m, 1H), 8.05 (m, 1H), 7.80 (m, 1H), 7.51 (s, 1H), 7.31 (m, 1H), 7.06 (m, 1H), 6.88 (m, 1H), 6.75 (m, 1H), 5.31 (tr, 1H), 4.44 (d, 2H), 3.76 (s, 3H).

Preparation of End Product (Alternative Preparation of Intermediate 1.2)

Thionyl chloride (0.19 ml; 2.55 mmol) was added dropwise to a stirred solution of (2-{[5-fluoro-4-(4-fluoro-2-methoxyphenyl)pyridin-2-yl]amino}pyridin-4-yl)methanol (350 mg; 1.01 mmol) in DCM (4.0 ml) and NMP (0.4 ml) at 0° C. The mixture was stirred for 7 hours at RT. The batch was diluted with aqueous sodium bicarbonate solution and aqueous sodium chloride solution and extracted with DCM (3×). The combined organic phases were filtered using a Whatman filter and concentrated to give crude N-[4-(chloromethyl)pyridin-2-yl]-5-fluoro-4-(4-fluoro-2-methoxyphenyl)pyridin-2-amine, that was used without further purification in the next step.

The residue was re-dissolved in EtOH (12.0 ml) and the resulting solution was cooled to 0° C. Sodium methanethiolate (158 mg; 2.26 mmol) was added portionwise to the stirred solution at 0° C. The mixture was stirred for 4 hours at RT before it was diluted with DCM and washed with aqueous sodium chloride solution. The organic phase was filtered using a Whatman filter and concentrated. The residue was purified by chromatography (DCM/EtOH 95:5) to give the desired product (301 mg; 0.81 mmol).

¹H NMR (400 MHz, CDCl₃, 300K) δ=8.15 (m, 2H), 7.61 (m, 1H), 7.40 (br, 2H), 7.29 (m, 1H), 6.82 (m, 1H), 6.75 (m, 2H), 3.83 (s, 3H), 3.62 (s, 2H), 2.03 (s, 3H).

Alternative Procedure for the Preparation of Example 1

Preparation of Intermediate 1.4

(rac)-2,2,2-Trifluoro-N-{[(2-{[5-fluoro-4-(4-fluoro-2-methoxyphenyl)pyridin-2-yl]amino}pyridin-4-yl)methyl](methyl)-λ$^4$-sulfanylidene}acetamide

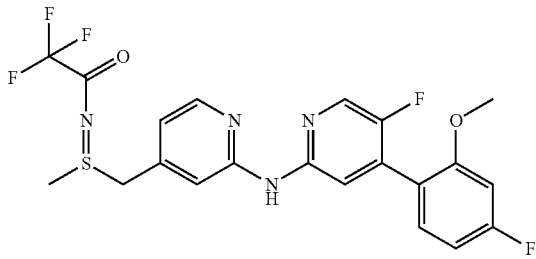 [SMILES: COc1cc(F)ccc1-c1cc(Nc2cc(CS(C)=NC(=O)C(F)(F)F)ccn2)ncc1F]

Under an atmosphere of argon, a solution of 2,2,2-trifluoroacetamide (2.53 g; 22.4 mmol) in THF (10.0 mL) was added dropwise to a solution of sodium tert.-butoxide (1.43 g; 14.9 mmol) in THF (12.0 mL), so that the temperature of the mixture remained below 10° C. Subsequently, a freshly prepared solution of 1,3-dibromo-5,5-dimethylhydantoin (3.20 g; 11.2 mmol) in THF (12.0 mL) was added dropwise to the stirred mixture, so that the temperature of the mixture remained below 10° C. Then the mixture was stirred for 10 minutes at 10° C. Finally, a solution of 5-fluoro-4-(4-fluoro-2-methoxyphenyl)-N-{4-[(methylsulfanyl)methyl]pyridin-2-yl}pyridin-2-amine (5.57 g; 14.9 mmol; Intermediate 1.2) in dioxane (12.0 mL) was added dropwise to the stirred mixture, so that the temperature of the mixture remained below 10° C. The mixture was stirred for 60 minutes at 10° C. The batch was diluted with toluene (40.0 mL) under cooling and an aqueous solution of sodium sulfite (1.88 g; 14.9 mmol in 40.0 mL water) was added so that the temperature of the mixture remained below 15° C. The batch was extracted three times (3×) with ethyl acetate. The combined organic layers were washed with an aqueous solution of sodium chloride, filtered using a Whatman filter and concentrated. The residue was purified by column chromatography on silica gel (DCM to DCM/EtOH 95:5) to give the desired product (4.71 g; 9.72 mmol).

$^1$H NMR (400 MHz, CDCl$_3$, 300K) δ=8.29 (m, 1H), 8.18 (m, 1H), 7.83 (s, 1H), 7.50 (br, 1H), 7.32 (m, 1H), 7.28 (m, 1H), 6.79 (m, 3H), 4.52 (d, 1H), 4.21 (d, 1H), 3.85 (s, 3H), 2.71 (s, 3H).

Alternative Preparation of End Product (Example 1)

An aqueous solution of potassium hydroxide (25%) was added dropwise to a stirred solution of 2,2,2-trifluoro-N-{[(2-{[5-fluoro-4-(4-fluoro-2-methoxyphenyl)pyridin-2-yl]amino}pyridin-4-yl)methyl](methyl)-λ$^4$-sulfanylidene}acetamide (4.64 g; 9.58 mmol) in DMF (350 mL), methanol (100 mL) and water (100 mL) to adjust the pH to 10.5. Oxone® (5.00 g; 8.14 mmol) was added and the mixture was stirred at room temperature for 4.5 hours. During this time, the pH was kept between 10-11, by dropwise addition of an aqueous solution of potassium hydroxide (25%), if necessary. The mixture was filtered and the filter cake was washed with plenty of DCM. The pH of the filtrate was adjusted to 6-7 using an aqueous solution of hydrogen chloride (15%). The filtrate was washed with an aqueous solution of sodium chloride, followed by an aqueous solution of sodium thiosulfate (10%). During evaporation of solvents using a rotary evaporator, a solid substance precipitated from the solution. The precipitated solid was isolated by suction filtration, washed with DCM and diisopropyl ether, and dried to give the desired product (2.61 g; 6.43 mmol).

$^1$H NMR (400 MHz, d$_6$-DMSO, 300K) δ=9.82 (s, 1H), 8.21 (m, 1H), 8.16 (m, 1H), 7.78 (m, 1H), 7.59 (m, 1H), 7.34 (m, 1H), 7.09 (m, 1H), 6.90 (m, 2H), 4.35 (m, 2H), 3.79 (s, 3H), 3.75 (s, 1H), 2.87 (s, 3H).

Example 2 and 3

Enantiomers of 5-Fluoro-4-(4-fluoro-2-methoxyphenyl)-N-{4-[(S-methylsulfonimidoyl)methyl]pyridin-2-yl}pyridin-2-amine

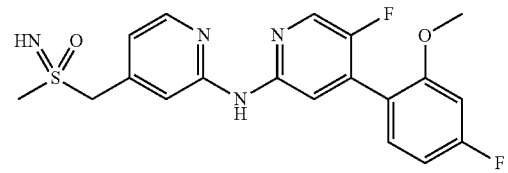 [SMILES: COc1cc(F)ccc1-c1cc(Nc2cc(CS(C)(=N)=O)ccn2)ncc1F]

(rac)-5-Fluoro-4-(4-fluoro-2-methoxyphenyl)-N-{4-[(S-methylsulfonimidoyl)methyl]pyridin-2-yl}pyridin-2-amine (3.47 g) was separated into the single enantiomers by preparative chiral HPLC.

| | |
|---|---|
| System: | Sepiatec: Prep SFC100, |
| Column: | Chiralpak IC 5 μm 250 × 30 mm |
| Solvent: | CO$_2$/2-propanol 70/30 + 0.4% DEA |
| Flow: | 100 mL/min |
| Pressure (outlet): | 150 bar |
| Temperature: | 40° C. |
| Solution: | 3.468 g/55 mL DCM/MeOH 2:1 |
| Injection: | 112 × 0.49 mL |
| Detection: | UV 254 nm |

| | Retention time in min | purity in % | yield | specific optical rotation: |
|---|---|---|---|---|
| Example 2 Enantiomer 1 | 7.0-8.1 | 99.15 | 1.31 g (3.24 mmol) | $[α]_D^{20}$ = 12.0° +/− 0.15° (DMSO, 589 nm, 20° C.). |
| Example 3 Enantiomer 2 | 8.5-10.5 | 96.98 | 1.32 g (3.26 mmol) | $[α]_D^{20}$ = −13.8° +/− 0.25° (DMSO, 589 nm, 20° C.). |

Example 2

(+)-5-Fluoro-4-(4-fluoro-2-methoxyphenyl)-N-{4-[(S-methylsulfonimidoyl)methyl]pyridin-2-yl}pyridin-2-amine $^1$H-NMR (300 MHz, DMSO-d$_6$, 300 K): δ [ppm]=9.80 (s, 1H), 8.20 (m, 1H), 8.16 (m, 1H), 7.78 (m, 1H), 7.59 (s, 1H), 7.34 (m, 1H), 7.09 (m, 1H), 6.90 (m, 2H), 4.37 (d, 1H), 4.33 (d, 1H), 3.79 (s, 3H), 3.72 (s, 1H), 2.87 (s, 3H).

Example 3

(−)-5-Fluoro-4-(4-fluoro-2-methoxyphenyl)-N-{4-[(S-methylsulfonimidoyl)methyl]pyridin-2-yl}pyridin-2-amine $^1$H-NMR (300 MHz, DMSO-d$_6$, 300 K): δ [ppm]=9.80 (s, 1H), 8.20 (m, 1H), 8.16 (m, 1H), 7.78 (m, 1H), 7.59 (s, 1H), 7.34 (m, 1H), 7.09 (m, 1H), 6.90 (m, 2H), 4.37 (d, 1H), 4.33 (d, 1H), 3.79 (s, 3H), 3.72 (s, 1H), 2.87 (s, 3H).

Example 4

(rac)-5-Fluoro-4-(4-fluoro-2-methoxyphenyl)-N-{6-methyl-4-[(S-methylsulfonimidoyl)methyl]pyridin-2-yl}pyridin-2-amine

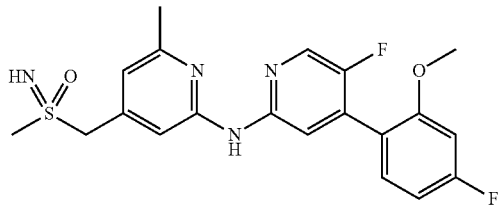 [SMILES: COc1cc(F)ccc1-c1cc(Nc2cc(CS(C)(=N)=O)cc(C)n2)ncc1F]

Preparation of Intermediate 4.1

5-Fluoro-4-(4-fluoro-2-methoxyphenyl)pyridin-2-amine

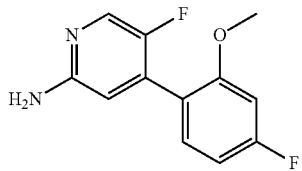 [SMILES: COc1cc(F)ccc1-c1cc(N)ncc1F]

A solution of lithium bis(trimethylsilyl)amide in THF (1M; 20.5 mL; 20.53 mmol; Aldrich Chemical Company Inc.) was added to a mixture of 2-chloro-5-fluoro-4-(4-fluoro-2-methoxyphenyl)pyridine (2.50 g; 9.78 mmol; Intermediate 1.1), tris(dibenzylideneacetone)dipalladium (0) (0.18 g; 0.20 mmol; Aldrich Chemical Company Inc.) and 2-(dicyclohexylphosphino)-2',4',6'-triisopropylbiphenyl (0.19 g; 0.39 mmol; Aldrich Chemical Company Inc.) in THF (16.3 mL) under an atmosphere of argon at room temperature. The mixture was stirred at 60° C. for 6 hours. The mixture was cooled to −40° C. and water (10 ml) was added. The mixture was slowly warmed to room temperature under stirring, solid sodium chloride was added and the mixture was extracted with ethyl acetate twice (2×). The combined organic layers were filtered using a Whatman filter and concentrated. The residue was purified by column chromatography on silica gel (hexane to hexane/ethyl acetate 60%) to give the desired product (2.04 g; 8.64 mmol).

$^1$H NMR (400 MHz, CDCl$_3$, 300K) δ=7.95 (m, 1H), 7.20 (m, 1H), 6.72 (m, 2H), 6.46 (m, 1H), 4.33 (br, 2H), 3.61 (s, 3H).

Preparation of Intermediate 4.2

(2-Chloro-6-methylpyridin-4-yl)methanol

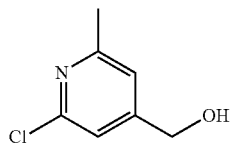

To a stirred solution of 2-chloro-6-methylpyridine-4-carboxylic acid (10.00 g; 55.4 mmol; Maybridge) in THF (100 mL) at 0° C. was added a 1M solution of borane-tetrahydrofuran complex in THF (221.5 mL; 221.5 mmol). The mixture was allowed to react at RT overnight. Then, MeOH (22 mL) was cautiously added to the stirred mixture while cooling with an ice bath. The batch was diluted with ethyl acetate and washed with aqueous sodium hydroxide solution (1N) and saturated aqueous sodium chloride solution. The organic layer was filtered using a Whatman filter and concentrated. The residue was purified by column chromatography on silica gel (DCM/EtOH 95:5) to give the pure product (7.24 g; 45.9 mmol).

$^1$H NMR (400 MHz, CDCl$_3$, 300K) δ=7.18 (s, 1H), 7.09 (s, 1H), 4.72 (d, 2H), 2.55 (s, 3H), 2.17 (tr, 1H).

Preparation of Intermediate 4.3

2-Chloro-6-methyl-4-[(methylsulfanyl)methyl]pyridine

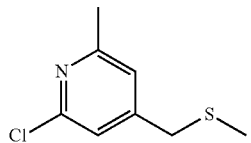

To a stirred solution of (2-chloro-6-methylpyridin-4-yl)methanol (7.20 g; 45.7 mmol) in DMF (200 mL) at 0° C. was added dropwise thionyl chloride (8.3 mL; 114.2 mmol). The mixture was allowed to react at 10° C. for 2 hours. Then, the mixture was concentrated to give the crude product 2-chloro-4-(chloromethyl)-6-methylpyridine (17.08 g).

Crude 2-chloro-4-(chloromethyl)-6-methylpyridine (8.04 g).was dissolved in acetone (250 mL) and an aqueous solution of sodium methanethiolate (21%, 18.3 mL, 54.8 mmol; Aldrich Chemical Company Inc.) was added dropwise under stirring. The mixture was stirred at RT for 3 hours before additional aqueous solution of sodium methanethiolate (21%, 15.3 mL, 45.7 mmol; Aldrich Chemical Company Inc.) was added and the mixture was stirred at RT overnight. Finally, additional aqueous solution of sodium methanethiolate (21%, 15.3 mL, 45.7 mmol; Aldrich Chemical Company Inc.) was added and the mixture was stirred at RT for 6 hours. The batch was diluted with ethyl acetate and an aqueous solution of sodium chloride. The mixture was extracted twice with ethyl acetate. The combined organic layers were filtered using a Whatman filter and concentrated. The residue was purified by column chromatography on silica gel (hexane to hexane/ethyl acetate 20%) to give the desired product (7.05 g; 37.6 mmol).

$^1$H NMR (400 MHz, CDCl$_3$, 300K) δ=7.12 (s, 1H), 7.05 (s, 1H), 3.58 (s, 2H), 2.54 (s, 3H), 2.03 (s, 3H).

Preparation of Intermediate 4.4

5-Fluoro-4-(4-fluoro-2-methoxyphenyl)-N-{6-methyl-4-[(methylsulfanyl)methyl]pyridin-2-yl}pyridin-2-amine

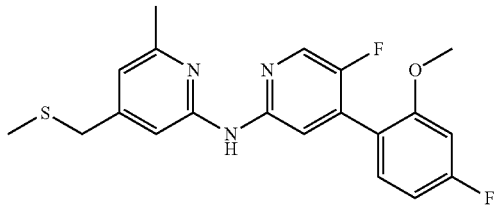 [SMILES: COc1cc(F)ccc1-c1cc(Nc2cc(CSC)cc(C)n2)ncc1F]

A batch containing 5-fluoro-4-(4-fluoro-2-methoxyphenyl)pyridin-2-amine (852 mg; 3.61 mmol), 2-chloro-6-methyl-4-[(methylsulfanyl)methyl]pyridine (677 mg; 3.61 mmol) and cesium carbonate (1410 mg; 4.33 mmol) in dioxane (8.3 mL) was degassed using argon. (9,9-Dimethyl-9H-xanthene-4,5-diyl)bis(diphenylphosphane) (81 mg; 0.14 mmol) and tris(dibenzylideneacetone)dipalladium(0) (69 mg; 0.08 mmol) were added under an atmosphere of argon and the batch was stirred in a closed pressure tube for 3 hours at 100° C. Additional (9,9-dimethyl-9H-xanthene-4,5-diyl)bis(diphenylphosphane) (81 mg; 0.14 mmol) and tris(dibenzylideneacetone)dipalladium(0) (69 mg; 0.08 mmol) were added under an atmosphere of argon and the batch was stirred in the closed pressure tube for additional 20 hours at 100° C.

After cooling, the mixture was diluted with ethyl acetate and washed with an aqueous solution of sodium chloride. The organic layer was filtered using a Whatman filter and concentrated. The residue was purified by column chromatography on silica gel (hexane to hexane/ethyl acetate 50%) to give the desired product (628 mg; 1.62 mmol).

Preparation of Intermediates 4.5 and 4.6

(rac)-2,2,2-Trifluoro-N-{[(2-{[5-fluoro-4-(4-fluoro-2-methoxyphenyl)pyridin-2-yl]amino}-6-methyl-pyridin-4-yl)methyl](methyl)-λ$^4$-sulfanylidene}acetamide and (rac)-N-{[(3-bromo-6-{[5-fluoro-4-(4-fluoro-2-methoxyphenyl)pyridin-2-yl]amino}-2-methylpyridin-4-yl)methyl](methyl)-λ$^4$-sulfanylidene}-2,2,2-trifluoroacetamide Intermediate 4.5

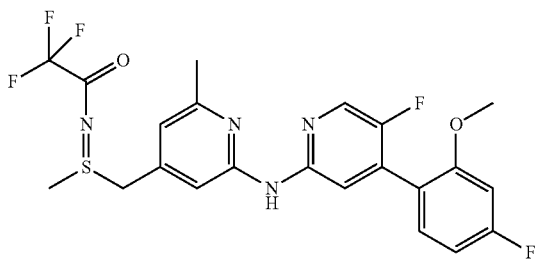

Intermediate 4.6

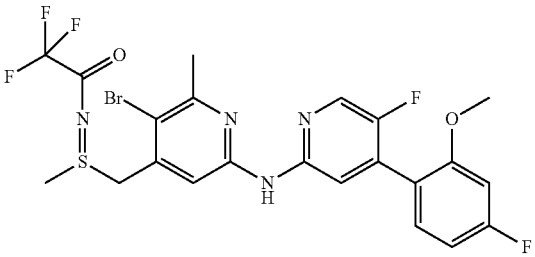

Under an atmosphere of argon, a solution of 2,2,2-trifluoroacetamide (125 mg; 1.11 mmol) in THF (1.0 mL) was added dropwise to a solution of sodium tert.-butoxide (71 mg; 0.74 mmol) in THF (1.0 mL), so that the temperature of the mixture remained below 10° C. Subsequently, a freshly prepared solution of 1,3-dibromo-5,5-dimethylhydantoin (158 mg; 0.55 mmol) in THF (1.0 mL) was added dropwise to the stirred mixture, so that the temperature of the mixture remained below 10° C. Then the mixture was stirred for 10 minutes at 10° C. Finally, a solution of 5-fluoro-4-(4-fluoro-2-methoxyphenyl)-N-{6-methyl-4-[(methylsulfanyl)methyl]pyridin-2-yl}pyridin-2-amine (286 mg; 0.74 mmol) in THF (1.5 mL) was added dropwise to the stirred mixture, so that the temperature of the mixture remained below 10° C. The mixture was stirred for 60 minutes at 10° C. The batch was diluted with toluene (4.0 mL) under cooling and an aqueous solution of sodium sulfite (93 mg; 0.74 mmol in 7.0 mL water) was added so that the temperature of the mixture remained below 15° C. The batch was extracted three times with ethyl acetate. The combined organic layers were washed with an aqueous solution of sodium chloride, filtered using a Whatman filter and concentrated. The residue was purified by column chromatography on silica gel (hexane to hexane/ethyl acetate 100%) to give the desired product 2,2,2-trifluoro-N-{[(2-{[5-fluoro-4-(4-fluoro-2-methoxyphenyl)pyridin-2-yl]amino}-6-methylpyridin-4-yl)methyl](methyl)-λ$^4$-sulfanylidene}acetamide (134 mg; 0.27 mmol) and the side product N-{[(3-bromo-6-{[5-fluoro-4-(4-fluoro-2-methoxyphenyl)pyridin-2-yl]amino}-2-methylpyridin-4-yl)methyl](methyl)-λ$^4$-sulfanylidene}-2,2,2-trifluoroacetamide (110 mg; 0.19 mmol).

Intermediate 4.5:

$^1$H NMR (400 MHz, CDCl$_3$, 300K) δ=8.18 (m, 1H), 7.70 (s, 1H), 7.33 (br, 1H), 7.29 (m, 1H), 7.24 (m, 1H), 6.79 (m, 2H), 6.68 (s, 1H), 4.49 (d, 1H), 4.16 (d, 1H), 3.86 (s, 3H), 2.70 (s, 3H), 2.48 (s, 3H).

Intermediate 4.6:

$^1$H NMR (400 MHz, CDCl$_3$, 300K) δ=8.18 (s, 1H), 7.84 (s, 1H), 7.33 (s, 1H), 7.29 (m, 1H), 7.23 (m, 1H), 6.78 (m, 2H), 4.77 (d, 1H), 4.36 (d, 1H), 3.86 (s, 3H), 2.80 (s, 3H), 2.63 (s, 3H).

Preparation of End Product:

An aqueous solution of potassium hydroxide (25%) was added dropwise to a stirred solution of 2,2,2-trifluoro-N-{[(2-{[5-fluoro-4-(4-fluoro-2-methoxyphenyl)pyridin-2-yl]amino}-6-methylpyridin-4-yl)methyl](methyl)-λ$^4$-sulfanylidene}acetamide (126 mg; 0.25 mmol) in methanol (5.0 mL) and water (1.8 mL) to adjust the pH to 10.5. Oxone® (132 mg; 0.22 mmol) was added and the mixture was stirred at room temperature for 4.5 hours. During this time, the pH was kept between 10-11, by dropwise addition of an aqueous solution of potassium hydroxide (25%), if necessary. After 4.5 hours, additional Oxone® (33 mg; 0.05 mmol) was added and the mixture was stirred at room temperature for additional 2.5 hours. The pH was kept between 10-11, by dropwise addition of an aqueous solution of potassium hydroxide (25%), if necessary. The mixture was filtered and the filter cake was washed with plenty of DCM. The filtrate was washed with an aqueous solution of sodium chloride, followed by an aqueous solution of sodium thiosulfate (10%). The organic layer was filtered using a Whatman filter and concentrated. The residue was purified by chromatography (DCM to DCM/ethanol 10%) to give the desired product (38 mg; 0.09 mmol).

$^1$H NMR (400 MHz, CDCl$_3$, 300K) δ=8.16 (s, 1H), 7.60 (s, 1H), 7.39 (m, 1H), 7.30 (m, 2H), 6.79 (m, 3H), 4.34 (d, 1H), 4.22 (d, 1H), 3.86 (s, 3H), 3.02 (s, 3H), 2.79 (br, 1H), 2.48 (s, 3H).

Alternative Procedure for the Preparation of Example 4

Preparation of Intermediate 4.1

5-Fluoro-4-(4-fluoro-2-methoxyphenyl)pyridin-2-amine

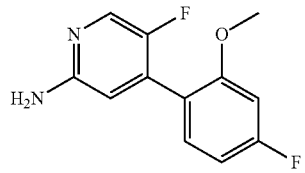

2-Chloro-5-fluoro-4-(4-fluoro-2-methoxyphenyl)pyridine (20.00 g; 78.23 mmol), tris(dibenzylideneacetone)dipalladium (0) (1.433 g; 1.563 mmol) and 2-(dicyclohexylphosphino)-2',4',6'-triisopropylbiphenyl (1.492 g; 3.129 mmol) in anhydrous THF (200 mL) were degassed three times with argon. After 10 minutes of stirring at RT a solution of lithium bis(trimethylsilyl)amide (156.5 mL; 1.0M; THF) was added and the reaction mixture was degassed three more times with argon. The reaction mixture was stirred 2.5 hours at 60° C.

The reaction mixture was cooled to −20° C. Diluted aqueous hydrochloric acid (1.0M) was added so that the pH was adjusted to approximately 5. The reaction mixture was allowed to reach RT and stirred for 10 minutes at this temperature. Then, the pH was adjusted to 10-11 with aqueous sodium hydroxide solution (5.0M). The reaction mixture was diluted with ethyl acetate and washed twice with half saturated sodium chloride solution. The organic layer was dried over magnesium sulfate and concentrated. The residue was purified by column chromatography on silica gel (gradient: hexane to ethyl acetate 100%, with 5% dichloromethane during the first 4 column volumes and afterwards 10% dichloromethane) to give the desired compound (12.04 g; 50.97 mmol).

$^1$H-NMR (300 MHz, DMSO-d$_6$, 300 K): δ [ppm]=7.85 (d, 1H), 7.25 (tr, 1H), 7.08-7.00 (m, 1H), 6.91-6.81 (m, 1H), 6.35 (d, 1H), 5.84 (s, 2H).

Preparation of Intermediate 4.3

2-Chloro-6-methyl-4-[(methylsulfanyl)methyl]pyridine

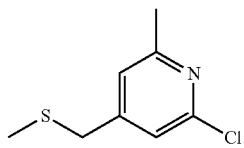

An aqueous solution of sodium methanethiolate (21%, 13.15 mL, 39.38 mmol) was added dropwise to a stirred solution of 4-(bromomethyl)-2-chloro-6-methylpyridine hydrochloride (4.60 g; 17.90 mmol; Aldlab Chemicals, LLC; for the free base see CAS 1227588-90-0) in acetone (100 mL) while cooling with a water bath at RT. The mixture was stirred at RT over night. EtOAc was added and the layers were separated. The organic layers were washed with saturated aqueous sodium chloride solution, dried over magnesium sulfate and concentrated. The residue was purified by column chromatography on silica gel (gradient: hexane to hexane/EtOAc 8:2) to give the desired product (2.60 g, 13.85 mmol).

$^1$H-NMR (300 MHz, DMSO-d$_6$, 300 K): δ [ppm]=7.24 (s, 1H), 7.20 (s, 1H), 3.66 (s, 2H), 2.42 (s, 3H), 1.95 (s, 3H).

Preparation of Intermediate 4.4

5-Fluoro-4-(4-fluoro-2-methoxyphenyl)-N-{6-methyl-4-[(methylsulfanyl)methyl]pyridin-2-yl}pyridin-2-amine

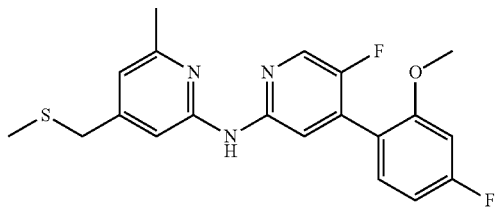 [SMILES: COc1cc(F)ccc1-c1cc(Nc2cc(CSC)cc(C)n2)ncc1F]

A batch containing 5-fluoro-4-(4-fluoro-2-methoxyphenyl)pyridin-2-amine (692.2 mg; 2.93 mmol), 2-chloro-6-methyl-4-[(methylsulfanyl)methyl]pyridine (500 mg; 2.66 mmol) and cesium carbonate (1302 mg; 4.00 mmol) in dioxane (15 mL) was degassed with argon. (9,9-Dimethyl-9H-xanthene-4,5-diyl)bis(diphenylphosphane) (67.8 mg; 0.117 mmol) and tris(dibenzylideneacetone)dipalladium(0) (36.6 mg; 0.04 mmol) were added under an atmosphere of argon and the batch was stirred in a closed pressure tube for 10 hours at 100° C.

Five of these batches were combined and diluted with EtOAc. The organic layer was washed twice with saturated aqueous sodium chloride solution, dried over magnesium sulfate and concentrated. The residue was purified by column chromatography on silica gel (gradient: hexane to hexane/EtOAc 1:1) affording the desired product (3.75 g; 9.68 mmol).

¹H-NMR (300 MHz, CDCl₃, 300 K): δ [ppm]=8.16 (d, 1H), 7.56 (d, 1H), 7.36-7.29 (m, 2H), 7.21 (s, 1H), 6.85-6.73 (m, 2H), 6.72 (s, 1H), 3.86 (s, 3H), 3.61 (s, 2H), 2.45 (s, 3H), 2.06 (s, 3H).

Preparation of Intermediate 4.5

(rac)-2,2,2-Trifluoro-N-{[(2-{[5-fluoro-4-(4-fluoro-2-methoxyphenyl)pyridin-2-yl]amino}-6-methylpyridin-4-yl)methyl](methyl)-λ⁴-sulfanylidene}acetamide

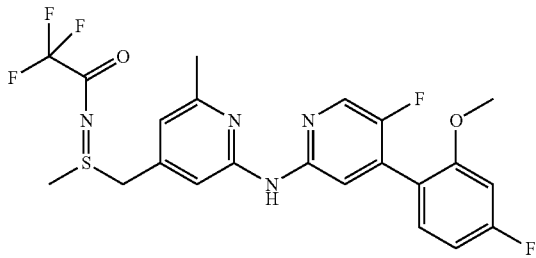 [SMILES: COc1cc(F)ccc1-c1cc(Nc2cc(CS(C)=NC(=O)C(F)(F)F)cc(C)n2)ncc1F]

Preparation of Intermediate 4.6

(rac)-N-{[(3-bromo-6-{[5-fluoro-4-(4-fluoro-2-methoxyphenyl)pyridin-2-yl]amino}-2-methylpyridin-4-yl)methyl](methyl)-λ⁴-sulfanylidene}-2,2,2-trifluoroacetamide

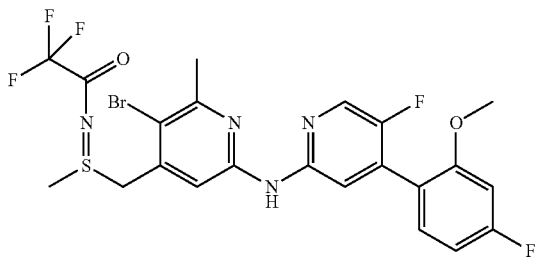 [SMILES: COc1cc(F)ccc1-c1cc(Nc2cc(CS(C)=NC(=O)C(F)(F)F)c(Br)c(C)n2)ncc1F]

Under an atmosphere of argon, a solution of 2,2,2-trifluoroacetamide (450.7 mg; 3.99 mmol) in anhydrous THF (2.0 mL) was added dropwise to sodium tert.-butoxide (255.5 mg; 2.60 mmol) in anhydrous THF (3.0 mL), so that the temperature of the mixture remained below 10° C. Subsequently, a freshly prepared solution of 1,3-dibromo-5,5-dimethylhydantoin (456.1 mg; 1.60 mmol) in anhydrous THF (3.0 mL) was added dropwise to the stirred mixture, so that the temperature of the mixture remained below 10° C. Then the mixture was stirred for 10 minutes at 10° C. Finally, a solution of 5-fluoro-4-(4-fluoro-2-methoxyphenyl)-N-{6-methyl-4-[(methylsulfanyl)methyl]pyridin-2-yl}pyridin-2-amine (1030 mg; 2.66 mmol) in anhydrous THF (3.0 mL) was added dropwise to the stirred mixture, so that the temperature of the mixture remained below 10° C. The mixture was stirred 1 hour at 10° C. The batch was diluted with toluene (8.0 mL) under cooling and an aqueous solution of sodium sulfite (335 mg; 2.66 mmol in 15.0 mL water) was added under cooling so that the temperature of the mixture remained below 15° C. After 10 minutes the batch was extracted three times with ethyl acetate. The combined organic phases were washed with saturated aqueous sodium chloride solution, dried over magnesium sulfate and concentrated. The residue was purified by column chromatography on silica gel (gradient: hexane to ethyl acetate 100%) to yield the desired product 2,2,2-trifluoro-N-{[(2-{[5-fluoro-4-(4-fluoro-2-methoxyphenyl)pyridin-2-yl]amino}-6-methylpyridin-4-yl)methyl](methyl)-λ⁴-sulfanylidene}acetamide (1202 mg; 2.41 mmol; containing 5,5-dimethylhydantoin) and the side product N-{[(3-bromo-6-{[5-fluoro-4-(4-fluoro-2-methoxyphenyl)pyridin-2-yl]amino}-2-methylpyridin-4-yl)methyl](methyl)-λ⁴-sulfanylidene}-2,2,2-trifluoroacetamide (7 mg; 0.012 mmol).

To remove the 5,5-dimethylhydantoin 3.76 g of the product from 4 batches were purified by column chromatography on silica gel (gradient: dichloromethane to dichloromethane/methanol 95:5) to yield the desired product (3.39 g; 6.80 mmol).

Intermediate 4.5:

¹H-NMR (300 MHz, DMSO-d₆, 300 K): δ [ppm]=9.85 (s, 1H), 8.17 (d, 1H), 7.65-7.57 (m, 2H), 7.34 (dd, 1H), 7.09 (dd, 1H), 6.96-6.87 (m, 1H), 6.66 (s, 1H), 4.56-4.48 (m, 1H), 4.42-4.33 (m, 1H), 3.80 (s, 3H), 2.77 (s, 3H), 2.34 (s, 3H).

Intermediate 4.6

(¹H-NMR was Taken from a Different Batch)

¹H-NMR (300 MHz, DMSO-d₆, 300 K): δ [ppm]=10.02 (s, 1H), 8.18 (d, 1H), 7.83 (s, 1H), 7.52 (d, 1H), 7.38-7.31 (m, 1H), 7.13-7.06 (m, 1H), 6.96-6.87 (s, 1H), 4.67-4.55 (m, 2H), 3.80 (s, 3H), 2.92 (s, 3H), 2.51 (br. s., 3H).

Preparation of Intermediates 4.7 and 4.8

3.76 g of racemic 2,2,2-trifluoro-N-{[(2-{[5-fluoro-4-(4-fluoro-2-methoxyphenyl)pyridin-2-yl]amino}-6-methylpyridin-4-yl)methyl](methyl)-λ⁴-sulfanylidene}acetamide were separated by chiral HPLC:

| | |
|---|---|
| System: | Agilent: Prep 1200, 2xPrep Pump, DLA, MWD, Prep FC |
| Column: | Chiralpak IA 5 μm 250 × 30 mm Nr.: 010 |
| Solvent: | hexane/ethanol/diethylamine 50:50:0.1 (v/v/v) |
| Flow: | 45 mL/min |
| Temperature: | RT |
| Solution: | 3760 mg/30.4 mL DCM/MeOH |
| Injection: | 38 × 0.8 mL |
| Detection: | UV 280 nm |

| Fractions | retention time in min | purity in % | yield | Specific optical rotation |
|---|---|---|---|---|
| Intermediate 4.7 | 5.3-6.8 min | 95.5%; ee: 100% | 1520 mg (3.05 mmol) | $[\alpha]_D^{20}$ = +113.4° (1.00, DMSO) |
| Intermediate 4.8 | 7.2-10.5 min | 97.1%; ee: 98.7% | 1480 mg (2.97 mmol) | $[\alpha]_D^{20}$ = −112.1° (1.00, DMSO) |

Intermediate 4.7

(+)-2,2,2-Trifluoro-N-{[(2-{[5-fluoro-4-(4-fluoro-2-methoxyphenyl)pyridin-2-yl]amino}-6-methylpyridin-4-yl)methyl](methyl)-$\lambda^4$-sulfanylidene}acetamide

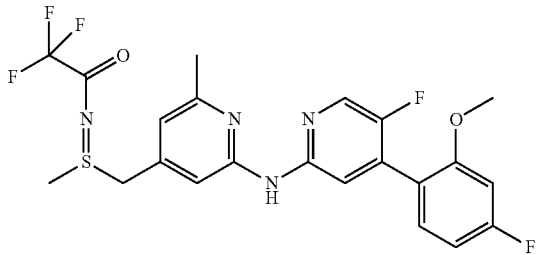

$^1$H-NMR (400 MHz, DMSO-d$_6$, 300 K): δ [ppm]=9.83 (s, 1H), 8.17 (d, 1H), 7.63-7.59 (m, 2H), 7.34 (dd, 1H), 7.09 (dd, 1H), 6.94-6.88 (m, 1H), 6.66 (s, 1H), 4.52 (d, 1H), 4.37 (d, 1H), 3.80 (s, 3H), 2.77 (s, 3H), 2.34 (s, 3H).

Intermediate 4.8

(−)-2,2,2-Trifluoro-N-{[(2-{[5-fluoro-4-(4-fluoro-2-methoxyphenyl)pyridin-2-yl]amino}-6-methylpyridin-4-yl)methyl](methyl)-$\lambda^4$-sulfanylidene}acetamide

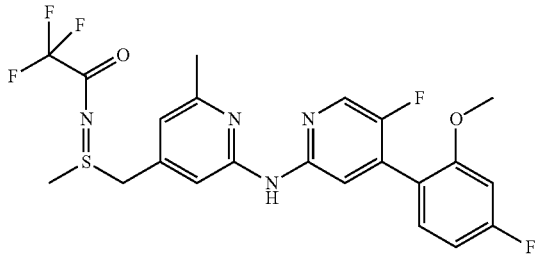 [SMILES: COc1cc(F)ccc1-c1cc(Nc2cc(CS(C)=NC(=O)C(F)(F)F)cc(C)n2)ncc1F]

$^1$H-NMR (400 MHz, DMSO-d$_6$, 300 K): δ [ppm]=9.83 (s, 1H), 8.17 (d, 1H), 7.63-7.59 (m, 2H), 7.34 (dd, 1H), 7.09 (dd, 1H), 6.94-6.88 (m, 1H), 6.66 (s, 1H), 4.52 (d, 1H), 4.37 (d, 1H), 3.80 (s, 3H), 2.77 (s, 3H), 2.34 (s, 3H).

Alternative Preparation of End Product (Example 4)

(rac)-5-Fluoro-4-(4-fluoro-2-methoxyphenyl)-N-{6-methyl-4-[(S-methylsulfonimidoyl)methyl]pyridin-2-yl}pyridin-2-amine

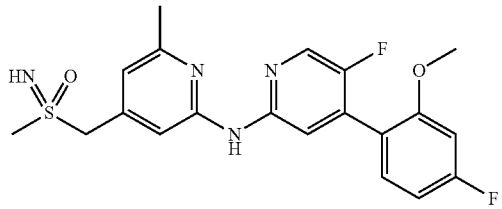 [SMILES: COc1cc(F)ccc1-c1cc(Nc2cc(CS(C)(=N)=O)cc(C)n2)ncc1F]

(rac)-2,2,2-Trifluoro-N-{[(2-{[5-fluoro-4-(4-fluoro-2-methoxyphenyl)pyridin-2-yl]amino}-6-methylpyridin-4-yl)methyl](methyl)-$\lambda^4$-sulfanylidene}acetamide (150 mg; 0.301 mmol) was dissolved in methanol (18.0 mL) and water (9.0 mL). At 0-5° C. the pH was adjusted to 9-10 with an aqueous potassium hydroxide solution (15%). At this temperature Oxone® (157.0 mg; 0.256 mmol) was added in several portions and the pH was held at 9-10. The mixture was stirred for 1 hour at 0-5° C. and the pH was held at 9-10.

The reaction mixture was adjusted with 2.0M hydrochloric acid to pH 6-7. Saturated aqueous sodium chloride solution was added and the reaction mixture was extracted three times with dichloromethane. The combined organic phases were washed with an aqueous sodium thiosulfate solution (10%), dried over magnesium sulfate and concentrated. The residue was purified by column chromatography on silica gel (gradient: dichloromethane to dichloromethane/ethanol 9:1) to afford the desired product (100 mg; 0.239 mmol).

$^1$H-NMR (300 MHz, DMSO-d$_6$, 300 K): δ [ppm]=9.76 (s, 1H), 8.18 (d, 1H), 7.67 (d, 1H), 7.57 (s, 1H), 7.38-7.30 (m, 1H), 7.13-7.06 (m, 1H), 6.96-6.87 (m, 1H), 6.77 (s, 1H), 4.37-4.25 (m, 2H), 3.80 (s, 3H), 3.71 (s, 1H), 2.87 (s, 3H), 2.35 (s, 3H).

Example 5

(rac)-5-Bromo-N-[5-fluoro-4-(4-fluoro-2-methoxyphenyl)pyridin-2-yl]-6-methyl-4-[(S-methylsulfonimidoyl)methyl]pyridin-2-amine

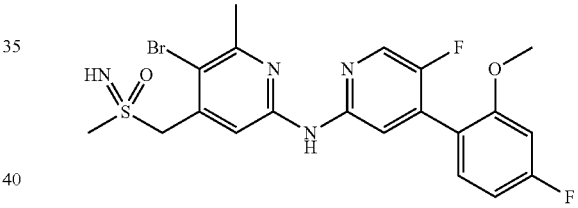

An aqueous solution of potassium hydroxide (25%) was added dropwise to a stirred solution of N-{[(3-bromo-6-{[5-fluoro-4-(4-fluoro-2-methoxyphenyl)pyridin-2-yl]amino}-2-methylpyridin-4-yl)methyl](methyl)-$\lambda^4$-sulfanylidene}-2,2,2-trifluoroacetamide (161 mg; 0.28 mmol, Intermediate 4.6) in methanol (15.0 mL) and water (5.0 mL) to adjust the pH to 10.5. Oxone® (146 mg; 0.24 mmol) was added and the mixture was stirred at room temperature for 4 hours. During this time, the pH was kept between 10-11, by dropwise addition of an aqueous solution of potassium hydroxide (25%), if necessary. After 4 hours, an additional portion of Oxone® (50 mg; 0.08 mmol) was added and the mixture was stirred at room temperature for additional 2.5 hours. The pH was kept between 10-11, by dropwise addition of an aqueous solution of potassium hydroxide (25%), if necessary. The mixture was filtered and the filter cake was washed with plenty of DCM/MeOH (2:1). The pH of the filtrate was adjusted to pH 6.5 using an aqueous solution of hydrogen chloride (15%), diluted with DCM and washed with an aqueous solution of sodium chloride. The organic layer was finally washed with an aqueous solution of sodium thiosulfate (10%). The organic phase was filtered using a Whatman filter and concentrated. The residue was purified by chromatography (DCM to DCM/ethanol 5%) to give the desired product (44 mg; 0.09 mmol).

$^1$H NMR (400 MHz, CDCl$_3$, 300K) δ=8.14 (m, 1H), 7.80 (s, 1H), 7.32 (m, 2H), 7.29 (m, 1H), 6.78 (m, 2H), 4.87 (d, 1H), 4.59 (d, 1H), 3.85 (s, 3H), 3.07 (s, 3H), 2.99 (br, 1H), 2.62 (s, 3H).

Example 6

(rac)-5-Fluoro-4-(4-fluoro-2-methoxyphenyl)-N-{6-methoxy-4-[(S-methylsulfonimidoyl)methyl]pyridin-2-yl}pyridin-2-amine

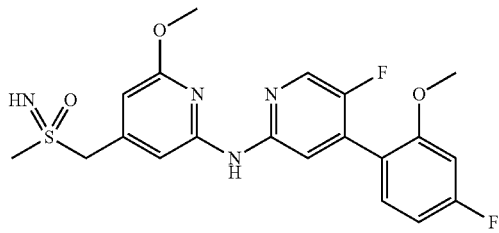 [SMILES: COc1cc(CS(C)(=N)=O)cc(Nc2cc(-c3ccc(F)cc3OC)c(F)cn2)n1]

Preparation of Intermediate 6.1:

2-Chloro-6-methoxy-4-[(methylsulfanyl)methyl]pyridine

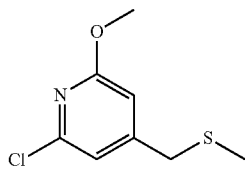

An aqueous solution of sodium methanethiolate (21%, 1.4 mL, 4.2 mmol; Aldrich Chemical Company Inc.) was added dropwise to a stirred solution of 4-(bromomethyl)-2-chloro-6-methoxypyridine (1000 mg; 4.2 mmol, ZereneX Molecular Limited) in acetone (50 mL) while cooling with a water bath at RT. The mixture was stirred at RT for 3 hours. The batch was diluted with ethyl acetate and an aqueous solution of sodium chloride. The mixture was extracted twice (2×) with ethyl acetate. The combined organic layers were filtered using a Whatman filter and concentrated. The residue was purified by column chromatography on silica gel (hexane to hexane/ethyl acetate 10%) to give the desired product (738 mg; 3.6 mmol).

$^1$H NMR (400 MHz, CDCl$_3$, 300K) δ=6.92 (s, 1H), 6.61 (s, 1H), 3.96 (s, 3H), 3.56 (s, 2H), 2.03 (s, 3H).

Preparation of Intermediate 6.2

5-Fluoro-4-(4-fluoro-2-methoxyphenyl)-N-{6-methoxy-4-[(methylsulfanyl)methyl]pyridin-2-yl}pyridin-2-amine

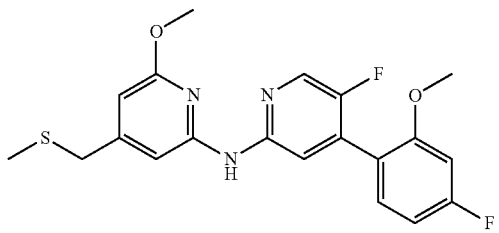 [SMILES: COc1cc(CSC)cc(Nc2cc(-c3ccc(F)cc3OC)c(F)cn2)n1]

A mixture of 5-fluoro-4-(4-fluoro-2-methoxyphenyl)pyridin-2-amine (1281 mg; 5.4 mmol, Intermediate 4.1), 2-chloro-6-methoxy-4-[(methylsulfanyl)methyl]pyridine (724 mg; 3.6 mmol), chloro(2-dicyclohexylphosphino-2',4',6'-tri-iso-propyl-1,1'-biphenyl)[2-(2-aminoethyl)phenyl] palladium(II) methyl-tert-butylether adduct (294 mg; 0.36 mmol; ABCR GmbH & CO. KG) and 2-(dicyclohexylphosphino)-2',4',6'-triisopropylbiphenyl (170 mg; 0.36 mmol; Aldrich Chemical Company Inc.) and potassium phosphate (3773 mg; 17.77 mmol) in toluene (84 ml) and NMP (10 mL) was stirred under an atmosphere of argon at 130° C. in a closed vessel for 4 hours. After cooling, the batch was diluted with DCM and washed with aqueous sodium chloride solution. The organic layer was filtered using a Whatman filter and concentrated. The residue was purified by column chromatography on silica gel (hexane to hexane/ethyl acetate 35%) to give the pure product (1212 mg; 3.00 mmol).

$^1$H NMR (400 MHz, CDCl$_3$, 300K) δ=8.15 (m, 1H), 7.91 (m, 1H), 7.29 (m, 1H), 7.21 (s, 1H), 6.77 (m, 3H), 6.28 (s, 1H), 3.87 (s, 3H), 3.85 (s, 3H), 3.58 (s, 2H), 2.06 (s, 3H).

Preparation of Intermediate 6.3

(rac)-2,2,2-Trifluoro-N-{[(2-{[5-fluoro-4-(4-fluoro-2-methoxyphenyl)pyridin-2-yl]amino}-6-methoxypyridin-4-yl)methyl](methyl)-λ$^4$-sulfanylidene}acetamide

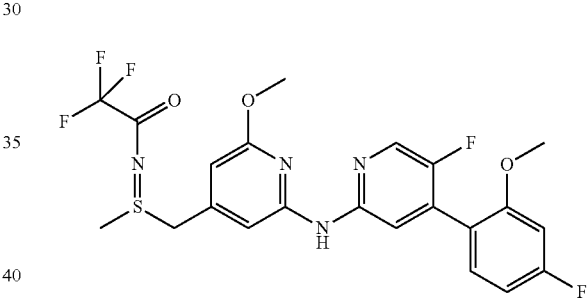

Under an atmosphere of argon, a solution of 2,2,2-trifluoroacetamide (252 mg; 2.23 mmol) in THF (2.0 mL) was added dropwise to a solution of sodium tert.-butoxide (143 mg; 1.49 mmol) in THF (2.0 mL), so that the temperature of the mixture remained below 10° C. Subsequently, a freshly prepared solution of 1,3-dibromo-5,5-dimethylhydantoin (255 mg; 0.89 mmol) in THF (2.0 mL) was added dropwise to the stirred mixture, so that the temperature of the mixture remained below 10° C. Then the mixture was stirred for 10 minutes at 10° C. Finally, a solution of 5-fluoro-4-(4-fluoro-2-methoxyphenyl)-N-{6-methoxy-4-[(methylsulfanyl)methyl]pyridin-2-yl}pyridin-2-amine (600 mg; 1.49 mmol) in THF (3.0 mL) was added dropwise to the stirred mixture, so that the temperature of the mixture remained below 10° C. The mixture was stirred for 3.5 hours at 10° C. The batch was diluted with toluene (8.0 mL) under cooling and an aqueous solution of sodium sulfite (187 mg; 1.49 mmol in 14.0 mL water) was added so that the temperature of the mixture remained below 15° C. The batch was extracted three times with ethyl acetate. The combined organic layers were washed with an aqueous solution of sodium chloride, filtered using a Whatman filter and concentrated. The residue was purified by column chromatography on silica gel (DCM to DCM/ethanol 5%) to give the desired product (37 mg; 0.07 mmol).

$^1$H NMR (400 MHz, CDCl$_3$, 300K) δ=8.18 (m, 1H), 7.56 (m, 1H), 7.29 (m, 2H), 7.12 (m, 1H), 6.78 (m, 2H), 6.25 (s, 1H), 4.52 (d, 1H), 4.07 (d, 1H), 3.89 (s, 3H), 3.85 (s, 3H), 2.70 (s, 3H).

Preparation of End Product:

An aqueous solution of potassium hydroxide (25%) was added dropwise to a stirred solution of 2,2,2-trifluoro-N-{[(2-{[5-fluoro-4-(4-fluoro-2-methoxyphenyl)pyridin-2-yl]amino}-6-methoxypyridin-4-yl)methyl](methyl)-λ$^4$-sulfanylidene}acetamide (32 mg; 0.06 mmol) in methanol (1.0 mL) and water (0.6 mL) to adjust the pH to 10.5. Oxone® (32 mg; 0.05 mmol) was added and the mixture was stirred at RT for 2.5 hours. During this time, the pH was kept between 10-11, by dropwise addition of an aqueous solution of potassium hydroxide (25%), if necessary. The mixture was filtered and the filter cake was washed with plenty of DCM. The filtrate was washed with an aqueous solution of sodium chloride, followed by an aqueous solution of sodium thiosulfate (10%). The organic layer was filtered using a Whatman filter and concentrated. The residue was purified by preparative HPLC to give the desired product (9 mg; 0.02 mmol).

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injection: | 1 × 2.5 mL |
| Detection: | DAD scan range 210-400 nm |
| | MS ESI+, ESI−, scan range 160-1000 m/z |

$^1$H NMR (400 MHz, CDCl$_3$, 300K) δ=8.16 (m, 1H), 7.78 (m, 1H), 7.26 (m, 2H), 7.00 (m, 1H), 6.77 (m, 2H), 6.36 (m, 1H), 4.30 (d, 1H), 4.19 (d, 1H), 3.88 (s, 3H), 3.85 (s, 3H), 3.01 (s, 3H), 2.79 (br, 1H).

Alternative Procedure for the Preparation of Example 6

(rac)-5-Fluoro-4-(4-fluoro-2-methoxyphenyl)-N-{6-methoxy-4-[(S-methylsulfonimidoyl)methyl]pyridin-2-yl}pyridin-2-amine

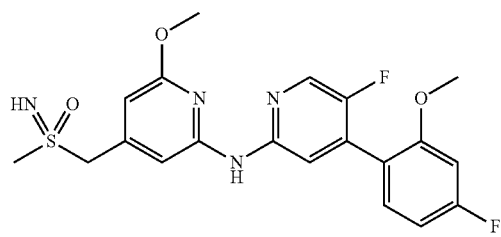 [SMILES: COc1cc(CS(C)(=N)=O)cc(Nc2cc(-c3ccc(F)cc3OC)c(F)cn2)n1]

A freshly prepared 1.5 M solution of sodium ethanolate in ethanol (1.5 mL; 2.25 mmol) was added under an atmosphere of argon to a solution of (rac)-ethyl{[(2-{[5-fluoro-4-(4-fluoro-2-methoxyphenyl)pyridin-2-yl]amino}-6-methoxypyridin-4-yl)methyl](methyl)oxido-λ$^6$-sulfanylidene}carbamate (290 mg; 0.57 mmol; Example 15) in ethanol (6.3 mL). The batch was stirred at 60° C. for 4 hours. After cooling the batch was diluted with an aqueous solution of sodium chloride and extracted three times with ethyl acetate. The combined organic layers were filtered using a Whatman filter and concentrated to give the desired product (257 mg; 0.0.59 mmol).

$^1$H NMR (400 MHz, CDCl$_3$, 300K) δ=8.16 (m, 1H), 7.78 (m, 1H), 7.26 (m, 2H), 7.00 (m, 1H), 6.77 (m, 2H), 6.36 (m, 1H), 4.30 (d, 1H), 4.19 (d, 1H), 3.88 (s, 3H), 3.85 (s, 3H), 3.01 (s, 3H), 2.79 (br, 1H).

Example 7

(rac)-N-{6-Chloro-4-[(S-methylsulfonimidoyl)methyl]pyridin-2-yl}-5-fluoro-4-(4-fluoro-2-methoxyphenyl)pyridin-2-amine

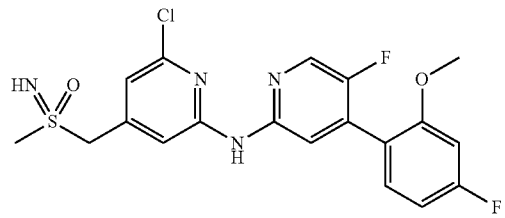

Preparation of Intermediate 7.1

2-Chloro-6-methoxy-4-[(methylsulfanyl)methyl]pyridine

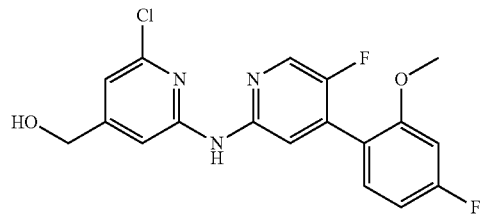 [SMILES: COc1cc(F)ccc1-c1cc(Nc2cc(CO)cc(Cl)n2)ncc1F]

A mixture of 5-fluoro-4-(4-fluoro-2-methoxyphenyl)pyridin-2-amine (2000 mg; 8.47 mmol, Intermediate 4.1), (2,6-dichloropyridin-4-yl)methanol (1507 mg; 8.47 mmol; ABCR GmbH & CO. KG), chloro(2-dicyclohexylphosphino-2',4',6'-tri-iso-propyl-1,1'-biphenyl)[2-(2-aminoethyl)phenyl]palladium(II) methyl-tert-butylether adduct (700 mg; 0.85 mmol; ABCR GmbH & CO. KG) and 2-(dicyclohexylphosphino)-2',4',6'-triisopropylbiphenyl (404 mg; 0.85 mmol; Aldrich Chemical Company Inc.) and potassium phosphate (8986 mg; 42.33 mmol) in toluene (40 ml) and NMP (4 mL) was stirred under an atmosphere of argon at 110° C. for 135 minutes. After cooling, the batch was diluted with ethyl acetate and washed with aqueous sodium chloride solution. The organic layer was filtered using a Whatman filter and concentrated. The residue was purified by column chromatography on silica gel (hexane to hexane/ethyl acetate 50%) to give the pure product (1350 mg; 3.57 mmol).

$^1$H NMR (400 MHz, d$_6$-DMSO, 300K) δ=10.06 (s, 1H), 8.25 (m, 1H), 7.71 (m, 1H), 7.56 (m, 1H), 7.35 (m, 1H), 7.10 (m, 1H), 6.93 (m, 1H), 6.85 (m, 1H), 5.47 (tr, 1H), 4.49 (d, 2H), 3.81 (s, 3H).

Preparation of Intermediate 7.2

N-{6-Chloro-4-[(methylsulfanyl)methyl]pyridin-2-yl}-5-fluoro-4-(4-fluoro-2-methoxyphenyl)pyridin-2-amine

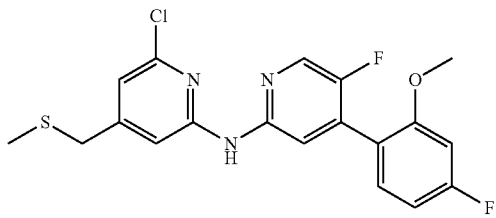

To a stirred solution of (2-chloro-6-{[5-fluoro-4-(4-fluoro-2-methoxyphenyl)pyridin-2-yl]amino}pyridin-4-yl)methanol (1.47 g; 3.89 mmol) in DMF (43 mL) at 0° C. was added dropwise thionyl chloride (0.71 mL; 9.73 mmol). The mixture was allowed to react at RT for 2 hours. Then, the mixture was concentrated to give crude N-[6-chloro-4-(chloromethyl)pyridin-2-yl]-5-fluoro-4-(4-fluoro-2-methoxyphenyl)pyridin-2-amine (2.85 g).

Crude N-[6-chloro-4-(chloromethyl)pyridin-2-yl]-5-fluoro-4-(4-fluoro-2-methoxyphenyl)pyridin-2-amine (2.85 g) was dissolved in acetone (87 mL) and an aqueous solution of sodium methanethiolate (21%, 5.2 mL, 15.58 mmol; Aldrich Chemical Company Inc.) was added dropwise under stirring. The mixture was stirred at RT for 6 hours. The mixture was diluted with an aqueous solution of sodium chloride and extracted twice with ethyl acetate. The combined organic layers were filtered using a Whatman filter and concentrated. The residue was purified by column chromatography on silica gel (hexane to hexane/ethyl acetate 20%) to give the desired product (1.24 g; 3.04 mmol).

$^1$H NMR (400 MHz, CDCl$_3$, 300K) δ=8.17 (s, 1H), 7.50 (m, 3H), 7.32 (m, 1H), 6.90 (s, 1H), 6.79 (m, 2H), 3.87 (s, 3H), 3.62 (s, 2H), 2.07 (s, 3H).

Preparation of Intermediate 7.3

(rac)-N-{[(2-chloro-6-{[5-fluoro-4-(4-fluoro-2-methoxyphenyl)pyridin-2-yl]amino}pyridin-4-yl)methyl](methyl)-λ$^4$-sulfanylidene}-2,2,2-trifluoroacetamide

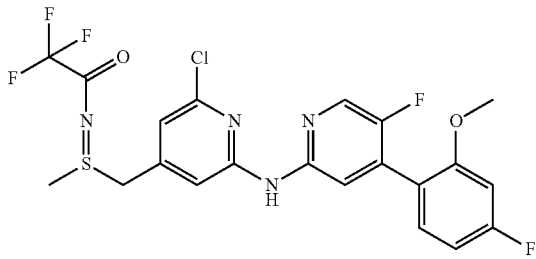 [SMILES: COc1cc(F)ccc1-c1cc(Nc2cc(CS(C)=NC(=O)C(F)(F)F)cc(Cl)n2)ncc1F]

Under an atmosphere of argon, a solution of 2,2,2-trifluoroacetamide (312 mg; 2.76 mmol) in THF (2.0 mL) was added dropwise to a solution of sodium tert.-butoxide (176 mg; 1.84 mmol) in THF (2.0 mL), so that the temperature of the mixture remained below 10° C. Subsequently, a freshly prepared solution of 1,3-dibromo-5,5-dimethylhydantoin (394 mg; 1.38 mmol) in THF (3.0 mL) was added dropwise to the stirred mixture, so that the temperature of the mixture remained below 10° C. Then the mixture was stirred for 10 minutes at 10° C. Finally, a solution of N-{6-chloro-4-[(methylsulfanyl)methyl]pyridin-2-yl}-5-fluoro-4-(4-fluoro-2-methoxyphenyl)pyridin-2-amine (750 mg; 1.84 mmol) in THF (3.0 mL) was added dropwise to the stirred mixture, so that the temperature of the mixture remained below 5° C. The mixture was stirred for 3 hours at 5° C. The batch was diluted with toluene (5.0 mL) under cooling and an aqueous solution of sodium sulfite (232 mg; 1.84 mmol in 5.0 mL water) was added so that the temperature of the mixture remained below 15° C. The batch was extracted three times with ethyl acetate. The combined organic layers were washed with an aqueous solution of sodium chloride, filtered using a Whatman filter and concentrated. The residue was purified by column chromatography on silica gel (hexane to hexane/ethyl acetate 85%) to give the desired product (363 mg; 0.70 mmol).

$^1$H NMR (400 MHz, CDCl$_3$, 300K) δ=8.18 (s, 1H), 8.12 (br, 1H), 7.84 (s, 1H), 7.37 (m, 1H), 7.31 (m, 1H), 6.80 (m, 3H), 4.46 (d, 1H), 4.24 (d, 1H), 3.87 (s, 3H), 2.75 (s, 3H).

Preparation of End Product:

An aqueous solution of potassium hydroxide (25%) was added dropwise to a stirred solution of N-{[(2-chloro-6-{[5-fluoro-4-(4-fluoro-2-methoxyphenyl)pyridin-2-yl]amino}pyridin-4-yl)methyl](methyl)-λ$^4$-sulfanylidene}-2,2,2-trifluoroacetamide (495 mg; 0.95 mmol) in methanol (15.0 mL) and water (6.7 mL) to adjust the pH to 10.5. Oxone® (498 mg; 0.81 mmol) was added and the mixture was stirred at RT for 90 minutes. During this time, the pH was kept between 10-11, by dropwise addition of an aqueous solution of potassium hydroxide (25%), if necessary. The mixture was filtered and the filter cake was washed with plenty of DCM and methanol. The pH of the filtrate was adjusted to 6-7 using an aqueous solution of hydrogen chloride (15%). The filtrate was washed with an aqueous solution of sodium chloride, followed by an aqueous solution of sodium thiosulfate (10%). The organic phase was filtered using a Whatman filter and concentrated. The residue was purified by chromatography (DCM to DCM/ethanol 50%) to give the desired product (118 mg; 0.27 mmol).

Example 8

(rac)-2-{S-[(2-{[5-Fluoro-4-(4-fluoro-2-methoxyphenyl)pyridin-2-yl]amino}pyridin-4-yl)methyl]sulfonimidoyl}ethanol

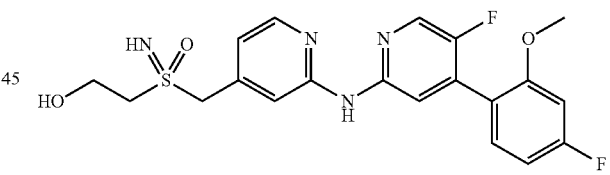

Preparation of Intermediate 8.1

2-{[(2-{[5-Fluoro-4-(4-fluoro-2-methoxyphenyl)pyridin-2-yl]amino}pyridin-4-yl)methyl]sulfanyl}ethanol

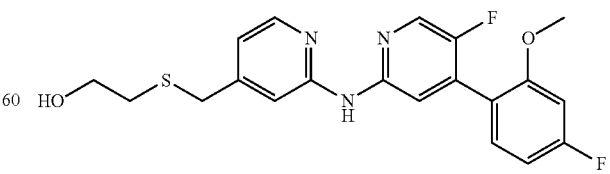

A batch containing 2-chloro-5-fluoro-4-(4-fluoro-2-methoxyphenyl)pyridine (1387 mg; 5.43 mmol, Intermediate 1.1), 2-{[(2-aminopyridin-4-yl)methyl]sulfanyl}ethanol (2000 mg; 10.85 mmol; UkrOrgSynthesis Ltd.), (9,9-dimethyl-9H-xanthene-4,5-diyl)bis(diphenylphosphane) (138 mg; 0.24 mmol) and cesium carbonate (2652 mg; 8.14 mmol) in dioxane (14.2 mL) was degassed using argon. Tris(dibenzylideneacetone)dipalladium(0) (75 mg; 0.08 mmol) was added under an atmosphere of argon and the batch was stirred for 23 hours in a closed vessel at 100° C. After cooling, the batch was diluted with DCM and washed with an aqueous solution of sodium chloride. The organic layer was filtered using a Whatman filter and concentrated. The residue was purified by column chromatography on silica gel (DCM to DCM/EtOH 5%) and finally crystallized from DCM/diisopropylether to give the desired product (1500 mg; 3.72 mmol).

$^1$H NMR (400 MHz, CDCl$_3$, 300K) δ=8.15 (m, 2H), 7.55 (m, 3H), 7.28 (m, 1H), 6.76 (m, 3H), 3.82 (s, 3H), 3.72 (tr, 2H), 3.68 (s, 2H), 2.66 (tr, 2H).

Preparation of Intermediate 8.2

N-(4-{[(2-{[tert-Butyl(dimethyl)silyl]oxy}ethyl)sulfanyl]methyl}pyridin-2-yl)-5-fluoro-4-(4-fluoro-2-methoxyphenyl)pyridin-2-amine

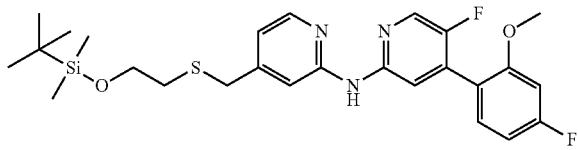 [SMILES: COc1cc(F)ccc1-c1cc(Nc2cc(CSCCO[Si](C)(C)C(C)(C)C)ccn2)ncc1F]

Tert-butyldimethylchlorosilane (556 mg; 3.69 mmol) was added to a stirred solution of 2-{[(2-{[5-fluoro-4-(4-fluoro-2-methoxyphenyl)pyridin-2-yl]amino}pyridin-4-yl)methyl]sulfanyl}ethanol (1490 mg; 3.69 mmol) and imidazole (254 mg; 3.73 mmol) in DCM (16 mL) at RT. The reaction mixture was stirred for 21 hours before additional imidazole (51 mg; 0.74 mmol) and tert-butyldimethylchlorosilane (111 mg; 0.74 mmol) were added. The reaction mixture was stirred for additional 30 hours at RT. The mixture was diluted with water and extracted three times with DCM. The combined organic layers were filtered using a Whatman filter and concentrated. The residue was purified by column chromatography on silica gel (DCM to DCM/EtOH 5%) to give the desired product (1358 mg; 2.62 mmol).

$^1$H NMR (400 MHz, CDCl$_3$, 300K) δ=8.17 (m, 2H), 7.64 (m 1H), 7.39 (m, 2H), 7.31 (m, 1H), 6.86 (m 1H), 6.78 (m, 2H), 3.85 (s, 3H), 3.79 (tr, 2H), 3.74 (s, 2H), 2.62 (tr, 2H), 0.92 (s, 9H), 0.08 (s, 6H).

Preparation of Intermediate 8.3

(rac)-N-{(2-{[tert-Butyl(dimethyl)silyl]oxy}ethyl)[(2-{[5-fluoro-4-(4-fluoro-2-methoxyphenyl)pyridin-2-yl]amino}pyridin-4-yl)methyl]-λ$^4$-sulfanylidene}-2,2,2-trifluoroacetamide

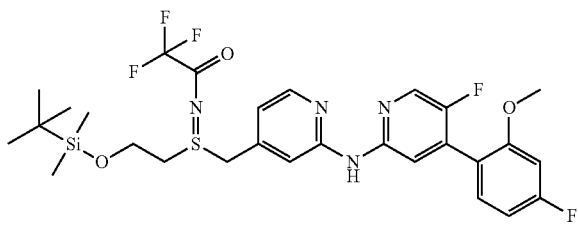 [SMILES: COc1cc(F)ccc1-c1cc(Nc2cc(CS(CCO[Si](C)(C)C(C)(C)C)=NC(=O)C(F)(F)F)ccn2)ncc1F]

Under an atmosphere of argon, a solution of 2,2,2-trifluoroacetamide (184 mg; 1.63 mmol) in THF (4.0 mL) was added dropwise to a solution of sodium tert.-butoxide (104 mg; 1.09 mmol) in THF (5.0 mL), so that the temperature of the mixture remained below 10° C. Subsequently, a freshly prepared solution of 1,3-dibromo-5,5-dimethylhydantoin (186 mg; 0.65 mmol) in THF (4.0 mL) was added dropwise to the stirred mixture, so that the temperature of the mixture remained below 10° C. Then the mixture was stirred for 10 minutes at 10° C. Finally, a solution of N-(4-{[(2-{[tert-butyl(dimethyl)silyl]oxy}ethyl)sulfanyl]methyl}pyridin-2-yl)-5-fluoro-4-(4-fluoro-2-methoxyphenyl)pyridin-2-amine (562 mg; 1.09 mmol) in THF (5.0 mL) was added dropwise to the stirred mixture, so that the temperature of the mixture remained below 5° C. The mixture was stirred for 5 hours at 5° C. The batch was diluted with toluene (5.0 mL) under cooling and an aqueous solution of sodium sulfite (137 mg; 1.09 mmol in 4.0 mL water) was added so that the temperature of the mixture remained below 15° C. The batch was extracted three times with ethyl acetate. The combined organic phases were washed with an aqueous solution of sodium chloride, filtered using a Whatman filter and concentrated. The residue was purified by chromatography (DCM to ECM/EtOH 5%) to give the desired product (293 mg; 0.47 mmol).

$^1$H NMR (400 MHz, CDCl$_3$, 300K) δ=8.27 (m, 1H), 8.17 (m, 1H), 7.72 (s, 1H), 7.38 (m, 2H), 7.30 (m, 1H), 6.79 (m, 3H), 4.50 (d, 1H), 4.41 (d, 1H), 4.09 (m, 2H), 3.85 (s, 3H), 3.18 (m, 2H), 0.92 (s, 9H), 0.13 (s, 3H), 0.12 (s, 3H).

Preparation of End Product:

An aqueous solution of potassium hydroxide (25%) was added dropwise to a stirred mixture of N-{(2-{[tert-butyl(dimethyl)silyl]oxy}ethyl)[(2-{[5-fluoro-4-(4-fluoro-2-methoxyphenyl)pyridin-2-yl]amino}pyridin-4-yl)methyl]-λ$^4$-sulfanylidene}-2,2,2-trifluoroacetamide (188 mg; 0.30 mmol) in methanol (45.0 mL) and water (10.0 mL) to adjust the pH to 10.5. Oxone® (156 mg; 0.25 mmol) was added and the mixture was stirred at RT for 17 hours. During this time, the pH was kept between 10-11, by dropwise addition of an aqueous solution of potassium hydroxide (25%), if necessary. The mixture was filtered and the filter cake was washed with plenty of DCM and methanol. The pH of the filtrate was adjusted to 6-7 using an aqueous solution of hydrogen chloride (15%). The filtrate was washed with an aqueous solution of sodium chloride, followed by an aqueous solution of sodium thiosulfate (10%). The organic layer was filtered using a Whatman filter and concentrated. The residue was purified by preparative HPLC to give the desired product (50 mg; 0.12 mmol).

| | |
|---|---|
| System: | Waters Autopurificationsystem: Pump 2545, Sample Manager 2767, CFO, DAD 2996, ELSD 2424, SQD 3001 |
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, d$_6$-DMSO, 300K) δ=9.89 (s, 1H), 8.18 (m, 2H), 7.71 (m, 1H), 7.66 (s, 1H), 7.34 (m, 1H), 7.09 (m, 1H), 6.91 (m, 1H), 6.80 (m, 1H), 5.30 (tr, 1H), 4.62 (d, 1H), 4.45 (d, 1H), 3.82 (m, 1H), 3.80 (s, 3H), 3.74 (m, 1H), 3.36 (m, 1H), 3.18 (m, 1H).

Example 9

(rac)-N-(4-{[S-(2-Aminoethyl)sulfonimidoyl]
methyl}pyridin-2-yl)-5-fluoro-4-(4-fluoro-2-
methoxyphenyl)pyridin-2-amine

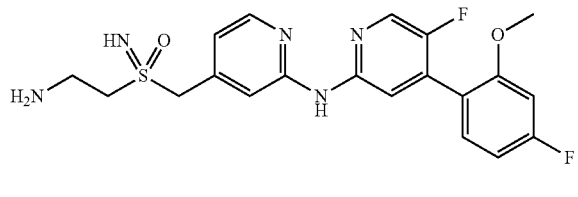 [SMILES: COc1cc(F)ccc1-c1cc(Nc2cc(CS(=N)(=O)CCN)ccn2)ncc1F]

Preparation of Intermediate 9.1 tert-Butyl (2-{S-[(2-{[5-fluoro-4-(4-fluoro-2-
methoxyphenyl)pyridin-2-yl]amino}pyridin-4-yl)
methyl]-N-(trifluoroacetyl)sulfinimidoyl}ethyl)car-
bamate

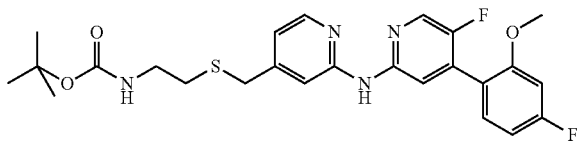 [SMILES: COc1cc(F)ccc1-c1cc(Nc2cc(CSCCNC(=O)OC(C)(C)C)ccn2)ncc1F]

Thionyl chloride (1.06 ml; 14.56 mmol) was added dropwise to a stirred solution of (2-{[5-fluoro-4-(4-fluoro-2-methoxyphenyl)pyridin-2-yl]amino}pyridin-4-yl)methanol (2000 mg; 5.83 mmol, Intermediate 1.3) in DMF (60 ml) at 0° C. The mixture was stirred for 2.5 hours at RT. The batch was diluted with aqueous sodium bicarbonate solution and aqueous sodium chloride solution and extracted five times with DCM. The combined organic layers were filtered using a Whatman filter and concentrated to give crude N-[4-(chloromethyl)pyridin-2-yl]-5-fluoro-4-(4-fluoro-2-methoxyphenyl)pyridin-2-amine (1730 mg), that was used without further purification in the next step.

The residue was dissolved in DMF (12.5 ml) and caesium carbonate (3116 mg; 9.56 mmol) and tert-butyl (2-sulfanylethyl)carbamate (874 mg; 4.78 mmol; Aldrich Chemical Company Inc.) were added under stirring. The mixture was stirred for 16 hours at RT before it was diluted with an aqueous solution of sodium chloride and extracted twice with ethyl acetate. The combined organic layers were filtered using a Whatman filter and concentrated. The residue was purified by column chromatography on silica gel (hexane to hexane/ethyl acetate 50%) to give the desired product (1260 mg; 2.51 mmol).

$^1$H NMR (400 MHz, CDCl$_3$, 300K) δ=8.18 (m, 2H), 7.59 (m, 1H), 7.49 (s, 1H), 7.38 (s, 1H), 7.31 (m, 1H), 6.84 (m, 1H), 6.75 (m, 2H), 4.93 (br, 1H), 3.85 (s, 3H), 3.69 (s, 2H), 3.32 (m, 2H), 2.61 (tr, 2H), 1.47 (s, 9H).

Preparation of Intermediate 9.2

(rac)-tert-Butyl (2-{S-[(2-{[5-fluoro-4-(4-fluoro-2-
methoxyphenyl)pyridin-2-yl]amino}pyridin-4-yl)
methyl]-N-(trifluoroacetyl)sulfinimidoyl}ethyl)car-
bamate

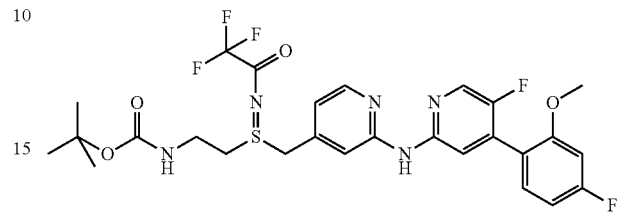

Under an atmosphere of argon, a solution of 2,2,2-trifluoroacetamide (202 mg; 1.79 mmol) in THF (0.6 mL) was added dropwise to a solution of sodium tert.-butoxide (115 mg; 1.19 mmol) in THF (1.0 mL), so that the temperature of the mixture remained below 10° C. Subsequently, a freshly prepared solution of 1,3-dibromo-5,5-dimethylhydantoin (222 mg; 0.78 mmol) in THF (1.0 mL) was added dropwise to the stirred mixture, so that the temperature of the mixture remained below 10° C. Then the mixture was stirred for 10 minutes at 10° C. Finally, a solution of tert-butyl (2-{[(2-{[5-fluoro-4-(4-fluoro-2-methoxyphenyl)pyridin-2-yl]amino}pyridin-4-yl)methyl]sulfanyl}ethyl)carbamate (600 mg; 1.19 mmol) in THF (1.0 mL) was added dropwise to the stirred mixture, so that the temperature of the mixture remained below 10° C. The mixture was stirred for 80 minutes at 10° C. The batch was diluted with toluene (3.0 mL) under cooling and an aqueous solution of sodium sulfite (150 mg; 1.19 mmol in 4.5 mL water) was added so that the temperature of the mixture remained below 15° C. The batch was extracted three times with ethyl acetate. The combined organic layers were washed with an aqueous solution of sodium chloride, filtered using a Whatman filter and concentrated. The residue was purified by column chromatography on silica gel (hexane to hexane/ethyl acetate 30%/70%) to give the desired product (579 mg; 0.94 mmol).

$^1$H NMR (400 MHz, CDCl$_3$, 300K) δ=8.48 (br, 1H), 8.25 (m, 1H), 8.18 (m, 1H), 7.77 (br, 1H), 7.48 (m, 1H), 7.30 (m, 1H), 6.80 (m, 3H), 5.77 (br, 1H), 4.40 (s, 2H), 3.85 (m, 4H), 3.71 (m, 1H), 3.45 (m, 1H), 3.32 (m, 1H), 1.45 (s, 9H).

Preparation of Intermediate 9.3

(rac)-tert-Butyl (2-{S-[(2-{[5-fluoro-4-(4-fluoro-2-
methoxyphenyl)pyridin-2-yl]amino}pyridin-4-yl)
methyl]sulfonimidoyl}ethyl)carbamate

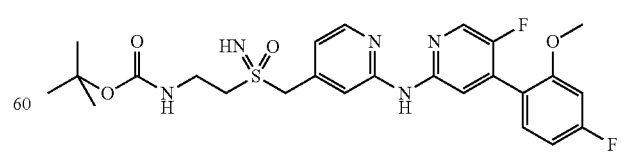

An aqueous solution of potassium hydroxide (25%) was added dropwise to a stirred mixture of tert-butyl (2-{S-[(2-{[5-fluoro-4-(4-fluoro-2-methoxyphenyl)pyridin-2-yl]amino}pyridin-4-yl)methyl]-N-(trifluoroacetyl)sulfinimidoyl}ethyl)carbamate (438 mg; 0.71 mmol) in methanol (14.0 mL) and water (5.0 mL) to adjust the pH to 10.5. Oxone® (373 mg; 0.61 mmol) was added and the mixture was stirred at RT for 2 hours. During this time, the pH was kept between 10-11, by dropwise addition of an aqueous solution of potassium hydroxide (25%), if necessary. The mixture was filtered and the filter cake was washed with plenty of DCM. The pH of the filtrate was adjusted to 6-7 using an aqueous solution of hydrogen chloride (15%). The filtrate was washed with an aqueous solution of sodium chloride, followed by an aqueous solution of sodium thiosulfate (10%). The organic phase was filtered using a Whatman filter and concentrated. The residue was purified by chromatography (hexane to ethyl acetate) to give the desired product (139 mg; 0.26 mmol).

$^1$H NMR (400 MHz, CDCl$_3$, 300K) δ=8.26 (m, 1H), 8.17 (s, 1H), 7.71 (s, 1H), 7.53 (m, 1H), 7.30 (m, 2H), 6.92 (m, 1H), 6.78 (m, 2H), 5.55 (br, 1H), 4.35 (d, 1H), 4.22 (d, 1H), 3.85 (s, 3H), 3.72 (m, 2H), 3.27 (m, 2H), 1.47 (s, 9H).

Preparation of End Product:

Trifluoroacetic acid (0.59 mL; 7.65 mmol) was added to a stirred solution of (rac)-tert-butyl (2-{S-[(2-{[5-fluoro-4-(4-fluoro-2-methoxyphenyl)pyridin-2-yl]amino}pyridin-4-yl)methyl]sulfonimidoyl}ethyl)carbamate (136 mg; 0.26 mmol) in DCM (10.7 mL) and the mixture was stirred overnight at RT. The batch was concentrated and the residue was purified by preparative HPLC to give the desired product (38 mg; 0.09 mmol).

| System: | Waters Autopurificationsystem: Pump 254, Sample Manager 2767, CFO, DAD 2996, SQD 3100 |
|---|---|
| Column: | XBrigde C18 5 μm 100 × 30 mm |
| Solvent: | A = H$_2$O + 0.2% Vol. NH$_3$ (32%) |
| | B = MeCN |
| Gradient: | 0.5 min Inlet (12% B, 25 mL/min); 0.5-5.5 min 25-50% B |
| Flow: | 70 mL/min |
| Temperature: | RT |
| Solution: | 182 mg/1.7 mL DMSO |
| Injection: | 4 × 0.425 mL |
| Detection: | DAD scan range 210-400 nm |
| | MS ESI+, ESI−, scan range 160-1000 m/z |

| Retention time in min | purity in % |
|---|---|
| 4.6-4.9 | 99 |

$^1$H NMR (400 MHz, CDCl$_3$, 300K) δ=8.24 (m, 1H), 8.13 (m, 1H), 7.67 (s, 1H), 7.46 (m, 1H), 7.38 (s, 1H), 7.28 (m, 1H), 6.91 (m, 1H), 6.75 (m, 2H), 4.40 (d, 1H), 4.28 (d, 1H), 3.83 (s, 3H), 3.32 (m, 2H), 3.17 (m, 2H).

Example 10

{[(2-{[5-Fluoro-4-(4-fluoro-2-methoxyphenyl)pyridin-2-yl]amino}pyridin-4-yl)methyl](methyl)oxido-λ$^6$-sulfanylidene}cyanamide

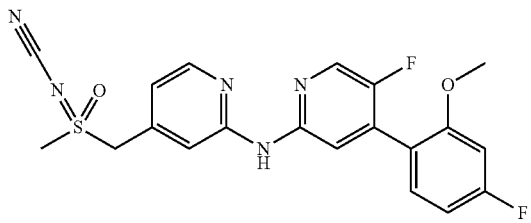 [SMILES: COc1cc(F)ccc1-c1cc(Nc2cc(CS(C)(=O)=NC#N)ccn2)ncc1F]

Cyanogen bromide (39 mg; 0.37 mmol) was added to a stirred solution of 5-fluoro-4-(4-fluoro-2-methoxyphenyl)-N-{4-[(S-methylsulfonimidoyl)methyl]pyridin-2-yl}pyridin-2-amine (75 mg; 0.19 mmol; example 3; enantiomer 2) and 4-dimethylaminopyridine in DCM (1.0 mL) at RT. The mixture was stirred for 24 hours at RT before it was concentrated under reduced pressure. The residue was purified by preparative HPLC to give the desired product (36 mg; 0.08 mmol).

| System: | Waters Autopurificationsystem: Pump 2545, Sample Manager 2767, CFO, DAD 2996, ELSD 2424, SQD 3001 |
|---|---|
| Column: | XBrigde C18 5 μm 100 × 30 mm |
| Solvent: | A = H$_2$O + 0.1% HCOOH |
| | B = MeCN |
| Gradient: | 0-1 min 1% B, 1-8 min 1-99% B, 8-10 min 99% B |
| Flow: | 50 mL/min |
| Temperature: | RT |
| Solution: | Max. 250 mg/max. 2.5 mL DMSO or DMF |
| Injektion: | 1 × 2.5 mL |
| Detection: | DAD scan range 210-400 nm |
| | MS ESI+, ESI−, scan range 160-1000 m/z |

$^1$H NMR (400 MHz, d$_6$-DMSO, 300K) δ=9.98 (s, 1H), 8.22 (m, 2H), 7.74 (m, 2H), 7.34 (m, 1H), 7.09 (m, 1H), 6.92 (m, 2H), 5.03 (m, 2H), 3.79 (s, 3H), 3.45 (s, 3H).

Example 11

(rac)-Ethyl{[(2-{[5-fluoro-4-(4-fluoro-2-methoxyphenyl)pyridin-2-yl]amino}pyridin-4-yl)methyl](methyl)oxido-λ$^6$-sulfanylidene}carbamate

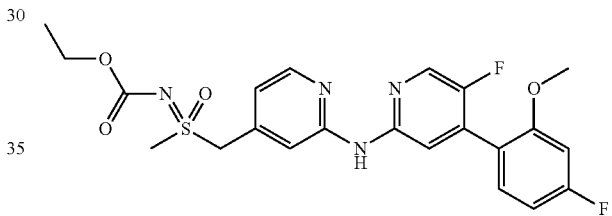

Ethyl chloroformate (26 mg; 0.24 mmol) was added dropwise to a stirred solution of (rac)-5-fluoro-4-(4-fluoro-2-methoxyphenyl)-N-{4-[(S-methylsulfonimidoyl)methyl]pyridin-2-yl}pyridin-2-amine (75 mg; 0.19 mmol; Example 1) in pyridine (2.0 mL) at 0° C. The ice bath was removed and the mixture was stirred for 5 hours at RT before it was concentrated under reduced pressure. The residue was dissolved in ethyl acetate and washed with an aqueous solution of sodium chloride. The organic layer was filtered using a Whatman filter and concentrated. The residue was purified by preparative HPLC to give the desired product (24 mg; 0.05 mmol).

| System: | Waters Autopurificationsystem: Pump 254, Sample Manager 2767, CFO, DAD 2996, ELSD 2424, SQD 3100 |
|---|---|
| Column: | XBrigde C18 5 μm 100 × 30 mm |
| Solvent: | A = H$_2$O + 0.2% Vol. NH$_3$ (32%) |
| | B = MeCN |
| Gradient: | 0-8 min 30-90% B |
| Flow: | 70 mL/min |
| Temperature: | RT |
| Solution: | 59.0 mg/1.5 mL DMSO |
| Injection: | 3 × 0.5 mL |
| Detection: | DAD scan range 210-400 nm |
| | MS ESI+, ESI−, scan range 160-1000 m/z |

| Retention time in min | purity in % |
|---|---|
| 4.6-5.0 | >99 |

¹H NMR (400 MHz, d₆-DMSO, 300K) δ=9.90 (s, 1H), 8.20 (m, 2H), 7.73 (m, 1H), 7.68 (s, 1H), 7.34 (m, 1H), 7.09 (m, 1H), 6.91 (m, 2H), 4.85 (m, 2H), 3.98 (q, 2H), 3.79 (s, 3H), 3.25 (s, 3H), 1.13 (tr, 3H).

Example 12

(rac)-1-Ethyl-3-{[(2-{[5-fluoro-4-(4-fluoro-2-methoxyphenyl)pyridin-2-yl]amino}pyridin-4-yl)methyl](methyl)oxido-λ⁶-sulfanylidene}urea

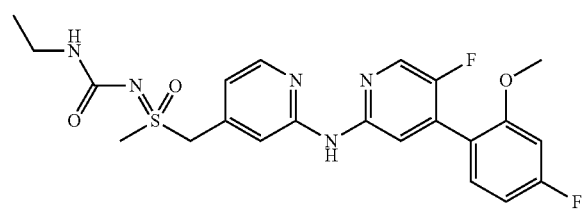

Ethyl isocyanate (13 mg; 0.19 mmol) was added to a stirred solution of (rac)-5-fluoro-4-(4-fluoro-2-methoxyphenyl)-N-{4-[(S-methylsulfonimidoyl)methyl]pyridin-2-yl}pyridin-2-amine (75 mg; 0.19 mmol; Example 1) and triethylamine (19 mg; 0.19 mmol) in DMF (2.0 mL) at RT. The mixture was stirred for 7 hours at RT before it was diluted with an aqueous solution of sodium chloride and extracted twice with ethyl acetate. The combined organic layers were filtered using a Whatman filter and concentrated. The residue was purified by preparative HPLC to give the desired product (24 mg; 0.05 mmol).

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = H₂O + 0.2% Vol. NH₃ (32%) |
|  | B = MeOH |
| Gradient: | 0-5.5 min 54-59% B |
| Flow: | 70 mL/min |
| Temperature: | RT |
| Solution: | 78 mg/2 mL DMSO/MeOH 1:1 |
| Injection: | 2 × 1 mL |
| Detection: | DAD scan range 210-400 nm |
|  | MS ESI+, ESI−, scan range 160-1000 m/z |

| Retention time in min | purity in % |
|---|---|
| 3.97-4.75 | 97 |

¹H NMR (400 MHz, d₆-DMSO, 300K) δ=9.83 (s, 1H), 8.19 (m, 2H), 7.72 (m, 1H), 7.67 (s, 1H), 7.33 (m, 1H), 7.09 (m, 1H), 6.90 (m, 2H), 6.76 (tr, 1H), 4.81 (m, 2H), 3.79 (s, 3H), 3.10 (s, 3H), 2.97 (m, 2H), 0.96 (tr, 3H).

Example 13

(rac)-N-{[(2-{[5-Fluoro-4-(4-fluoro-2-methoxyphenyl)pyridin-2-yl]amino}pyridin-4-yl)methyl](methyl)oxido-λ⁶-sulfanylidene}acetamide

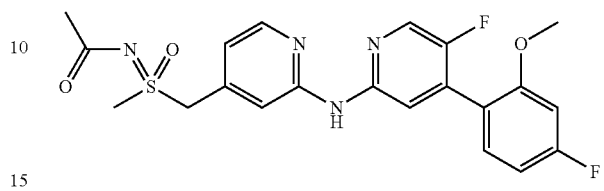

Acetyl chloride (16 mg; 0.20 mmol) was added dropwise to a stirred solution of (rac)-5-fluoro-4-(4-fluoro-2-methoxyphenyl)-N-{4-[(S-methylsulfonimidoyl)methyl]pyridin-2-yl}pyridin-2-amine (75 mg; 0.19 mmol; Example 1) and triethylamine (19 mg; 0.19 mmol) in DCM (2.0 mL) at 0° C. The ice bath was removed and the mixture was stirred for 16 hours at RT before it was diluted with water and extracted twice with ethyl acetate. The combined organic layers were filtered using a Whatman filter and concentrated. The residue was purified by preparative HPLC to give the desired product (8 mg; 0.02 mmol).

| System: | Waters Autopurificationsystem: Pump 254, Sample Manager 2767, CFO, DAD 2996, ELSD 2424, SQD 3100 |
|---|---|
| Column: | XBrigde C18 5 µm 100 × 30 mm |
| Solvent: | A = H₂O + 0.1% Vol. HCOOH (99%) |
|  | B = MeCN |
| Gradient: | 0-8 min 25-45% B |
| Flow: | 70 mL/min |
| Temperature: | RT |
| Solution: | 68.0 mg/1.5 mL DMSO |
| Injection: | 6 × 0.25 mL |
| Detection: | DAD scan range 210-400 nm |
|  | MS ESI+, ESI−, scan range 160-1000 m/z |

| Retention time in min | purity in % |
|---|---|
| 3.10-4.50 | >99 |

¹H NMR (400 MHz, d₆-DMSO, 300K) δ=9.90 (s, 1H), 8.20 (m, 2H), 7.73 (m, 1H), 7.68 (s, 1H), 7.34 (m, 1H), 7.09 (m, 1H), 6.90 (m, 2H), 4.84 (m, 2H), 3.79 (s, 3H), 3.21 (s, 3H), 1.93 (s, 3H).

Example 14

5-Fluoro-4-(4-fluoro-2-methoxyphenyl)-N-{4-[(S-methylsulfonimidoyl)methyl]pyridin-2-yl}pyridin-2-amine hydrochloride; enantiomer 2

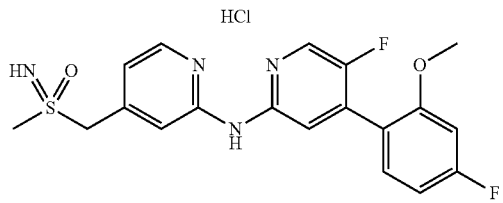 [SMILES: Cl ; COc1cc(F)ccc1-c1cc(Nc2cc(CS(C)(=N)=O)ccn2)ncc1F]

A solution of hydrogen chloride in dioxane (4N, 0.03 mL; 0.12 mmol) was added to a stirred solution of example 3 (50 mg; 0.12 mmol) in MeCN (6.0 mL) and the batch was stirred for 1 hour at RT. The batch was concentrated to give the desired product (50 mg; 0.11 mmol).

¹H NMR (500 MHz, d₆-DMSO, 300K) δ=8.34 (m, 2H), 7.68 (s, 1H), 7.55 (m, 1H), 7.39 (m, 1H), 7.21 (m, 1H), 7.14 (m, 1H), 6.95 (m, 1H), 5.15 (m, 2H), 3.82 (s, 3H), 3.47 (s, 3H).

Example 15

(rac)-Ethyl{[(2-{[5-fluoro-4-(4-fluoro-2-methoxyphenyl)pyridin-2-yl]amino}-6-methoxypyridin-4-yl)methyl](methyl)oxido-λ⁶-sulfanylidene}carbamate

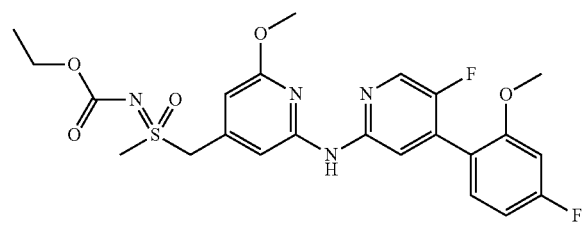 [SMILES: CCOC(=O)N=S(C)(=O)Cc1cc(Nc2cc(-c3ccc(F)cc3OC)c(F)cn2)nc(OC)c1]

Preparation of Intermediate 15.1

2-Chloro-6-methoxy-4-[(methylsulfanyl)methyl]pyridine

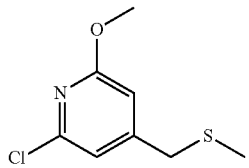

An aqueous solution of sodium methanethiolate (21%, 7.06 mL, 21.1 mmol) was added dropwise to a stirred solution of 4-(bromomethyl)-2-chloro-6-methoxypyridine (5.00 g; 21.4 mmol) in acetone (250 mL) while cooling with a water bath at RT. The mixture was stirred at RT for 150 minutes. EtOAc was added and the layers were separated. The organic layers were washed with saturated aqueous sodium chloride solution, filtered over a Whatman filter and concentrated. The residue was purified by column chromatography on silica gel (gradient: hexane to hexane/EtOAc 9:1) to give the desired product (4.06 g, 19.9 mmol).

¹H-NMR (300 MHz, CDCl₃, 300 K): δ [ppm]=6.92 (s, 1H), 6.61 (s, 1H), 3.96 (s, 3H), 3.56 (s, 2H), 2.03 (s, 3H).

Preparation of Intermediate 15.2

(rac)-2-Chloro-6-methoxy-4-[(methylsulfinyl)methyl]pyridine

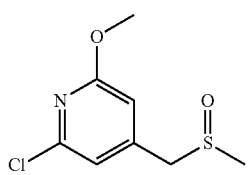

Iron(III)chloride (12 mg; 0.07 mmol) was added to a solution of 2-chloro-6-methoxy-4-[(methylsulfanyl)methyl]pyridine (500 mg; 2.46 mmol) in acetonitrile (6.0 mL) and the batch was stirred at 0° C. for 10 minutes. Periodic acid (599 mg; 2.63 mmol) was added in one portion and the mixture was stirred at 0° C. for 60 minutes before it was added to a stirred solution of sodium thiosulfate pentahydrate (3.41 g; 13.75 mmol) in ice water (71 mL). The batch was saturated with solid sodium chloride and extracted with ethyl acetate and DCM. The combined organic layers were filtered using a Whatman filter and concentrated to give the desired product (533 mg; 2.43 mmol).

¹H NMR (400 MHz, d₆-DMSO, 300K) δ=7.03 (s, 1H), 6.77 (s, 1H), 4.15 (d, 1H), 3.93 (d, 1H), 3.85 (s, 3H), 3.30 (s, 3H).

Preparation of Intermediate 15.3

(rac)-2-Chloro-6-methoxy-4-[(S-methylsulfonimidoyl)methyl]pyridine

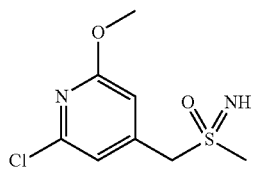

To a suspension of (rac)-2-chloro-6-methoxy-4-[(methylsulfinyl)methyl]pyridine (4.30 g; 19.57 mmol), trifluoroacetamide (4.43 g; 39.15 mmol), magnesium oxide (3.16 g; 78.30 mmol) and rhodium(II)-acetate dimer (0.22 g; 0.49 mmol) in DCM (146 mL) was added iodobenzene diacetate (9.46 g; 29.36 mmol) at room temperature. The mixture was stirred for 18 hours at room temperature. The suspension was filtered through a pad of celite and the filtrate was concentrated under reduced pressure. The residue was dissolved in MeOH (1694 mL) and potassium carbonate (5.41 g; 39.15 mmol) was added. The mixture was stirred for 90 minutes before it was concentrated under reduced pressure to circa 150 mL. The batch was diluted with plenty of THF/EE (1:1) and washed with an aqueous solution of sodium chloride. The organic layer was filtered using a Whatman filter and concentrated. The residue was re-dissolved in EtOAc/MeOH (1:1), filtered and concentrated. The residue was purified by column chromatography on silica gel (hexane/ethyl acetate 50% to pure ethyl acetate) to give the desired product (2.715 g; 11.55 mmol).

¹H NMR (400 MHz, d₆-DMSO, 300K) δ=7.15 (m, 1H), 6.90 (m, 1H), 4.45 (d, 1H), 4.35 (d, 1H), 3.89 (s, 1H), 3.85 (s, 3H), 2.61 (s, 3H).

Preparation of Intermediate 15.4

(rac)-Ethyl{[(2-chloro-6-methoxypyridin-4-yl)methyl](methyl)oxido-λ⁶-sulfanylidene}carbamate

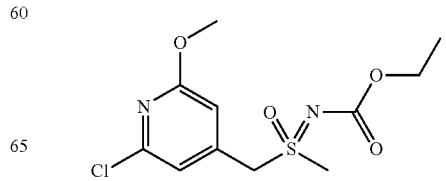

Ethyl chloroformate (0.265 mL; 2.77 mmol) was added dropwise to a stirred solution of (rac)-2-chloro-6-methoxy-4-[(S-methylsulfonimidoyl)methyl]pyridine (500 mg; 2.13 mmol) in pyridine (10.0 mL) at 0° C. The ice bath was removed and the mixture was stirred at RT overnight before it was concentrated under reduced pressure. The residue was dissolved in ethyl acetate and washed with an aqueous solution of sodium chloride. The organic layer was filtered using a Whatman filter and concentrated to give the crude product (660 mg), that was used without further purification.

$^1$H NMR (400 MHz, CDCl$_3$, 300K) δ=7.00 (m, 1H), 6.74 (m, 1H), 4.71 (d, 1H), 4.63 (d, 1H), 4.20 (q, 2H), 3.96 (s, 3H), 3.08 (s, 3H), 1.34 (tr, 3H).

Preparation of End Product:

A mixture of 5-fluoro-4-(4-fluoro-2-methoxyphenyl)pyridin-2-amine (381 mg; 1.61 mmol), (rac)-ethyl{[(2-chloro-6-methoxypyridin-4-yl)methyl](methyl)oxido-λ$^6$-sulfanylidene}carbamate (330 mg; 1.08 mmol), chloro(2-dicyclohexylphosphino-2',4',6'-tri-iso-propyl-1,1'-biphenyl)[2-(2-aminoethyl)phenyl]palladium(II) methyl-tert-butylether adduct (89 mg; 0.11 mmol; ABCR GmbH & CO. KG) and 2-(dicyclohexylphosphino)-2',4',6'-triisopropylbiphenyl (51 mg; 0.11 mmol; Aldrich Chemical Company Inc.) and potassium phosphate (1142 mg; 5.38 mmol) in toluene (25 ml) and NMP (3 mL) was stirred under an atmosphere of argon at 130° C. for 2 hours. After cooling, the batch was diluted with ethyl acetate/THF (1:1) and washed with aqueous sodium chloride solution. The organic layer was filtered using a Whatman filter and concentrated. The residue was purified by column chromatography on silica gel (hexane to hexane/ethyl acetate 80%) to give the pure product (292 mg; 0.57 mmol).

$^1$H NMR (400 MHz, d$_6$-DMSO, 300K) δ=8.17 (m, 1H), 7.66 (m, 1H), 7.29 (m, 1H), 7.25 (m, 1H), 7.09 (s, 1H), 6.77 (m, 2H), 6.35 (m, 1H), 4.68 (m, 2H), 4.20 (q, 2H), 3.89 (s, 3H), 3.85 (s, 3H), 3.09 (s, 3H), 1.33 (tr, 3H).

Example 16

5-Fluoro-4-(4-fluoro-2-methoxyphenyl)-N-{4-[(S-methylsulfonimidoyl)methyl]pyridin-2-yl}pyridin-2-amine hydrochloride; enantiomer 1

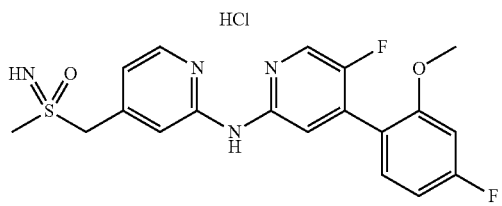 [SMILES: Cl ; COc1cc(F)ccc1-c1cc(Nc2cc(CS(C)(=N)=O)ccn2)ncc1F]

A solution of hydrogen chloride in dioxane (4N, 0.06 mL; 0.25 mmol) was added to a stirred solution of example 2 (100 mg; 0.25 mmol) in MeCN (12.0 mL) at RT. The batch was treated with ultrasound for 5 minutes and then was concentrated to give the desired product (112 mg; 0.25 mmol).

$^1$H NMR (500 MHz, d$_6$-DMSO, 300K) δ=8.34 (m, 2H), 7.68 (s, 1H), 7.55 (m, 1H), 7.39 (m, 1H), 7.21 (m, 1H), 7.14 (m, 1H), 6.95 (m, 1H), 5.15 (m, 2H), 3.82 (s, 3H), 3.47 (s, 3H).

Example 17

(rac)-5-Fluoro-4-(4-fluoro-2-methoxyphenyl)-N-{6-fluoro-4-[(S-methylsulfonimidoyl)methyl]pyridin-2-yl}pyridin-2-amine

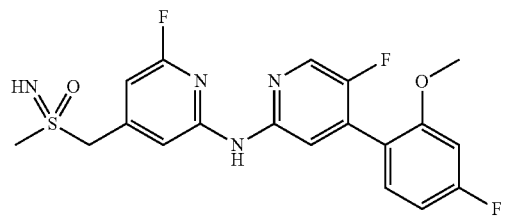

Example 18

(rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)oxido-λ$^6$-sulfanylidene}acetamide

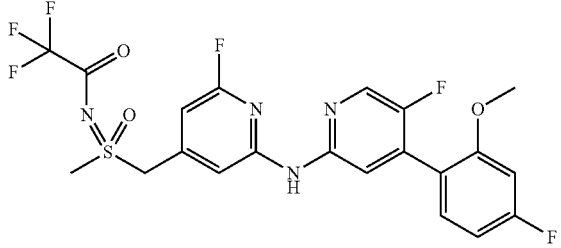 [SMILES: COc1cc(F)ccc1-c1cc(Nc2cc(CS(C)(=O)=NC(=O)C(F)(F)F)cc(F)n2)ncc1F]

Preparation of Intermediate 17.1

(2,6-Difluoropyridin-4-yl)methanol

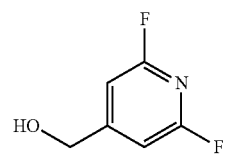

To a stirred solution of 2,6-difluoropyridine-4-carboxylic acid (5.32 g; 32.8 mmol; Matrix Scientific, CAS #88912-23-6) in THF (85 mL) at 0° C. was added a 1M solution of borane-tetrahydrofuran complex in THF (13.2 mL; 131.2 mmol). The mixture was allowed to react at RT overnight. Then, MeOH (15.9 mL) was cautiously added to the stirred mixture while cooling with an ice bath. The batch was diluted with ethyl acetate and washed with aqueous sodium hydroxide solution (1N) and saturated aqueous sodium chloride solution. The organic layer was filtered using a Whatman filter and concentrated to yield the title compound (4.85 g), which was used without further purification.

$^1$H-NMR (400 MHz, DMSO-d$_6$): δ [ppm]=7.06 (s, 2H), 5.68 (t, 1H), 4.62 (d, 2H).

Preparation of Intermediate 17.2

(2-Amino-6-fluoropyridin-4-yl)methanol

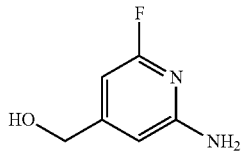

A mixture of (2,6-difluoropyridin-4-yl)methanol (330 mg; 2.27 mmol) and 33% w/w aqueous solution of ammonia (19.8 ml) was placed into a microwave tube. The mixture was allowed to react at 110° C. for 6 hours in the sealed tube under microwave irradiation. Then, the mixture was diluted with water and extracted with ethyl acetate. The combined organic layers were washed with saturated aqueous sodium chloride solution and dried over sodium sulfate. After evaporation the residue was purified by column chromatography on silica gel (dichloromethane/methanol) to yield the title compound (209 mg, 1.41 mmol).

$^1$H-NMR (400 MHz, DMSO-$d_6$): δ [ppm]=6.28 (dd, 1H), 6.22 (s, 2H), 5.99 (s, 1H), 5.28 (t, 1H), 4.37 (d, 2H).

Preparation of Intermediate 17.3

4-(Chloromethyl)-6-fluoropyridin-2-amine

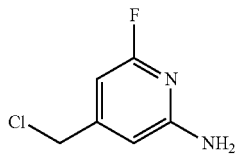

To a stirred solution of (2-amino-6-fluoropyridin-4-yl)methanol (194 mg; 1.36 mmol,) in DCM (6.6 ml) and NMP (0.44 ml) at 0° C. was added dropwise thionyl chloride (0.25 mL; 3.41 mmol). The mixture was allowed to react at room temperature overnight. The batch was diluted with aqueous sodium bicarbonate solution and aqueous sodium chloride solution and extracted three times with DCM. The combined organic layers were filtered, dried over sodium sulfate, and concentrated. The crude material was purified by column chromatography on silica gel (dichloromethane/methanol) to yield the desired product (161 mg; 0.94 mmol).

$^1$H-NMR (400 MHz, DMSO-$d_6$): δ [ppm]=6.45 (s, 1H), 6.34 (d, 1H), 6.13 (s, 1H), 4.61 (s, 2H).

Preparation of Intermediate 17.4

6-Fluoro-4-[(methylsulfanyl)methyl]pyridin-2-amine

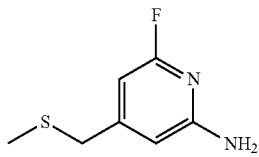

Sodium methanethiolate (99 mg; 1.34 mmol) was added to a stirred solution of 4-(chloromethyl)-6-fluoropyridin-2-amine (110 mg; 0.67 mmol) in ethanol (5.5 mL) at 0° C. The cold bath was removed and the batch was stirred at room temperature for 3 hours. The batch was diluted with saturated aqueous sodium chloride solution and extracted twice with ethyl acetate. The combined organic layers were washed with water, dried (sodium sulfate), filtered and concentrated to give the desired product (117 mg).

$^1$H-NMR (400 MHz, DMSO-$d_6$): δ [ppm]=6.29 (s, 2H), 6.24 (d, 1H), 6.04 (s, 1H), 3.54 (s, 2H), 1.97 (s, 3H).

Preparation of Intermediate 17.5

5-Fluoro-4-(4-fluoro-2-methoxyphenyl)-N-{6-fluoro-4-[(methylsulfanyl)methyl]pyridin-2-yl}pyridin-2-amine

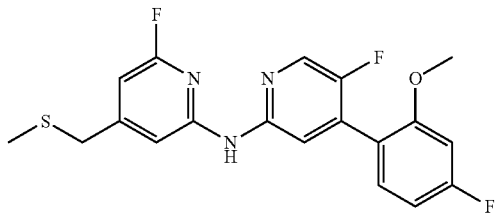 [SMILES: COc1cc(F)ccc1-c1cc(Nc2cc(CSC)cc(F)n2)ncc1F]

A mixture of 6-fluoro-4-[(methylsulfanyl)methyl]pyridin-2-amine (95 mg; 0.57 mmol), 2-chloro-5-fluoro-4-(4-fluoro-2-methoxyphenyl)pyridine (217 mg; 0.8 mmol; Intermediate 1.1), chloro(2-dicyclohexylphosphino-2',4',6'-tri-isopropyl-1,1'-biphenyl)[2-(2-aminoethyl)phenyl]palladium(II) methyl-tert-butylether adduct (44 mg; 0.054 mmol; ABCR GmbH & Co. KG) and 2-(dicyclohexylphosphino)-2',4',6'-triisopropylbiphenyl (25.6 mg; 0.054 mmol; Aldrich Chemical Company Inc.) and potassium phosphate (570 mg; 2.68 mmol) in toluene (12.1 ml) and NMP (0.94 mL) was stirred under an atmosphere of argon at 130° C. for 3 hours. After cooling, the batch was diluted with ethyl acetate and washed with aqueous sodium chloride solution. The organic layer was filtered using a Whatman filter and concentrated. The residue was purified by column chromatography on silica gel (hexane/ethyl acetate) to yield the title compound (174 mg; 0.44 mmol).

$^1$H-NMR (400 MHz, DMSO-$d_6$): δ [ppm]=10.02 (s, 1H), 8.27 (d, 1H), 7.60-7.55 (m, 2H), 7.36 (dd, 1H), 7.11 (dd, 1H), 6.93 (trd, 1H), 6.51 (s, 1H), 3.81 (s, 3H), 3.70 (s, 2H), 2.02 (s, 3H).

Preparation of Intermediate 17.6

(rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)-$\lambda^4$-sulfanylidene}acetamide

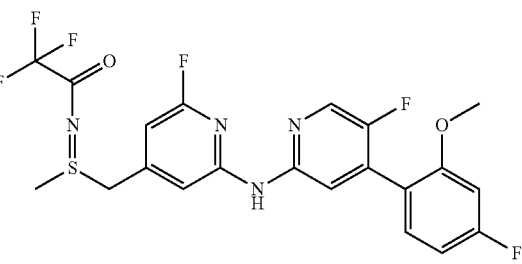

Under an atmosphere of argon, a solution of 2,2,2-trifluoroacetamide (60 mg; 0.51 mmol) in dioxane (1 mL) was added dropwise to a solution of sodium tert.-butoxide (25.3 mg; 0.25 mmol) in dioxane (1 mL), so that the temperature of the mixture remained below 10° C. Subsequently, a freshly prepared solution of 1,3-dibromo-5,5-dimethylhydantoin (55 mg; 0.19 mmol) in dioxane (1 mL) was added dropwise to the stirred mixture, so that the temperature of the mixture remained below 10° C. Then the mixture was stirred for 10 minutes at ambient temperature. Finally, a solution of 5-fluoro-4-(4-fluoro-2-methoxyphenyl)-N-{6-fluoro-4-[(methylsulfanyl)methyl]pyridin-2-yl}pyridin-2-amine (100 mg; 0.25 mmol) in dioxane (1 mL) was added dropwise to the stirred mixture. The mixture was stirred for 30 minutes. The batch was diluted with ethyl acetate and an aqueous solution of sodium sulfite (10%) was added. The batch was extracted three times with ethyl acetate. The combined organic layers were washed with an aqueous solution of sodium chloride, dried over sodium sulfate and concentrated. The residue was purified by column chromatography on silica gel (hexanes/ethyl aceate) to yield the title compound (52 mg; 0.1 mmol).

$^1$H-NMR (400 MHz, DMSO-d$_6$): δ [ppm]=10.19 (s, 1H), 8.24 (d, 1H), 7.68 (s, 1H), 7.52 (d, 1H), 7.36 (dd, 1H), 7.11 (dd, 1H), 6.93 (td, 1H), 6.52 (s, 1H), 4.65-4.43 (m, 2H), 3.81 (s, 3H), 2.81 (s, 3H).

Preparation of End Products:

(rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)-λ$^4$-sulfanylidene}acetamide (318 mg; 0.63 mmol) was dissolved in methanol (25 ml). To this solution water was added (0.66 ml). A solution of Oxone® (331 mg: 0.538 mmol) in water (2 ml) was added to the first solution and the resulting mixture was stirred. The pH was kept between 6.8-7.2 by addition of an aqueous solution of potassium hydroxide (5%). After 100 minutes of reaction time an additional amount of Oxone® (156 mg; 0.253 mmol) was added. The pH was kept between 7.8-8.2. After additional 20 minutes of stirring the batch was diluted with water (300 ml). The suspension was extracted with ethyl acetate. The organic layer was washed with an aqueous solution of sodium sulfite (10%), dried over sodium sulfate, filtered, and concentrated. The residue was purified by column chromatography on silica gel (ethyl acetate/methanol) to yield (rac)-5-fluoro-4-(4-fluoro-2-methoxyphenyl)-N-{6-fluoro-4-[(S-methylsulfonimidoyl)methyl]pyridin-2-yl}pyridin-2-amine (66 mg; 0.16 mmol; example 17) and (rac)-2,2,2-trifluoro-N-[(2-fluoro-6-{[5-fluoro-4-(4-fluoro-2-methoxyphenyl)pyridin-2-yl]amino}pyridin-4-yl)methyl](methyl)oxido-λ$^6$-sulfanylidene acetamide 126 mg; 0.24 mmol; example 18).

Example 17

$^1$H-NMR (400 MHz, DMSO-d$_6$): δ [ppm]=10.09 (s, 1H), 8.25 (d, 1H), 7.63 (s, 1H), 7.58 (d, 1H), 7.36 (dd, 1H), 7.11 (dd, 1H), 6.93 (trd, 1H), 6.62 (s, 1H), 4.44 (s, 2H), 3.84 (s, 1H), 3.81 (s, 3H), 2.90 (s, 3H).

Example 18

$^1$H-NMR (400 MHz, DMSO-d$_6$): δ [ppm]=10.24 (s, 1H), 8.24 (d, 1H), 7.77 (s, 1H), 7.53 (d, 1H), 7.36 (dd, 1H), 7.11 (dd, 1H), 6.93 (trd, 1H), 6.61 (s, 1H), 5.16 (s, 2H), 3.81 (s, 3H), 3.55 (s, 3H).

Examples 19 and 20

Enantiomers of 5-Fluoro-4-(4-fluoro-2-methoxyphenyl)-N-{6-fluoro-4-[(S-methylsulfonimidoyl)-methyl]pyridin-2-yl}pyridin-2-amine

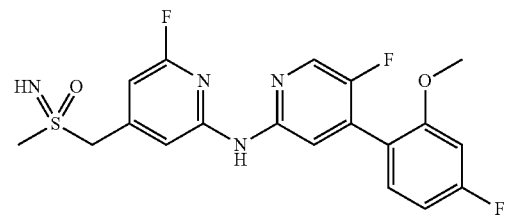

(rac)-5-Fluoro-4-(4-fluoro-2-methoxyphenyl)-N-{6-fluoro-4-[(S-methylsulfonimidoyl)-methyl]pyridin-2-yl}-pyridin-2-amine (Example 17, 178 mg) was separated into the single enantiomers by preparative chiral HPLC.

| | |
|---|---|
| System: | Agilent: Prep 1200, 2xPrep Pump, DLA, MWD, Gilson: Liquid Handler 215 |
| Column: | Chiralpak IA 5 µm 250 × 20 mm |
| Solvent: | MeCN/ethanol/diethylamine 90:10:0.1 (v/v/v) |
| Flow: | 25 mL/min |
| Temperature: | RT |
| Solution: | 178 mg/6 mL DCM/MeOH |
| Injection: | 10 × 0.6 mL |
| Detection: | UV 254 nm |

| | Retention time in min | purity in % | yield | specific optical rotation: |
|---|---|---|---|---|
| Example 19 Enantiomer 1 | 4.4-5.7 | 82.5 | 32 mg (0.07 mmol) | $[α]_D^{20}$ = 12.6° +/− 0.15° (DMSO, 589 nm, 20° C.). |
| Example 20 Enantiomer 2 | 5.7-8.4 | 97.2 | 70 mg (0.16 mmol) | $[α]_D^{20}$ = −12.9° +/− 0.25° (DMSO, 589 nm, 20° C.). |

Example 21

(rac)-5-Fluoro-4-(4-fluoro-2-methoxyphenyl)-N-{4-[(S-methylsulfonimidoyl)methyl]-6-(trifluoromethyl)pyridin-2-yl}pyridin-2-amine

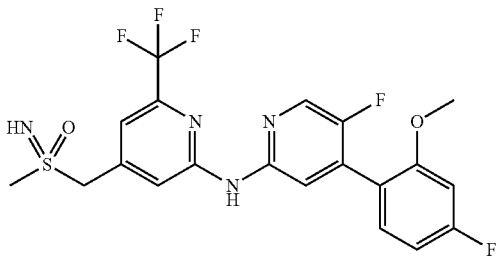 [SMILES: COc1cc(F)ccc1-c1cc(Nc2cc(CS(C)(=N)=O)cc(C(F)(F)F)n2)ncc1F]

Preparation of Intermediate 21.1

2-Chloro-4-[(methylsulfanyl)methyl]-6-(trifluoromethyl)pyridine

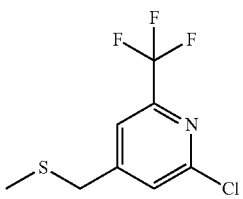

Sodium methanethiolate (254 mg; 3.6 mmol) was added to a stirred solution of 2-chloro-4-(chloromethyl)-6-(trifluoromethyl)pyridine (490 mg; 1.18 mmol; Anichem LLC; CAS #1196154-47-8) in ethanol (15 mL) at 0° C. The cold bath was removed and the batch was stirred at room temperature for 3 hours. The batch was diluted with saturated aqueous sodium chloride solution and extracted twice with ethyl acetate. The combined organic layers were washed with water, dried (sodium sulfate), filtered and concentrated to give the crude product. Purification by column chromatography on silica gel (hexanes/ethyl acetate) yielded the title compound (446 mg; 1.68 mmol).

$^1$H-NMR (400 MHz, DMSO-$d_6$): δ [ppm]=7.91 (s, 1H), 7.82 (s, 1H), 3.84 (s, 2H), 1.97 (s, 3H).

Preparation of Intermediate 21.2

5-Fluoro-4-(4-fluoro-2-methoxyphenyl)-N-{4-[(methylsulfanyl)methyl]-6-(trifluoromethyl)pyridin-2-yl}pyridin-2-amine

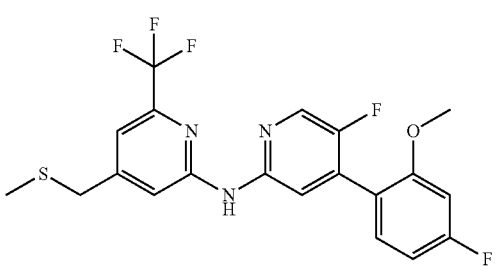 [SMILES: COc1cc(F)ccc1-c1cc(Nc2cc(CSC)cc(C(F)(F)F)n2)ncc1F]

A mixture of 2-chloro-4-[(methylsulfanyl)methyl]-6-(trifluoromethyl)pyridine (246 mg; 0.38 mmol;), 5-fluoro-4-(4-fluoro-2-methoxyphenyl)pyridin-2-amine (157 mg; 0.66 mmol; Intermediate 4.1), chloro(2-dicyclohexylphosphino-2',4',6'-tri-iso-propyl-1,1'-biphenyl)[2-(2-aminoethyl)phenyl]palladium(II) methyl-tert-butylether adduct (31.1 mg; 0.038 mmol; ABCR GmbH & CO. KG) and 2-(dicyclohexylphosphino)-2',4',6'-triisopropylbiphenyl (17.9 mg; 0.038 mmol; Aldrich Chemical Company Inc.) and potassium phosphate (400 mg; 1.88 mmol) in toluene (10 ml) and NMP (1 mL) was stirred under an atmosphere of argon at 130° C. for 180 minutes. After cooling, the batch was diluted with ethyl acetate and washed with aqueous sodium chloride solution. The organic layer was filtered using a Whatman filter and concentrated. The residue was purified by column chromatography on silica gel (hexanes/ethyl acetate) to yield the title compound (160 mg; 0.36 mmol).

$^1$H-NMR (400 MHz, DMSO-$d_6$): δ [ppm]=10.23 (s, 1H), 8.28 (d, 1H), 7.87 (s, 1H), 7.79 (d, 1H), 7.34 (dd, 1H), 7.28 (s, 1H), 7.11 (dd, 1H), 6.93 (trd, 1H), 3.80 (s, 3H), 3.77 (s, 2H), 2.01 (s, 3H).

Preparation of Intermediate 21.3

(rac)-2,2,2-Trifluoro-N-[{2-{[5-fluoro-4-(4-fluoro-2-methoxyphenyl)pyridin-2-yl]amino}-6-(trifluoromethyl)pyridin-4-yl]methyl}(methyl) -λ$^4$-sulfanylidene]acetamide

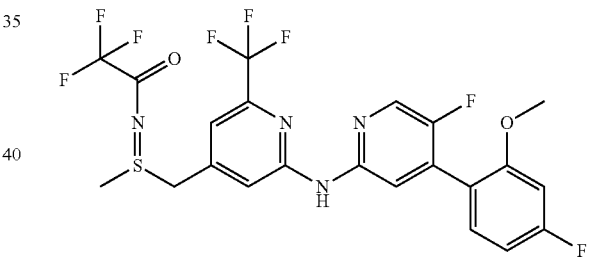

A solution of 2,2,2-trifluoroacetamide (99.8 mg; 0.86 mmol) in dioxane (1.5 mL) was added dropwise to a solution of sodium tert.-butoxide (42.4 mg; 0.42 mmol) in dioxane (1.5 mL). Subsequently, a freshly prepared solution of 1,3-dibromo-5,5-dimethylhydantoin (122.4 mg; 0.43 mmol) in dioxane (2 mL) was added dropwise to the stirred mixture. Then the mixture was stirred for 10 minutes at ambient temperature. Finally, a solution of 5-fluoro-4-(4-fluoro-2-methoxyphenyl)-N-{4-[(methylsulfanyl)methyl]-6-(trifluoromethyl)pyridin-2-yl}pyridin-2-amine (225 mg; 0.43 mmol) in dioxane (2 mL) was added dropwise to the stirred mixture. The mixture was stirred for 1 hour. The batch was diluted with ethyl acetate and an aqueous solution of sodium sulfite (10%) was added. The batch was extracted three times with ethyl acetate. The combined organic layers were washed with an aqueous solution of sodium chloride, dried over sodium sulfate and concentrated. The residue was purified by column chromatography on silica gel (hexanes/ethyl aceate) to yield the title compound (123 mg; 0.22 mmol).

¹H-NMR (400 MHz, DMSO-d₆): δ [ppm]=10.40 (s, 1H), 8.26 (d, 1H), 8.00 (s, 1H), 7.71 (d, 1H), 7.35 (dd, 1H), 7.23 (d, 1H), 7.11 (dd, 1H), 6.93 (trd, 1H), 4.80-4.45 (m, 2H), 3.80 (s, 3H), 2.82 (s, 3H).

Intermediate 21.4 and 21.5

Enantiomers of (rac)-2,2,2-Trifluoro-N-[{[2-{[5-fluoro-4-(4-fluoro-2-methoxyphenyl)pyridin-2-yl]amino}-6-(trifluoromethyl)pyridin-4-yl]methyl}(methyl)-λ⁴-sulfanylidene]acetamide (rac)-2,2,2-Trifluoro-N-[{[2-{[5-fluoro-4-(4-fluoro-2-methoxyphenyl)pyridin-2-yl]amino}-6-(trifluoromethyl)pyridin-4-yl]methyl}(methyl)-λ⁴-sulfanylidene]acetamide (638 mg) was separated into the single enantiomers by preparative chiral HPLC.

| System: | Agilent: Prep 1200, 2xPrep Pump, DLA, MWD, Prep FC, |
|---|---|
| Column: | Chiralpak AD-H 5 µm 250 × 30 mm |
| Solvent: | Hexane/Ethanol 70:30 (v/v) |
| Flow: | 50 mL/min |
| Temperature: | RT |
| Solution: | 638 mg/8 mL MeOH, |
| Injection: | 23 × 0.35 mL |
| Detection: | UV 254 nm |

| | Retention time in min | purity in % | yield | specific optical rotation: |
|---|---|---|---|---|
| Intermediate 21.4 Enantiomer 1 | 10.26-11.50 | 98.59 | 178 mg (0.31 mmol) | $[\alpha]_D^{20} = 110.1° +/- 0.13°$ (DMSO, 589 nm, 20° C.). |
| Intermediate 21.5. Enantiomer 2 | 12.63-14.15 | 97.27 | 137 mg (0.25 mmol) | $[\alpha]_D^{20} = -116.3° +/- 0.08°$ (DMSO, 589 nm, 20° C.). |

Intermediate 21.4, (+)-Enantiomer of Intermediate 21.3

¹H-NMR (400 MHz, DMSO-d₆): δ [ppm]=10.40 (s, 1H), 8.26 (d, 1H), 8.00 (s, 1H), 7.71 (d, 1H), 7.35 (dd, 1H), 7.23 (s, 1H), 7.11 (dd, 1H), 6.93 (trd, 1H), 4.76-4.47 (m, 2H), 3.80 (s, 3H), 2.82 (s, 3H), 2.08 (s, 2H).

Intermediate 21.5, (−)-Enantiomer of Intermediate 21.3

¹H-NMR (400 MHz, DMSO-d₆): δ [ppm]=10.40 (s, 1H), 8.26 (d, 1H), 8.00 (s, 1H), 7.71 (d, 1H), 7.35 (dd, 1H), 7.23 (d, 1H), 7.11 (dd, 1H), 6.93 (trd, 1H), 4.77-4.46 (m, 2H), 3.80 (s, 3H), 2.82 (s, 3H).

Preparation of End Product:
A solution of (rac)-2,2,2-trifluoro-N-[{[2-{[5-fluoro-4-(4-fluoro-2-methoxyphenyl)pyridin-2-yl]amino}-6-(trifluoromethyl)pyridin-4-yl]methyl}(methyl)-λ⁴-sulfanylidene]acetamide (122 mg; 0.22 mmol; Intermediate 21.3) in methanol (3.6 ml)/water (0.32 ml) was adjusted to pH 10.5 by addition of an aqueous solution of potassium hydroxide (10%). Oxone® (115 mg; 0.187 mmol) was added. The resulting mixture was stirred for 90 min The pH was kept between 10 and 11 by addition of aqueous solution of potassium hydroxide (10%), if necessary. An additional amount of Oxone® (34 mg; 0.055 mmol) was added and the mixture was stirred for 60 min at a pH between 10 and 11. Then, the batch was neutralized, diluted with water (40 ml) and extracted with DCM. The combined organic layers were washed with an aqueous solution of sodium sulfite (10%), dried over sodium sulfate and concentrated. The residue was purified by column chromatography on silica gel (ethyl acetate/methanol) to yield the title compound (43 mg; 0.09 mmol).

¹H-NMR (400 MHz, DMSO-d₆): δ [ppm]=10.31 (s, 1H), 8.27 (d, 1H), 7.96 (s, 1H), 7.77 (d, 1H), 7.39 (d, 1H), 7.35 (dd, 1H), 7.11 (dd, 1H), 6.93 (td, 1H), 4.52 (s, 2H), 3.89 (s, 1H), 3.80 (s, 3H), 2.91 (s, 3H).

Examples 22 and 23

Enantiomers of 5-fluoro-4-(4-fluoro-2-methoxyphenyl)-N-{4-[(S-methylsulfonimidoyl)methyl]-6-(trifluoromethyl)pyridin-2-yl}pyridin-2-amine

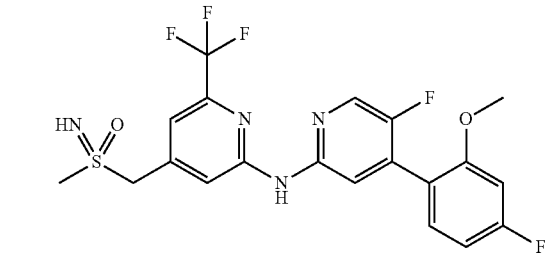 [SMILES: COc1cc(F)ccc1-c1cc(Nc2cc(CS(C)(=N)=O)cc(C(F)(F)F)n2)ncc1F]

(rac)-5-Fluoro-4-(4-fluoro-2-methoxyphenyl)-N-{4-[(S-methylsulfonimidoyl)methyl]-6-(trifluoro-methyl)pyridin-2-yl}pyridin-2-amine (Example 21) was separated into the single enantiomers by preparative chiral HPLC.

| | | | |
|---|---|---|---|
| System: | Agilent: Prep 1200, 2xPrep Pump, DLA, MWD, Prep FC | | |
| Column: | Chiralpak ID 5 μm 250 × 30 mm Nr.: 022 | | |
| Solvent: | Hexane/2-Propanol/diethylamine 70:30:0.1 (v/v/v) | | |
| Flow: | 50 mL/min | | |
| Temperature: | RT | | |
| Solution: | 380 mg/5.6 mL DCM/MeOH 1:1 | | |
| Injection: | 6 × 0.93 mL | | |
| Detection: | UV 280 nm | | |

| | Retention time in min | purity in % | yield | specific optical rotation: |
|---|---|---|---|---|
| Example 22 Enantiomer 1 | 10.5-12.8 | >99.9% | 105 mg (0.21 mmol) | $[\alpha]_D^{20} = 16.6° +/- 0.15°$ (DMSO, 589 nm, 20° C.). |
| Example 23 Enantiomer 2 | 13.1-16.7 | 98.9% | 115 mg (0.23 mmol) | $[\alpha]_D^{20} = -14.7° +/- 0.15°$ (DMSO, 589 nm, 20° C.). |

Example 22

(+)-Enantiomer $^1$H-NMR (400 MHz, DMSO-$d_6$): δ [ppm]=10.31 (s, 1H), 8.27 (d, 1H), 7.96 (s, 1H), 7.77 (d, 1H), 7.39 (s, 1H), 7.35 (dd, 1H), 7.11 (dd, 1H), 6.93 (td, 1H), 4.52 (s, 2H), 3.90 (s, 1H), 3.80 (s, 3H), 2.91 (s, 3H).

Example 23

(−)-Enantiomer $^1$H-NMR (400 MHz, DMSO-$d_6$): δ [ppm]=10.31 (s, 1H), 8.27 (d, 1H), 7.96 (s, 1H), 7.77 (d, 1H), 7.39 (s, 1H), 7.35 (dd, 1H), 7.11 (dd, 1H), 6.93 (td, 1H), 4.52 (s, 2H), 3.90 (s, 1H), 3.80 (s, 3H), 2.91 (s, 3H).

Alternative Preparation of Example 22

(+)-5-Fluoro-4-(4-fluoro-2-methoxyphenyl)-N-{4-[(S-methylsulfonimidoyl)methyl]-6-(trifluoromethyl)pyridin-2-yl}pyridin-2-amine Examples 22 and 24 were prepared under similar conditions as described in the preparation of examples 17 and 18 using (+)-2,2,2-trifluoro-N-[{[2-{[5-fluoro-4-(4-fluoro-2-methoxyphenyl)pyridin-2-yl]amino}-6-(trifluoromethyl)pyridin-4-yl]methyl}(methyl)-$\lambda^4$-sulfanylidene]acetamide (175 mg; 0.3 mmol; Intermediate 21.4). Column chromatography on silica gel (ethyl acetate/methanol) gave (+)-5-fluoro-4-(4-fluoro-2-methoxyphenyl)-N-{4-[(S-methylsulfonimidoyl)methyl]-6-(trifluoromethyl)pyridin-2-yl}pyridin-2-amine (94 mg; 0.2 mmol; example 22) and (+)-2,2,2-trifluoro-N-[{[2-{[5-fluoro-4-(4-fluoro-2-methoxyphenyl)pyridin-2-yl]amino}-6-(trifluoromethyl)pyridin-4-yl]methyl}(methyl)oxido-$\lambda^6$-sulfanylidene]acetamide (20 mg; 0.03 mmol example 24).

$^1$H-NMR (400 MHz, DMSO-$d_6$): δ [ppm]=10.46 (s, 1H), 8.26 (d, 1H), 8.10 (s, 1H), 7.72 (d, 1H), 7.37-7.32 (m, 2H), 7.11 (dd, 1H), 6.93 (trd, 1H), 5.29-5.20 (m, 2H), 3.81 (s, 3H), 3.59 (s, 3H).

Alternative Preparation Example 23

(−)-5-Fluoro-4-(4-fluoro-2-methoxyphenyl)-N-{4-[(S-methylsulfonimidoyl)methyl]-6-(trifluoromethyl)pyridin-2-yl}pyridin-2-amine

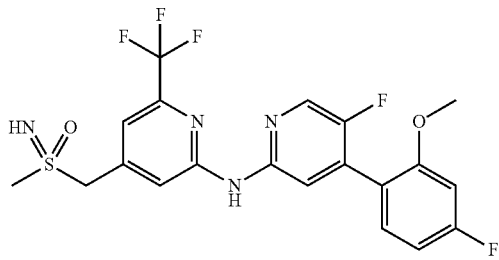 [SMILES: COc1cc(F)ccc1-c1cc(Nc2cc(CS(C)(=N)=O)cc(C(F)(F)F)n2)ncc1F]

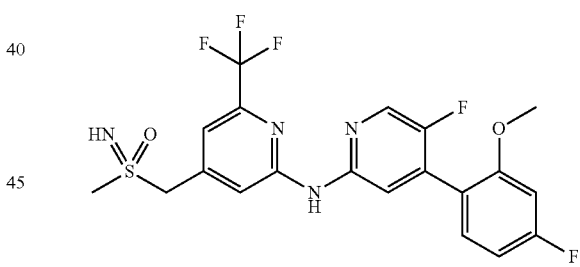

Example 24

(+)-2,2,2-Trifluoro-N-[{[2-{[5-fluoro-4-(4-fluoro-2-methoxyphenyl)pyridin-2-yl]amino}-6-(trifluoromethyl)pyridin-4-yl]methyl}(methyl)oxido-$\lambda^6$-sulfanylidene]acetamide

Example 25

(−)-2,2,2-Trifluoro-N-[{[2-{[5-fluoro-4-(4-fluoro-2-methoxyphenyl)pyridin-2-yl]amino}-6-(trifluoromethyl)pyridin-4-yl]methyl}(methyl)oxido-$\lambda^6$-sulfanylidene]acetamide

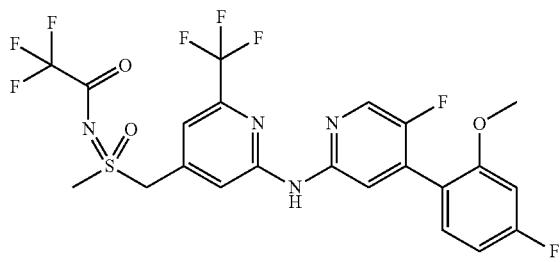 [SMILES: COc1cc(F)ccc1-c1cc(Nc2cc(CS(C)(=O)=NC(=O)C(F)(F)F)cc(C(F)(F)F)n2)ncc1F]

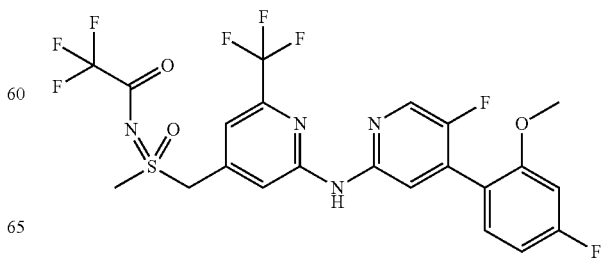

Examples 23 and 25 were prepared under similar conditions as described in the preparation of examples 17 and 18 using (−)-2,2,2-trifluoro-N-[{[2-{[5-fluoro-4-(4-fluoro-2-methoxyphenyl)pyridin-2-yl]amino}-6-(trifluoromethyl)pyridin-4-yl]methyl}(methyl)-λ⁴-sulfanylidene]acetamide (165 mg; 0.295 mmol; Intermediate 21.5). Column chromatography on silica gel (ethyl acetate/methanol) gave (−)-5-fluoro-4-(4-fluoro-2-methoxyphenyl)-N-{4-[(S-methylsulfonimidoyl)methyl]-6-(trifluoromethyl)pyridin-2-yl}pyridin-2-amine (85 mg; 0.18 mmol; example 23) and (−)-2,2,2-trifluoro-N-[{[2-{[5-fluoro-4-(4-fluoro-2-methoxyphenyl)pyridin-2-yl]amino}-6-(trifluoromethyl)pyridin-4-yl]methyl}(methyl)oxido-λ⁶-sulfanylidene]acetamide (5 mg; 0.008 mmol example 25).

¹H-NMR (400 MHz, DMSO-d₆): δ [ppm]=10.46 (s, 1H), 8.26 (d, 1H), 8.10 (s, 1H), 7.72 (d, 1H), 7.38-7.31 (m, 2H), 7.11 (dd, 1H), 6.93 (trd, 1H), 5.28-5.19 (m, 2H), 3.80 (s, 4H), 3.59 (s, 3H).

Example 26

(rac)-4-(2-Ethoxy-4-fluorophenyl)-5-fluoro-N-{6-fluoro-4-[(S-methylsulfonimidoyl)methyl]pyridin-2-yl}pyridin-2-amine

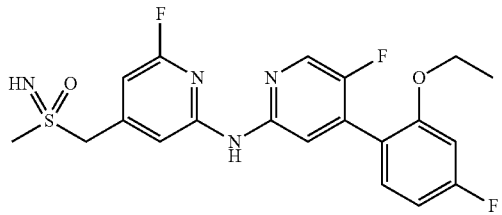 [SMILES: CCOc1cc(F)ccc1-c1cc(Nc2cc(CS(C)(=N)=O)cc(F)n2)ncc1F]

Example 27

(rac)-N-{[(2-{[4-(2-Ethoxy-4-fluorophenyl)-5-fluoropyridin-2-yl]amino}-6-fluoropyridin-4-yl)methyl](methyl)oxido-λ⁶-sulfanylidene}-2,2,2-trifluoroacetamide

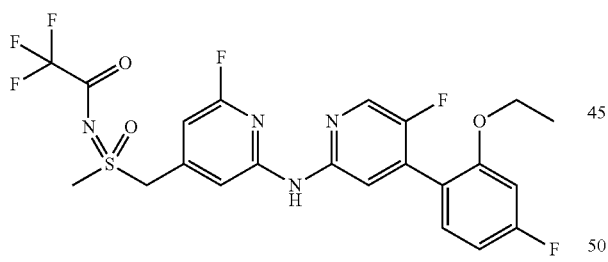

Preparation of Intermediate 26.1

2-Chloro-4-(2-ethoxy-4-fluorophenyl)-5-fluoropyridine

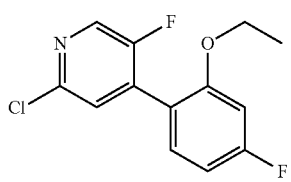 [SMILES: CCOc1cc(F)ccc1-c1cc(Cl)ncc1F]

Intermediate 26.1 was prepared under similar conditions as described in the preparation of intermediate 1.1 using 2-chloro-5-fluoro-4-iodopyridine (Manchester Organics, CAS #884494-49-9) and (2-ethoxy-4-fluorophenyl)boronic acid (ABCR, CAS #480438-58-2).

¹H-NMR (400 MHz, DMSO-d₆): δ [ppm]=8.49 (d, 1H), 7.61 (d, 1H), 7.42 (dd, 1H), 7.10 (dd, 1H), 6.92 (trd, 1H), 4.10 (q, 2H), 1.23 (tr, 3H).

Preparation of Intermediate 26.2

5-Fluoro-4-(4-fluoro-2-methoxyphenyl)-N-{6-fluoro-4-[(methylsulfanyl)methyl]pyridin-2-yl}pyridin-2-amine

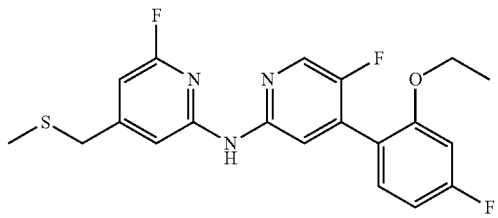 [SMILES: CCOc1cc(F)ccc1-c1cc(Nc2cc(CSC)cc(F)n2)ncc1F]

Intermediate 26.2 was prepared under similar conditions as described in the preparation of intermediate 17.5 using 6-fluoro-4-[(methylsulfanyl)methyl]pyridin-2-amine (Intermediate 17.4) and 2-chloro-4-(2-ethoxy-4-fluorophenyl)-5-fluoropyridine.

¹H-NMR (400 MHz, DMSO-d₆): δ [ppm]=10.03 (s, 1H), 8.27 (d, 1H), 7.63 (d, 1H), 7.57 (s, 1H), 7.35 (dd, 1H), 7.09 (dd, 1H), 6.91 (trd, 1H), 6.51 (s, 1H), 4.10 (q, 2H), 3.70 (s, 2H), 2.02 (s, 3H), 1.24 (tr, 3H).

Preparation of Intermediate 26.3

(rac)-N-[(2-{[4-(2-Ethoxy-4-fluorophenyl)-5-fluoropyridin-2-yl]amino}-6-fluoropyridin-4-yl)methyl](methyl)-λ⁴-sulfanylidene]-2,2,2-trifluoroacetamide

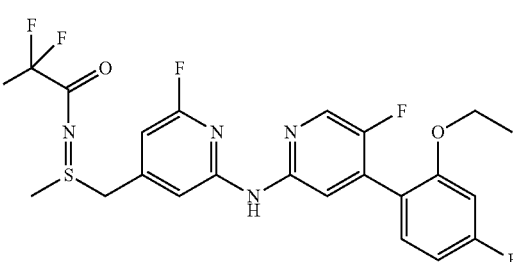

Intermediate 26.3 was prepared under similar conditions as described in the preparation of intermediate 17.6 using 5-fluoro-4-(4-fluoro-2-methoxyphenyl)-N-{6-fluoro-4-[(methylsulfanyl)methyl]pyridin-2-yl}pyridin-2-amine.

¹H-NMR (400 MHz, DMSO-d₆): δ [ppm]=10.20 (s, 1H), 8.25 (d, 1H), 7.68 (s, 1H), 7.56 (d, 1H), 7.36 (dd, 1H), 7.09 (dd, 1H), 6.91 (trd, 1H), 6.51 (s, 1H), 4.66-4.44 (m, 2H), 4.10 (q, 2H), 2.81 (s, 3H), 1.27-1.22 (m, 5H).

Preparation of End Products:

Examples 26 and 27 were prepared under similar conditions as described in the preparation of examples 17 and 18 using (rac)-N-[[(2-{[4-(2-ethoxy-4-fluorophenyl)-5-fluoropyridin-2-yl]amino}-6-fluoropyridin-4-yl)methyl](methyl)-λ⁴-sulfanylidene]-2,2,2-trifluoroacetamide.

Example 26

$^1$H-NMR (400 MHz, DMSO-$d_6$): δ [ppm]=10.10 (s, 1H), 8.26 (d, 1H), 7.65-7.59 (m, 2H), 7.36 (dd, 1H), 7.09 (dd, 1H), 6.91 (trd, 1H), 6.62 (s, 1H), 4.44 (s, 2H), 4.11 (q, 2H), 3.84 (s, 1H), 2.90 (s, 3H), 1.25 (tr, 3H).

Example 27

$^1$H-NMR (400 MHz, DMSO-$d_6$): δ [ppm]=10.25 (s, 1H), 8.24 (d, 1H), 7.77 (s, 1H), 7.57 (d, 1H), 7.36 (dd, 1H), 7.09 (dd, 1H), 6.91 (trd, 1H), 6.61 (s, 1H), 5.16 (s, 2H), 4.10 (q, 2H), 3.55 (s, 3H), 1.24 (tr, 3H).

Examples 28 and 29

Enantiomers of 4-(2-Ethoxy-4-fluorophenyl)-5-fluoro-N-{6-fluoro-4-[(S-methylsulfonimidoyl)-methyl]pyridin-2-yl}pyridin-2-amine

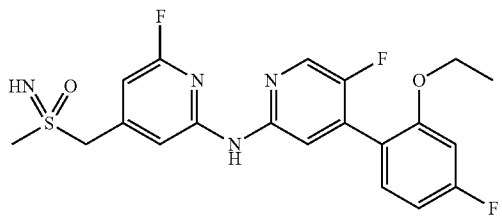

(rac)-4-(2-Ethoxy-4-fluorophenyl)-5-fluoro-N-{6-fluoro-4-[(S-methylsulfonimidoyl)-methyl]pyridin-2-yl}pyridin-2-amine (95 mg, Example 26) was separated into the single enantiomers by preparative chiral HPLC.

| System: | Agilent: Prep 1200, 2xPrep Pump, DLA, MWD, Prep FC, |
| --- | --- |
| Column: | Chiralpak IA 5 μm 250 × 20 mm |
| Solvent: | Acetonitrile/ethanol 90:10 (v/v) + 0.1% DEA |
| Flow: | 31 mL/min |
| Temperature: | RT |
| Solution: | 95 mg/2 mL MeOH |
| Injection: | 7 × 0.3 mL |
| Detection: | UV 254 nm |

| | Retention time in min | purity in % | yield | specific optical rotation: |
| --- | --- | --- | --- | --- |
| Example 28 Enantiomer 1 | 3.0-6.0 | 96.1 | 35 mg (0.08 mmol) | $[α]_D^{20}$ = 6.3° (DMSO, 589 nm, 20° C.). |
| Example 29 Enantiomer 2 | 8.0-16.0 | 96.5 | 25 mg (0.06 mmol) | $[α]_D^{20}$ = −10.7° (DMSO, 589 nm, 20° C.). |

Example 28

(+)-Enantiomer $^1$H-NMR (400 MHz, DMSO-$d_6$): δ [ppm]=10.10 (s, 1H), 8.26 (s, 1H), 7.66-7.59 (m, 2H), 7.36 (tr, 1H), 7.08 (dd, 1H), 6.91 (trd, 1H), 6.62 (s, 1H), 4.44 (s, 2H), 4.10 (q, 2H), 3.85 (br. s., 1H), 2.90 (s, 3H), 1.24 (tr, 3H).

Example 29

(−)-Enantiomer $^1$H-NMR (400 MHz, DMSO-$d_6$): δ [ppm]=10.10 (s, 1H), 8.26 (d, 1H), 7.66-7.59 (m, 2H), 7.40-7.32 (m, 1H), 7.09 (dd, 1H), 6.91 (trd, 1H), 6.62 (s, 1H), 4.44 (s, 2H), 4.10 (q, 2H), 3.84 (s, 1H), 2.90 (s, 3H), 1.24 (tr, 3H).

Example 30

(rac)-N-{4-[(S-Ethylsulfonimidoyl)methyl]pyridin-2-yl}-5-fluoro-4-(4-fluoro-2-methoxyphenyl)pyridin-2-amine

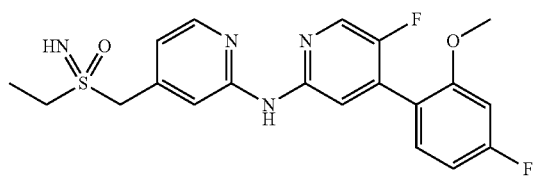 [SMILES: CCS(=N)(=O)Cc1ccnc(Nc2cc(-c3ccc(F)cc3OC)c(F)cn2)c1]

Preparation of Intermediate 30.1

N-{4-[(Ethylsulfanyl)methyl]pyridin-2-yl}-5-fluoro-4-(4-fluoro-2-methoxyphenyl)pyridin-2-amine

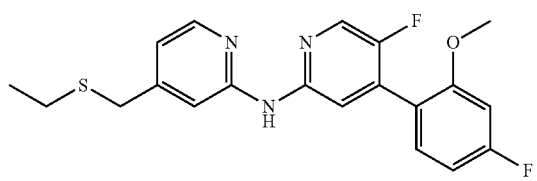 [SMILES: CCSCc1ccnc(Nc2cc(-c3ccc(F)cc3OC)c(F)cn2)c1]

Intermediate 30.1 was prepared under similar conditions as described in the preparation of intermediate 17.5 using 4-[(ethylsulfanyl)methyl]pyridin-2-amine (purchased from Enamine) and 2-chloro-5-fluoro-4-(4-fluoro-2-methoxyphenyl)pyridine (Intermediate 1.1).

$^1$H-NMR (400 MHz, DMSO-$d_6$): δ [ppm]=9.73 (s, 1H), 8.22 (d, 1H), 8.10 (d, 1H), 7.81 (d, 1H), 7.54 (s, 1H), 7.34 (dd, 1H), 7.09 (dd, 1H), 6.95-6.88 (m, 1H), 6.81 (dd, 1H), 3.80 (s, 3H), 3.68 (s, 2H), 2.45 (q, 2H), 1.18 (tr, 3H).

Preparation of Intermediate 30.2

(rac)-N-{Ethyl[(2-{[5-fluoro-4-(4-fluoro-2-methoxyphenyl)pyridin-2-yl]amino}pyridin-4-yl)methyl]-$\lambda^4$-sulfanylidene}-2,2,2-trifluoroacetamide

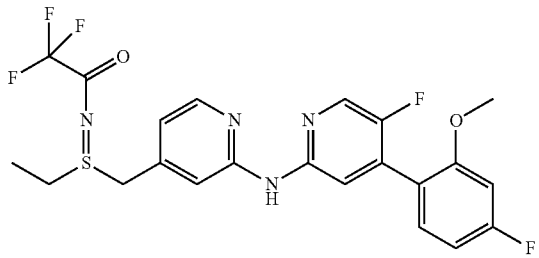 [SMILES: CCS(Cc1ccnc(Nc2cc(-c3ccc(F)cc3OC)c(F)cn2)c1)=NC(=O)C(F)(F)F]

Intermediate 30.2 was prepared under similar conditions as described in the preparation of intermediate 17.6 using N-{4-[(ethylsulfanyl)methyl]pyridin-2-yl}-5-fluoro-4-(4-fluoro-2-methoxyphenyl)pyridin-2-amine.

$^1$H-NMR (400 MHz, DMSO-d$_6$): δ [ppm]=9.90 (s, 1H), 8.23-8.17 (m, 2H), 7.72 (d, 1H), 7.67 (s, 1H), 7.35 (dd, 1H), 7.10 (dd, 1H), 6.92 (trd, 1H), 6.83 (dd, 1H), 4.58-4.37 (m, 2H), 3.80 (s, 3H), 3.30-3.22 (m, 1H), 3.12-3.01 (m, 1H), 1.27 (tr, 3H).

Preparation of End Product:

Example 30 was prepared under similar conditions as described in the preparation of example 21 using (rac)-N-{ethyl[(2-{[5-fluoro-4-(4-fluoro-2-methoxyphenyl)pyridin-2-yl]amino}pyridin-4-yl)methyl]-$\lambda^4$-sulfanylidene}-2,2,2-trifluoroacetamide.

$^1$H-NMR (400 MHz, DMSO-d$_6$): δ [ppm]=9.80 (s, 1H), 8.21 (d, 1H), 8.16 (d, 1H), 7.79 (d, 1H), 7.60 (s, 1H), 7.35 (dd, 1H), 7.10 (dd, 1H), 6.95-6.88 (m, 2H), 4.36-4.25 (m, 2H), 3.80 (s, 3H), 3.68 (s, 1H), 2.97 (q, 2H), 1.25 (t, 3H).

Example 31

(rac)-N-{6-(Difluoromethyl)-4-[(S-methylsulfonimidoyl)methyl]pyridin-2-yl}-5-fluoro-4-(4-fluoro-2-methoxyphenyl)pyridin-2-amine

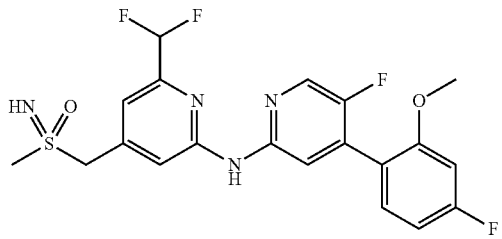 [SMILES: COc1cc(F)ccc1-c1cc(Nc2cc(CS(C)(=N)=O)cc(C(F)F)n2)ncc1F]

Preparation of Intermediate 31.1

(rac)-2-Chloro-6-(difluoromethyl)-4-[(methylsulfinyl)methyl]pyridine

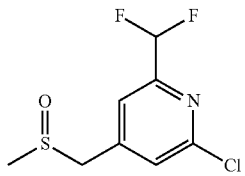

To a solution of 2-chloro-4-[(methylsulfanyl)methyl]pyridine (500 mg, 2.88 mmol; UkrOrgSynthesis Ltd.) and zinc difluoromethanesulfinate (DFMS; Baran et al, J. Am. Chem. Soc. 2012, 134, 1494) (1702 mg; 5.76 mmol) in DCM (10.0 mL) and water (4.0 mL) at RT was added trifluoroacetic acid (0.22 mL; 2.88 mmol) followed by slow addition of tert-butylhydroperoxide (70% solution in water; 1.23 mL; 8.64 mmol) with vigorous stirring. After 24 hours a second addition of DFMS (1702 mg; 5.76 mmol) and tert-butylhydroperoxide (70% solution in water; 1.23 mL; 8.64 mmol) was added and the batch was stirred for 22 hours at RT. The reaction was partitioned between DCM and an aqueous solution of sodium bicarbonate. The organic layer was separated, and the aqueous layer was extracted twice with DCM. The combined organic layers were filtered using a Whatman filter and concentrated. The residue was purified by column chromatography on silica gel (DCM/EtOH 95:5) to give the desired product (130 mg; 0.54 mmol).

$^1$H-NMR (300 MHz, CDCl$_3$, 300 K): δ=7.53 (s, 1H), 7.46 (s, 1H), 6.82 (tr, 1H), 4.05 (d, 1H), 3.91 (d, 1H), 2.60 (s, 3H).

Preparation of Intermediate 31.2

(rac)-N-[{[2--Chloro-6-(difluoromethyl)pyridin-4-yl]methyl}(methyl)oxido-$\lambda^6$-sulfanylidene]-2,2,2-trifluoroacetamide

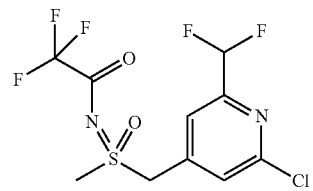 [SMILES: CS(=O)(Cc1cc(Cl)nc(C(F)F)c1)=NC(=O)C(F)(F)F]

To a suspension of (rac)-2-Chloro-6-(difluoromethyl)-4-[(methylsulfinyl)methyl]pyridine (124 mg; 0.52 mmol), trifluoroacetamide (117 mg; 1.04 mmol), magnesium oxide (83 mg; 2.07 mmol) and rhodium(II)-acetate dimer (6 mg; 0.01 mmol) in DCM (3 mL) was added iodobenzene diacetate (250 mg; 0.78 mmol) at RT. The mixture was stirred for 18 hours at RT. The suspension was filtered through a pad of celite and the filtrate was concentrated under reduced pressure. The residue was purified by column chromatography on silica gel (DCM to DCM/EtOH 95:5) to give the desired product (77 mg; 0.22 mmol).

$^1$H NMR (400 MHz, CDCl$_3$, 300K) δ=7.65 (s, 1H), 7.56 (s, 1H), 6.64 (tr, 1H), 4.88 (d, 1H), 4.72 (d, 1H), 3.35 (s, 3H).

Preparation of End Product:

A mixture of (rac)-N-[{[2-chloro-6-(difluoromethyl)pyridin-4-yl]methyl}(methyl)oxido-$\lambda^6$-sulfanylidene]-2,2,2-trifluoroacetamide (72.0 mg; 0.21 mmol;), 5-fluoro-4-(4-fluoro-2-methoxyphenyl)pyridin-2-amine (72.7 mg; 0.31 mmol; Intermediate 4.1), chloro(2-dicyclohexylphosphino-2',4',6'-tri-iso-propyl-1,1'-biphenyl) [2-(2-aminoethyl)phenyl]palladium(II) methyl-tert-butylether adduct (17.0 mg; 0.02 mmol; ABCR GmbH & CO. KG) and 2-(dicyclohexylphosphino)-2',4',6'-triisopropylbiphenyl (9.8 mg; 0.02 mmol; Aldrich Chemical Company Inc.) and potassium phosphate (218 mg; 1.03 mmol) in toluene (4.8 ml) and NMP (0.6 mL) was stirred under an atmosphere of argon at 130° C. for 2 hours. After cooling, the batch was diluted with DCM and washed with aqueous sodium chloride solution. The organic layer was filtered using a Whatman filter and concentrated. The residue was purified by preparative TLC to yield the desired product (3.4 mg; 0.01 mmol).

$^1$H-NMR (400 MHz, DMSO-$d_6$): δ [ppm]=8.18 (s, 1H), 7.86 (s, 1H), 7.50 (m, 2H), 7.30 (m, 1H), 7.21 (s, 1H), 6.80 (m, 2H), 6.51 (tr, 1H), 4.43 (d, 1H), 4.31 (d, 1H), 3.86 (s, 3H), 3.05 (s, 3H), 2.87 (br, 1H).

Examples 32 and 33

Enantiomers of 5-fluoro-4-(4-fluoro-2-methoxyphenyl)-N-{6-methyl-4-[(S-methylsulfonimidoyl)methyl]pyridin-2-yl}pyridin-2-amine

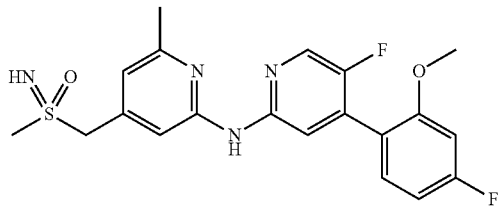 [SMILES: COc1cc(F)ccc1-c1cc(Nc2cc(CS(C)(=N)=O)cc(C)n2)ncc1F]

86 mg of racemic 5-fluoro-4-(4-fluoro-2-methoxyphenyl)-N-{6-methyl-4-[(S-methylsulfonimidoyl)methyl]pyridin-2-yl}pyridin-2-amine (Example 4) were separated by preparative chiral HPLC:

| System: | Agilent: Prep 1200, 2xPrep Pump, DLA, MWD, Prep FC |
|---|---|
| Column: | Chiralpak IC 5 μm 250 × 30 mm Nr.: 009 |
| Solvent: | hexane/2-propanol/diethylamine 70:30:0.1 (v/v/v) |
| Flow: | 50 mL/min |
| Temperature: | RT |
| Solution: | 86 mg/2 mL DCM/MeOH 1:1 |
| Injection: | 2 × 1.0 mL |
| Detection: | UV 280 nm |

| Fraktions | Retention time in min | purity in % | yield | Specific optical rotation |
|---|---|---|---|---|
| Example 32 Enantiomer 1 | 17.0-18.8 min | >99.9% | 28 mg (0.067 mmol) | $[α]_D^{20}$ = +15.1° (1.00, DMSO) |
| Example 33 Enantiomer 2 | 20.8-23.0 min | >99.9% | 30 mg (0.072 mmol) | $[α]_D^{20}$ = −11.6° (1.00, DMSO) |

Example 32

(+)-5-Fluoro-4-(4-fluoro-2-methoxyphenyl)-N-{6-methyl-4-[(S-methylsulfonimidoyl)methyl]pyridin-2-yl}pyridin-2-amine

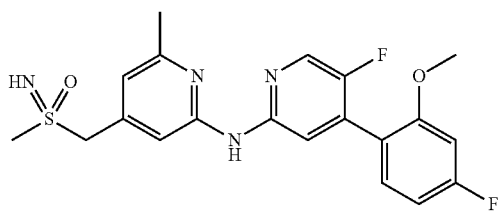 [SMILES: COc1cc(F)ccc1-c1cc(Nc2cc(CS(C)(=N)=O)cc(C)n2)ncc1F]

$^1$H-NMR (300 MHz, DMSO-$d_6$, 300 K): δ [ppm]=9.73 (s, 1H), 8.18 (d, 1H), 7.67 (d, 1H), 7.56 (s, 1H), 7.38-7.30 (m, 1H), 7.12-7.05 (m, 1H), 6.95-6.87 (m, 1H), 6.77 (s, 1H), 4.37-4.25 (m, 2H), 3.80 (s, 3H), 3.69 (s, 1H), 2.87 (s, 3H), 2.35 (s, 3H).

Example 33

(−)-5-Fluoro-4-(4-fluoro-2-methoxyphenyl)-N-{6-methyl-4-[(S-methylsulfonimidoyl)methyl]pyridin-2-yl}pyridin-2-amine

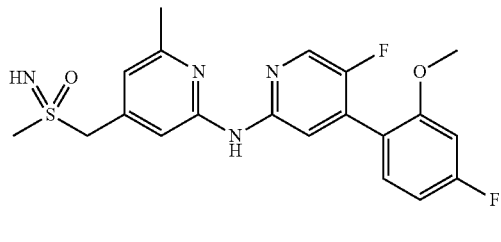 [SMILES: COc1cc(F)ccc1-c1cc(Nc2cc(CS(C)(=N)=O)cc(C)n2)ncc1F]

$^1$H-NMR (300 MHz, DMSO-$d_6$, 300 K): δ [ppm]=9.73 (s, 1H), 8.18 (d, 1H), 7.67 (d, 1H), 7.56 (s, 1H), 7.37-7.31 (m, 1H), 7.12-7.06 (m, 1H), 6.95-6.87 (m, 1H), 6.77 (s, 1H), 4.37-4.25 (m, 2H), 3.80 (s, 3H), 3.69 (d, 1H), 2.87 (s, 3H), 2.35 (s, 3H).

Alternative to Example 32

(+)-5-Fluoro-4-(4-fluoro-2-methoxyphenyl)-N-{6-methyl-4-[(S-methylsulfonimidoyl)methyl]pyridin-2-yl}pyridin-2-amine

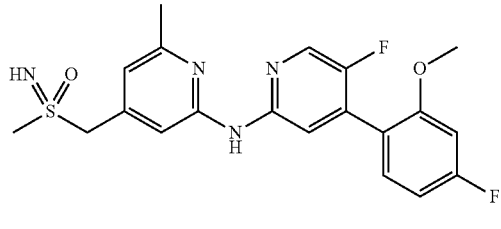 [SMILES: COc1cc(F)ccc1-c1cc(Nc2cc(CS(C)(=N)=O)cc(C)n2)ncc1F]

(+)-2,2,2-Trifluoro-N-{[(2-{[5-fluoro-4-(4-fluoro-2-methoxyphenyl)pyridin-2-yl]amino}-6-methylpyridin-4-yl)methyl](methyl)-$λ^4$-sulfanylidene}acetamide (300 mg; 0.602 mmol; Intermediate 4.7) was dissolved in methanol (36.0 mL) and water (18.0 mL). At 0-5° C. the pH was adjusted to 9-10 with an aqueous potassium hydroxide solution (15%). At this temperature Oxone® (315.0 mg; 0.512 mmol) was added in several portions and the pH was held at 9-10. The mixture was stirred for 1 hour at 0-5° C. and the pH was held at 9-10.

The reaction mixture was adjusted with 2.0M hydrochloric acid to pH 6-7. Saturated aqueous sodium chloride solution was added and the reaction mixture was extracted three times with dichloromethane. The combined organic layers were washed with an aqueous sodium thiosulfate solution (10%), dried over magnesium sulfate and concentrated.

Five such batches were combined and purified by column chromatography on silica gel (gradient: dichloromethane to dichloromethane/ethanol 9:1) yielding the desired product (800 mg; 1.91 mmol). $[\alpha]_D^{20} = +11.4°$ (1.00, DMSO)

$^1$H-NMR (300 MHz, DMSO-$d_6$, 300 K): δ [ppm]=9.75 (s, 1H), 8.20-8.17 (m, 1H), 7.67 (d, 1H), 7.59-7.55 (m, 1H), 7.38-7.30 (m, 1H), 7.13-7.06 (m, 1H), 6.95-6.87 (m, 1H), 6.77 (s, 1H), 4.38-4.25 (m, 2H), 3.80 (s, 3H), 3.71 (s, 1H), 2.87 (s, 3H), 2.35 (s, 3H).

Alternative to Example 33

(−)-5-Fluoro-4-(4-fluoro-2-methoxyphenyl)-N-{6-methyl-4-[(S-methylsulfonimidoyl)methyl]pyridin-2-yl}pyridin-2-amine

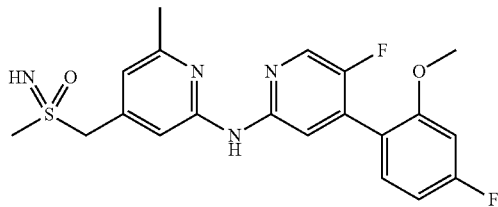

(−)-2,2,2-Trifluoro-N-{[(2-{[5-fluoro-4-(4-fluoro-2-methoxyphenyl)pyridin-2-yl]amino}-6-methylpyridin-4-yl)methyl](methyl)-$\lambda^4$-sulfanylidene}acetamide (296 mg; 0.594 mmol; Intermediate 4.8) was dissolved in methanol (35.5 mL) and water (17.8 mL). At 0-5° C. the pH adjusted to 9-10. with an aqueous potassium hydroxide solution (15%). At this temperature Oxone® (310.0 mg; 0.505 mmol) was added in several portions and the pH was held at 9-10. The mixture was stirred for 1 hour at 0-5° C. and the pH was held at 9-10.

The reaction mixture was adjusted with 2.0M hydrochloric acid to pH 6-7. Saturated aqueous sodium chloride solution was added and the reaction mixture was extracted three times with dichloromethane. The combined organic layers were washed with an aqueous sodium thiosulfate solution (10%), dried over magnesium sulfate and concentrated.

Five such batches were combined and purified by column chromatography on silica gel (gradient: dichloromethane to dichloromethane/ethanol 9:1) yielding the desired product (800 mg; 1.91 mmol). $[\alpha]_D^{20} = -14.0°$ (1.00, DMSO)

$^1$H-NMR (400 MHz, DMSO-$d_6$, 300 K): δ [ppm]=9.75 (s, 1H), 8.19 (d, 1H), 7.68 (d, 1H), 7.58 (s, 1H), 7.35 (dd, 1H), 7.09 (dd, 1H), 6.92 (dtr, 1H), 6.78 (s, 1H), 4.38-4.27 (m, 2H), 3.81 (s, 3H), 3.71 (s, 1H), 2.88 (s, 3H), 2.36 (s, 3H).

The following Table 1 provides an overview on the compounds described in the example section:

TABLE 1

| Example No. | Structure | Name of compound |
| --- | --- | --- |
| 1 | 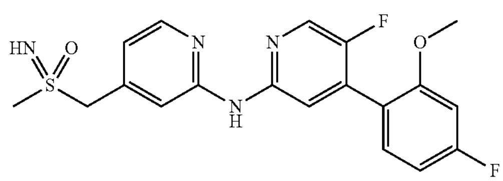 [SMILES: COc1cc(F)ccc1-c1cc(Nc2cc(CS(C)(=N)=O)ccn2)ncc1F] | (rac)-5-Fluoro-4-(4-fluoro-2-methoxyphenyl)-N-{4-[(S-methylsulfonimidoyl)methyl]pyridin-2-yl}pyridin-2-amine |
| 2 | 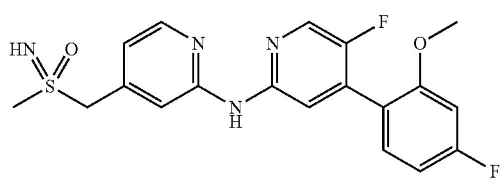 [SMILES: COc1cc(F)ccc1-c1cc(Nc2cc(CS(C)(=N)=O)ccn2)ncc1F] | (+)-5-Fluoro-4-(4-fluoro-2-methoxyphenyl)-N-{4-[(S-methylsulfonimidoyl)methyl]pyridin-2-yl}pyridin-2-amine |
| 3 | 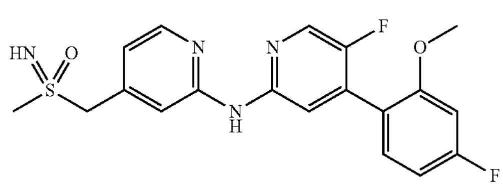 [SMILES: COc1cc(F)ccc1-c1cc(Nc2cc(CS(C)(=N)=O)ccn2)ncc1F] | (−)-5-Fluoro-4-(4-fluoro-2-methoxyphenyl)-N-{4-[(S-methylsulfonimidoyl)methyl]pyridin-2-yl}pyridin-2-amine |

TABLE 1-continued

| Example No. | Structure | Name of compound |
|---|---|---|
| 4 | 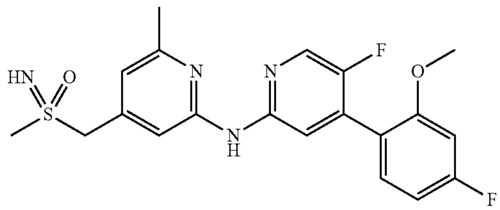 [SMILES: COc1cc(F)ccc1-c1cc(Nc2cc(CS(C)(=N)=O)cc(C)n2)ncc1F] | (rac)-5-Fluoro-4-(4-fluoro-2-methoxyphenyl)-N-{6-methyl-4-[(S-methylsulfonimidoyl)methyl]pyridin-2-yl}pyridin-2-amine |
| 5 | 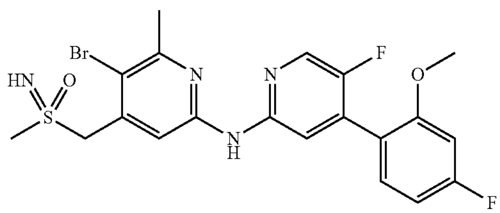 [SMILES: COc1cc(F)ccc1-c1cc(Nc2cc(CS(C)(=N)=O)c(Br)c(C)n2)ncc1F] | (rac)-5-Bromo-N-[5-fluoro-4-(4-fluoro-2-methoxyphenyl)pyridin-2-yl]-6-methyl-4-[(S-methylsulfonimidoyl)methyl]pyridin-2-amine |
| 6 | 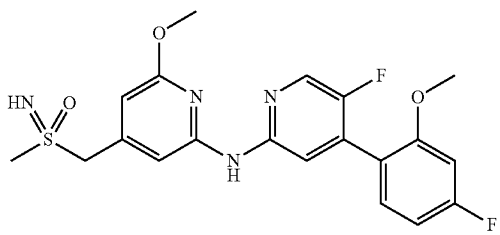 [SMILES: COc1cc(CS(C)(=N)=O)cc(Nc2cc(-c3ccc(F)cc3OC)c(F)cn2)n1] | (rac)-5-Fluoro-4-(4-fluoro-2-methoxyphenyl)-N-{6-methoxy-4-[(S-methylsulfonimidoyl)methyl]pyridin-2-yl}pyridin-2-amine |
| 7 | 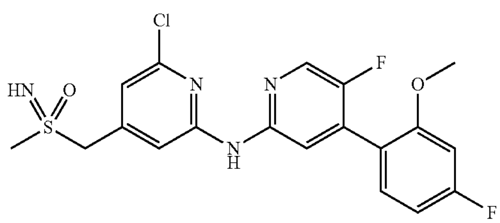 | (rac)-N-{6-Chloro-4-[(S-methylsulfonimidoyl)methyl]pyridin-2-yl}-5-fluoro-4-(4-fluoro-2-methoxyphenyl)pyridin-2-amine |
| 8 | 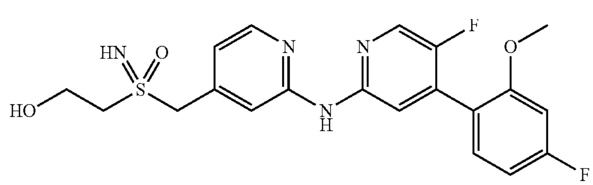 [SMILES: COc1cc(F)ccc1-c1cc(Nc2cc(CS(=N)(=O)CCO)ccn2)ncc1F] | (rac)-2-{S-[(2-{[5-Fluoro-4-(4-fluoro-2-methoxyphenyl)pyridin-2-yl]amino}pyridin-4-yl)methyl]sulfonimidoyl}ethanol |
| 9 | 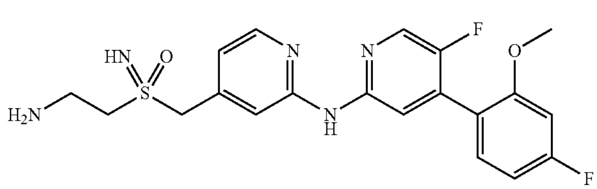 [SMILES: COc1cc(F)ccc1-c1cc(Nc2cc(CS(=N)(=O)CCN)ccn2)ncc1F] | (rac)-N-(4-{[S-(2-Aminoethyl)sulfonimidoyl]methyl}pyridin-2-yl)-5-fluoro-4-(4-fluoro-2-methoxyphenyl)pyridin-2-amine |
| 10 | 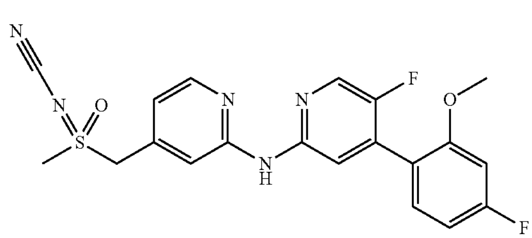 [SMILES: COc1cc(F)ccc1-c1cc(Nc2cc(CS(C)(=O)=NC#N)ccn2)ncc1F] | {[(2-{[5-Fluoro-4-(4-fluoro-2-methoxyphenyl)pyridin-2-yl]amino}pyridin-4-yl)methyl](methyl)oxido-$\lambda^6$-sulfanylidene}cyanamide(single stereoisomer); |

TABLE 1-continued

| Example No. | Structure | Name of compound |
|---|---|---|
| 11 | 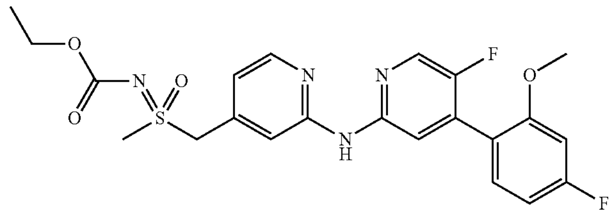 [SMILES: CCOC(=O)N=S(C)(=O)Cc1ccnc(Nc2cc(-c3ccc(F)cc3OC)c(F)cn2)c1] | (rac)-Ethyl {[(2-{[5-fluoro-4-(4-fluoro-2-methoxyphenyl)pyridin-2-yl]amino}pyridin-4-yl)methyl](methyl)oxido-$\lambda^6$-sulfanylidene}carbamate |
| 12 | 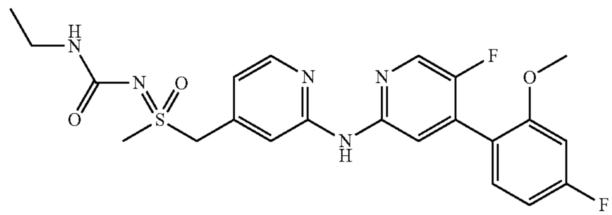 [SMILES: CCNC(=O)N=S(C)(=O)Cc1ccnc(Nc2cc(-c3ccc(F)cc3OC)c(F)cn2)c1] | (rac)-1-Ethyl-3-{[(2-{[5-fluoro-4-(4-fluoro-2-methoxyphenyl)pyridin-2-yl]amino}pyridin-4-yl)methyl](methyl)oxido-$\lambda^6$-sulfanylidene}urea |
| 13 | 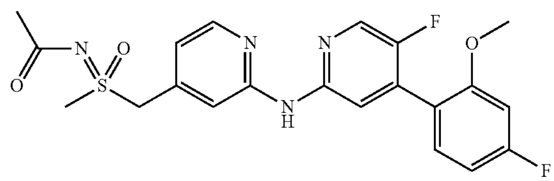 [SMILES: COc1cc(F)ccc1-c1cc(Nc2cc(CS(C)(=O)=NC(C)=O)ccn2)ncc1F] | (rac)-N-{[(2-{[5-Fluoro-4-(4-fluoro-2-methoxyphenyl)pyridin-2-yl]amino}pyridin-4-yl)methyl](methyl)oxido-$\lambda^6$-sulfanylidene}acetamide |
| 14 | 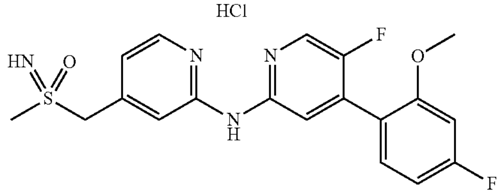 [SMILES: Cl ; COc1cc(F)ccc1-c1cc(Nc2cc(CS(C)(=N)=O)ccn2)ncc1F] | 5-Fluoro-4-(4-fluoro-2-methoxyphenyl)-N-{4-[(S-methylsulfonimidoyl)methyl]pyridin-2-yl}pyridin-2-amine hydrochloride; enantiomer 2 |
| 15 | 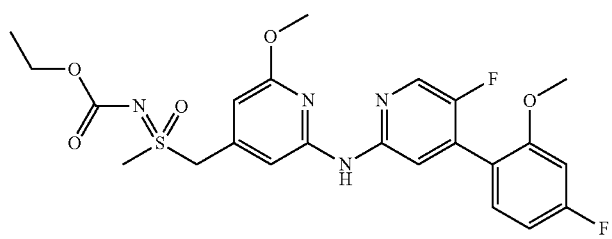 [SMILES: CCOC(=O)N=S(C)(=O)Cc1cc(Nc2cc(-c3ccc(F)cc3OC)c(F)cn2)nc(OC)c1] | (rac)-Ethyl {[(2-{[5-fluoro-4-(4-fluoro-2-methoxyphenyl)pyridin-2-yl]amino}-6-methoxypyridin-4-yl)methyl](methyl)oxido-$\lambda^6$-sulfanylidene}carbamate |
| 16 | 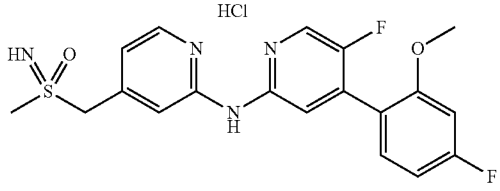 [SMILES: Cl ; COc1cc(F)ccc1-c1cc(Nc2cc(CS(C)(=N)=O)ccn2)ncc1F] | 5-Fluoro-4-(4-fluoro-2-methoxyphenyl)-N-{4-[(S-methylsulfonimidoyl)methyl]pyridin-2-yl}pyridin-2-amine hydrochloride; enantiomer 1 |
| 17 | 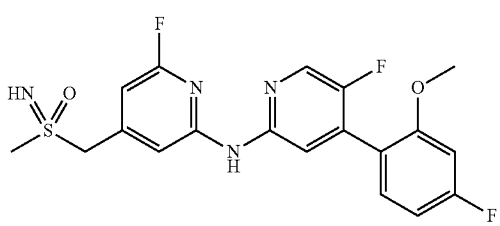 | (rac)-5-Fluoro-4-(4-fluoro-2-methoxyphenyl)-N-{6-fluoro-4-[(S-methylsulfonimidoyl)methyl]pyridin-2-yl}pyridin-2-amine |

TABLE 1-continued

| Example No. | Structure | Name of compound |
|---|---|---|
| 18 | 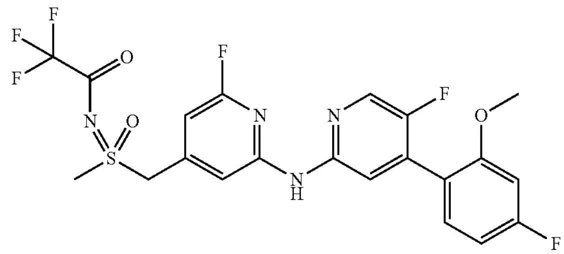 [SMILES: COc1cc(F)ccc1-c1cc(Nc2cc(CS(C)(=O)=NC(=O)C(F)(F)F)cc(F)n2)ncc1F] | (rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)oxido-$\lambda^6$-sulfanylidene}acetamide |
| 19 | 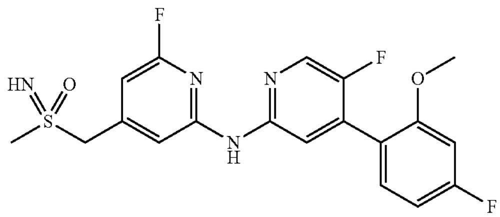 [SMILES: COc1cc(F)ccc1-c1cc(Nc2cc(CS(C)(=N)=O)cc(F)n2)ncc1F] | (+)-5-Fluoro-4-(4-fluoro-2-methoxyphenyl)-N-{6-fluoro-4-[(S-methylsulfonimidoyl)methyl]pyridin-2-yl}pyridin-2-amine |
| 20 | 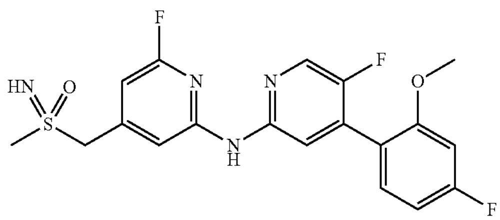 [SMILES: COc1cc(F)ccc1-c1cc(Nc2cc(CS(C)(=N)=O)cc(F)n2)ncc1F] | (−)-5-Fluoro-4-(4-fluoro-2-methoxyphenyl)-N-{6-fluoro-4-[(S-methylsulfonimidoyl)methyl]pyridin-2-yl}pyridin-2-amine |
| 21 | 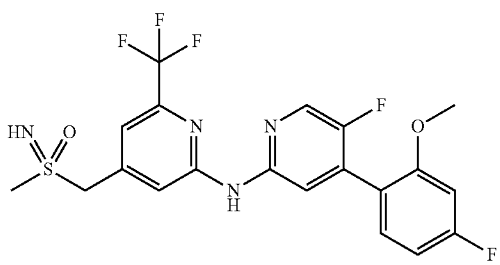 [SMILES: COc1cc(F)ccc1-c1cc(Nc2cc(CS(C)(=N)=O)cc(C(F)(F)F)n2)ncc1F] | (rac)-5-Fluoro-4-(4-fluoro-2-methoxyphenyl)-N-{4-[(S-methylsulfonimidoyl)methyl]-6-(trifluoromethyl)pyridin-2-yl}pyridin-2-amine |
| 22 | 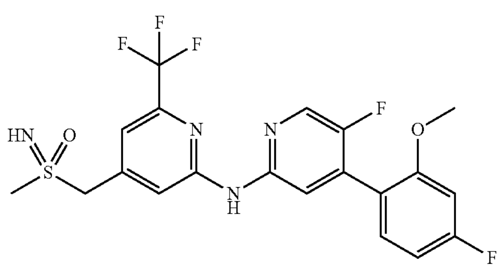 [SMILES: COc1cc(F)ccc1-c1cc(Nc2cc(CS(C)(=N)=O)cc(C(F)(F)F)n2)ncc1F] | (+)-5-Fluoro-4-(4-fluoro-2-methoxyphenyl)-N-{4-[(S-methylsulfonimidoyl)methyl]-6-(trifluoromethyl)pyridin-2-yl}pyridin-2-amine |
| 23 | 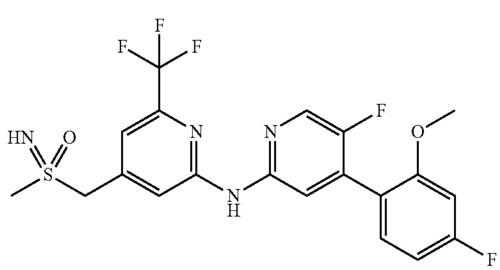 [SMILES: COc1cc(F)ccc1-c1cc(Nc2cc(CS(C)(=N)=O)cc(C(F)(F)F)n2)ncc1F] | (−)-5-Fluoro-4-(4-fluoro-2-methoxyphenyl)-N-{4-[(S-methylsulfonimidoyl)methyl]-6-(trifluoromethyl)pyridin-2-yl}pyridin-2-amine |

TABLE 1-continued

| Example No. | Structure | Name of compound |
|---|---|---|
| 24 | 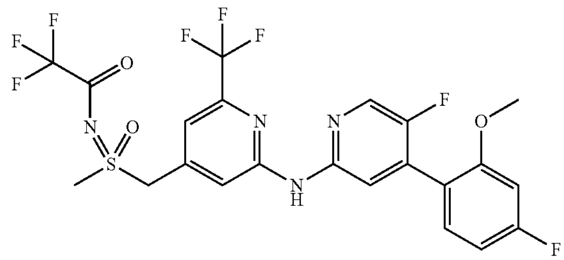 [SMILES: COc1cc(F)ccc1-c1cc(Nc2cc(CS(C)(=O)=NC(=O)C(F)(F)F)cc(C(F)(F)F)n2)ncc1F] | (+)-2,2,2-Trifluoro-N-[{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide |
| 25 | 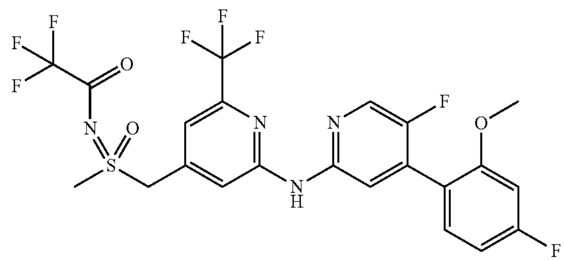 [SMILES: COc1cc(F)ccc1-c1cc(Nc2cc(CS(C)(=O)=NC(=O)C(F)(F)F)cc(C(F)(F)F)n2)ncc1F] | (−)-2,2,2-Trifluoro-N-{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide |
| 26 | 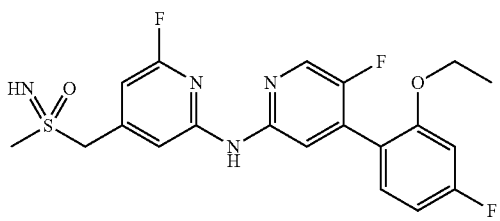 | (rac)-4-(2-Ethoxy-4-fluorophenyl)-5-fluoro-N-{6-fluoro-4-[(S-methylsulfonimidoyl)methyl]pyridin-2-yl}pyridin-2-amine |
| 27 | 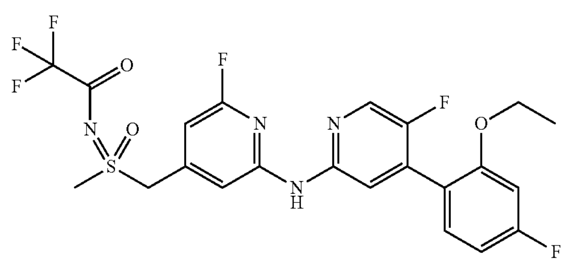 [SMILES: CCOc1cc(F)ccc1-c1cc(Nc2cc(CS(C)(=O)=NC(=O)C(F)(F)F)cc(F)n2)ncc1F] | (rac)-N-{[(2-{[4-(2-Ethoxy-4-fluorophenyl)-5-fluoropyridin-2-yl]amino}-6-fluoropyridin-4-yl)methyl]-(methyl)oxido-$\lambda^6$-sulfanylidene}-2,2,2-trifluoroacetamide |
| 28 | 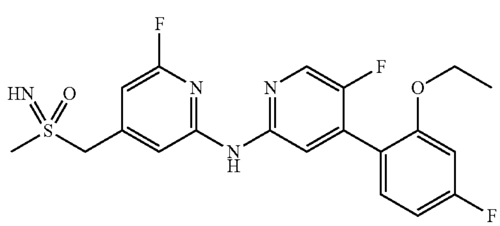 [SMILES: CCOc1cc(F)ccc1-c1cc(Nc2cc(CS(C)(=N)=O)cc(F)n2)ncc1F] | (+)-4-(2-Ethoxy-4-fluorophenyl)-5-fluoro-N-{6-fluoro-4-[(S-methylsulfonimidoyl)methyl]pyridin-2-yl}pyridin-2-amine |
| 29 | 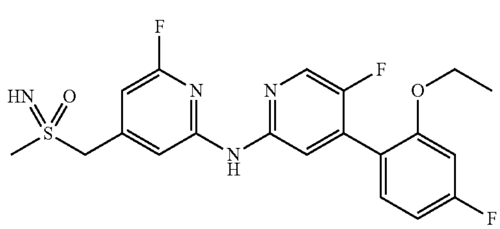 [SMILES: CCOc1cc(F)ccc1-c1cc(Nc2cc(CS(C)(=N)=O)cc(F)n2)ncc1F] | (−)-4-(2-Ethoxy-4-fluorophenyl)-5-fluoro-N-{6-fluoro-4-[(S-methylsulfonimidoyl)methyl]pyridin-2-yl}pyridin-2-amine |

TABLE 1-continued

| Example No. | Structure | Name of compound |
|---|---|---|
| 30 | 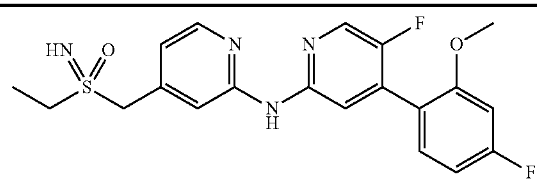 | (rac)-N-{4-[(S-Ethylsulfonimidoyl)-methyl]pyridin-2-yl}-5-fluoro-4-(4-fluoro-2-methoxyphenyl)pyridin-2-amine |
| 31 | 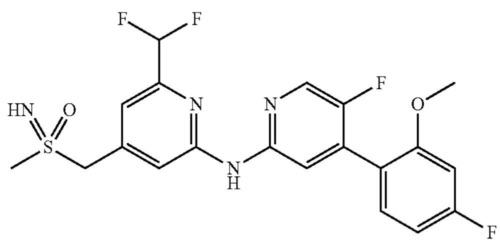 [SMILES: COc1cc(F)ccc1-c1cc(Nc2cc(CS(C)(=N)=O)cc(C(F)F)n2)ncc1F] | (rac)-N-{6-(Difluoromethyl)-4-[(S-methylsulfonimidoyl)methyl]pyridin-2-yl}-5-fluoro-4-(4-fluoro-2-methoxyphenyl)pyridin-2-amine |
| 32 | 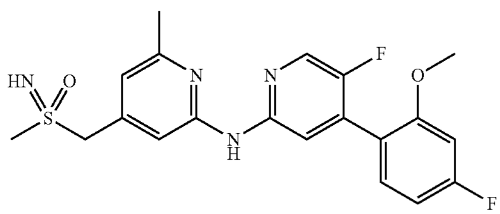 [SMILES: COc1cc(F)ccc1-c1cc(Nc2cc(CS(C)(=N)=O)cc(C)n2)ncc1F] | (+)-5-Fluoro-4-(4-fluoro-2-methoxyphenyl)-N-{6-methyl-4-[(S-methylsulfonimidoyl)methyl]pyridin-2-yl}pyridin-2-amine |
| 33 | 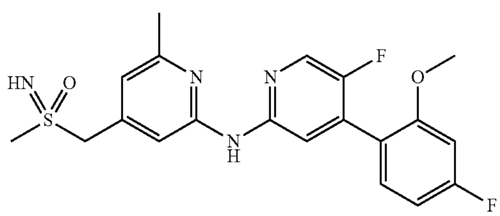 [SMILES: COc1cc(F)ccc1-c1cc(Nc2cc(CS(C)(=N)=O)cc(C)n2)ncc1F] | (−)-5-Fluoro-4-(4-fluoro-2-methoxyphenyl)-N-{6-methyl-4-[(S-methylsulfonimidoyl)methyl]pyridin-2-yl}pyridin-2-amine |

Results:

Table 2: Inhibition for CDK9 and CDK2 of compounds according to the present invention The $IC_{50}$ (inhibitory concentration at 50% of maximal effect) values are indicated in nM, "n.t." means that the compounds have not been tested in this assay.

①: Example Number

②: CDK9: CDK9/CycT1 kinase assay as described under Method 1a. of Materials and Methods ③: CDK2: CDK2/CycE kinase assay as described under Method 2. of Materials and Methods ④: high ATP CDK9: CDK9/CycT1 kinase assay as described under Method 1b. of Materials and Methods ⑤: high CDK2: CDK2/CycE kinase assay as described under Method 2b. of Materials and Methods

TABLE 2

| ① | Structure | ② | ③ | ④ | ⑤ |
|---|---|---|---|---|---|
| 1 | 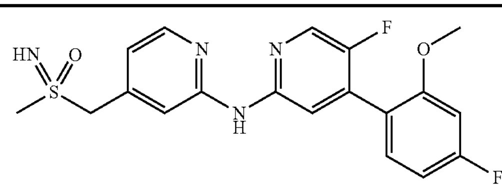 | 4 | 410 | 10 | 5860 |
| 2 | 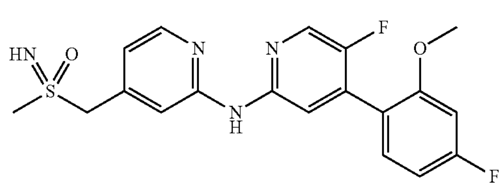 [SMILES: COc1cc(F)ccc1-c1cc(Nc2cc(CS(C)(=N)=O)ccn2)ncc1F] | 3 | 360 | 4 | 2920 |

| ① | Structure | ② | ③ | ④ | ⑤ |
|---|---|---|---|---|---|
| 3 | 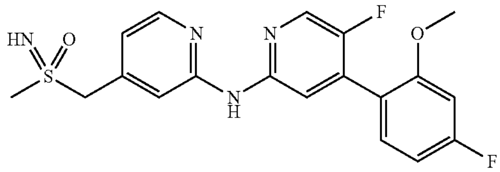 [SMILES: COc1cc(F)ccc1-c1cc(Nc2cc(CS(C)(=N)=O)ccn2)ncc1F] | 2 | 240 | 3 | 2490 |
| 4 | 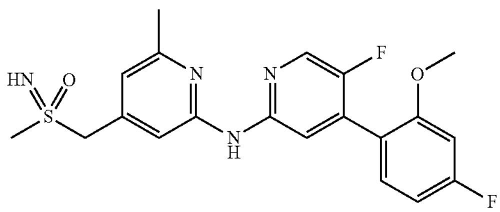 [SMILES: COc1cc(F)ccc1-c1cc(Nc2cc(CS(C)(=N)=O)cc(C)n2)ncc1F] | 4 | 120 | 2 | 1010 |
| 5 | 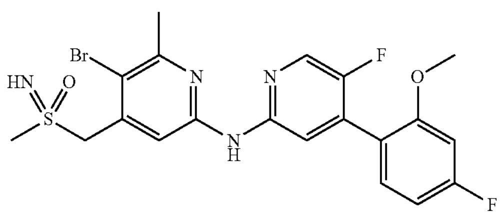 [SMILES: COc1cc(F)ccc1-c1cc(Nc2cc(CS(C)(=N)=O)c(Br)c(C)n2)ncc1F] | 5 | 140 | 3 | 1770 |
| 6 | 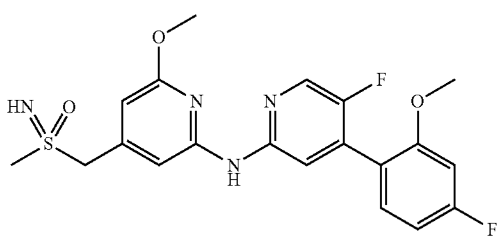 [SMILES: COc1cc(CS(C)(=N)=O)cc(Nc2cc(-c3ccc(F)cc3OC)c(F)cn2)n1] | 2 | 4 | 1 | 84 |
| 7 | 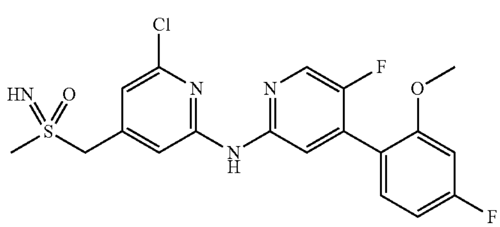 | 2 | 44 | 2 | 630 |
| 8 | 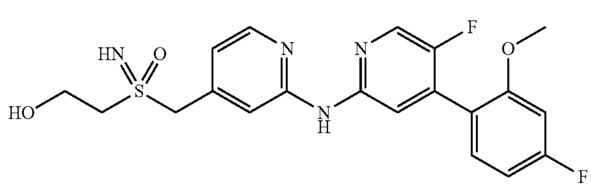 [SMILES: COc1cc(F)ccc1-c1cc(Nc2cc(CS(=N)(=O)CCO)ccn2)ncc1F] | 13 | 430 | 14 | 4190 |
| 9 | 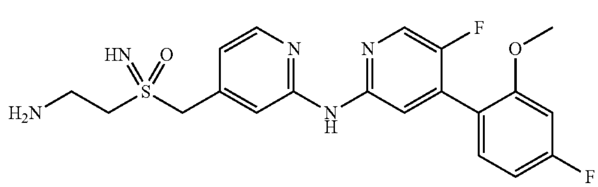 [SMILES: COc1cc(F)ccc1-c1cc(Nc2cc(CS(=N)(=O)CCN)ccn2)ncc1F] | 8 | 240 | 6 | 4230 |

TABLE 2-continued

| ① | Structure | ② | ③ | ④ | ⑤ |
|---|---|---|---|---|---|
| 10 | [structure] | 4 | 72 | 1 | 1420 |
| 11 | [structure] | 1 | 170 | 1 | 2920 |
| 12 | [structure] | 2 | 140 | 2 | 3070 |
| 13 | [structure] | 1 | 130 | 1 | 3690 |
| 14 | [structure] | 3 | 200 | 1 | 3410 |
| 15 | [structure] | 2 | 10 | 1 | 123 |
| 16 | [structure] | 3 | 430 | 8 | 5150 |

TABLE 2-continued

| ① | Structure | ② | ③ | ④ | ⑤ |
|---|---|---|---|---|---|
| 17 | 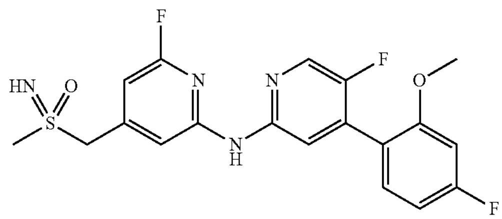 [SMILES: COc1cc(F)ccc1-c1cc(Nc2cc(CS(C)(=N)=O)cc(F)n2)ncc1F] | 0.9 | 49 | 1.8 | 886 |
| 18 | 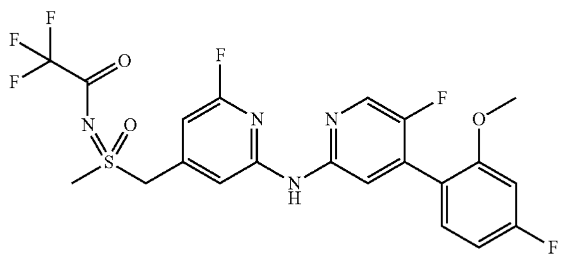 [SMILES: COc1cc(F)ccc1-c1cc(Nc2cc(CS(C)(=O)=NC(=O)C(F)(F)F)cc(F)n2)ncc1F] | 3 | 39 | 4 | n.t. |
| 19 | 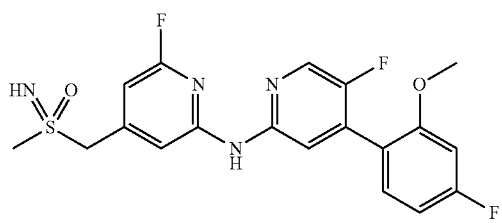 [SMILES: COc1cc(F)ccc1-c1cc(Nc2cc(CS(C)(=N)=O)cc(F)n2)ncc1F] | 5 | 94 | 19 | 1370 |
| 20 | 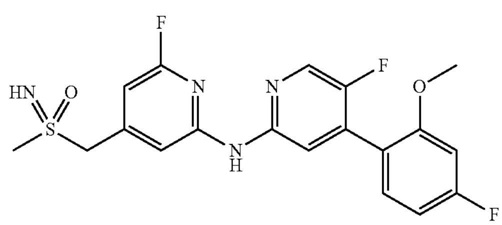 [SMILES: COc1cc(F)ccc1-c1cc(Nc2cc(CS(C)(=N)=O)cc(F)n2)ncc1F] | 2 | 72 | 1 | 815 |
| 21 | 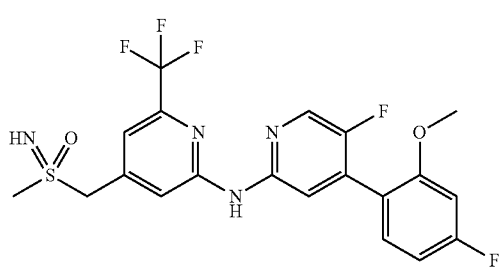 [SMILES: COc1cc(F)ccc1-c1cc(Nc2cc(CS(C)(=N)=O)cc(C(F)(F)F)n2)ncc1F] | 2 | 11 | 2 | 133 |
| 22 | 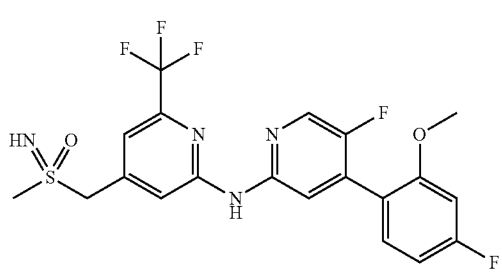 [SMILES: COc1cc(F)ccc1-c1cc(Nc2cc(CS(C)(=N)=O)cc(C(F)(F)F)n2)ncc1F] | 2 | 18 | 1 | 233 |

TABLE 2-continued

| ① | Structure | ② | ③ | ④ | ⑤ |
|---|---|---|---|---|---|
| 23 | 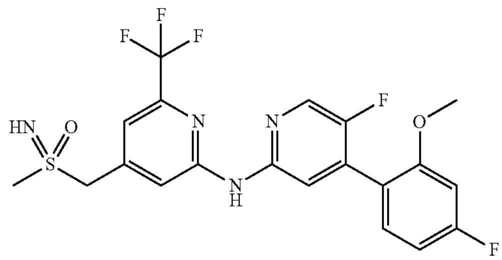 [SMILES: COc1cc(F)ccc1-c1cc(Nc2cc(CS(C)(=N)=O)cc(C(F)(F)F)n2)ncc1F] | 2 | 22 | 2 | 283 |
| 24 | 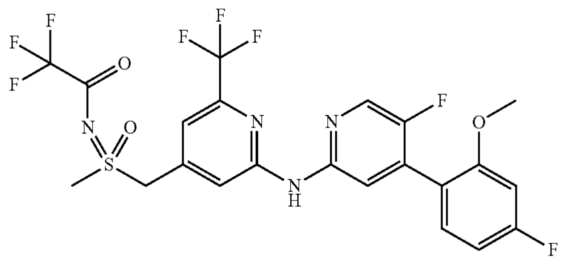 [SMILES: COc1cc(F)ccc1-c1cc(Nc2cc(CS(C)(=O)=NC(=O)C(F)(F)F)cc(C(F)(F)F)n2)ncc1F] | 18 | 250 | 27 | 4000 |
| 25 | 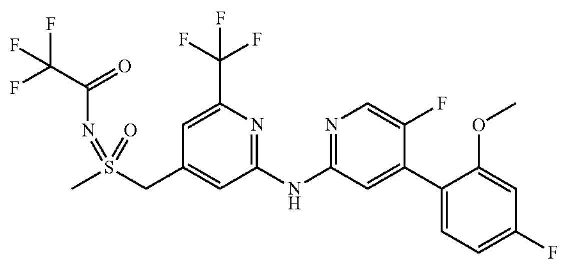 [SMILES: COc1cc(F)ccc1-c1cc(Nc2cc(CS(C)(=O)=NC(=O)C(F)(F)F)cc(C(F)(F)F)n2)ncc1F] | 15 | 110 | 13 | 2640 |
| 26 | 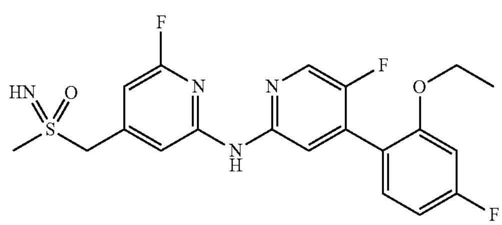 [SMILES: CCOc1cc(F)ccc1-c1cc(Nc2cc(CS(C)(=N)=O)cc(F)n2)ncc1F] | 3 | 110 | 4 | 1200 |
| 27 | 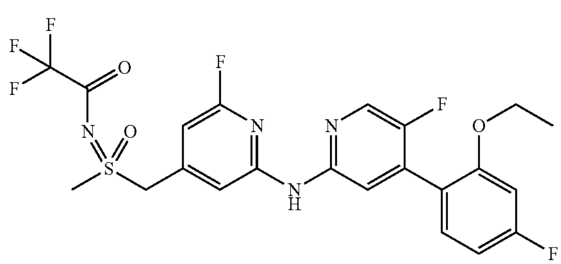 [SMILES: CCOc1cc(F)ccc1-c1cc(Nc2cc(CS(C)(=O)=NC(=O)C(F)(F)F)cc(F)n2)ncc1F] | 9 | 1200 | 22 | 20000 |
| 28 | 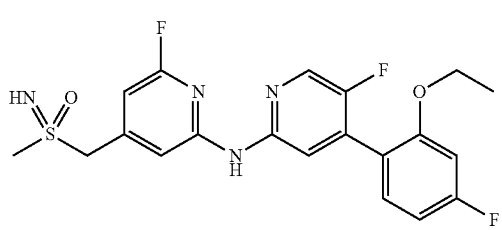 [SMILES: CCOc1cc(F)ccc1-c1cc(Nc2cc(CS(C)(=N)=O)cc(F)n2)ncc1F] | 5 | 120 | 4 | 1170 |

TABLE 2-continued

| ① Example | Structure | ② | ③ | ④ | ⑤ |
|---|---|---|---|---|---|
| 29 | (structure) | 3 | 98 | 4 | 1710 |
| 30 | (structure) | 3 | 210 | 5 | 300 |
| 31 | (structure) | 3 | 10 | 1 | 229 |
| 32 | (structure) | n.t. | 120 | 2 | 1120 |
| 33 | (structure) | n.t. | 67 | 1 | 680 |

Tables 3a and 3b: Inhibition of proliferation of HeLa, HeLa-MaTu-ADR, NCI-H460, DU145, Caco-2, B16F10, A2780 and MOLM-13 cells by compounds according to the present invention, determined as described under Method 3. of Materials and Methods. All $IC_{50}$ (inhibitory concentration at 50% of maximal effect) values are indicated in nM, "n.t." means that the compounds have not been tested in this assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation
⑨: Inhibition of MOLM-13 cell proliferation

TABLE 3a

Indications represented by cell lines

| Cell line | Source | Indication |
|---|---|---|
| HeLa | ATCC | Human cervical tumour |
| NCI-H460 | ATCC | Human non-small cell lung carcinoma |
| A2780 | ECACC | Human ovarian carcinoma |
| DU 145 | ATCC | Hormone-independent human prostate carcinoma |
| HeLa-MaTu-ADR | EPO-GmbH Berlin | Multidrug-resistant human cervical carcinoma |

TABLE 3a-continued

Indications represented by cell lines

| Cell line | Source | Indication |
|---|---|---|
| Caco-2 | ATCC | Human colorectal carcinoma |
| B16F10 | ATCC | Mouse melanoma |
| MOLM-13 | DSMZ | Human acute myeloid leukemia |

TABLE 3b

Inhibition of proliferation

| ① | Structure | ② | ③ | ④ | ⑤ | ⑥ | ⑦ | ⑧ | ⑨ |
|---|---|---|---|---|---|---|---|---|---|
| 1 | 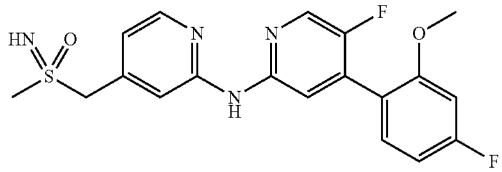 [SMILES: COc1cc(F)ccc1-c1cc(Nc2cc(CS(C)(=N)=O)ccn2)ncc1F] | 95 | 61 | 62 | 37 | 45 | 110 | 26 | 19 |
| 2 | 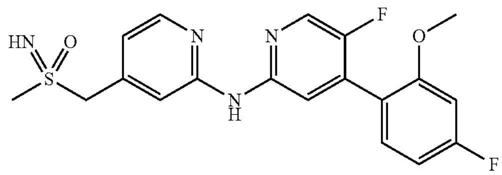 [SMILES: COc1cc(F)ccc1-c1cc(Nc2cc(CS(C)(=N)=O)ccn2)ncc1F] | 110 | 33 | 75 | 33 | 62 | 240 | 110 | 29 |
| 3 | 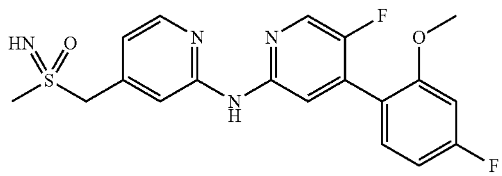 [SMILES: COc1cc(F)ccc1-c1cc(Nc2cc(CS(C)(=N)=O)ccn2)ncc1F] | 100 | 37 | 65 | 37 | 58 | 310 | 52 | 40 |
| 4 | 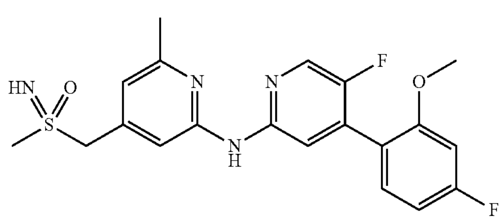 [SMILES: COc1cc(F)ccc1-c1cc(Nc2cc(CS(C)(=N)=O)cc(C)n2)ncc1F] | 35 | 34 | 97 | 67 | 68 | 100 | 37 | 35 |
| 5 | 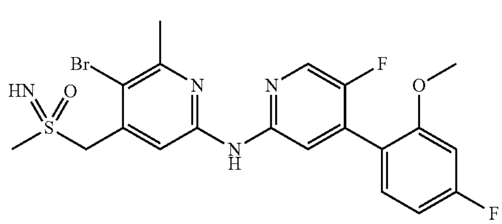 [SMILES: COc1cc(F)ccc1-c1cc(Nc2cc(CS(C)(=N)=O)c(Br)c(C)n2)ncc1F] | 93 | n.t. | 120 | 110 | 110 | 120 | n.t. | n.t. |
| 6 | 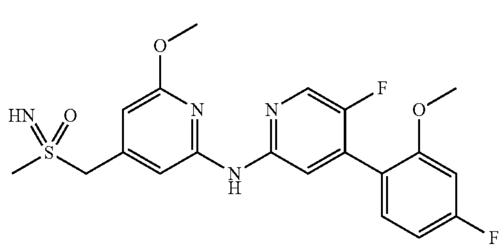 [SMILES: COc1cc(CS(C)(=N)=O)cc(Nc2cc(-c3ccc(F)cc3OC)c(F)cn2)n1] | 21 | 30 | 33 | 30 | 31 | 33 | 11 | 11 |

TABLE 3b-continued

Inhibition of proliferation

| ① | Structure | ② | ③ | ④ | ⑤ | ⑥ | ⑦ | ⑧ | ⑨ |
|---|-----------|---|---|---|---|---|---|---|---|
| 7 | 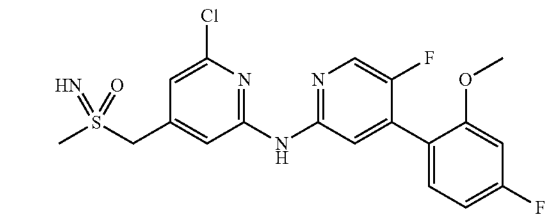 | 32 | 32 | 47 | 37 | 41 | 34 | 27 | 28 |
| 8 | 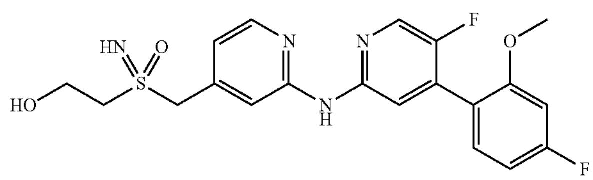 [SMILES: COc1cc(F)ccc1-c1cc(Nc2cc(CS(=N)(=O)CCO)ccn2)ncc1F] | 140 | 200 | 290 | 110 | 160 | 186 | 45 | 55 |
| 9 | 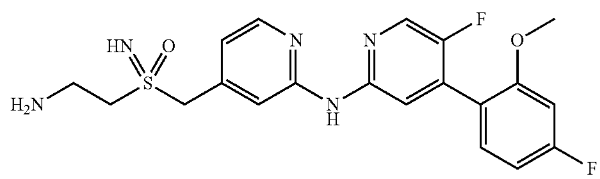 [SMILES: COc1cc(F)ccc1-c1cc(Nc2cc(CS(=N)(=O)CCN)ccn2)ncc1F] | 410 | n.t. | n.t. | n.t. | n.t. | n.t. | 210 | 120 |
| 10 | 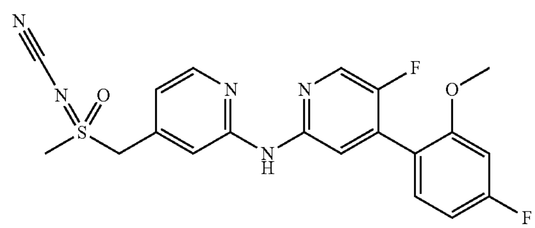 [SMILES: COc1cc(F)ccc1-c1cc(Nc2cc(CS(C)(=O)=NC#N)ccn2)ncc1F] | 31 | 32 | 39 | 34 | 38 | 63 | 10 | 12 |
| 11 | 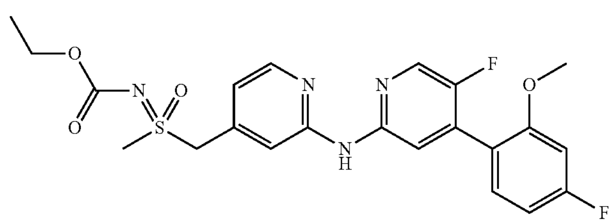 [SMILES: CCOC(=O)N=S(C)(=O)Cc1ccnc(Nc2cc(-c3ccc(F)cc3OC)c(F)cn2)c1] | 72 | 100 | 110 | 110 | 110 | 180 | 23 | 42 |
| 12 | 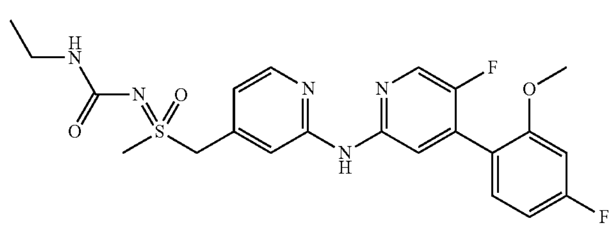 [SMILES: CCNC(=O)N=S(C)(=O)Cc1ccnc(Nc2cc(-c3ccc(F)cc3OC)c(F)cn2)c1] | 34 | 100 | 100 | 77 | 98 | 130 | 26 | 29 |
| 13 | 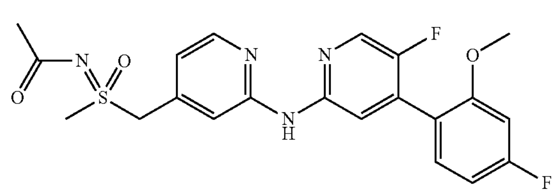 [SMILES: COc1cc(F)ccc1-c1cc(Nc2cc(CS(C)(=O)=NC(C)=O)ccn2)ncc1F] | 100 | 110 | 110 | 110 | 120 | 180 | 23 | 29 |

TABLE 3b-continued

Inhibition of proliferation

| ① | Structure | ② | ③ | ④ | ⑤ | ⑥ | ⑦ | ⑧ | ⑨ |
|---|---|---|---|---|---|---|---|---|---|
| 14 | (structure with HCl) | 42 | 46 | 30 | 33 | 37 | 73 | n.t. | n.t. |
| 15 | (structure) | 40 | 31 | 32 | 31 | 39 | 45 | n.t. | n.t. |
| 16 | (structure with HCl) | 63 | 110 | 130 | 120 | 120 | 150 | n.t. | n.t. |
| 17 | (structure) | 46 | 33 | 45 | 48 | 57 | 67 | 14 | 20 |
| 18 | (structure) | 61 | 35 | 110 | 41 | 43 | 68 | n.t. | n.t. |
| 19 | (structure) | n.t. | 64 | 110 | 58 | n.t. | 95. | n.t. | n.t. |
| 20 | (structure) | 30 | 38 | 100 | 58 | 45 | 54 | n.t. | n.t. |

TABLE 3b-continued
| ① | Structure | ② | ③ | ④ | ⑤ | ⑥ | ⑦ | ⑧ | ⑨ |
|---|---|---|---|---|---|---|---|---|---|
| 21 | 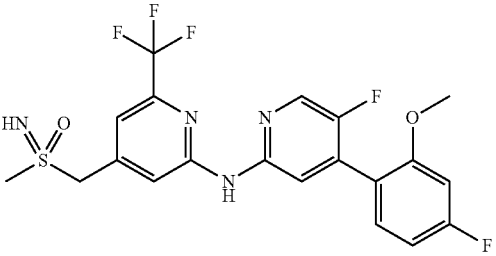 [SMILES: COc1cc(F)ccc1-c1cc(Nc2cc(CS(C)(=N)=O)cc(C(F)(F)F)n2)ncc1F] | 29 | 30 | 33 | 30 | 32 | 38 | 17 | 17 |
| 22 | 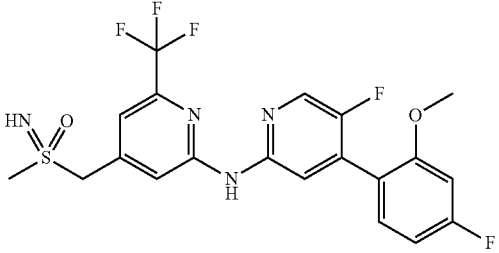 [SMILES: COc1cc(F)ccc1-c1cc(Nc2cc(CS(C)(=N)=O)cc(C(F)(F)F)n2)ncc1F] | 30 | 30 | 34 | 32 | 38 | 51 | 12 | 10 |
| 23 | 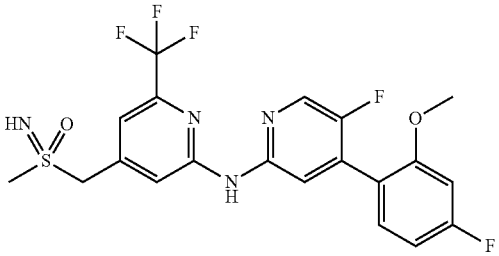 [SMILES: COc1cc(F)ccc1-c1cc(Nc2cc(CS(C)(=N)=O)cc(C(F)(F)F)n2)ncc1F] | 30 | 30 | 35 | 34 | 34 | 47 | 11 | 10 |
| 24 | 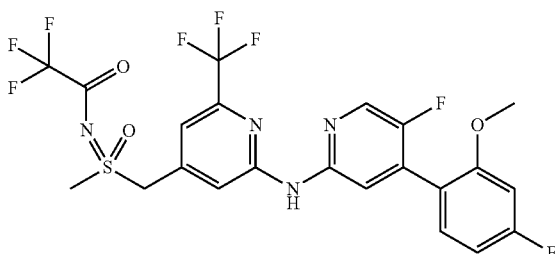 | 32 | 30 | 33 | 33 | 41 | 43 | n.t. | n.t. |
| 25 | 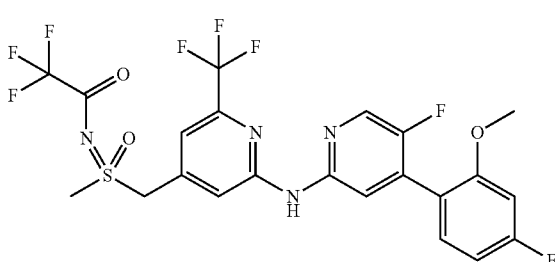 | 35 | 30 | 36 | 37 | 45 | 50 | n.t. | n.t. |
| 26 | 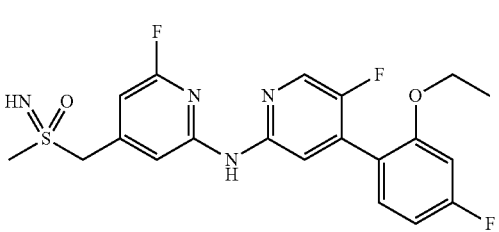 [SMILES: CCOc1cc(F)ccc1-c1cc(Nc2cc(CS(C)(=N)=O)cc(F)n2)ncc1F] | 43 | 49 | 120 | 110 | 86 | 150 | 36 | 44 |

TABLE 3b-continued
| ① | Structure | ② | ③ | ④ | ⑤ | ⑥ | ⑦ | ⑧ | ⑨ |
|---|---|---|---|---|---|---|---|---|---|
| 27 | 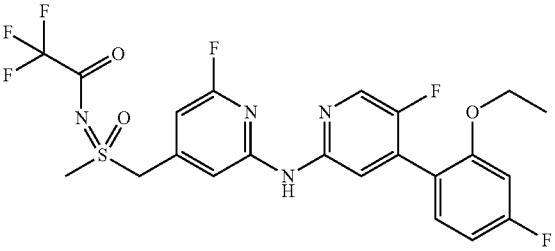 [SMILES: CCOc1cc(F)ccc1-c1cc(Nc2cc(CS(C)(=O)=NC(=O)C(F)(F)F)cc(F)n2)ncc1F] | 100 | 110 | 120 | 110 | 130 | 150 | n.t. | n.t. |
| 28 | 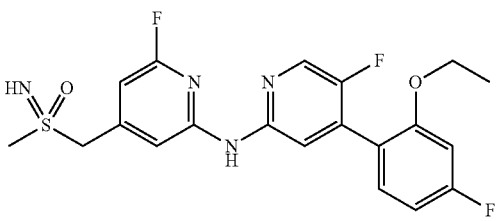 [SMILES: CCOc1cc(F)ccc1-c1cc(Nc2cc(CS(C)(=N)=O)cc(F)n2)ncc1F] | 99 | 120 | 190 | 120 | 120 | 150 | n.t. | n.t. |
| 29 | 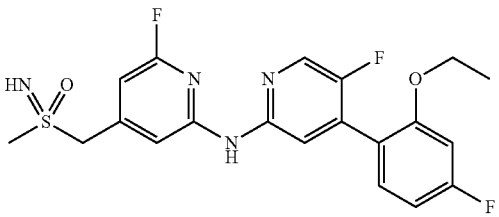 [SMILES: CCOc1cc(F)ccc1-c1cc(Nc2cc(CS(C)(=N)=O)cc(F)n2)ncc1F] | 110 | 81 | 150 | 110 | 100 | 110 | n.t. | n.t. |
| 30 | 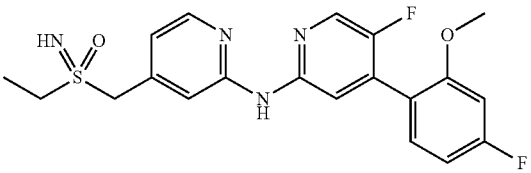 [SMILES: CCS(=N)(=O)Cc1ccnc(Nc2cc(-c3ccc(F)cc3OC)c(F)cn2)c1] | 100 | 74 | 120 | 82 | 52 | 120 | n.t. | n.t. |
| 31 | 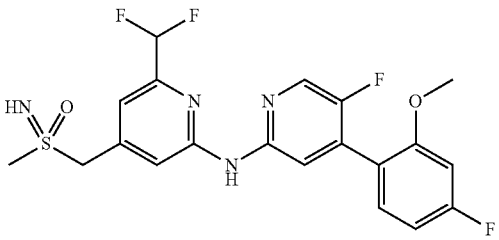 [SMILES: COc1cc(F)ccc1-c1cc(Nc2cc(CS(C)(=N)=O)cc(C(F)F)n2)ncc1F] | 8 | n.t. | n.t. | n.t. | n.t. | n.t. | n.t. | n.t. |
| 32 | 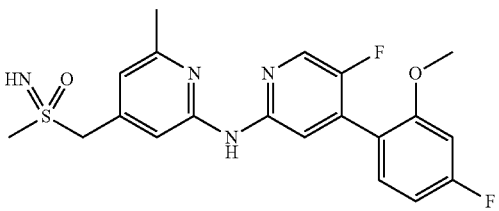 [SMILES: COc1cc(F)ccc1-c1cc(Nc2cc(CS(C)(=N)=O)cc(C)n2)ncc1F] | 31 | 53 | 100 | 38 | 40 | 98 | 10 | 17 |

TABLE 3b-continued

Inhibition of proliferation

| ① | Structure | ② | ③ | ④ | ⑤ | ⑥ | ⑦ | ⑧ | ⑨ |
|---|---|---|---|---|---|---|---|---|---|
| 33 | [structure] | 19 | 27 | 30 | 31 | 30 | 54 | 10 | 23 |

Table 4: Thermodynamic solubility of compounds according to the present invention in water at pH 6.5 and in aqueous Citrate buffer solution at pH 4, which is a clinical standard formulation for iv application, as determined by the equilibrium shake flask method described under Method 4. of Materials and Methods.

①: Example Number

②: Solubility in water at pH 6.5 in mg/l.

③: Solubility in mg/l in aqueous Citrate buffer pH4

| ① | Structure of compound | ② | ③ |
|---|---|---|---|
| 1 | [structure] | 13 | 489 |
| 2 | [structure] | 25 | n.t. |
| 3 | [structure] | 27 | 699 |
| 4 | [structure] | n.t. | 470 |
| 8 | [structure] | n.t. | 730 |

-continued
| ① | Structure of compound | ② | ③ |
|---|---|---|---|
| 9 | 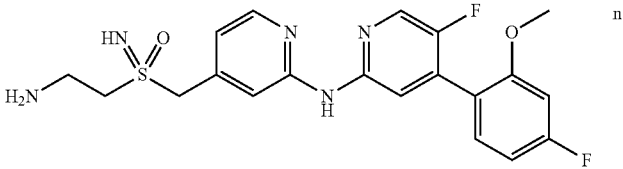 | n.t. | 660 |
| 10 | 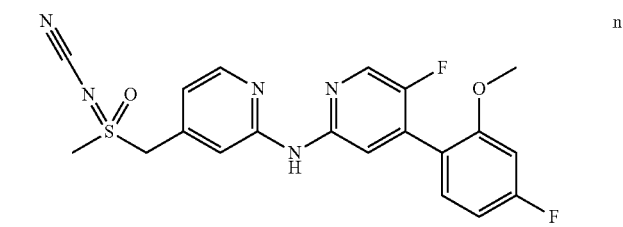 | n.t. | 102 |
| 11 | 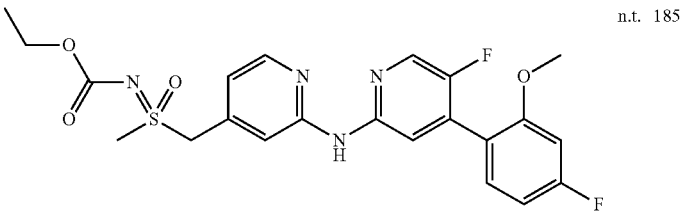 | n.t. | 185 |
| 12 | 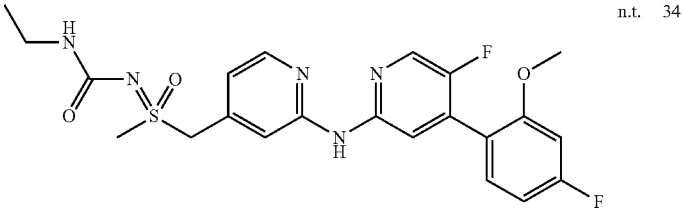 | n.t. | 34 |
| 14 | 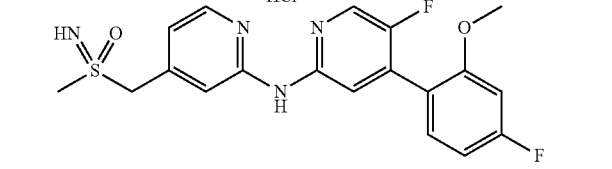 [SMILES: COc1cc(F)ccc1-c1cc(Nc2cc(CS(C)(=N)=O)ccn2)ncc1F] | n.t. | 600 |
| 17 | 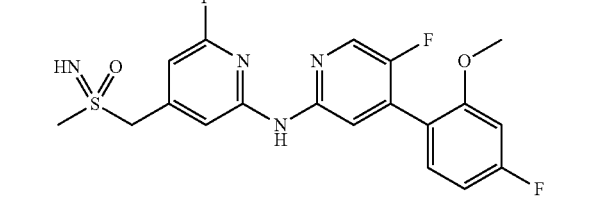 | n.t. | 3 |
| 22 | 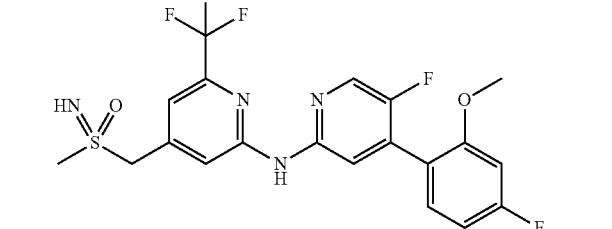 | n.t. | 52 |

-continued

| ① | Structure of compound | ② | ③ |
|---|---|---|---|
| 23 | (structure) | n.t. | 45 |

Table 5: Caco-2 permeation of compounds according to the present invention, determined as described under Method 5. of Materials and Methods.
①: Example Number
②: Concentration of test compound indicated in μM.
③: $P_{app}$ A-B ($M_{ari}$) indicated in [nm/s]
④: $P_{app}$ B-A ($M_{ari}$) indicated in [nm/s]
⑤: Efflux ratio

TABLE 5

| ① | Structure of compound | ② | ③ | ④ | ⑤ |
|---|---|---|---|---|---|
| 1 | (structure) | 2 | 155 | 180 | 1.16 |
| 2 | (structure) | 2 | 166 | 186 | 1.12 |
| 3 | (structure) | 2 | 133 | 197 | 1.48 |
| 4 | (structure) | 2 | 196 | 149 | 0.76 |
| 8 | (structure) | 2 | 41 | 246 | 6 |

TABLE 5-continued
| ① | Structure of compound | ② | ③ | ④ | ⑤ |
|---|---|---|---|---|---|
| 17 | 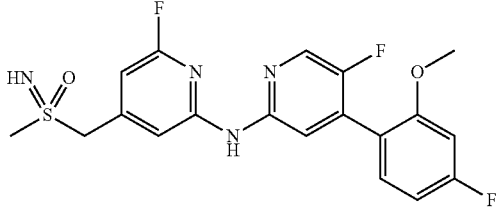 | 2 | 141 | 135 | 0.96 |
| 21 | 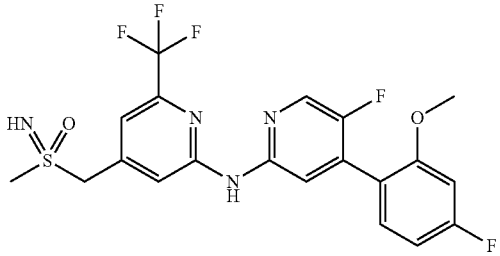 [SMILES: COc1cc(F)ccc1-c1cc(Nc2cc(CS(C)(=N)=O)cc(C(F)(F)F)n2)ncc1F] | 2 | 51 | 33 | 0.64 |
| 22 | 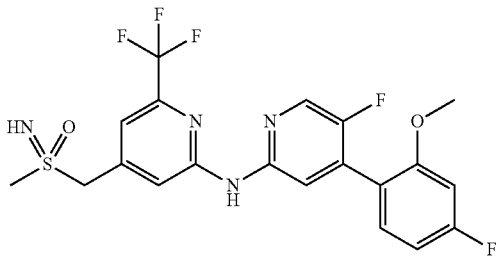 [SMILES: COc1cc(F)ccc1-c1cc(Nc2cc(CS(C)(=N)=O)cc(C(F)(F)F)n2)ncc1F] | 2 | 48 | 53 | 1.1 |
| 23 | 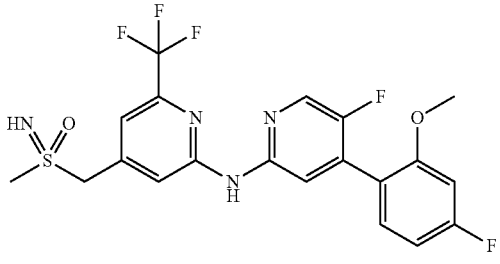 [SMILES: COc1cc(F)ccc1-c1cc(Nc2cc(CS(C)(=N)=O)cc(C(F)(F)F)n2)ncc1F] | 2 | 47 | 62 | 1.3 |
| 30 | 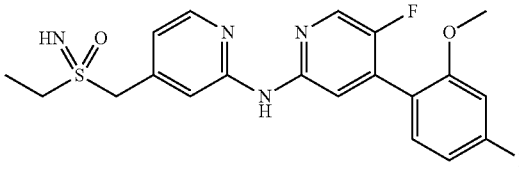 | 2 | 186 | 172 | 0.92 |

Table 6: Inhibition of Carbonic anhydrase-1 and Carbonic anhydrase-2 as determined as described under Method 6. of Materials and Methods.
①: Compound Number
②: Inhibition of Carbonic anhydrase-1: the $IC_{50}$ (inhibitory concentration at 50% of maximal effect) values are indicated in nM.
③ Inhibition of Carbonic anhydrase-2: the $IC_{50}$ (inhibitory concentration at 50% of maximal effect) values are indicated in nM.

TABLE 6

| ① | Structure of compound | ② | ③ |
|---|---|---|---|
| 1 | 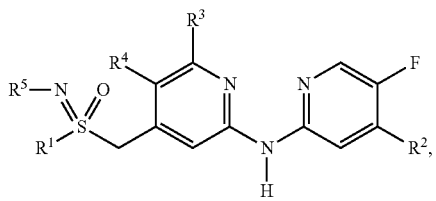 | >10000 | >10000 |

The invention claimed is:
1. A compound of formula (I)

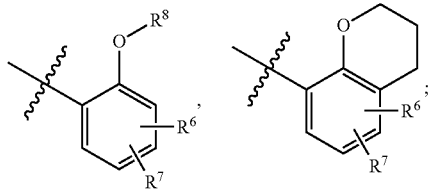
(I)

wherein
$R^1$ is a $C_1$-$C_6$-alkyl- or $C_3$-$C_5$-cycloalkyl group,
wherein said group is optionally substituted with one substituent selected from the group consisting of hydroxy, $C_1$-$C_3$-alkoxy-, —$NH_2$, alkylamino-, dialkylamino-, cyclic amines, and —OP(O)(OH)$_2$;
$R^2$ is a group selected from

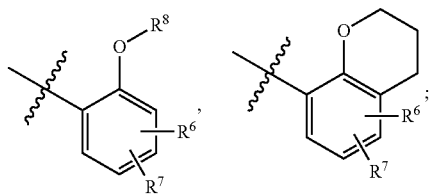

$R^3$ is a hydrogen atom, fluoro atom, chloro atom, $C_1$-$C_3$-alkyl, $C_1$-$C_3$-alkoxy or fluoro-$C_1$-$C_3$-alkyl group;
$R^4$ is a hydrogen atom, fluoro atom or bromo atom;
$R^5$ is a group selected from a hydrogen atom, cyano, —C(O)$R^9$, —C(O)O$R^9$, —C(O)N$R^{10}R^{11}$, —P(O)(O$R^{12}$)$_2$, —CH$_2$OP(O$R^{12}$)$_2$ and $C_1$-$C_3$-alkyl-,
wherein said $C_1$-$C_3$-alkyl group is optionally substituted with one substituent selected from —$NH_2$, alkylamino-, dialkylamino-, and cyclic amines;
$R^6$ and $R^7$ are, independently from each other, a group selected from a hydrogen atom, fluoro atom and chloro atom;

$R^8$ is a group selected from
a) a $C_1$-$C_3$-alkyl group, which is optionally substituted with one or two or three substituents, identically or differently, selected from halogen and halo-$C_1$-$C_3$-alkyl-; and
b) a phenyl-$C_1$-$C_3$-alkyl- group, the phenyl group of which is optionally substituted with one or two or three substituents, identically or differently, selected from the group consisting of halogen, cyano, $C_1$-$C_3$-alkyl-, halo-$C_1$-$C_3$-alkyl-, $C_1$-$C_3$-fluoroalkoxy-, and $C_1$-$C_3$-alkoxy-;
$R^9$ is a group selected from $C_1$-$C_3$-alkyl-, halo-$C_1$-$C_3$-alkyl-, and a benzyl group, the phenyl group of which is optionally substituted with one or two substituents, identically or differently, selected from the group consisting of halogen, $C_1$-$C_3$-alkyl-, $C_1$-$C_3$-alkoxy-, —$NH_2$, alkylamino-, and dialkylamino-;
$R^{10}$ and $R^{11}$ are, independently from each other, a group selected from a hydrogen atom, $C_1$-$C_3$-alkyl-, and benzyl,
or
$R^{10}$ and $R^{11}$ are taken together with the nitrogen atom to which they are attached to form a cyclic amine; and
$R^{12}$ is a group selected from a hydrogen atom and $C_1$-$C_2$-alkyl,
or an enantiomer, diastereomer, or salt thereof.
2. The compound of formula (I) according to claim 1, wherein
$R^1$ is a $C_1$-$C_6$-alkyl group,
wherein said group is optionally substituted with one substituent selected from the group consisting of hydroxy, $C_1$-$C_3$-alkoxy, —$NH_2$, alkylamino-, dialkylamino-, and cyclic amines;
$R^2$ is a group selected from $R^3$ is a hydrogen atom, fluoro atom, chloro atom, methyl, methoxy, difluoromethyl or trifluoromethyl group;
$R^4$ is a hydrogen atom or bromo atom;
$R^5$ is a group selected from a hydrogen atom, cyano, —C(O)$R^9$, —C(O)O$R^9$, and —C(O)N$R^{10}R^{11}$;
$R^6$ and $R^7$ are, independently from each other, a group selected from a hydrogen atom, fluoro atom and chloro atom;

173

R⁸ is a $C_1$-$C_3$-alkyl group;
R⁹ is a $C_1$-$C_3$-alkyl group, a benzyl group, or trifluoromethyl; and
R¹⁰ and R¹¹ are, independently from each other, a group selected from a hydrogen atom and $C_1$-$C_2$-alkyl-,
or an enantiomer, diastereomer, or salt thereof.

3. The compound of formula (I) according to claim 1, wherein
R¹ is a $C_1$-$C_3$-alkyl group,
   wherein said group is optionally substituted with one substituent selected from the group consisting of hydroxyl and —NH₂;
R² is a group

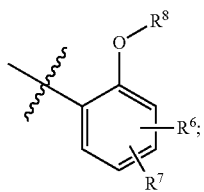

R³ is a hydrogen atom, fluoro atom, chloro atom, methyl, methoxy, difluoromethyl or trifluoromethyl group;
R⁴ is a hydrogen atom or bromo atom;
R⁵ is a group selected from a hydrogen atom, cyano, —C(O)R⁹, —C(O)OR⁹, and —C(O)NR¹⁰R¹¹;
R⁶ is a fluoro atom;
R⁷ is a hydrogen atom;
R⁸ is a methyl or ethyl group;
R⁹ is a methyl, ethyl or trifluoromethyl group; and
R¹⁰ and R¹¹ are, independently from each other, a group selected from a hydrogen atom and $C_1$-$C_2$-alkyl-,
or an enantiomer, diastereomer, or salt thereof.

4. The compound of formula (I) according to claim 1, wherein
R¹ is a methyl, ethyl, 2-hydroxyethyl or 2-aminoethyl group;
R² is a 4-fluoro-2-methoxyphenyl or 4-fluoro-2-ethoxyphenyl group;
R³ is a hydrogen atom, fluoro atom, chloro atom, methyl, methoxy, difluoromethyl or trifluoromethyl group;
R⁴ is a hydrogen atom or bromo atom; and
R⁵ is a hydrogen atom or a group selected from cyano, —C(O)CH₃, —C(O)CF₃, —C(O)OC₂H, and —C(O)N(H)C₂H₅,
or an enantiomer, diastereomer, or salt thereof.

5. The compound according to claim 1, which is
(rac)-5-Fluoro-4-(4-fluoro-2-methoxyphenyl)-N-{4-[(S-methylsulfonimidoyl)methyl]pyridin-2-yl}pyridin-2-amine;
(+)-5-Fluoro-4-(4-fluoro-2-methoxyphenyl)-N-{4-[(S-methylsulfonimidoyl)methyl]pyridin-2-yl}pyridin-2-amine;
(−)-5-Fluoro-4-(4-fluoro-2-methoxyphenyl)-N-{4-[(S-methylsulfonimidoyl)methyl]pyridin-2-yl}pyridin-2-amine;
(rac)-5-Fluoro-4-(4-fluoro-2-methoxyphenyl)-N-{6-methyl-4-[(S-methylsulfonimidoyl)methyl]pyridin-2-yl}pyridin-2-amine;

174

(rac)-5-Bromo-N-[5-fluoro-4-(4-fluoro-2-methoxyphenyl)pyridin-2-yl]-6-methyl-4-[(S-methylsulfonimidoyl)methyl]pyridin-2-amine;
(rac)-5-Fluoro-4-(4-fluoro-2-methoxyphenyl)-N-{6-methoxy-4-[(S-methylsulfonimidoyl)methyl]pyridin-2-yl}pyridin-2-amine;
(rac)-N-{6-Chloro-4-[(S-methylsulfonimidoyl)methyl]pyridin-2-yl}-5-fluoro-4-(4-fluoro-2-methoxyphenyl)pyridin-2-amine;
(rac)-2-{S-[(2-{[5-Fluoro-4-(4-fluoro-2-methoxyphenyl)pyridin-2-yl]amino}pyridin-4-yl)methyl]sulfonimidoyl}ethanol;
(rac)-N-(4-{[S-(2-Aminoethyl)sulfonimidoyl]methyl}pyridin-2-yl)-5-fluoro-4-(4-fluoro-2-methoxyphenyl)pyridin-2-amine;
{[(2-{[5-Fluoro-4-(4-fluoro-2-methoxyphenyl)pyridin-2-yl]amino}pyridin-4-yl)methyl](methyl)oxido-$\lambda^6$-sulfanylidene}cyanamide;
(rac)-Ethyl{[(2-{[5-fluoro-4-(4-fluoro-2-methoxyphenyl)pyridin-2-yl]amino}pyridin-4-yl)methyl](methyl)oxido-$\lambda^6$-sulfanylidene}carbamate;
(rac)-1-Ethyl-3-{[(2-{[5-fluoro-4-(4-fluoro-2-methoxyphenyl)pyridin-2-yl]amino}pyridin-4-yl)methyl](methyl)oxido-$\lambda^6$-sulfanylidene}urea;
(rac)-N-{[(2-{[5-Fluoro-4-(4-fluoro-2-methoxyphenyl)pyridin-2-yl]amino}pyridin-4-yl)methyl](methyl)oxido-$\lambda^6$-sulfanylidene}acetamide;
5-Fluoro-4-(4-fluoro-2-methoxyphenyl)-N-{4-[(S-methylsulfonimidoyl)methyl]pyridin-2-yl}pyridin-2-amine hydrochloride; enantiomer 2;
(rac)-Ethyl{[(2-{[5-fluoro-4-(4-fluoro-2-methoxyphenyl)pyridin-2-yl]amino}-6-methoxypyridin-4-yl)methyl](methyl)oxido-$\lambda^6$-sulfanylidene}carbamate;
5-Fluoro-4-(4-fluoro-2-methoxyphenyl)-N-{4-[(S-methylsulfonimidoyl)methyl]pyridin-2-yl}pyridin-2-amine hydrochloride; enantiomer 1;
(rac)-5-Fluoro-4-(4-fluoro-2-methoxyphenyl)-N-{6-fluoro-4-[(S-methylsulfonimidoyl)methyl]pyridin-2-yl}pyridin-2-amine;
(rac)-2,2,2-Trifluoro-N-{[(2-fluoro-6-{[5-fluoro-4-(4-fluoro-2-methoxyphenyl)pyridin-2-yl]amino}pyridin-4-yl)methyl](methyl)oxido-$\lambda^6$-sulfanylidene}acetamide;
(+)-5-Fluoro-4-(4-fluoro-2-methoxyphenyl)-N-{6-fluoro-4-[(S-methylsulfonimidoyl)methyl]pyridin-2-yl}pyridin-2-amine;
(−)-5-Fluoro-4-(4-fluoro-2-methoxyphenyl)-N-{6-fluoro-4-[(S-methylsulfonimidoyl)methyl]pyridin-2-yl}pyridin-2-amine;
(rac)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
(+)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
(−)-5-Fluoro-4-(4-fluoro-2-methoxyphenyl)-N-{4-[(S-methylsulfonimidoyl)methyl]-6-(trifluoromethyl)pyridin-2-yl}pyridin-2-amine;
(+)-2,2,2-Trifluoro-N-[{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide;
(−)-2,2,2-Trifluoro-N-[{[2-{[5-fluoro-4-(4-fluoro-2-methoxyphenyl)pyridin-2-yl]amino}-6-(trifluoromethyl)-pyridin-4-yl]methyl}(methyl)oxido-$\lambda^6$-sulfanylidene]acetamide;

(rac)-4-(2-Ethoxy-4-fluorophenyl)-5-fluoro-N-{6-fluoro-4-[(S-methylsulfonimidoyl)methyl]pyridin-2-yl}pyridin-2-amine;

(rac)-N-{[(2-{[4-(2-Ethoxy-4-fluoro-phenyl)-5-fluoro-pyridin-2-yl]amino}-6-fluoropyridin-4-yl)methyl]-(methyl)oxido-λ$^6$-sulfanylidene}-2,2,2-trifluoroacetamide;

(+)-4-(2-Ethoxy-4-fluorophenyl)-5-fluoro-N-{6-fluoro-4-[(S-methylsulfonimidoyl)methyl]pyridin-2-yl}pyridin-2-amine;

(−)-4-(2-Ethoxy-4-fluorophenyl)-5-fluoro-N-{6-fluoro-4-[(S-methylsulfonimidoyl)methyl]pyridin-2-yl}pyridin-2-amine;

(rac)-N-{4-[(S-Ethylsulfonimidoyl)-methyl]pyridin-2-yl}-5-fluoro-4-(4-fluoro-2-methoxyphenyl)pyridin-2-amine;

(rac)-N-{6-(Difluoromethyl)-4-[(S-methylsulfonimidoyl)methyl]pyridin-2-yl}-5-fluoro-4-(4-fluoro-2-methoxyphenyl)pyridin-2-amine;

(+)-5-Fluoro-4-(4-fluoro-2-methoxyphenyl)-N-{6-methyl-4-[(S-methylsulfonimidoyl)methyl]pyridin-2-yl}pyridin-2-amine; or (−)-5-Fluoro-4-(4-fluoro-2-methoxyphenyl)-N-{6-methyl-4-[(S-methylsulfonimidoyl)methyl]pyridin-2-yl}pyridin-2-amine, or an enantiomer, diastereomer, or salt thereof.

6. A pharmaceutical composition comprising the compound according to claim 1 in combination with an inert, nontoxic, pharmaceutically suitable adjuvant.

7. The compound according to claim 5, which is (rac)-5-Fluoro-4-(4-fluoro-2-methoxyphenyl)-N-{4-[(S-methylsulfonimidoyl)methyl]pyridin-2-yl}pyridin-2-amine, or a salt thereof.

8. The compound according to claim 5, which is (+)-5-Fluoro-4-(4-fluoro-2-methoxyphenyl)-N-{4-[(S-methylsulfonimidoyl)methyl]pyridin-2-yl}pyridin-2-amine, or a salt thereof.

9. The compound according to claim 5, which is (-)-5-Fluoro-4-(4-fluoro-2-methoxyphenyl)-N-{4-[(S-methylsulfonimidoyl)methyl]pyridin-2-yl}pyridin-2-amine, or a salt thereof.

\* \* \* \* \*